US007413888B2

(12) United States Patent
Fidantsef et al.

(10) Patent No.: US 7,413,888 B2
(45) Date of Patent: Aug. 19, 2008

(54) VARIANTS OF BETA-GLUCOSIDASES

(75) Inventors: Ana Fidantsef, Davis, CA (US); Michael Lamsa, Davis, CA (US); Brian Gorre Clancy, Elk Grove, CA (US)

(73) Assignee: Novozymes, Inc., Dan's, CA (US)

( * ) Notice: Subject to any disclaimer, the term of this patent is extended or adjusted under 35 U.S.C. 154(b) by 370 days.

(21) Appl. No.: 10/836,063

(22) Filed: Apr. 30, 2004

(65) Prior Publication Data

US 2004/0253702 A1    Dec. 16, 2004

Related U.S. Application Data

(60) Provisional application No. 60/467,767, filed on May 2, 2003, provisional application No. 60/528,342, filed on Dec. 9, 2003.

(51) Int. Cl.
*C12N 9/42* (2006.01)
*C12N 1/21* (2006.01)
*C12Q 1/68* (2006.01)
*C07H 21/04* (2006.01)

(52) U.S. Cl. .......................... 435/209; 435/69.1; 435/6; 435/252.3; 435/320.1; 536/23.2

(58) Field of Classification Search .................... 435/4, 435/6, 69.1, 183, 200, 252.3, 252.7, 252.74, 435/254.1, 254.3, 320.1; 530/23.2, 23.4, 530/23.6, 23.7, 23.74
See application file for complete search history.

(56) References Cited

FOREIGN PATENT DOCUMENTS

WO    0126586    5/2001

OTHER PUBLICATIONS

Iwashita K et al. (GenBank Accession No. P87076, 1997).*
Kawaguchi T et al. (GenBank Accession No. JC4939, 1996).*
Shu et al. (GenBank Accession No. AAB82320, 2001).*
Kawaguchi et al., Cloning and sequencing of the cDNA encoding Beta-glucosidase 1 from *Aspergillus aculeatus*, Gene, 1996, v. 173, pp. 287-288.
Iwashita et al., The bgIA gene of *Aspergillus kawachii* encodes both extracellular and cell wall-bound Beta-glucosidases, Applied and Environmental Microbiology, Dec. 1999, pp. 5546-5553.

* cited by examiner

*Primary Examiner*—Rebecca Prouty
*Assistant Examiner*—Younus Meah
(74) *Attorney, Agent, or Firm*—Robert L. Starnes

(57) ABSTRACT

The present invention relates to variants of a parent beta-glucosidase, comprising a substitution at one or more positions corresponding to positions 142, 183, 266, and 703 of amino acids 1 to 842 of SEQ ID NO: 2 or corresponding to positions 142, 183, 266, and 705 of amino acids 1 to 844 of SEQ ID NO: 70, wherein the variant has beta-glucosidase activity. The present invention also relates to nucleotide sequences encoding the variant beta-glucosidases and to nucleic acid constructs, vectors, and host cells comprising the nucleotide sequences.

16 Claims, 38 Drawing Sheets

| | | | | | | | | | | | | | | | | |
|---|---|---|---|---|---|---|---|---|---|---|---|---|---|---|---|---|
| atg | aag | ctt | ggt | tgg | atc | gag | gtg | gcc | gca | ttg | gcg | gct | gcc | tca | gta | 48 |
| Met | Lys | Leu | Gly | Trp | Ile | Glu | Val | Ala | Ala | Leu | Ala | Ala | Ala | Ser | Val | |
| 1 | | | | 5 | | | | | 10 | | | | | 15 | | |
| gtc | agt | gcc | aag | gat | gat | ctc | gcg | tac | tcc | cct | cct | ttc | tac | cct | tcc | 96 |
| Val | Ser | Ala | Lys | Asp | Asp | Leu | Ala | Tyr | Ser | Pro | Pro | Phe | Tyr | Pro | Ser | |
| | | 20 | | | | | 25 | | | | | 30 | | | | |
| cca | tgg | gca | gat | ggt | cag | ggt | gaa | tgg | gcg | gaa | gta | tac | aaa | cgc | gct | 144 |
| Pro | Trp | Ala | Asp | Gly | Gln | Gly | Glu | Trp | Ala | Glu | Val | Tyr | Lys | Arg | Ala | |
| | | 35 | | | | | 40 | | | | | 45 | | | | |
| gta | gac | ata | gtt | tcc | cag | atg | acg | ttg | aca | gag | aaa | gtc | aac | tta | acg | 192 |
| Val | Asp | Ile | Val | Ser | Gln | Met | Thr | Leu | Thr | Glu | Lys | Val | Asn | Leu | Thr | |
| | | 50 | | | | | 55 | | | | | 60 | | | | |
| act | gga | aca | gga | tgg | caa | cta | gag | agg | tgt | gtt | gga | caa | act | ggc | agt | 240 |
| Thr | Gly | Thr | Gly | Trp | Gln | Leu | Glu | Arg | Cys | Val | Gly | Gln | Thr | Gly | Ser | |
| 65 | | | | | 70 | | | | | 75 | | | | | 80 | |
| gtt | ccc | aga | ctc | aac | atc | ccc | agc | ttg | tgt | ttg | cag | gat | agt | cct | ctt | 288 |
| Val | Pro | Arg | Leu | Asn | Ile | Pro | Ser | Leu | Cys | Leu | Gln | Asp | Ser | Pro | Leu | |
| | | | | 85 | | | | | 90 | | | | | 95 | | |

Fig. 9A

```
ggt att cgt ttc tcg gac tac aat tca gct ttc cct gcg ggt gtt aat   336
Gly Ile Arg Phe Ser Asp Tyr Asn Ser Ala Phe Pro Ala Gly Val Asn
        100                     105                     110 gtc gct gcc acc tgg gac aag acg ctc gcc tac ctt cgt ggt cag gca   384
Val Ala Ala Thr Trp Asp Lys Thr Leu Ala Tyr Leu Arg Gly Gln Ala
        115                     120                     125 atg ggt gag gag ttc agt gat aag ggt att gac gtt cag ctg ggt cct   432
Met Gly Glu Glu Phe Ser Asp Lys Gly Ile Asp Val Gln Leu Gly Pro
        130                     135                     140 gct ggc cct ctc ggt gct cat ccg gat ggc ggt aga aac tgg gaa cct   480
Ala Gly Pro Leu Gly Ala His Pro Asp Gly Gly Arg Asn Trp Glu Pro
        145                     150                     155     160 gga ttc tca cca gat cca gcc ctc acc ggt gta ctt ttt gcg gag acg   528
Gly Phe Ser Pro Asp Pro Ala Leu Thr Gly Val Leu Phe Ala Glu Thr
        165                     170                     175 att aag ggt caa gat gct ggt gtc att gcg aca gct aag cat tat        576
Ile Lys Gly Gln Asp Ala Gly Val Ile Ala Thr Ala Lys His Tyr
        180                     185                     190
```

Fig. 9B

| | | | | | | | | | | | |
|---|---|---|---|---|---|---|---|---|---|---|---|
| atc | atg | aac | gaa | caa | gag | cat | ttc | cgc | caa | ccc | gag | gct | ggt | 624 |
| Ile | Met | Asn | Glu | Gln | Glu | His | Phe | Arg | Gln | Pro | Glu | Ala | Gly | |
| 195 | | | | | | 200 | | | | | 205 | | | |

| tac | gga | ttc | aac | gta | agc | gac | agt | ttg | agt | tcc | aac | gtt | gat | gac | aag | 672 |
|---|---|---|---|---|---|---|---|---|---|---|---|---|---|---|---|---|
| Tyr | Gly | Phe | Asn | Val | Ser | Asp | Ser | Leu | Ser | Ser | Asn | Val | Asp | Asp | Lys |
| 210 | | | | 215 | | | | | 220 | | | | | | |

| act | atg | cat | gaa | ttg | tac | ctc | tgg | ccc | ttc | gcg | gat | gca | gta | cgc | gct | 720 |
|---|---|---|---|---|---|---|---|---|---|---|---|---|---|---|---|---|
| Thr | Met | His | Glu | Leu | Tyr | Leu | Trp | Pro | Phe | Ala | Asp | Ala | Val | Arg | Ala |
| 225 | | | | 230 | | | | 235 | | | | | 240 | | |

| gga | gtc | ggt | gct | gtc | atg | tgc | tct | tac | aac | caa | atc | aac | agc | tac | 768 |
|---|---|---|---|---|---|---|---|---|---|---|---|---|---|---|---|
| Gly | Val | Gly | Ala | Val | Met | Cys | Ser | Tyr | Asn | Gln | Ile | Asn | Ser | Tyr | |
| | 245 | | | | | 250 | | | | | 255 | | | | |

| ggt | tgc | gag | aat | agc | gaa | act | ctg | aac | aag | ctt | ttg | aag | gcg | gag | ctt | 816 |
|---|---|---|---|---|---|---|---|---|---|---|---|---|---|---|---|---|
| Gly | Cys | Glu | Asn | Ser | Glu | Thr | Leu | Asn | Lys | Leu | Leu | Lys | Ala | Glu | Leu |
| 260 | | | | | 265 | | | | | 270 | | | | | |

| ggt | ttc | caa | ggc | ttc | gtc | atg | agt | gat | tgg | acc | gct | cat | cac | agc | ggc | 864 |
|---|---|---|---|---|---|---|---|---|---|---|---|---|---|---|---|---|
| Gly | Phe | Gln | Gly | Phe | Val | Met | Ser | Asp | Trp | Thr | Ala | His | His | Ser | Gly |
| 275 | | | | | 280 | | | | | 285 | | | | | |

Fig. 9C

| gta | ggc | gct | gct | tta | gca | ggt | ctg | gat | atg | tcg | atg | ccc | ggt | ggt | gtt | 912 |
|-----|-----|-----|-----|-----|-----|-----|-----|-----|-----|-----|-----|-----|-----|-----|-----|-----|
| Val | Gly | Ala | Ala | Leu | Ala | Gly | Leu | Asp | Met | Ser | Met | Pro | Gly | Asp | Val | |
| 290 | | | | | 295 | | | | | 300 | | | | | | |

| acc | ttc | gat | agt | ggt | acg | ggt | tct | ttc | tgg | ggt | gca | aac | ttg | acg | gtc | ggt | 960 |
|-----|-----|-----|-----|-----|-----|-----|-----|-----|-----|-----|-----|-----|-----|-----|-----|-----|-----|
| Thr | Phe | Asp | Ser | Gly | Thr | Gly | Ser | Phe | Trp | Gly | Ala | Asn | Leu | Thr | Val | Gly | |
| 305 | | | | | 310 | | | | | 315 | | | | | 320 | | |

| gtc | ctt | aac | ggt | aca | atc | ccc | caa | tgg | cgt | gtt | gat | gac | atg | gct | gtc | 1008 |
|-----|-----|-----|-----|-----|-----|-----|-----|-----|-----|-----|-----|-----|-----|-----|-----|------|
| Val | Leu | Asn | Gly | Thr | Ile | Pro | Gln | Trp | Arg | Val | Asp | Asp | Met | Ala | Val | |
| 325 | | | | | | | 330 | | | | | 335 | | | | |

| cgt | atc | atg | gcc | tat | tac | aag | gtt | ggc | cgc | gac | acc | aaa | tac | acc | 1056 |
|-----|-----|-----|-----|-----|-----|-----|-----|-----|-----|-----|-----|-----|-----|-----|------|
| Arg | Ile | Met | Ala | Tyr | Tyr | Lys | Val | Gly | Arg | Asp | Thr | Lys | Tyr | Thr | |
| | 340 | | | | | 345 | | | | 350 | | | | | |

| cct | ccc | aac | ttt | agc | tcg | tgg | acc | agg | gac | gaa | tat | ggt | ttc | gcg | cat | 1104 |
|-----|-----|-----|-----|-----|-----|-----|-----|-----|-----|-----|-----|-----|-----|-----|-----|------|
| Pro | Pro | Asn | Phe | Ser | Ser | Trp | Thr | Arg | Asp | Glu | Tyr | Gly | Phe | Ala | His | |
| 355 | | | | | | 360 | | | | | 365 | | | | | |

| aac | cat | gtt | tcg | gaa | ggt | gct | gca | tac | gag | agg | gtc | aac | gaa | gtg | gac | 1152 |
|-----|-----|-----|-----|-----|-----|-----|-----|-----|-----|-----|-----|-----|-----|-----|-----|------|
| Asn | His | Val | Ser | Glu | Gly | Ala | Ala | Tyr | Glu | Arg | Val | Asn | Glu | Val | Asp | |
| 370 | | | | | 375 | | | | | 380 | | | | | | |

Fig. 9D

```
gtg caa cgc gat cat gcc gac cta atc cgt cgc atc ggc gcg cag agc    1200
Val Gln Arg Asp His Ala Asp Leu Ile Arg Arg Ile Gly Ala Gln Ser
385                 390                 395                 400 act gtt ctg ctg aag aac aag ggt gcc ttg ccc ttg agc cgc aag gaa    1248
Thr Val Leu Leu Lys Asn Lys Gly Ala Leu Pro Leu Ser Arg Lys Glu
        405                 410                 415 aag ctg gtc gcc ctt ctg gga gag gat gcg gcg ggt tcc aac tcg tgg ggc  1296
Lys Leu Val Ala Leu Leu Gly Glu Asp Ala Ala Gly Ser Asn Ser Trp Gly
    420                 425                 430 gct aac ggc tgt gat gac cgt gga gag gat tgc gat aac ggt acc ctt gcc atg  1344
Ala Asn Gly Cys Asp Asp Arg Gly Glu Asp Cys Asp Asn Gly Thr Leu Ala Met
435                 440                 445 gcc tgg ggt agc ggt act gcg aat ttc cca tac ctc gtg aca cca gag    1392
Ala Trp Gly Ser Gly Thr Ala Asn Phe Pro Tyr Leu Val Thr Pro Glu
        450                 455                 460 cag gcg att cag aac gaa gtt ctt cag ggc cgt ggt aat gtc ttc gcc    1440
Gln Ala Ile Gln Asn Glu Val Leu Gln Gly Arg Gly Asn Val Phe Ala
465                 470                 475                 480
```

Fig. 9E

| gtg | acc | gac | agt | tgg | gcg | ctc | gac | aag | atc | gct | gcg | gct | cag | 1488 |
| Val | Thr | Asp | Ser | Trp | Ala | Leu | Asp | Lys | Ile | Ala | Ala | Ala | Arg | Gln |
|     |     |     |     | 485 |     |     |     | 490 |     |     |     | 495 |     |

| gcc | agc | gta | tct | ctc | gtg | ttc | gtc | aac | tcc | gac | tca | gga | gaa | tat | 1536 |
| Ala | Ser | Val | Ser | Leu | Val | Phe | Val | Asn | Ser | Asp | Ser | Gly | Glu | Gly | Tyr |
|     |     | 500 |     |     |     |     | 505 |     |     |     |     | 510 |     |     |

| ctt | agt | gtg | gat | gga | gag | ggc | gat | cgt | aac | atc | act | ctg | tgg | 1584 |
| Leu | Ser | Val | Asp | Gly | Glu | Gly | Asp | Arg | Asn | Ile | Thr | Leu | Trp |
|     | 515 |     |     |     |     | 520 |     |     |     |     | 525 |     |     |

| aag | aac | ggc | gac | aat | gtg | gtc | aag | acc | gca | gcg | aat | aac | tgt | aac | aac | 1632 |
| Lys | Asn | Gly | Asp | Asn | Val | Val | Lys | Thr | Ala | Ala | Asn | Asn | Cys | Asn | Asn |
| 530 |     |     |     |     | 535 |     |     |     |     | 540 |     |     |     |     |

| acc | gat | gac | atc | atc | cac | tcc | gga | cca | gtt | ttg | atc | gat | gaa | tgg | 1680 |
| Thr | Asp | Asp | Ile | Ile | His | Ser | Gly | Pro | Val | Leu | Ile | Asp | Glu | Trp |
| 545 |     |     |     | 550 |     |     |     |     | 555 |     |     |     |     | 560 |

| tat | gac | cac | ccc | aat | gtc | act | ggt | att | ctc | tgg | gct | ggt | ctg | cca | ggc | 1728 |
| Tyr | Asp | His | Pro | Asn | Val | Thr | Gly | Ile | Leu | Trp | Ala | Gly | Leu | Pro | Gly |
|     |     | 565 |     |     |     |     | 570 |     |     |     |     | 575 |     |     |

Fig. 9F

```
cag gag tct ggt aac tcc att gcc gat gtg ctg tac ggt cgt gtc aac    1776
Gln Glu Ser Gly Asn Ser Ile Ala Asp Val Leu Tyr Gly Arg Val Asn
            580                 585                 590 cct ggc gcc aag tct cct ttc act tgg ggc aag acc cgg gag tcg tat    1824
Pro Gly Ala Lys Ser Pro Phe Thr Trp Gly Lys Thr Arg Glu Ser Tyr
        595                 600                 605 ggt tct ccc ttg gtc aag gat gcc aac aat ggc aac gga gcg ccc cag    1872
Gly Ser Pro Leu Val Lys Asp Ala Asn Asn Gly Asn Gly Ala Pro Gln
    610                 615                 620 tct gat ttc acc cag ggt ttc atc tac cct atc gat tac cgc cat ttc    1920
Ser Asp Phe Thr Gln Gly Phe Ile Tyr Pro Ile Asp Tyr Arg His Phe
625                 630                 635                 640 ttc aat gag acc cct atc tac gag ttt ggc tac ggc ttg agc tac acc    1968
Phe Asn Glu Thr Pro Ile Tyr Glu Phe Gly Tyr Gly Leu Ser Tyr Thr
                645                 650                 655 acc ttc gag ctc tcc gac ctc cat gtt cag ccc ctg aac gcg tcc cga    2016
Thr Phe Glu Leu Ser Asp Leu His Val Gln Pro Leu Asn Ala Ser Arg
            660                 665                 670
```

Fig. 9G

| tac | act | ccc | acc | agt | ggc | atg | act | gaa | gct | gca | aag | aac | ttt | ggt | gaa | 2064 |
| Tyr | Thr | Pro | Thr | Ser | Gly | Met | Thr | Glu | Ala | Ala | Lys | Asn | Phe | Gly | Glu | |
| 675 | | | | | | 680 | | | | | 685 | | | | | |

| att | ggc | gat | gcg | tcg | gag | tac | gtg | tat | ccg | gag | ggg | ctg | gaa | agg | atc | 2112 |
| Ile | Gly | Asp | Ala | Ser | Glu | Tyr | Val | Tyr | Pro | Glu | Gly | Leu | Glu | Arg | Ile | |
| 690 | | | | | 695 | | | | | 700 | | | | | | |

| cat | gag | ttt | atc | tat | ccc | tgg | atc | aac | tct | acc | gac | ctg | aag | gca | tcg | 2160 |
| His | Glu | Phe | Ile | Tyr | Pro | Trp | Ile | Asn | Ser | Thr | Asp | Leu | Lys | Ala | Ser | |
| 705 | | | | 710 | | | | | 715 | | | | | | 720 | |

| tct | gac | gat | tct | aac | tac | ggc | tgg | gaa | gac | tcc | aag | tat | att | ccc | gaa | 2208 |
| Ser | Asp | Asp | Ser | Asn | Tyr | Gly | Trp | Glu | Asp | Ser | Lys | Tyr | Ile | Pro | Glu | |
| | | | 725 | | | | | 730 | | | | | 735 | | | |

| ggc | gcc | acg | gat | ggg | tct | gcc | cag | ccc | cgt | ttg | ccc | gct | agt | ggt | ggt | 2256 |
| Gly | Ala | Thr | Asp | Gly | Ser | Ala | Gln | Pro | Arg | Leu | Pro | Ala | Ser | Gly | Gly | |
| | 740 | | | | | 745 | | | | | 750 | | | | | |

| gcc | gga | gga | aac | ccc | ggt | ctg | tac | gag | gat | ttt | cgc | gtc | tct | gtg | | 2304 |
| Ala | Gly | Gly | Asn | Pro | Gly | Leu | Tyr | Glu | Asp | Phe | Arg | Val | Ser | Val | | |
| 755 | | | | | 760 | | | | | 765 | | | | | | |

Fig. 9H

| aag | gtc | aac | acg | ggc | aat | gtc | gcc | ggt | gat | gaa | gtt | cct | cag | ctg | 2352 |
| Lys | Val | Asn | Thr | Gly | Asn | Val | Ala | Gly | Asp | Glu | Val | Pro | Gln | Leu | |
| 770 | | | | 775 | | | | | 780 | | | | | | |

| tac | gtt | tcc | cta | ggc | ggc | ggt | ggc | ccg | aat | gag | gtg | gta | ctg | cgc | aag | 2400 |
| Tyr | Val | Ser | Leu | Gly | Gly | Gly | Pro | Asn | Glu | Val | Val | Leu | Arg | Lys | |
| 785 | | | | 790 | | | | | 795 | | | | | 800 | |

| ttt | gag | cgt | att | cac | ttg | gcc | cct | tcg | cag | gag | gcc | gtg | acg | acg | 2448 |
| Phe | Glu | Arg | Ile | His | Leu | Ala | Pro | Ser | Gln | Glu | Ala | Val | Thr | Thr | |
| | | | | 805 | | | | | 810 | | | | | 815 | |

| acc | ctt | acc | cgt | gac | ctt | gca | aac | tgg | gac | gtt | tcg | gct | cag | gac | 2496 |
| Thr | Leu | Thr | Arg | Asp | Leu | Ala | Asn | Trp | Asp | Val | Ser | Ala | Gln | Asp | |
| | | 820 | | | | | 825 | | | | | 830 | | | |

| tgg | acc | gtc | act | cct | tac | ccc | aag | acg | atc | tac | gtt | gga | aac | tcc | tca | 2544 |
| Trp | Thr | Val | Thr | Pro | Tyr | Pro | Lys | Thr | Ile | Tyr | Val | Gly | Asn | Ser | Ser |
| 835 | | | | | 840 | | | | | 845 | | | | | |

| cgg | aaa | ctg | ccg | ctc | cag | gcc | tcg | ctg | cct | aag | gcc | cag | taa | | 2586 |
| Arg | Lys | Leu | Pro | Leu | Gln | Ala | Ser | Leu | Pro | Lys | Ala | Gln | | | |
| 850 | | | | | 855 | | | | | 860 | | | | | |

Fig. 9I

ATG CGT TCC TCC CCC CTC CTC CGC TCC GCC GTT GTG GCC GCC CTG CCG GTG TTG GCC CTT GCC
M   R   S   S   P   L   L   R   S   A   V   V   A   A   L   P   V   L   A   L   A

Fig. 10

```
ATGAGATTCGGTTGGCTCGAGGTGGCCGCTCTGACGGCCGCTCTGTAGCCAATGCCAGTTTGTGATGCTTTCCGTCATTGTTCGATATAGTTGA  100
 M  R  F  G  W  L  E  V  A  A  L  T  A  A  S  V  A  N  A  Q
CAATAGTCATGGAAATCAGAATTGGCTTTCTCCTCCACCATTCTACCCTTCGCCTTGGGCTGATGGCCAGGAGAGTGGGACAGATGCCAATGACGC  200
                  E  L  A  F  S  P  P  F  Y  P  S  P  W  A  D  G  Q  G  E  W  A  D  A  H  R  R
GCCGTCGAGATCGTTCTCAGATGACACTCTGGCCGAGAAGGTTAACCTTACAACGGGTCGGTTGCGACTTTTTTGTTGACAGTGAGCTTTCTTC  300
 A  V  E  I  V  S  Q  M  T  L  A  E  K  V  N  L  T  T  G  T  G
ACTGACCATCTACACAGATGGGAAATGGACCGGTGTCTATCAACGGTCGGTCCCAGTAAGCTTGCAATTCTGCAACAACGTGCAAGTGTAGTT  400
 T  D  H  Y  T  D  G  K  W  T  G  V  Y  Q  R  S  V  P  S  S  L  Q  F  C  N  N  V  Q  V
GCTAAAACGCCGGTGCGTGCAGACTTGGTATCAACTGGGGCTCTTTGTGGCCAGGATTCCCCCTTGGGTATCCGTTCTTCTGTGAGCTATACCCCGGGAGTCTTT  500
                  W  E  M  D  R  C  V  G  Q  T  G  S  V  P  P  R
                                 L  G  I  N  W  G  L  C  G  Q  D  S  P  L  G  I  R  F
CAGTCCTTGTATTATGCTGCTGAAGGCCATGGGTGAGAATCAACGACAAGGCCGTGAGAATTCAACGACAAGGCCGTGAGGAATTCAAGAAATCGCCGACATGGACAAGACACT  600
                  S  D  L  N  S  A  F  P  A  G  T  N  V  A  A  T  W  D  K  T  L
CGCCTACCTTCGTGCCAAGGCCATGGGTGAGAATTCAACGACAAGGCCGTGACATTTGCTGGGGCCTCGTGCTGTCTCCGCAAATACCCGGAC  700
 A  Y  L  R  K  A  M  G  E  E  F  N  D  K  G  V  D  I  L  L  G  P  A  A  G  P  L  G  K  Y  P  D
GGCGGCAGAATCTGGGAAGGCTTCTCTCCTGATCCGGTTCTCACTGGTGTACTTTTCGCGAACTATCAAGGATATCCAAGACGCGGTGATTGCTA  800
 G  G  R  I  W  E  G  F  S  P  D  D  P  V  L  T  G  V  L  F  A  E  T  I  K  G  I  Q  D  A  G  V  I  A
CTGCCAAGCATTACATTCTGAATGAACAGAGCATTTCGACAGGTTGGCGAGGCCAGGATATGTTACAACATCACGGAGACGATCAGCTCCAACGT  900
 T  A  K  H  Y  I  L  N  E  Q  H  F  R  Q  V  G  E  A  Q  G  Y  G  Y  N  I  T  E  T  I  S  S  N  V
GGATGACAAGACCATGCACGAGTTGTACCTTTTGGTGAGACTTGACCTCGCGACGAAGAAATCGCTGACGAACCATCGTAGCTGTGCGCTGTCATGTGTTCCTA  1000
 D  D  K  T  M  H  E  L  Y  L  W                                                  P  F  A
AGATGCTGTGCGCGTAAGATTTTCCGTAGACTTGTCAAAACAGTTGTCAAAACAGTCAACACTCTCAACAAGCTCCTCGAGCTTCGTGGGCTTGAGCTCATGAGTGACTGG  1100
 D  A  V  R                                                  A  G  V  G  A  V  M  C  S  Y
CAATCAAATCAACAACAGCTACGGTTGTCAAAACAGTTGTCAAAACAGTCTGCGCGTGTCGCGCGGGCTGTCCGCTGGGTTGGATATGTCGATGCCTGGAGACATTCCTTCGACGACGGGACTCTCCTTCTGGGCACGA  1200
 N  Q  I  N  N  S  Y  G  C  Q  N  S  Q  T  L  N  K  L  L  K  A  E  L  G  F  Q  Q  G  F  V  M  S  D  W
AGCGCTCCACCAGCGGTGTCGCGGCGTCGGCAAAGCTGGACATGTCGATGCCTGGAGACATTCCTTCGACGACGGGACTCTCCTTCTGGGGCACGA  1300
 S  A  H  H  S  G  V  G  A  A  L  A  G  L  D  M  S  M  P  G  D  I  S  F  D  D  G  L  S  F  W  G  T
ACCTAACTGTCAGTGTTCTTAACGGCACCGTTCCAGCGTTCAGCTCCTGGACCCGGATGAGTACGGCCGATGAGAGCCTGGACCAAGGTGAACGACTTC  1400
 N  L  T  V  S  V  L  N  G  T  V  P  A  W  R  V  D  D  M  A  V  R  I  M  T  A  Y  Y  K  V  G  R  D  R
TCTTCGTATTCCCCCTAACTTCAGCTCCTCAGATCATCCTGAGATTCGTGAGATTGGTGCCGCTAGTACGGTGCTGCTCAAGAATACGGGTGCTGCTTCCTTTGACCGGCAAGG  1500
 L  R  I  P  P  N  F  S  S  W  T  R  D  E  Y  G  W  E  H  S  A  V  S  E  G  A  W  T  K  V  N  D  F
GTCAATGTGCAGCGCGTGGGTTCTCGGTGAAGACGCTGGTTCAACCGTGTTCCAACCCGTGGGGTGCTAACGCCTATCAGCAGCGGGAGAGGTCATCAGCAGCGGCAATGTCTTGCCTGACT  1600
 V  N  V  Q  R  S  H  S  Q  I  H  R  E  I  G  A  A  S  T  V  L  L  K  N  T  G  A  L  P  L  T  G  K
AGGTTAAAGTGGGTGTTCTCGGTGGCGGCGATGCTGGAAGCAATCCGTGGGGTGCTAACGGCCAGGCTGCAATCCAGCGCGAGAGGGTCATCAGCAATGGCGGCAATGTCTTTTGCTGTGACT  1700
 E  V  K  V  G  V  L  G  B  D  A  G  S  N  P  W  G  A  N  G  C  P  D  D  R  G  C  D  N  G  T  L  A  M  A
CTGGGGTAGTGGTACTGCCAACTTCCCTTACCTTGTCATCTCAATCCAGGTGAGTGCGCGCGGGCCAATCCGAGGAGGTCATCAGCAATGGCGGCAATGTCTTCGCTGTGACT  1800
 W  G  S  G  T  A  N  F  P  Y  L  V  T  P  E  Q  A  I  Q  R  E  V  I  S  N  G  G  N  V  F  A  V  T
GATAACGGGGCTCTCAGCCAGATGGCAGATGTGCATCTCAATCCAGGTGAGTGCGCGCGGGCCAATCCGAGGAGGTCATCAGCAATGGCGGCAATGTCTTCTCTGAATGAAGTTTTTTAACCA  1900
 D  N  G  A  L  S  Q  M  A  D  V  A  S  Q  S
```

Fig. 21A

```
TTGCGAACAGCGTGTCTTTGTGTTTGTCAACGCCGACTCTGACGAGAGGTTTCATCAGTGTCGACGGCAACGAGGGTGACCGCAAAATCTCACTCTGTG  2000
   V  S  L  V  F  F  V  N  A  D  S  G  E  G  F  I  S  V  D  G  N  E  G  D  R  K  N  L  T  L  W
GAAGAACGGCGAGGCCGTCATTGACACTGTTGTCAGCCACTGCAACAACACGATTGTGGTTATTCACAGTGTTGGCCCGTCTTGATGACCGGTGGTAT  2100
   K  N  G  E  A  V  I  D  T  V  V  S  H  C  N  N  T  I  V  V  I  H  S  V  G  P  V  L  I  D  R  W  Y
GATAACCCCAACGTCACTGCCATCATCTGGGCCGGTCAAGACTCGGGCGAGTCTTACGGGCAAGCCTAACAATGGCTGTCTCCCCAGGATGATTTCAA  2200
   D  N  P  N  V  T  A  I  I  W  A  G  L  P  G  Q  E  S  G  N  S  L  V  D  V  L  Y  G  R  V  N  P  S
CCAAGAACCCCGTTCACCTGGGCAAGACTCGGGAGTCTTACGGGCAAGCCTAACAATGGCTGTCTCCCCAGGATGATTTCAA  2300
   A  K  T  P  F  F  T  W  G  K  T  R  E  S  Y  G  A  P  L  T  E  P  N  N  G  A  P  Q  D  D  F  N
CGAGGGCGGTCTTCATTGACTACCGTCACTTTGACAAGCGCAATGAGACGCCATTTATGAGTTTGGCCATGGCTTGAGCTACACCACCTTTGGTTACTCT  2400
   E  G  V  F  I  D  Y  R  H  F  D  K  R  N  E  T  P  I  Y  E  F  G  H  G  L  S  Y  T  T  F  G  Y  S
CACCTTCGGGTTCAGCCCCTCAATAGTTCGGAGTTCGGACATATGTCCGACTAGCGGAGAGACAAGCCTGCCGCCAACCTATGGTGAGATCGGTAGTGCCG  2500
   H  L  R  V  Q  A  L  N  S  S  S  A  Y  V  P  T  S  G  E  T  K  P  A  P  T  Y  G  E  I  G  S  A
CCGACTACCTGTATCCCGAGGGTCTCAAAGAATTACCAAGTTTATTCCCTGGCTCGAGGATTCTTCTGACGACCGAACTA  2600
   A  D  Y  L  Y  P  E  G  L  K  R  I  T  K  F  I  Y  P  W  L  N  S  T  D  L  E  D  S  D  D  P  N  Y
CGGCTGGAGGACTCTTGTTAGGGTGTCGCGGCAGTACATTCCCGAAGGCTAGGATGGCTCTCCTCAACCCTCCTGGTGGTAACCCTACCCTT  2700
   G  W  E  D  S  E  Y  I  P  E  G  A  R  D  S  P  Q  P  L  L  K  A  G  G  A  P  G  G  N  P  T  L
TATCAGGATCTTGTTAGGGTGTCGCTTCTAGTAACTGGAAGTCCCTCAATTGTGAGTGACCGCATGTTCCTTGCG  2800
   Y  Q  D  L  V  R  V  S  A  T  I  T  N  T  G  N  V  A  G  Y  E  V  P  Q  L
TTGCAATTTGGCTAACTCGCTTCTAGTAACCGACTCTTAACCGTCGTGATCTCCCAATTGGGATGTGGAGCTCAGAGTGCCGCAATCTTCCTGGCTCCTGG  2900
        V  S  L  G  G  P  N  E  P  R  V  L  R  K  F  D  R  I  F  L  A  P  G
GGAGCAAAAGGTTTGACCACGACTCTTAACCGTCGTGATCTCCCAATTGGGATGTGGAGCTCAGAGTGCCGCAATCTTCCTGGCTCCTGG  3000
   E  Q  K  V  W  T  T  T  L  N  R  R  D  L  A  N  W  D  V  E  A  Q  D  W  V  I  T  K  Y  P  P  K  K  V
CACGTCGGCAGCTCCTCGCAGCTGCCTCTGAGAGCCGCCTCTGCCCCGTGTCTACTAG 3060
   H  V  G  S  S  R  K  L  P  L  R  A  P  L  P  P  R  V  Y
```

Fig. 21B

SEQUENCE LISTING

<160> NUMBER OF SEQ ID NOS: 92

<210> SEQ ID NO 1
<211> LENGTH: 2586
<212> TYPE: DNA
<213> ORGANISM: Aspergillus oryzae
<220> FEATURE:
<221> NAME/KEY: CDS
<222> LOCATION: (1)..(2583)

<400> SEQUENCE: 1

```
atg aag ctt ggt tgg atc gag gtg gcc gca ttg gcg gct gcc tca gta        48
Met Lys Leu Gly Trp Ile Glu Val Ala Ala Leu Ala Ala Ala Ser Val
1               5                   10                  15 gtc agt gcc aag gat gat ctc gcg tac tcc cct cct ttc tac cct tcc        96
Val Ser Ala Lys Asp Asp Leu Ala Tyr Ser Pro Pro Phe Tyr Pro Ser
                20                  25                  30 cca tgg gca gat ggt cag ggt gaa tgg gcg gaa gta tac aaa cgc gct       144
Pro Trp Ala Asp Gly Gln Gly Glu Trp Ala Glu Val Tyr Lys Arg Ala
            35                  40                  45 gta gac ata gtt tcc cag atg acg ttg aca gag aaa gtc aac tta acg       192
Val Asp Ile Val Ser Gln Met Thr Leu Thr Glu Lys Val Asn Leu Thr
        50                  55                  60 act gga aca gga tgg caa cta gag agg tgt gtt gga caa act ggc agt       240
Thr Gly Thr Gly Trp Gln Leu Glu Arg Cys Val Gly Gln Thr Gly Ser
65                  70                  75                  80 gtt ccc aga ctc aac atc ccc agc ttg tgt ttg cag gat agt cct ctt       288
Val Pro Arg Leu Asn Ile Pro Ser Leu Cys Leu Gln Asp Ser Pro Leu
                85                  90                  95 ggt att cgt ttc tcg gac tac aat tca gct ttc cct gcg ggt gtt aat       336
Gly Ile Arg Phe Ser Asp Tyr Asn Ser Ala Phe Pro Ala Gly Val Asn
            100                 105                 110 gtc gct gcc acc tgg gac aag acg ctc gcc tac ctt cgt ggt cag gca       384
Val Ala Ala Thr Trp Asp Lys Thr Leu Ala Tyr Leu Arg Gly Gln Ala
        115                 120                 125 atg ggt gag gag ttc agt gat aag ggt att gac gtt cag ctg ggt cct       432
Met Gly Glu Glu Phe Ser Asp Lys Gly Ile Asp Val Gln Leu Gly Pro
    130                 135                 140 gct gct ggc cct ctc ggt gct cat ccg gat ggc ggt aga aac tgg gaa       480
Ala Ala Gly Pro Leu Gly Ala His Pro Asp Gly Gly Arg Asn Trp Glu
145                 150                 155                 160 ggt ttc tca cca gat cca gcc ctc acc ggt gta ctt ttt gcg gag acg       528
Gly Phe Ser Pro Asp Pro Ala Leu Thr Gly Val Leu Phe Ala Glu Thr
```

-continued

```
                        165                 170                 175
att aag ggt att caa gat gct ggt gtc att gcg aca gct aag cat tat        576
Ile Lys Gly Ile Gln Asp Ala Gly Val Ile Ala Thr Ala Lys His Tyr
                    180                 185                 190 atc atg aac gaa caa gag cat ttc cgc caa caa ccc gag gct gcg ggt        624
Ile Met Asn Glu Gln Glu His Phe Arg Gln Gln Pro Glu Ala Ala Gly
                195                 200                 205 tac gga ttc aac gta agc gac agt ttg agt tcc aac gtt gat gac aag        672
Tyr Gly Phe Asn Val Ser Asp Ser Leu Ser Ser Asn Val Asp Asp Lys
            210                 215                 220 act atg cat gaa ttg tac ctc tgg ccc ttc gcg gat gca gta cgc gct        720
Thr Met His Glu Leu Tyr Leu Trp Pro Phe Ala Asp Ala Val Arg Ala
225                 230                 235                 240 gga gtc ggt gct gtc atg tgc tct tac aac caa atc aac aac agc tac        768
Gly Val Gly Ala Val Met Cys Ser Tyr Asn Gln Ile Asn Asn Ser Tyr
                245                 250                 255 ggt tgc gag aat agc gaa act ctg aac aag ctt ttg aag gcg gag ctt        816
Gly Cys Glu Asn Ser Glu Thr Leu Asn Lys Leu Leu Lys Ala Glu Leu
            260                 265                 270 ggt ttc caa ggc ttc gtc atg agt gat tgg acc gct cat cac agc ggc        864
Gly Phe Gln Gly Phe Val Met Ser Asp Trp Thr Ala His His Ser Gly
        275                 280                 285 gta ggc gct gct tta gca ggt ctg gat atg tcg atg ccc ggt gat gtt        912
Val Gly Ala Ala Leu Ala Gly Leu Asp Met Ser Met Pro Gly Asp Val
    290                 295                 300 acc ttc gat agt ggt acg tct ttc tgg ggt gca aac ttg acg gtc ggt        960
Thr Phe Asp Ser Gly Thr Ser Phe Trp Gly Ala Asn Leu Thr Val Gly
305                 310                 315                 320 gtc ctt aac ggt aca atc ccc caa tgg cgt gtt gat gac atg gct gtc       1008
Val Leu Asn Gly Thr Ile Pro Gln Trp Arg Val Asp Asp Met Ala Val
                325                 330                 335 cgt atc atg gcc gct tat tac aag gtt ggc cgc gac acc aaa tac acc       1056
Arg Ile Met Ala Ala Tyr Tyr Lys Val Gly Arg Asp Thr Lys Tyr Thr
            340                 345                 350 cct ccc aac ttc agc tcg tgg acc agg gac gaa tat ggt ttc gcg cat       1104
Pro Pro Asn Phe Ser Ser Trp Thr Arg Asp Glu Tyr Gly Phe Ala His
        355                 360                 365 aac cat gtt tcg gaa ggt gct tac gag agg gtc aac gaa ttc gtg gac       1152
Asn His Val Ser Glu Gly Ala Tyr Glu Arg Val Asn Glu Phe Val Asp
    370                 375                 380 gtg caa cgc gat cat gcc gac cta atc cgt cgc atc ggc gcg cag agc       1200
Val Gln Arg Asp His Ala Asp Leu Ile Arg Arg Ile Gly Ala Gln Ser
385                 390                 395                 400 act gtt ctg ctg aag aac aag ggt gcc ttg ccc ttg agc cgc aag gaa       1248
Thr Val Leu Leu Lys Asn Lys Gly Ala Leu Pro Leu Ser Arg Lys Glu
                405                 410                 415 aag ctg gtc gcc ctt ctg gga gag gat gcg ggt tcc aac tcg tgg ggc       1296
Lys Leu Val Ala Leu Leu Gly Glu Asp Ala Gly Ser Asn Ser Trp Gly
            420                 425                 430 gct aac ggc tgt gat gac cgt ggt tgc gat aac ggt acc ctt gcc atg       1344
Ala Asn Gly Cys Asp Asp Arg Gly Cys Asp Asn Gly Thr Leu Ala Met
        435                 440                 445 gcc tgg ggt agc ggt act gcg aat ttc cca tac ctc gtg aca cca gag       1392
Ala Trp Gly Ser Gly Thr Ala Asn Phe Pro Tyr Leu Val Thr Pro Glu
    450                 455                 460 cag gcg att cag aac gaa gtt ctt cag ggc cgt ggt aat gtc ttc gcc       1440
Gln Ala Ile Gln Asn Glu Val Leu Gln Gly Arg Gly Asn Val Phe Ala
465                 470                 475                 480 gtg acc gac agt tgg gcg ctc gac aag atc gct gcg gct gcc cgc cag       1488
```

```
                    Val Thr Asp Ser Trp Ala Leu Asp Lys Ile Ala Ala Ala Arg Gln
                                485                 490                 495 gcc agc gta tct ctc gtg ttc gtc aac tcc gac tca gga gaa ggc tat          1536
Ala Ser Val Ser Leu Val Phe Val Asn Ser Asp Ser Gly Glu Gly Tyr
            500                 505                 510 ctt agt gtg gat gga aat gag ggc gat cgt aac aac atc act ctg tgg          1584
Leu Ser Val Asp Gly Asn Glu Gly Asp Arg Asn Asn Ile Thr Leu Trp
        515                 520                 525 aag aac ggc gac aat gtg gtc aag acc gca gcg aat aac tgt aac aac          1632
Lys Asn Gly Asp Asn Val Val Lys Thr Ala Ala Asn Asn Cys Asn Asn
    530                 535                 540 acc gtt gtc atc atc cac tcc gtc gga cca gtt ttg atc gat gaa tgg          1680
Thr Val Val Ile Ile His Ser Val Gly Pro Val Leu Ile Asp Glu Trp
545                 550                 555                 560 tat gac cac ccc aat gtc act ggt att ctc tgg gct ggt ctg cca ggc          1728
Tyr Asp His Pro Asn Val Thr Gly Ile Leu Trp Ala Gly Leu Pro Gly
                565                 570                 575 cag gag tct ggt aac tcc att gcc gat gtg ctg tac ggt cgt gtc aac          1776
Gln Glu Ser Gly Asn Ser Ile Ala Asp Val Leu Tyr Gly Arg Val Asn
            580                 585                 590 cct ggc gcc aag tct cct ttc act tgg ggc aag acc cgg gag tcg tat          1824
Pro Gly Ala Lys Ser Pro Phe Thr Trp Gly Lys Thr Arg Glu Ser Tyr
        595                 600                 605 ggt tct ccc ttg gtc aag gat gcc aac aat ggc aac gga gcg ccc cag          1872
Gly Ser Pro Leu Val Lys Asp Ala Asn Asn Gly Asn Gly Ala Pro Gln
    610                 615                 620 tct gat ttc acc cag ggt gtt ttc atc gat tac cgc cat ttc gat aag          1920
Ser Asp Phe Thr Gln Gly Val Phe Ile Asp Tyr Arg His Phe Asp Lys
625                 630                 635                 640 ttc aat gag acc cct atc tac gag ttt ggc tac ggc ttg agc tac acc          1968
Phe Asn Glu Thr Pro Ile Tyr Glu Phe Gly Tyr Gly Leu Ser Tyr Thr
                645                 650                 655 acc ttc gag ctc tcc gac ctc cat gtt cag ccc ctg aac gcg tcc cga          2016
Thr Phe Glu Leu Ser Asp Leu His Val Gln Pro Leu Asn Ala Ser Arg
            660                 665                 670 tac act ccc acc agt ggc atg act gaa gct gca aag aac ttt ggt gaa          2064
Tyr Thr Pro Thr Ser Gly Met Thr Glu Ala Ala Lys Asn Phe Gly Glu
        675                 680                 685 att ggc gat gcg tcg gag tac gtg tat ccg gag ggg ctg gaa agg atc          2112
Ile Gly Asp Ala Ser Glu Tyr Val Tyr Pro Glu Gly Leu Glu Arg Ile
    690                 695                 700 cat gag ttt atc tat ccc tgg atc aac tct acc gac ctg aag gca tcg          2160
His Glu Phe Ile Tyr Pro Trp Ile Asn Ser Thr Asp Leu Lys Ala Ser
705                 710                 715                 720 tct gac gat tct aac tac ggc tgg gaa gac tcc aag tat att ccc gaa          2208
Ser Asp Asp Ser Asn Tyr Gly Trp Glu Asp Ser Lys Tyr Ile Pro Glu
                725                 730                 735 ggc gcc acg gat ggg tct gcc cag ccc cgt ttg ccc gct agt ggt ggt          2256
Gly Ala Thr Asp Gly Ser Ala Gln Pro Arg Leu Pro Ala Ser Gly Gly
            740                 745                 750 gcc gga gga aac ccc ggt ctg tac gag gat ctt ttc cgc gtc tct gtg          2304
Ala Gly Gly Asn Pro Gly Leu Tyr Glu Asp Leu Phe Arg Val Ser Val
        755                 760                 765 aag gtc aag aac acg ggc aat gtc gcc ggt gat gaa gtt cct cag ctg          2352
Lys Val Lys Asn Thr Gly Asn Val Ala Gly Asp Glu Val Pro Gln Leu
    770                 775                 780 tac gtt tcc cta ggc ggc ccg aat gag ccc aag gtg gta ctg cgc aag          2400
Tyr Val Ser Leu Gly Gly Pro Asn Glu Pro Lys Val Val Leu Arg Lys
785                 790                 795                 800
```

```
ttt gag cgt att cac ttg gcc cct tcg cag gag gcc gtg tgg aca acg    2448
Phe Glu Arg Ile His Leu Ala Pro Ser Gln Glu Ala Val Trp Thr Thr
                805                 810                 815 acc ctt acc cgt cgt gac ctt gca aac tgg gac gtt tcg gct cag gac    2496
Thr Leu Thr Arg Arg Asp Leu Ala Asn Trp Asp Val Ser Ala Gln Asp
            820                 825                 830 tgg acc gtc act cct tac ccc aag acg atc tac gtt gga aac tcc tca    2544
Trp Thr Val Thr Pro Tyr Pro Lys Thr Ile Tyr Val Gly Asn Ser Ser
        835                 840                 845 cgg aaa ctg ccg ctc cag gcc tcg ctg cct aag gcc cag taa            2586
Arg Lys Leu Pro Leu Gln Ala Ser Leu Pro Lys Ala Gln
    850                 855                 860

<210> SEQ ID NO 2
<211> LENGTH: 861
<212> TYPE: PRT
<213> ORGANISM: Aspergillus oryzae

<400> SEQUENCE: 2

Met Lys Leu Gly Trp Ile Glu Val Ala Ala Leu Ala Ala Ala Ser Val
1               5                   10                  15

Val Ser Ala Lys Asp Asp Leu Ala Tyr Ser Pro Pro Phe Tyr Pro Ser
            20                  25                  30

Pro Trp Ala Asp Gly Gln Gly Glu Trp Ala Glu Val Tyr Lys Arg Ala
        35                  40                  45

Val Asp Ile Val Ser Gln Met Thr Leu Thr Glu Lys Val Asn Leu Thr
    50                  55                  60

Thr Gly Thr Gly Trp Gln Leu Glu Arg Cys Val Gly Gln Thr Gly Ser
65                  70                  75                  80

Val Pro Arg Leu Asn Ile Pro Ser Leu Cys Leu Gln Asp Ser Pro Leu
                85                  90                  95

Gly Ile Arg Phe Ser Asp Tyr Asn Ser Ala Phe Pro Ala Gly Val Asn
            100                 105                 110

Val Ala Ala Thr Trp Asp Lys Thr Leu Ala Tyr Leu Arg Gly Gln Ala
        115                 120                 125

Met Gly Glu Glu Phe Ser Asp Lys Gly Ile Asp Val Gln Leu Gly Pro
    130                 135                 140

Ala Ala Gly Pro Leu Gly Ala His Pro Asp Gly Gly Arg Asn Trp Glu
145                 150                 155                 160

Gly Phe Ser Pro Asp Pro Ala Leu Thr Gly Val Leu Phe Ala Glu Thr
                165                 170                 175

Ile Lys Gly Ile Gln Asp Ala Gly Val Ile Ala Thr Ala Lys His Tyr
            180                 185                 190

Ile Met Asn Glu Gln Glu His Phe Arg Gln Pro Glu Ala Ala Gly
        195                 200                 205

Tyr Gly Phe Asn Val Ser Asp Ser Leu Ser Ser Asn Val Asp Asp Lys
    210                 215                 220

Thr Met His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
                245                 250                 255

Gly Cys Glu Asn Ser Glu Thr Leu Asn Lys Leu Leu Lys Ala Glu Leu
            260                 265                 270

Gly Phe Gln Gly Phe Val Met Ser Asp Trp Thr Ala His His Ser Gly
        275                 280                 285

Val Gly Ala Ala Leu Ala Gly Leu Asp Met Ser Met Pro Gly Asp Val
```

-continued

```
            290                 295                 300
Thr Phe Asp Ser Gly Thr Ser Phe Trp Gly Ala Asn Leu Thr Val Gly
305                 310                 315                 320

Val Leu Asn Gly Thr Ile Pro Gln Trp Arg Val Asp Met Ala Val
                325                 330                 335

Arg Ile Met Ala Ala Tyr Tyr Lys Val Gly Arg Asp Thr Lys Tyr Thr
                340                 345                 350

Pro Pro Asn Phe Ser Ser Trp Thr Arg Asp Glu Tyr Gly Phe Ala His
                355                 360                 365

Asn His Val Ser Glu Gly Ala Tyr Glu Arg Val Asn Glu Phe Val Asp
370                 375                 380

Val Gln Arg Asp His Ala Asp Leu Ile Arg Arg Ile Gly Ala Gln Ser
385                 390                 395                 400

Thr Val Leu Leu Lys Asn Lys Gly Ala Leu Pro Leu Ser Arg Lys Glu
                405                 410                 415

Lys Leu Val Ala Leu Leu Gly Glu Asp Ala Gly Ser Asn Ser Trp Gly
                420                 425                 430

Ala Asn Gly Cys Asp Asp Arg Gly Cys Asp Asn Gly Thr Leu Ala Met
                435                 440                 445

Ala Trp Gly Ser Gly Thr Ala Asn Phe Pro Tyr Leu Val Thr Pro Glu
                450                 455                 460

Gln Ala Ile Gln Asn Glu Val Leu Gln Gly Arg Gly Asn Val Phe Ala
465                 470                 475                 480

Val Thr Asp Ser Trp Ala Leu Asp Lys Ile Ala Ala Ala Arg Gln
                485                 490                 495

Ala Ser Val Ser Leu Val Phe Val Asn Ser Asp Ser Gly Glu Gly Tyr
                500                 505                 510

Leu Ser Val Asp Gly Asn Glu Gly Asp Arg Asn Asn Ile Thr Leu Trp
                515                 520                 525

Lys Asn Gly Asp Asn Val Val Lys Thr Ala Ala Asn Cys Asn Asn
530                 535                 540

Thr Val Ile Ile His Ser Val Gly Pro Val Leu Ile Asp Glu Trp
545                 550                 555                 560

Tyr Asp His Pro Asn Val Thr Gly Ile Leu Trp Ala Gly Leu Pro Gly
                565                 570                 575

Gln Glu Ser Gly Asn Ser Ile Ala Asp Val Leu Tyr Gly Arg Val Asn
                580                 585                 590

Pro Gly Ala Lys Ser Pro Phe Thr Trp Gly Lys Thr Arg Glu Ser Tyr
                595                 600                 605

Gly Ser Pro Leu Val Lys Asp Ala Asn Gly Asn Gly Ala Pro Gln
610                 615                 620

Ser Asp Phe Thr Gln Gly Val Phe Ile Asp Tyr Arg His Phe Asp Lys
625                 630                 635                 640

Phe Asn Glu Thr Pro Ile Tyr Glu Phe Gly Tyr Gly Leu Ser Tyr Thr
                645                 650                 655

Thr Phe Glu Leu Ser Asp Leu His Val Gln Pro Leu Asn Ala Ser Arg
                660                 665                 670

Tyr Thr Pro Thr Ser Gly Met Thr Glu Ala Ala Lys Asn Phe Gly Glu
                675                 680                 685

Ile Gly Asp Ala Ser Glu Tyr Val Tyr Pro Glu Gly Leu Glu Arg Ile
                690                 695                 700

His Glu Phe Ile Tyr Pro Trp Ile Asn Ser Thr Asp Leu Lys Ala Ser
705                 710                 715                 720
```

```
Ser Asp Asp Ser Asn Tyr Gly Trp Glu Asp Ser Lys Tyr Ile Pro Glu
            725                 730                 735

Gly Ala Thr Asp Gly Ser Ala Gln Pro Arg Leu Pro Ala Ser Gly Gly
            740                 745                 750

Ala Gly Gly Asn Pro Gly Leu Tyr Glu Asp Leu Phe Arg Val Ser Val
            755                 760                 765

Lys Val Lys Asn Thr Gly Asn Val Ala Gly Asp Glu Val Pro Gln Leu
            770                 775                 780

Tyr Val Ser Leu Gly Gly Pro Asn Glu Pro Lys Val Val Leu Arg Lys
785                 790                 795                 800

Phe Glu Arg Ile His Leu Ala Pro Ser Gln Glu Ala Val Trp Thr Thr
                805                 810                 815

Thr Leu Thr Arg Arg Asp Leu Ala Asn Trp Asp Val Ser Ala Gln Asp
            820                 825                 830

Trp Thr Val Thr Pro Tyr Pro Lys Thr Ile Tyr Val Gly Asn Ser Ser
            835                 840                 845

Arg Lys Leu Pro Leu Gln Ala Ser Leu Pro Lys Ala Gln
    850                 855                 860

<210> SEQ ID NO 3
<211> LENGTH: 32
<212> TYPE: DNA
<213> ORGANISM: Aspergillus oryzae

<400> SEQUENCE: 3
gcagatctac catgaagctt ggttggatcg ag                                   32

<210> SEQ ID NO 4
<211> LENGTH: 30
<212> TYPE: DNA
<213> ORGANISM: Aspergillus oryzae

<400> SEQUENCE: 4
gcctcgagtt actgggcctt aggcagcgag                                      30

<210> SEQ ID NO 5
<211> LENGTH: 29
<212> TYPE: DNA
<213> ORGANISM: Trichoderma reesei

<400> SEQUENCE: 5
aacgttaatt aaggaatcgt tttgtgttt                                       29

<210> SEQ ID NO 6
<211> LENGTH: 29
<212> TYPE: DNA
<213> ORGANISM: Trichoderma reesei

<400> SEQUENCE: 6
agtactagta gctccgtggc gaaagcctg                                       29

<210> SEQ ID NO 7
<211> LENGTH: 31
<212> TYPE: DNA
<213> ORGANISM: Escherichia coli

<400> SEQUENCE: 7
ttgaattgaa aatagattga tttaaaactt c                                    31
```

```
<210> SEQ ID NO 8
<211> LENGTH: 25
<212> TYPE: DNA
<213> ORGANISM: Escherichia coli

<400> SEQUENCE: 8
ttgcatgcgt aatcatggtc atagc                                        25

<210> SEQ ID NO 9
<211> LENGTH: 26
<212> TYPE: DNA
<213> ORGANISM: Saccharomyces cerevisiae

<400> SEQUENCE: 9
ttgaattcat gggtaataac tgatat                                       26

<210> SEQ ID NO 10
<211> LENGTH: 32
<212> TYPE: DNA
<213> ORGANISM: Saccharomyces cerevisiae

<400> SEQUENCE: 10
aaatcaatct attttcaatt caattcatca tt                                32

<210> SEQ ID NO 11
<211> LENGTH: 45
<212> TYPE: DNA
<213> ORGANISM: Aspergillus niger

<400> SEQUENCE: 11
ggatgctgtt gactccggaa atttaacggt ttggtcttgc atccc                  45

<210> SEQ ID NO 12
<211> LENGTH: 44
<212> TYPE: DNA
<213> ORGANISM: Aspergillus niger

<400> SEQUENCE: 12
ggtattgtcc tgcagacggc aatttaacgg cttctgcgaa tcgc                   44

<210> SEQ ID NO 13
<211> LENGTH: 29
<212> TYPE: DNA
<213> ORGANISM: Humicola insolens

<400> SEQUENCE: 13
aagcttaagc atgcgttcct cccccctcc                                    29

<210> SEQ ID NO 14
<211> LENGTH: 32
<212> TYPE: DNA
<213> ORGANISM: Humicola insolens

<400> SEQUENCE: 14
ctgcagaatt ctacaggcac tgatggtacc ag                                32

<210> SEQ ID NO 15
<211> LENGTH: 32
<212> TYPE: DNA
<213> ORGANISM: Humicola insolens

<400> SEQUENCE: 15
ctgcagaatt ctacaggcac tgatggtacc ag                                32
```

<210> SEQ ID NO 16
<211> LENGTH: 36
<212> TYPE: DNA
<213> ORGANISM: Humicola insolens

<400> SEQUENCE: 16
accgcggact gcgcatcatg cgttcctccc ccctcc        36

<210> SEQ ID NO 17
<211> LENGTH: 29
<212> TYPE: DNA
<213> ORGANISM: Trichoderma reesei

<400> SEQUENCE: 17
aaacgtcgac cgaatgtagg attgttatc        29

<210> SEQ ID NO 18
<211> LENGTH: 17
<212> TYPE: DNA
<213> ORGANISM: Trichoderma reesei

<400> SEQUENCE: 18
gatgcgcagt ccgcggt        17

<210> SEQ ID NO 19
<211> LENGTH: 29
<212> TYPE: DNA
<213> ORGANISM: Trichoderma reesei

<400> SEQUENCE: 19
aaacgtcgac cgaatgtagg attgttatc        29

<210> SEQ ID NO 20
<211> LENGTH: 36
<212> TYPE: DNA
<213> ORGANISM: Trichoderma reesei

<400> SEQUENCE: 20
ggagggggga ggaacgcatg atgcgcagtc cgcggt        36

<210> SEQ ID NO 21
<211> LENGTH: 29
<212> TYPE: DNA
<213> ORGANISM: Trichoderma reesei

<400> SEQUENCE: 21
aaacgtcgac cgaatgtagg attgttatc        29

<210> SEQ ID NO 22
<211> LENGTH: 32
<212> TYPE: DNA
<213> ORGANISM: Trichoderma reesei

<400> SEQUENCE: 22
ctgcagaatt ctacaggcac tgatggtacc ag        32

<210> SEQ ID NO 23
<211> LENGTH: 46
<212> TYPE: DNA
<213> ORGANISM: Aspergillus oryzae

<400> SEQUENCE: 23
atagtcaacc gcggactgcg catcatgaag cttggttgga tcgagg        46

<210> SEQ ID NO 24
<211> LENGTH: 26
<212> TYPE: DNA
<213> ORGANISM: Aspergillus oryzae

<400> SEQUENCE: 24
actagtttac tgggccttag gcagcg                                  26

<210> SEQ ID NO 25
<211> LENGTH: 26
<212> TYPE: DNA
<213> ORGANISM: Trichoderma reesei

<400> SEQUENCE: 25
gtcgactcga agcccgaatg taggat                                  26

<210> SEQ ID NO 26
<211> LENGTH: 45
<212> TYPE: DNA
<213> ORGANISM: Trichoderma reesei

<400> SEQUENCE: 26
cctcgatcca accaagcttc atgatgcgca gtccgcggtt gacta             45

<210> SEQ ID NO 27
<211> LENGTH: 42
<212> TYPE: DNA
<213> ORGANISM: Aspergillus oryzae

<400> SEQUENCE: 27
tgccggtgtt ggcccttgcc aaggatgatc tcgcgtactc cc                42

<210> SEQ ID NO 28
<211> LENGTH: 28
<212> TYPE: DNA
<213> ORGANISM: Aspergillus oryzae

<400> SEQUENCE: 28
gactagtctt actgggcctt aggcagcg                                28

<210> SEQ ID NO 29
<211> LENGTH: 63
<212> TYPE: DNA
<213> ORGANISM: Humicola insolens

<400> SEQUENCE: 29
atgcgttcct cccccctcct ccgctccgcc gttgtggccg ccctgccggt gttggccctt    60
gcc                                                           63

<210> SEQ ID NO 30
<211> LENGTH: 30
<212> TYPE: DNA
<213> ORGANISM: Aspergillus oryzae

<400> SEQUENCE: 30
acgcgtcgac cgaatgtagg attgttatcc                              30

<210> SEQ ID NO 31
<211> LENGTH: 42
<212> TYPE: DNA
<213> ORGANISM: Aspergillus oryzae

```
<400> SEQUENCE: 31
gggagtacgc gagatcatcc ttggcaaggg ccaacaccgg ca                        42

<210> SEQ ID NO 32
<211> LENGTH: 40
<212> TYPE: DNA
<213> ORGANISM: Aspergillus oryzae

<400> SEQUENCE: 32
aatccgacta gtggatctac catgcgttcc tcccccctcc                           40

<210> SEQ ID NO 33
<211> LENGTH: 32
<212> TYPE: DNA
<213> ORGANISM: Aspergillus oryzae

<400> SEQUENCE: 33
gcgggcctcg agttactggg ccttaggcag cg                                   32

<210> SEQ ID NO 34
<211> LENGTH: 17
<212> TYPE: DNA
<213> ORGANISM: Aspergillus oryzae

<400> SEQUENCE: 34
agggtgaatg ggcggaa                                                    17

<210> SEQ ID NO 35
<211> LENGTH: 20
<212> TYPE: DNA
<213> ORGANISM: Aspergillus oryzae

<400> SEQUENCE: 35
gacatttttg ctgtcagtca                                                 20

<210> SEQ ID NO 36
<211> LENGTH: 20
<212> TYPE: DNA
<213> ORGANISM: Aspergillus oryzae

<400> SEQUENCE: 36
aatgttacat gcgtacacgc                                                 20

<210> SEQ ID NO 37
<211> LENGTH: 17
<212> TYPE: DNA
<213> ORGANISM: Aspergillus oryzae

<400> SEQUENCE: 37
gtttcggctc aggactg                                                    17

<210> SEQ ID NO 38
<211> LENGTH: 17
<212> TYPE: DNA
<213> ORGANISM: Aspergillus oryzae

<400> SEQUENCE: 38
acttccgccc attcacc                                                    17

<210> SEQ ID NO 39
<211> LENGTH: 17
<212> TYPE: DNA
<213> ORGANISM: Aspergillus oryzae
```

```
<400> SEQUENCE: 39
agggtgaatg ggcggaa                                                    17

<210> SEQ ID NO 40
<211> LENGTH: 17
<212> TYPE: DNA
<213> ORGANISM: Aspergillus oryzae

<400> SEQUENCE: 40
ggcggaaatg ctcttgt                                                    17

<210> SEQ ID NO 41
<211> LENGTH: 18
<212> TYPE: DNA
<213> ORGANISM: Aspergillus oryzae

<400> SEQUENCE: 41
sggatggcgg tagaaact                                                   18

<210> SEQ ID NO 42
<211> LENGTH: 17
<212> TYPE: DNA
<213> ORGANISM: Aspergillus oryzae

<400> SEQUENCE: 42
gcggtccaat cactcat                                                    17

<210> SEQ ID NO 43
<211> LENGTH: 17
<212> TYPE: DNA
<213> ORGANISM: Aspergillus oryzae

<400> SEQUENCE: 43
gctacggttg cgagaat                                                    17

<210> SEQ ID NO 44
<211> LENGTH: 17
<212> TYPE: DNA
<213> ORGANISM: Aspergillus oryzae

<400> SEQUENCE: 44
ctcaagggca aggcacc                                                    17

<210> SEQ ID NO 45
<211> LENGTH: 17
<212> TYPE: DNA
<213> ORGANISM: Aspergillus oryzae

<400> SEQUENCE: 45
ggtgccttgc ccttgag                                                    17

<210> SEQ ID NO 46
<211> LENGTH: 17
<212> TYPE: DNA
<213> ORGANISM: Aspergillus oryzae

<400> SEQUENCE: 46
ttcgctgcgg tcttgac                                                    17

<210> SEQ ID NO 47
<211> LENGTH: 17
<212> TYPE: DNA
```

```
<213> ORGANISM: Aspergillus oryzae

<400> SEQUENCE: 47
gtggaagaac ggcgaca                                                    17

<210> SEQ ID NO 48
<211> LENGTH: 17
<212> TYPE: DNA
<213> ORGANISM: Aspergillus oryzae

<400> SEQUENCE: 48
cccagccgta gttagaa                                                    17

<210> SEQ ID NO 49
<211> LENGTH: 17
<212> TYPE: DNA
<213> ORGANISM: Aspergillus oryzae

<400> SEQUENCE: 49
cgtcccgata cactccc                                                    17

<210> SEQ ID NO 50
<211> LENGTH: 17
<212> TYPE: DNA
<213> ORGANISM: Aspergillus oryzae

<400> SEQUENCE: 50
cctggagcgg cagtttc                                                    17

<210> SEQ ID NO 51
<211> LENGTH: 18
<212> TYPE: DNA
<213> ORGANISM: Aspergillus oryzae

<400> SEQUENCE: 51
ggtcggtgtc cttaacgg                                                   18

<210> SEQ ID NO 52
<211> LENGTH: 20
<212> TYPE: DNA
<213> ORGANISM: Aspergillus oryzae

<400> SEQUENCE: 52
actatcctgc aaacacaagc                                                 20

<210> SEQ ID NO 53
<211> LENGTH: 16
<212> TYPE: DNA
<213> ORGANISM: Aspergillus oryzae

<400> SEQUENCE: 53
cctttcactt ggggca                                                     16

<210> SEQ ID NO 54
<211> LENGTH: 20
<212> TYPE: DNA
<213> ORGANISM: Aspergillus oryzae

<400> SEQUENCE: 54
ggagttacca gactcctggc                                                 20

<210> SEQ ID NO 55
<211> LENGTH: 20
```

-continued

```
<212> TYPE: DNA
<213> ORGANISM: Aspergillus oryzae

<400> SEQUENCE: 55
accttccgaa acatggttat                                                    20

<210> SEQ ID NO 56
<211> LENGTH: 39
<212> TYPE: DNA
<213> ORGANISM: Aspergillus oryzae
<220> FEATURE:
<221> NAME/KEY: misc_feature
<222> LOCATION: (16)..(17)
<223> OTHER INFORMATION: n is a, c, g, or t

<400> SEQUENCE: 56
ggtagaaact gggaannstt ctcaccagat ccagccctc                                39

<210> SEQ ID NO 57
<211> LENGTH: 33
<212> TYPE: DNA
<213> ORGANISM: Aspergillus oryzae
<220> FEATURE:
<221> NAME/KEY: misc_feature
<222> LOCATION: (16)..(17)
<223> OTHER INFORMATION: n is a, c, g, or t

<400> SEQUENCE: 57
gcctacgccg ctgtgnnsag cggtccaatc act                                     33

<210> SEQ ID NO 58
<211> LENGTH: 22
<212> TYPE: DNA
<213> ORGANISM: Aspergillus nidulens

<400> SEQUENCE: 58
gtgccccatg atacgcctcc gg                                                 22

<210> SEQ ID NO 59
<211> LENGTH: 26
<212> TYPE: DNA
<213> ORGANISM: Aspergillus nidulens

<400> SEQUENCE: 59
gagtcgtatt tccaaggctc ctgacc                                             26

<210> SEQ ID NO 60
<211> LENGTH: 23
<212> TYPE: DNA
<213> ORGANISM: Aspergillus nidulens

<400> SEQUENCE: 60
ggaggccatg aagtggacca acg                                                23

<210> SEQ ID NO 61
<211> LENGTH: 45
<212> TYPE: DNA
<213> ORGANISM: Aspergillus niger

<400> SEQUENCE: 61
caccgtgaaa gccatgctct ttccttcgtg tagaagacca gacag                        45

<210> SEQ ID NO 62
<211> LENGTH: 45
<212> TYPE: DNA
```

<213> ORGANISM: Aspergillus niger

<400> SEQUENCE: 62
ctggtcttct acacgaagga aagagcatgg ctttcacggt gtctg    45

<210> SEQ ID NO 63
<211> LENGTH: 44
<212> TYPE: DNA
<213> ORGANISM: Aspergillus niger

<400> SEQUENCE: 63
ctatatacac aactggattt accatgggcc cgcggccgca gatc    44

<210> SEQ ID NO 64
<211> LENGTH: 44
<212> TYPE: DNA
<213> ORGANISM: Aspergillus niger

<400> SEQUENCE: 64
gatctgcggc cgcgggccca tggtaaatcc agttgtgtat atag    44

<210> SEQ ID NO 65
<211> LENGTH: 30
<212> TYPE: DNA
<213> ORGANISM: Aspergillus oryzae

<400> SEQUENCE: 65
actggattta ccatgaagct tggttggatc    30

<210> SEQ ID NO 66
<211> LENGTH: 30
<212> TYPE: DNA
<213> ORGANISM: Aspergillus oryzae

<400> SEQUENCE: 66
agtcacctct agttattact gggccttagg    30

<210> SEQ ID NO 67
<211> LENGTH: 31
<212> TYPE: DNA
<213> ORGANISM: Aspergillus fumigatus

<400> SEQUENCE: 67
actggattta ccatgagatt cggttggctc g    31

<210> SEQ ID NO 68
<211> LENGTH: 31
<212> TYPE: DNA
<213> ORGANISM: Aspergillus fumigatus

<400> SEQUENCE: 68
agtcacctct agttactagt agacacgggg c    31

<210> SEQ ID NO 69
<211> LENGTH: 3060
<212> TYPE: DNA
<213> ORGANISM: Aspergillus fumigatus

<400> SEQUENCE: 69
atgagattcg gttggctcga ggtggccgct ctgacggccg cttctgtagc caatgcccag    60
gtttgtgatg ctttcccgtc attgtttcgg atatagttga caatagtcat ggaaataatc    120
aggaattggc tttctctcca ccattctacc cttcgccttg gctgatggc caggagagt    180

-continued

```
gggcagatgc ccatcgacgc gccgtcgaga tcgtttctca gatgacactg gcggagaagg      240
ttaaccttac aacgggtact gggtgggttg cgactttttt gttgacagtg agctttcttc      300
actgaccatc tacacagatg ggaaatggac cgatgcgtcg gtcaaaccgg cagcgttccc      360
aggtaagctt gcaattctgc aacaacgtgc aagtgtagtt gctaaaacgc ggtggtgcag      420
acttggtatc aactgggtgc tttgtggcca ggattcccct ttgggtatcc gtttctgtga      480
gctatacccg cggagtcttt cagtccttgt attatgtgct gatgattgtc tctgtatagc      540
tgacctcaac tccgccttcc ctgctggtac taatgtcgcc gcgacatggg acaagacact      600
cgcctacctt cgtggcaagg ccatgggtga ggaattcaac gacaagggcg tggacatttt      660 gctgggcct gctgctggtc ctctcggcaa atacccggac ggcggcagaa tctgggaagg       720
cttctctcct gatccggttc tcactggtgt acttttcgcc gaaactatca agggtatcca      780
agacgcgggt gtgattgcta ctgccaagca ttacattctg aatgaacagg agcatttccg      840
acaggttggc gaggcccagg gatatggtta caacatcacg gagacgatca gctccaacgt      900
ggatgacaag accatgcacg agttgtacct tggtgagta gttgacactg caaatgagga      960
ccttgattga tttgactgac ctggaatgca ggccctttgc agatgctgtg cgcggtaaga     1020
ttttccgtag acttgacctc gcgacgaaga atcgctgac gaaccatcgt agctggcgtt      1080
ggcgctgtca tgtgttccta caatcaaatc aacaacagct acggttgtca aaacagtcaa     1140
actctcaaca agctcctcaa ggctgagctg gcttccaag gcttcgtcat gagtgactgg      1200
agcgctcacc acagcggtgt cggcgctgcc ctcgctgggt tggatatgtc gatgcctgga     1260
gacatttcct tcgacgacgg actctccttc tggggcacga acctaactgt cagtgttctt     1320
aacggcaccg ttccagcctg gcgtgtcgat gacatggctg ttcgtatcat gaccgcgtac     1380
tacaaggttg gtcgtgaccg tcttcgtatt cccctaact tcagctcctg gacccgggat      1440
gagtacggct gggagcattc tgctgtctcc gagggagcct ggaccaaggt gaacgacttc     1500
gtcaatgtgc agcgcagtca ctctcagatc atccgtgaga ttggtgccgc tagtacagtg     1560
ctcttgaaga acacgggtgc tcttcctttg accggcaagg aggttaaagt gggtgttctc     1620
ggtgaagacg ctggttccaa cccgtggggt gctaacggct gccccgaccg cggctgtgat     1680
aacggcactc ttgctatggc ctggggtagt ggtactgcca acttccctta ccttgtcacc     1740
cccgagcagg ctatccagcg agaggtcatc agcaacggcg gcaatgtctt tgctgtgact     1800
gataacgggg ctctcagcca gatggcagat gttgcatctc aatccaggtg agtgcgggct     1860
cttagaaaaa gaacgttctc tgaatgaagt tttttaacca ttgcgaacag cgtgtctttg     1920
gtgtttgtca acgccgactc tggagagggt ttcatcagtg tcgacggcaa cgagggtgac     1980
cgcaaaaatc tcactctgtg gaagaacggc gaggccgtca ttgacactgt tgtcagccac     2040
tgcaacaaca cgattgtggt tattcacagt gttgggcccg tcttgatcga ccggtggtat     2100
gataacccca acgtcactgc catcatctgg gccggcttgc ccggtcagga gagtggcaac     2160
tccctggtcg acgtgctcta tggccgcgtc aaccccagcg ccaagacccc gttcacctgg     2220
ggcaagactc gggagtctta cggggctccc ttgctcaccg agcctaacaa tggcaatggt     2280
gctccccagg atgatttcaa cgagggcgtc ttcattgact accgtcactt tgacaagcgc     2340
aatgagaccc ccatttatga gtttggccat ggcttgagct acaccacctt tggttactct     2400
caccttcggg ttcaggccct caatagttcg agttcggcat atgtcccgac tagcggagag     2460
accaagcctg cgccaaccta tggtgagatc ggtagtgccg ccgactacct gtatcccgag     2520
```

```
ggtctcaaaa gaattaccaa gtttatttac ccttggctca actcgaccga cctcgaggat    2580
tcttctgacg acccgaacta cggctgggag gactcggagt acattcccga aggcgctagg    2640
gatgggtctc ctcaaccccT cctgaaggct ggcggcgctc ctggtggtaa ccctacccTt    2700
tatcaggatc ttgttagggt gtcggccacc ataaccaaca ctggtaacgt cgccggttat    2760
gaagtccctc aattggtgag tgacccgcat gttccttgcg ttgcaatttg gctaactcgc    2820
ttctagtatg tttcactggg cggaccgaac gagcctcggg tcgttctgcg caagttcgac    2880
cgaatcttcc tggctcctgg ggagcaaaag gtttggacca cgactcttaa ccgtcgtgat    2940
ctcgccaatt gggatgtgga ggctcaggac tgggtcatca caaagtaccc caagaaagtg    3000
cacgtcggca gctcctcgcg taagctgcct ctgagagcgc ctctgccccg tgtctactag    3060
```

<210> SEQ ID NO 70
<211> LENGTH: 863
<212> TYPE: PRT
<213> ORGANISM: Aspergillus fumigatus

<400> SEQUENCE: 70

```
Met Arg Phe Gly Trp Leu Glu Val Ala Ala Leu Thr Ala Ala Ser Val
1               5                   10                  15

Ala Asn Ala Gln Glu Leu Ala Phe Ser Pro Pro Phe Tyr Pro Ser Pro
                20                  25                  30

Trp Ala Asp Gly Gln Gly Glu Trp Ala Asp Ala His Arg Arg Ala Val
            35                  40                  45

Glu Ile Val Ser Gln Met Thr Leu Ala Glu Lys Val Asn Leu Thr Thr
        50                  55                  60

Gly Thr Gly Trp Glu Met Asp Arg Cys Val Gly Gln Thr Gly Ser Val
65                  70                  75                  80

Pro Arg Leu Gly Ile Asn Trp Gly Leu Cys Gly Gln Asp Ser Pro Leu
                85                  90                  95

Gly Ile Arg Phe Ser Asp Leu Asn Ser Ala Phe Pro Ala Gly Thr Asn
                100                 105                 110

Val Ala Ala Thr Trp Asp Lys Thr Leu Ala Tyr Leu Arg Gly Lys Ala
            115                 120                 125

Met Gly Glu Glu Phe Asn Asp Lys Gly Val Asp Ile Leu Leu Gly Pro
        130                 135                 140

Ala Ala Gly Pro Leu Gly Lys Tyr Pro Asp Gly Gly Arg Ile Trp Glu
145                 150                 155                 160

Gly Phe Ser Pro Asp Pro Val Leu Thr Gly Val Leu Phe Ala Glu Thr
                165                 170                 175

Ile Lys Gly Ile Gln Asp Ala Gly Val Ile Ala Thr Ala Lys His Tyr
                180                 185                 190

Ile Leu Asn Glu Gln Glu His Phe Arg Gln Val Gly Glu Ala Gln Gly
            195                 200                 205

Tyr Gly Tyr Asn Ile Thr Glu Thr Ile Ser Ser Asn Val Asp Asp Lys
        210                 215                 220

Thr Met His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
                245                 250                 255

Gly Cys Gln Asn Ser Gln Thr Leu Asn Lys Leu Leu Lys Ala Glu Leu
                260                 265                 270

Gly Phe Gln Gly Phe Val Met Ser Asp Trp Ser Ala His His Ser Gly
            275                 280                 285
```

```
Val Gly Ala Ala Leu Ala Gly Leu Asp Met Ser Met Pro Gly Asp Ile
    290                 295                 300

Ser Phe Asp Asp Gly Leu Ser Phe Trp Gly Thr Asn Leu Thr Val Ser
305                 310                 315                 320

Val Leu Asn Gly Thr Val Pro Ala Trp Arg Val Asp Asp Met Ala Val
                325                 330                 335

Arg Ile Met Thr Ala Tyr Tyr Lys Val Gly Arg Asp Arg Leu Arg Ile
                340                 345                 350

Pro Pro Asn Phe Ser Ser Trp Thr Arg Asp Glu Tyr Gly Trp Glu His
            355                 360                 365

Ser Ala Val Ser Glu Gly Ala Trp Thr Lys Val Asn Asp Phe Val Asn
    370                 375                 380

Val Gln Arg Ser His Ser Gln Ile Ile Arg Glu Ile Gly Ala Ala Ser
385                 390                 395                 400

Thr Val Leu Leu Lys Asn Thr Gly Ala Leu Pro Leu Thr Gly Lys Glu
                405                 410                 415

Val Lys Val Gly Val Leu Gly Glu Asp Ala Gly Ser Asn Pro Trp Gly
                420                 425                 430

Ala Asn Gly Cys Pro Asp Arg Gly Cys Asp Asn Gly Thr Leu Ala Met
            435                 440                 445

Ala Trp Gly Ser Gly Thr Ala Asn Phe Pro Tyr Leu Val Thr Pro Glu
    450                 455                 460

Gln Ala Ile Gln Arg Glu Val Ile Ser Asn Gly Gly Asn Val Phe Ala
465                 470                 475                 480

Val Thr Asp Asn Gly Ala Leu Ser Gln Met Ala Asp Val Ala Ser Gln
                485                 490                 495

Ser Ser Val Ser Leu Val Phe Val Asn Ala Asp Ser Gly Glu Gly Phe
            500                 505                 510

Ile Ser Val Asp Gly Asn Glu Gly Asp Arg Lys Asn Leu Thr Leu Trp
    515                 520                 525

Lys Asn Gly Glu Ala Val Ile Asp Thr Val Val Ser His Cys Asn Asn
    530                 535                 540

Thr Ile Val Val Ile His Ser Val Gly Pro Val Leu Ile Asp Arg Trp
545                 550                 555                 560

Tyr Asp Asn Pro Asn Val Thr Ala Ile Ile Trp Ala Gly Leu Pro Gly
                565                 570                 575

Gln Glu Ser Gly Asn Ser Leu Val Asp Val Leu Tyr Gly Arg Val Asn
            580                 585                 590

Pro Ser Ala Lys Thr Pro Phe Thr Trp Gly Lys Thr Arg Glu Ser Tyr
    595                 600                 605

Gly Ala Pro Leu Leu Thr Glu Pro Asn Asn Gly Asn Gly Ala Pro Gln
610                 615                 620

Asp Asp Phe Asn Glu Gly Val Phe Ile Asp Tyr Arg His Phe Asp Lys
625                 630                 635                 640

Arg Asn Glu Thr Pro Ile Tyr Glu Phe Gly His Gly Leu Ser Tyr Thr
                645                 650                 655

Thr Phe Gly Tyr Ser His Leu Arg Val Gln Ala Leu Asn Ser Ser Ser
            660                 665                 670

Ser Ala Tyr Val Pro Thr Ser Gly Glu Thr Lys Pro Ala Pro Thr Tyr
    675                 680                 685

Gly Glu Ile Gly Ser Ala Ala Asp Tyr Leu Tyr Pro Glu Gly Leu Lys
690                 695                 700
```

```
Arg Ile Thr Lys Phe Ile Tyr Pro Trp Leu Asn Ser Thr Asp Leu Glu
705                 710                 715                 720

Asp Ser Ser Asp Asp Pro Asn Tyr Gly Trp Glu Asp Ser Glu Tyr Ile
            725                 730                 735

Pro Glu Gly Ala Arg Asp Gly Ser Pro Gln Pro Leu Leu Lys Ala Gly
        740                 745                 750

Gly Ala Pro Gly Gly Asn Pro Thr Leu Tyr Gln Asp Leu Val Arg Val
    755                 760                 765

Ser Ala Thr Ile Thr Asn Thr Gly Asn Val Ala Gly Tyr Glu Val Pro
770                 775                 780

Gln Leu Tyr Val Ser Leu Gly Gly Pro Asn Glu Pro Arg Val Val Leu
785                 790                 795                 800

Arg Lys Phe Asp Arg Ile Phe Leu Ala Pro Gly Glu Gln Lys Val Trp
                805                 810                 815

Thr Thr Thr Leu Asn Arg Arg Asp Leu Ala Asn Trp Asp Val Glu Ala
            820                 825                 830

Gln Asp Trp Val Ile Thr Lys Tyr Pro Lys Lys Val His Val Gly Ser
        835                 840                 845

Ser Ser Arg Lys Leu Pro Leu Arg Ala Pro Leu Pro Arg Val Tyr
    850                 855                 860

<210> SEQ ID NO 71
<211> LENGTH: 2589
<212> TYPE: DNA
<213> ORGANISM: Aspergillus fumigatus

<400> SEQUENCE: 71
atgagattcg gttggctcga ggtggccgct ctgacggccg cttctgtagc caatgcccag      60
gaattggctt tctctccacc attctaccct tcgccttggg ctgatggcca gggagagtgg     120
gcagatgccc atcgacgcgc cgtcgagatc gtttctcaga tgacactggc ggagaaggtt     180
aaccttacaa cgggtactgg atgggaaatg gaccgatgcg tcggtcaaac cggcagcgtt     240
cccagacttg gtatcaactg ggtctttgt  ggccaggatt cccctttggg tatccgtttc     300
tctgacctca actccgcctt ccctgctggt actaatgtcg ccgcgacatg ggacaagaca     360
ctcgcctacc ttcgtggcaa ggccatgggt gaggaattca cgacaaggg  cgtggacatt     420 ttgctgggc  ctgctgctgg tcctctcggc aaatacccgg acggcggcag aatctgggaa     480
ggcttctctc ctgatccggc tctcactggt gtactttcg  ccgaaactat caagggtatc     540
caagacgcgg gtgtgattgc tactgccaag cattacattc tgaatgaaca ggagcatttc     600
cgacaggttg cgaggcccca gggatatggt tacaacatca cggagacgat cagctccaac     660
gtggatgaca agaccatgca cgagttgtac ctttggccct tgcagatgc  cgtgcgcgct     720 ggcgttggcg ctgtcatgtg ttcctacaat caaatcaaca acagctacgg ttgtcaaaac     780
agtcaaactc tcaacaagct cctcaaggct gagctgggct ccaaggctt  cgtcatgagt     840 gactggagcg ctcaccacag cggtgtcggc gctgccctcg ctgggttgga tatgtcgatg     900 cccgagagaca tttccttcga cgacggactc tccttctggg cacgaacct  aactgtcagt     960 gttcttaacg gcaccgttcc agcctggcgt gtcgatgaca tggctgttcg tatcatgacc    1020
gcgtactaca aggttggtcg tgaccgtctt cgtattcccc ctaacttcag ctcctggacc    1080
cgggatgagt acggctggga gcattctgct gtctccgagg gagcctggac caaggtgaac    1140
gacttcgtca atgtgcagcg cagtcactct cagatcatcc gtgagattgg tgccgctagt    1200
acagtgctct tgaagaacac gggtgctctt ccttgaccg  gcaaggaggt taaagtgggt    1260
```

```
gttctcggtg aagacgctgg ttccaacccg tggggtgcta acggctgccc cgaccgcggc    1320
tgtgataacg gcactcttgc tatggcctgg ggtagtggta ctgccaactt cccttacctt    1380 gtcaccccg agcaggctat ccagcgagag gtcatcagca acggcggcaa tgtctttgct    1440
gtgactgata acgggctct cagccagatg gcagatgttg catctcaatc cagcgtgtct    1500
ttggtgtttg tcaacgccga ctctggagag ggtttcatca gtgtcgacgg caacgagggt    1560
gaccgcaaaa atctcactct gtggaagaac ggcgaggccg tcattgacac tgttgtcagc    1620
cactgcaaca acacgattgt ggttattcac agtgttgggc ccgtcttgat cgaccggtgg    1680
tatgataacc ccaacgtcac tgccatcatc tgggccggct tgcccggtca ggagagtggc    1740
aactccctgg tcgacgtgct ctatggccgc gtcaacccca cgccaagac cccgttcacc    1800 tggggcaaga ctcgggagtc ttacggggct cccttgctca ccgagcctaa caatggcaat    1860
ggtgctcccc aggatgattt caacgagggc gtcttcattg actaccgtca ctttgacaag    1920
cgcaatgaga cccccattta tgagtttggc catggcttga gctacaccac ctttggttac    1980
tctcaccttc gggttcaggc cctcaatagt tcgagttcgg catatgtccc gactagcgga    2040
gagaccaagc ctgcgccaac ctatggtgag atcggtagtg ccgccgacta cctgtatccc    2100
gagggtctca aaagaattac caagtttatt taccccttggc tcaactcgac cgacctcgag    2160
gattcttctg acgacccgaa ctacggctgg caggactcga gtacattcc cgaaggcgct    2220 agggatgggt ctcctcaacc cctcctgaag gctggcggcg ctcctggtgg taaccctacc    2280
ctttatcagg atcttgttag ggtgtcggcc accataacca acactggtaa cgtcgccggt    2340
tatgaagtcc ctcaattgta tgtttcattg ggcggaccga acgagcctcg ggtcgttctg    2400
cgcaagttcg accgaatctt cctggctcct ggggagcaaa aggtttggac cacgactctt    2460
aaccgtcgtg atctcgccaa ttgggatgtg gaggctcagg actgggtcat cacaaagtac    2520
cccaagaaag tgcacgtcgg cagctcctcg cgtaagctgc ctctgagagc gcctctgccc    2580
cgtgtctac                                                           2589

<210> SEQ ID NO 72
<211> LENGTH: 29
<212> TYPE: DNA
<213> ORGANISM: Aspergillus fumigatus

<400> SEQUENCE: 72
ggctcatgag attcggttgg ctcgaggtc                                      29

<210> SEQ ID NO 73
<211> LENGTH: 30
<212> TYPE: DNA
<213> ORGANISM: Aspergillus fumigatus

<400> SEQUENCE: 73
gccgttatca cagccgcggt cggggcagcc                                     30

<210> SEQ ID NO 74
<211> LENGTH: 30
<212> TYPE: DNA
<213> ORGANISM: Aspergillus fumigatus

<400> SEQUENCE: 74
ggctgccccg accgcggctg tgataacggc                                     30

<210> SEQ ID NO 75
```

-continued

<210> SEQ ID NO 75
<211> LENGTH: 35
<212> TYPE: DNA
<213> ORGANISM: Aspergillus fumigatus

<400> SEQUENCE: 75
gcttaattaa tctagtagac acggggcaga ggcgc                      35

<210> SEQ ID NO 76
<211> LENGTH: 16
<212> TYPE: DNA
<213> ORGANISM: Aspergillus fumigatus

<400> SEQUENCE: 76
acactggcgg agaagg                                           16

<210> SEQ ID NO 77
<211> LENGTH: 18
<212> TYPE: DNA
<213> ORGANISM: Aspergillus fumigatus

<400> SEQUENCE: 77
gcccagggat atggttac                                         18

<210> SEQ ID NO 78
<211> LENGTH: 19
<212> TYPE: DNA
<213> ORGANISM: Aspergillus fumigatus

<400> SEQUENCE: 78
cgactctgga gagggtttc                                        19

<210> SEQ ID NO 79
<211> LENGTH: 19
<212> TYPE: DNA
<213> ORGANISM: Aspergillus fumigatus

<400> SEQUENCE: 79
ggactgggtc atcacaaag                                        19

<210> SEQ ID NO 80
<211> LENGTH: 17
<212> TYPE: DNA
<213> ORGANISM: Aspergillus fumigatus

<400> SEQUENCE: 80
gcgagaggtc atcagca                                          17

<210> SEQ ID NO 81
<211> LENGTH: 17
<212> TYPE: DNA
<213> ORGANISM: Aspergillus fumigatus

<400> SEQUENCE: 81
gtaaaacgac ggccagt                                          17

<210> SEQ ID NO 82
<211> LENGTH: 16
<212> TYPE: DNA
<213> ORGANISM: Aspergillus fumigatus

<400> SEQUENCE: 82
caggaaacag ctatga                                           16

```
<210> SEQ ID NO 83
<211> LENGTH: 69
<212> TYPE: DNA
<213> ORGANISM: Aspergillus fumigatus

<400> SEQUENCE: 83
cttcttgtta gtgcaatatc atatagaagt catcgactag tggatctacc atgagattcg      60
gttggctcg                                                             69

<210> SEQ ID NO 84
<211> LENGTH: 61
<212> TYPE: DNA
<213> ORGANISM: Aspergillus fumigatus

<400> SEQUENCE: 84
gcgtgaatgt aagcgtgaca taactaatta catgactcga gctagtagac acggggcaga      60
g                                                                     61

<210> SEQ ID NO 85
<211> LENGTH: 60
<212> TYPE: DNA
<213> ORGANISM: Aspergillus fumigatus

<400> SEQUENCE: 85
ccgctccgcc gttgtggccg ccctgccggt gttggccctt ccgaattgg ctttctctcc       60

<210> SEQ ID NO 86
<211> LENGTH: 17
<212> TYPE: DNA
<213> ORGANISM: Aspergillus fumigatus

<400> SEQUENCE: 86
ctggcgttgg cgctgtc                                                    17

<210> SEQ ID NO 87
<211> LENGTH: 30
<212> TYPE: DNA
<213> ORGANISM: Aspergillus fumigatus

<400> SEQUENCE: 87
gcggcagaat ctgggaaagc ttctctcctg                                      30

<210> SEQ ID NO 88
<211> LENGTH: 30
<212> TYPE: DNA
<213> ORGANISM: Aspergillus fumigatus

<400> SEQUENCE: 88
caggagagaa gctttcccag attctgccgc                                      30

<210> SEQ ID NO 89
<211> LENGTH: 29
<212> TYPE: DNA
<213> ORGANISM: Aspergillus fumigatus

<400> SEQUENCE: 89
tgactggagc gctcaacaca gcggtgtcg                                       29

<210> SEQ ID NO 90
<211> LENGTH: 29
<212> TYPE: DNA
<213> ORGANISM: Aspergillus fumigatus
```

-continued

```
<400> SEQUENCE: 90
cgacaccgct gtgttgagcg ctccagtca                                29

<210> SEQ ID NO 91
<211> LENGTH: 30
<212> TYPE: DNA
<213> ORGANISM: Aspergillus fumigatus

<400> SEQUENCE: 91
gaggattctt ctggcgaccc gaactacggc                               30

<210> SEQ ID NO 92
<211> LENGTH: 30
<212> TYPE: DNA
<213> ORGANISM: Aspergillus fumigatus

<400> SEQUENCE: 92
gccgtagttc gggtcgccag aagaatcctc                               30
```

VARIANTS OF BETA-GLUCOSIDASES

CROSS-REFERENCE TO RELATED APPLICATIONS

This application claims the benefit of U.S. Provisional Applications No. 60/467,767, filed May 2, 2003, and 60/528,342, filed Dec. 9, 2003, which applications are incorporated herein by reference.

STATEMENT AS TO RIGHTS TO INVENTIONS MADE UNDER FEDERALLY SPONSORED RESEARCH AND DEVELOPMENT

This invention was made with Government support under NREL Subcontract No. ZCO-30017-02, Prime Contract DE-AC36-98GO10337 awarded by the Department of Energy. The government has certain rights in this invention.

BACKGROUND OF THE INVENTION

1. Field of the Invention

The present invention relates to variants of beta-glucosidases having one or more improved properties relative to its parent enzyme, nucleic acids encoding the variants, methods of producing the variants, and methods for using the variants.

2. Description of the Related Art

Cellulose is a polymer of the simple sugar glucose covalently bonded by beta-1,4-linkages. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

The conversion of cellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the cellulose is converted to glucose, the glucose is easily fermented by yeast into ethanol. Since glucose is readily fermented to ethanol by a variety of yeasts while cellobiose is not, any cellobiose remaining at the end of the hydrolysis represents a loss of yield of ethanol. More importantly, cellobiose is a potent inhibitor of endoglucanases and cellobiohydrolases. The accumulation of cellobiose during hydrolysis is extremely undesirable for ethanol production.

Cellobiose accumulation has been a major problem in enzymatic hydrolysis because cellulase-producing microorganisms produce little beta-glucosidase. The low amount of beta-glucosidase results in a shortage of capacity to hydrolyze the cellobiose to glucose. Several approaches have been used to increase the amount of beta-glucosidase in cellulose conversion to glucose.

One approach is to produce beta-glucosidase using microorganisms that produce little cellulase, and add the beta-glucosidase exogenously to endoglucanase and cellobiohydrolase to enhance the hydrolysis. However, the quantities required are too costly for a commercial biomass to ethanol operation.

A second approach is to carry out cellulose hydrolysis simultaneously with fermentation of the glucose by yeast. This process is known as simultaneous saccharification and fermentation (SSF). In an SSF system, fermentation of the glucose removes it from solution. However, SSF systems are not yet commercially viable because the operating temperature for yeast of 28° C. is too low for the 50° C. conditions required.

A third approach to overcome the shortage of beta-glucosidase is to overexpress the beta-glucosidase in a host, thereby increasing the yield of beta-glucosidase.

It would be an advantage in the art to provide beta-glucosidase variants with improved properties for converting cellulosic materials to monosaccharides, disaccharides, and polysaccharides. Improved properties include altered temperature-dependent activity profiles, thermostability, pH activity, pH stability, substrate specificity, product specificity, and chemical stability.

It is an object of the present invention to provide variants of beta-glucosidases with improved properties compared to their parent enzymes.

SUMMARY OF THE INVENTION

The present invention relates to isolated variants of a parent beta-glucosidase, comprising a substitution at one or more positions corresponding to positions 142, 183, 266, and 703 of amino acids 1 to 842 of SEQ ID NO: 2 or corresponding to positions 142, 183, 266, and 705 of amino acids 1 to 844 of SEQ ID NO: 70, wherein the variant has beta-glucosidase activity.

The present invention also relates to isolated polypeptides having beta-glucosidase activity, wherein the amino acid sequence of the polypeptide differs from amino acids 1 to 842 of SEQ ID NO: 2 or amino acids 1 to 844 of SEQ ID NO: 70 at one or more positions corresponding to positions 142, 183, 266, and 703 of amino acids 1 to 842 of SEQ ID NO: 2 or corresponding to positions 142, 183, 266, and 705 of amino acids 1 to 844 of SEQ ID NO: 70.

The present invention also relates to isolated nucleotide sequences encoding the variant beta-glucosidases or polypeptides having beta-glucosidase activity and to nucleic acid constructs, vectors, and host cells comprising the nucleotide sequences.

The present invention also relates to methods for producing a variant of a parent beta-glucosidase or polypeptides having beta-glucosidase activity in a host cell.

The present invention also relates to methods for obtaining a variant of a parent beta-glucosidase, comprising:

(a) introducing a substitution at one or more positions corresponding to positions 142, 183, 266, and 703 of amino acids 1 to 842 of SEQ ID NO: 2 or corresponding to positions 142, 183, 266, and 705 of amino acids 1 to 844 of SEQ ID NO: 70, wherein the variant has beta-glucosidase activity; and (b) recovering the variant.

The present invention also relates to detergent compositions comprising beta-glucosidase variants and polypeptides having beta-glucosidase activity.

The present invention also relates to plants encoding beta-glucosidase variants or polypeptides having beta-glucosidase activity.

The present invention further relates to using the beta-glucosidase variants and polypeptides having beta-glucosidase activity in the conversion of cellulose to glucose.

BRIEF DESCRIPTION OF THE FIGURES

FIG. 9 shows the cDNA sequence of an *Aspergillus oryzae* beta-glucosidase gene (SEQ ID NO: 93) and the deduced amino acid sequence thereof (SEQ ID NO: 94). The predicted signal peptide is underlined.
FIG. 10 shows 63 bp of the putative *Humicola insolens* endoglucanase V signal sequence (ATG start codon to Ala-21, SEQ ID NO: 29).
FIG. 21 shows the genomic DNA sequence and the deduced amino acid sequence of an *Aspergillus fumigatus* beta-glucosidase (SEQ ID NOS: 95 and 96, respectively). The predicted signal peptide is underlined and predicted introns are italicized.

DETAILED DESCRIPTION OF THE INVENTION

Figure 1:
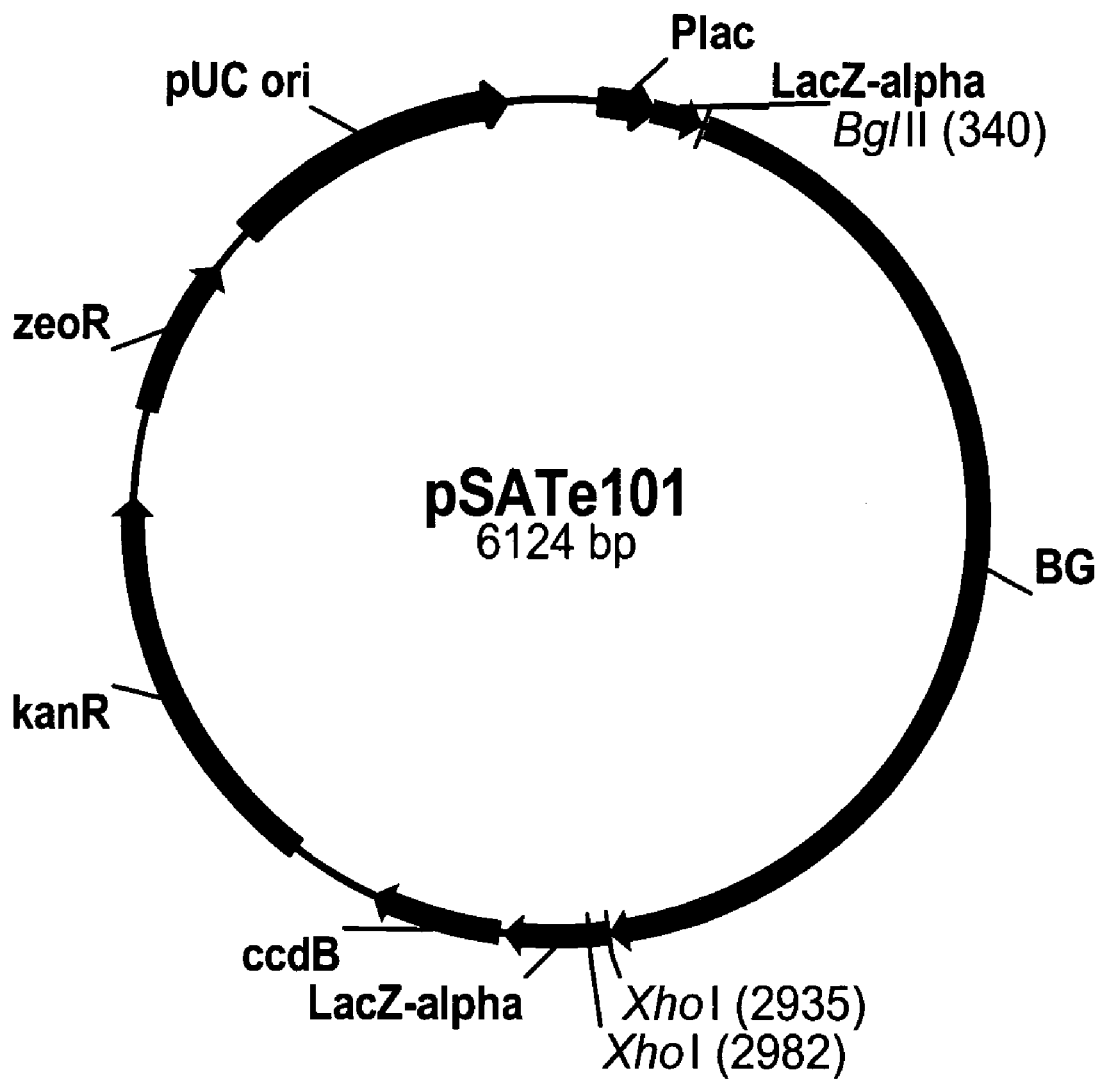
FIG. 1 shows a restriction map of pSATe101.

The present invention relates to isolated variants of a parent beta-glucosidase, comprising a substitution at one or more positions corresponding to positions 142, 183, 266, and 703 of amino acids 1 to 842 of SEQ ID NO: 2 or corresponding to positions 142, 183, 266, and 705 of amino acids 1 to 844 of SEQ ID NO: 70, wherein the variant has beta-glucosidase activity.

Definitions

The term "beta-glucosidase" is defined herein as a beta-D-glucoside glucohydrolase (E.C. 3.2.1.21) which catalyzes the hydrolysis of terminal non-reducing beta-D-glucose residues with the release of beta-D-glucose. For purposes of the present invention, beta-glucosidase activity is determined according to the basic procedure described by Venturi et al., 2002, *J. Basic Microbiol*. 42: 55-66, except various temperatures and pH 5 are employed herein. One unit of beta-glucosidase activity is defined as 1.0 μmole of beta-D-glucose produced per minute at 25° C., pH 5.

The term "variant" is defined herein as a beta-glucosidase comprising one or more alterations, such as substitutions, insertions, deletions, and/or truncations of one or more specific amino acid residues at one or more specific positions in the polypeptide.

The term "wild-type" beta-glucosidase denotes a beta-glucosidase expressed by a naturally occurring microorganism, such as a yeast or filamentous fungus found in nature.

The term "parent" beta-glucosidase as used herein means a beta-glucosidase to which modifications, e.g., substitution(s), insertion(s), deletion(s), and/or truncation(s), are made to produce the enzyme variants of the present invention. This term also refers to the polypeptide with which a variant is compared and aligned. The parent may be a naturally occurring (wild type) polypeptide, or it may even be a variant thereof, prepared by any suitable means. For instance, the parent protein may be a variant of a naturally occurring polypeptide which has been modified or altered in the amino acid sequence. A parent may also be an allelic variant which is any of two or more alternative forms of a gene occupying the same chromosomal locus. An allelic variant of a polypeptide is a polypeptide encoded by the corresponding allelic variant of a gene.

The term "shuffling" means recombination of nucleotide sequence(s) between two or more homologous nucleotide sequences resulting in recombined nucleotide sequences (i.e., nucleotide sequences having been subjected to a shuffling cycle) having a number of nucleotides exchanged, in comparison to the starting nucleotide sequences.

The term "randomized library", "variant library", or "library" is defined herein as a library of variant polypeptides. Diversity in the variant library can be generated via mutagenesis of the genes encoding the variants at the DNA triplet level, such that individual codons are variegated, e.g., by using primers of partially randomized sequences in a PCR reaction. Several techniques have been described, by which one can create a diverse combinatorial library by variegating several nucleotide positions in a gene and recombining them, for instance, where these positions are too far apart to be covered by a single (spiked or doped) oligonucleotide primer. These techniques include the use of in vivo recombination of the individually diversified gene segments as described in WO 97/07205 on page 3, lines 8 to 29. They also include the use of DNA shuffling techniques to create a library of full length genes, wherein several gene segments are combined, and wherein each segment may be diversified, e.g., by spiked mutagenesis (Stemmer, 1994, *Nature* 370: 389-391; U.S. Pat. No. 5,811,238; U.S. Pat. No. 5,605,793; and U.S. Pat. No. 5,830,721). One can use a gene encoding a protein "backbone" (wild type parent polypeptide) as a template polynucleotide, and combine this with one or more single or double-stranded oligonucleotides as described in WO 98/41623 and WO 98/41622. The single-stranded oligonucleotides can be partially randomized during synthesis. The double-stranded oligonucleotides can be PCR products incorporating diversity in a specific region. In both cases, one can dilute the diversity with corresponding segments encoding the sequence of the backbone protein in order to limit the average number of changes that are introduced.

The term "recombination" is defined herein as a process wherein nucleic acids associate with each other in regions of homology, leading to interstrand DNA exchange between those sequences.

For purposes of the present invention, homologous recombination is determined according to the procedures summarized by Paques and Haber, 1999, *Microbiology and Molecular Biology Reviews* 63: 349-404. "Homologous recombination" is defined herein as recombination in which no changes in the nucleotide sequences occurs within the regions of homology relative to the input nucleotide sequences. For perfect homologous recombination, the regions should contain a sufficient number of nucleic acids, such as 100 to 1,500 base pairs, preferably 400 to 1,500 base pairs, and most preferably 800 to 1,500 base pairs, which are highly homologous with the corresponding nucleic acid sequence to enhance the probability of homologous recombination. The recombination may also occur by non-homologous recombination. "Non-homologous recombination" is defined herein as recombination where any mode of DNA repair incorporating strand exchange results in a nucleotide sequence different from any of the recombining sequences.

The term "improved property" is defined herein as a characteristic associated with a variant which is improved compared to the parent beta-glucosidase. Such improved properties include, but are not limited to, altered temperature-dependent activity profile, thermostability, pH activity, pH stability, substrate specificity, product specificity, and chemical stability.

The term "improved thermal activity" is defined herein as a variant enzyme displaying an alteration of the temperature-dependent activity profile of a beta-glucosidase variant at a specific temperature relative to the temperature-dependent activity profile of the parent beta-glucosidase. The thermal activity value provides a measure of the enzyme's efficiency in performing catalysis of a hydrolysis reaction over a range of temperatures. A beta-glucosidase has a specific temperature range wherein the protein is stable and retains its enzymatic activity, but becomes less stable and thus less active with increasing temperature. Furthermore, the initial rate of a reaction catalyzed by a beta-glucosidase can be accelerated by an increase in temperature which is measured by determining thermal activity of a variant. A more thermoactive variant will lead to an increase in the rate of hydrolysis decreasing the time required and/or decreasing the enzyme concentration required for hydrolysis. Alternatively, a variant with a reduced thermal activity will catalyze a hydrolysis reaction at a temperature lower than the temperature optimum of the parent enzyme defined by the temperature-dependent activity profile of the parent.

The term "improved thermostability" is defined herein as a variant enzyme displaying retention of enzymatic activity after a period of incubation at elevated temperature relative to the parent enzyme. Such a variant may or may not display an altered thermal activity profile relative to the parent, e.g., it may have an improved ability to refold following incubation at elevated temperature relative to the parent.

In a preferred embodiment, the thermal activity of the variant beta-glucosidase is at least 1.5-fold, preferably at least 2-fold, more preferably at least 5-fold, most preferably at least 7-fold, and even most preferably at least 20-fold more thermally active than the parent enzyme when residual activity is compared using methylumbelliferyl-beta-D-glucopyranoside as substrate at 60° C. and pH 5 for 15 hours.

The term "improved product specificity" is defined herein as a variant enzyme displaying an altered product profile relative to the parent in which the altered product profile improves the performance of the variant in a given application relative to the parent. The term "product profile" is defined herein as the chemical composition of the reaction products produced by enzymatic hydrolysis.

The term "improved chemical stability" is defined herein as a variant enzyme displaying retention of enzymatic activity after a period of incubation in the presence of a chemical or chemicals, either naturally occurring or synthetic, that reduce the enzymatic activity of the parent enzyme. Improved chemical stability may also result in variants better able to catalyze a reaction in the presence of such chemicals.

Conventions for Designation of Variants

In the present invention, a specific numbering of amino acid residue positions in the beta-glucosidase variants is employed. For example, by aligning the amino acid sequences of known beta-glucosidases, it is possible to designate an amino acid position number to any amino acid residue in any beta-glucosidase enzyme.

Using the numbering system originating from the amino acid sequence of the beta-glucosidase disclosed in SEQ ID NO: 2 or SEQ ID NO: 70, aligned with the amino acid sequence of a number of other beta-glucosidases, it is possible to indicate the position of an amino acid residue in a beta-glucosidase in regions of structural homology.

Multiple alignments of protein sequences may be made, for example, using "ClustalW" (Thompson, J. D., Higgins, D. G. and Gibson, T. J., 1994, CLUSTAL W: Improving the sensitivity of progressive multiple sequence alignment through sequence weighting, positions-specific gap penalties and weight matrix choice, *Nucleic Acids Research* 22: 4673-4680). Multiple alignments of DNA sequences may be done using the protein alignment as a template, replacing the amino acids with the corresponding codon from the DNA sequence.

Pairwise sequence comparison algorithms in common use are adequate to detect similarities between protein sequences that have not diverged beyond the point of approximately 20-30% sequence identity (Doolittle, 1992, *Protein Sci.* 1: 191-200; Brenner et al., 1998, *Proc. Natl. Acad. Sci. USA* 95, 6073-6078). However, truly homologous proteins with the same fold and similar biological function have often diverged to the point where traditional sequence-based comparison fails to detect their relationship (Lindahl and Elofsson, 2000, *J. Mol. Biol.* 295: 613-615). Greater sensitivity in sequence-based searching can be attained using search programs that utilize probabilistic representations of protein families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the protein of interest has one or more representatives in the protein structure databases. Programs such as GenTHREADER (Jones 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the protein of interest, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. These alignments can be used to predict the structurally and functionally corresponding amino acid residues in proteins within the same structural superfamily. This information, along with information derived from homology modeling and profile searches, can be used to predict which residues to mutate when moving mutations of interest from one protein to a close or remote homolog.

In describing the various beta-glucosidase variants of the present invention, the nomenclature described below is adapted for ease of reference. In all cases, the accepted IUPAC single letter or triple letter amino acid abbreviations are employed.

Substitutions. For an amino acid substitution, the following nomenclature is used: [Original amino acid, position, substituted amino acid]. Accordingly, the substitution of threonine with alanine at position 226 is designated as "Thr226Ala" or "T226A". Multiple mutations are separated by addition marks ("+"), e.g., "Gly205Arg+Ser411Phe" or "G205R+S411F", representing mutations at positions 205 and 411 substituting glycine (G) with arginine (R), and serine (S) with phenylalanine (F), respectively.

Deletions. For an amino acid deletion, the following nomenclature is used: [Original amino acid, position*]. Accordingly, the deletion of glycine at position 195 is designated as "Gly195*" or "G195*". Multiple deletions are separated by addition marks ("+"), e.g., "Gly195*+Ser411*" or "G195*+S411*".

Insertions. For an amino acid insertion, the following nomenclature is used: [Original amino acid, position, original amino acid, new inserted amino acid]. Accordingly the insertion of lysine after glycine at position 195 is designated "Gly195GlyLys" or "G195GK". Multiple insertions of amino acids are designated [Original amino acid, position, original amino acid, new inserted amino acid #1, new inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example the sequences would thus be:

| Parent: | Variant: |
|---------|----------|
| 195     | 195 195a 195b |
| G       | G - K - A |

Degenerate indications. For degenerate indications where an amino acid residue identical to the existing amino acid residue is inserted, degeneracy in the nomenclature arises. For example, a glycine inserted after the glycine in the above example would be indicated by "G195GG". Given that an alanine were present in position 194, the same actual change could just as well be indicated as "A194AG":

|              | Parent: | Variant: |
|--------------|---------|----------|
| Numbering I: | 194 195 | 194 195 195a |
| Sequence:    | A - G   | A - G - G |
| Numbering II:|         | 194 194a 195 |

Such instances will be apparent to the skilled person, and the indication "G195GG" and corresponding indications for this type of insertion is thus meant to comprise such equivalent degenerate indications.

If amino acid sequence segments are repeated in the parent polypeptide and/or in the variant, equivalent degenerate indications arise, also when alterations other than insertions are listed such as deletions and/or substitutions. For instance, the deletion of two consecutive amino acids "AG" in the sequence "AGAG" from position 194-97 may be written as "A194*+G195*" or "A196*+G197*":

|              | Parent: | Variant: |
|--------------|---------|----------|
| Numbering I: | 194 195 196 197 | 194 195 |
| Sequence:    | A - G - A - G | A - G |
| Numbering II:|         | 196 197 |

Multiple modifications. Variants comprising multiple modifications are separated by addition marks ("+"), e.g., "Arg170Tyr+Gly195Glu" or "R170Y+G195E" representing modifications in positions 170 and 195 substituting tyrosine and glutamic acid for arginine and glycine, respectively. Thus, "Tyr167Gly,Ala,Ser,Thr+Arg170Gly,Ala,Ser,Thr" designates the following variants:
"Tyr167Gly+Arg170Gly", "Tyr167Gly+Arg170Ala",
"Tyr167Gly+Arg170Ser",
"Tyr167Gly+Arg170Thr", "Tyr167Ala+Arg170Gly",
"Tyr167Ala+Arg170Ala",
"Tyr167Ala+Arg170Ser", "Tyr167Ala+Arg170Thr",
"Tyr167Ser+Arg170Gly",
"Tyr167Ser+Arg170Ala", "Tyr167Ser+Arg170Ser",
"Tyr167Ser+Arg170Thr",
"Tyr167Thr+Arg170Gly", "Tyr167Thr+Arg170Ala",
"Tyr167Thr+Arg170Ser", and
"Tyr167Thr+Arg170Thr".

This nomenclature is particularly relevant to modifications involving substituting, inserting or deleting amino acid residues having specific common properties. Such modifications are referred to as conservative amino acid modification(s). Examples of conservative modifications are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid modifications, which do not generally alter the specific activity are known in the art and are described, for example, by H. Neurath and R. L. Hill, 1979, *In, The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as the reverse (Taylor, 1986, *Journal of Theoretical Biology* 119: 205-218; http://www.compbio.dundee.ac.uk/papers/amas/amas3d.html).

Parent Beta-Glucosidases

In the present invention, the parent beta-glucosidase is (a) a polypeptide comprising an amino acid sequence which has at least 70% identity with amino acids 1 to 842 of SEQ ID NO: 2 or amino acids 1 to 844 of SEQ ID NO: 70; or (b) a polypeptide encoded by a nucleotide sequence which hybridizes under at least low stringency conditions with nucleotides 58 to 2583 of SEQ ID NO: 1 or nucleotides 58 to 2589 of SEQ ID NO: 71, or their complementary strands.

In a first aspect, the parent beta-glucosidase comprise an amino acid sequence which has a degree of identity to amino acids 1 to 842 of SEQ ID NO: 2 or amino acids 1 to 844 of SEQ ID NO: 70 (i.e., the mature polypeptides) of at least about 70%, preferably at least about 75%, more preferably at least about 80%, more preferably at least about 85%, even more preferably at least about 90%, most preferably at least about 95%, and even most preferably at least about 97%, which have beta-glucosidase activity (hereinafter "homologous polypeptides"). In a preferred embodiment, the homologous polypeptides have an amino acid sequence which differs by five amino acids, preferably by four amino acids, more preferably by three amino acids, even more preferably by two amino acids, and most preferably by one amino acid from amino acids 1 to 842 of SEQ ID NO: 2 or amino acids 1 to 844 of SEQ ID NO: 70. For purposes of the present invention, the degree of identity between two amino acid sequences is determined by the Clustal method (Higgins, 1989, *CABIOS* 5: 151-153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=1, gap penalty=3, windows=5, and diagonals=5.

Substantially homologous parent beta-glucosidases may have one or more amino acid substitutions, deletions or additions. These changes are preferably of a minor nature, that is conservative amino acid substitutions as described above and other substitutions that do not significantly affect the three-dimensional folding or activity of the protein or polypeptide; small deletions, typically of one to about 30 amino acids; and small amino- or carboxyl-terminal extensions, such as an amino-terminal methionine residue, a small linker peptide of up to about 20-25 residues, or a small extension that facilitates purification (an affinity tag), such as a poly-histidine tract, or protein A (Nilsson et al., 1985, *EMBO J.* 4: 1075; Nilsson et al., 1991, *Methods Enzymol.* 198: 3. See, also, in general, Ford et al., 1991, *Protein Expression and Purification* 2: 95-107.

Although the changes described above preferably are of a minor nature, such changes may also be of a substantive nature such as fusion of larger polypeptides of up to 300 amino acids or more both as amino- or carboxyl-terminal extensions.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type beta-glucosidase. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Preferably, the parent beta-glucosidase comprises the amino acid sequence of SEQ ID NO: 2 or SEQ ID NO: 70; or an allelic variant thereof; or a fragment thereof that has beta-glucosidase activity. In a preferred embodiment, the parent polypeptide comprises the amino acid sequence of SEQ ID NO: 2 or SEQ ID NO: 70. In another preferred embodiment, the parent polypeptide comprises amino acids 1 to 842 of SEQ ID NO: 2 or amino acids 1 to 844 of SEQ ID NO: 70; or an allelic variant thereof; or a fragment thereof that has beta-glucosidase activity. In another preferred embodiment, the parent polypeptide comprises amino acids 1 to 842 of SEQ ID NO: 2 or amino acids 1 to 844 of SEQ ID NO: 70. In another preferred embodiment, the parent polypeptide consists of the amino acid sequence of SEQ ID NO: 2 or SEQ ID NO: 70; or an allelic variant thereof; or a fragment thereof that has beta-glucosidase activity. In another preferred embodiment, the parent polypeptide consists of the amino acid sequence of SEQ ID NO: 2 or SEQ ID NO: 70. In another preferred embodiment, the parent polypeptide consists of amino acids 1 to 842 of SEQ ID NO: 2 or amino acids 1 to 844 of SEQ ID NO: 70 or an allelic variant thereof; or a fragment thereof that has beta-glucosidase activity. In another preferred embodiment, the parent polypeptide consists of amino acids 1 to 842 of SEQ ID NO: 2 or amino acids 1 to 844 of SEQ ID NO: 70. In another preferred embodiment, the parent polypeptide is encoded by the nucleotide sequence contained in *Escherichia coli* DSM 14240, wherein the nucleic acid sequence encodes a polypeptide having beta-glucosidase activity. In another preferred embodiment, the parent polypeptide is encoded by the mature polypeptide coding region contained in *Escherichia coli* DSM 14240. In another preferred embodiment, the parent polypeptide is encoded by the nucleotide sequence contained in plasmid pEJG113 which is contained in *Escherichia coli* NRRL B-30695, wherein the nucleic acid sequence encodes a polypeptide having beta-glucosidase activity. In another preferred embodiment, the parent polypeptide is encoded by the mature polypeptide coding region contained in plasmid pEJG113 which is contained in *Escherichia coli* NRRL B-30695.

A fragment of SEQ ID NO: 2 or SEQ ID NO: 70 is a polypeptide having one or more amino acids deleted from the amino and/or carboxyl terminus of this amino acid sequence. Preferably, a fragment contains at least 770 amino acid residues, more preferably at least 800 amino acid residues, and most preferably at least 830 amino acid residues.

In a second aspect, the parent beta-glucosidase is encoded by a nucleotide sequence which hybridizes under low stringency conditions, preferably medium stringency conditions, more preferably medium-high stringency conditions, even more preferably high stringency conditions, and most preferably very high stringency conditions with a nucleotide probe which hybridizes under the same conditions with (i) nucleotides 58 to 2583 of SEQ ID NO: 1 or nucleotides 58 to 2589 of SEQ ID NO: 71, (ii) the genomic nucleotide sequence comprising nucleotides 58 to 2583 of SEQ ID NO: 1 or nucleotides 58 to 2589 of SEQ ID NO: 71, (iii) a subsequence of (i) or (ii), or (iv) a complementary strand of (i), (ii), or (iii) (J. Sambrook, E. F. Fritsch, and T. Maniatus, 1989, *Molecular Cloning, A Laboratory Manual*, 2d edition, Cold Spring Harbor, N.Y.). The subsequence of SEQ ID NO: 1 may be at least 100 contiguous nucleotides or preferably at least 200 contiguous nucleotides. Moreover, the subsequence may encode a polypeptide fragment which has beta-glucosidase activity.

A subsequence of SEQ ID NO: 1 or SEQ ID NO: 71, or homologue thereof, is a nucleotide sequence where one or more nucleotides have been deleted from the 5'-and/or 3'-end. Preferably, a subsequence contains at least 2310 nucleotides, more preferably at least 2400 nucleotides, and most preferably at least 2490 nucleotides.

The parent polypeptides may also be allelic variants of the polypeptides that have beta-glucosidase activity. An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The nucleotide sequence of SEQ ID NO: 1 or a subsequence thereof, as well as the amino acid sequence of SEQ ID NO: 2 or SEQ ID NO: 70, or a fragment thereof, may be used to design nucleotide probes to identify and clone DNA encoding parent polypeptides having beta-glucosidase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 35 nucleotides in length. Longer probes can also be used. Both DNA and RNA probes can be used. The probes are typically labeled for detecting the corresponding gene (for example, with $^{32}$P, $^{3}$H, $^{35}$S, biotin, or avidin).

A genomic DNA or cDNA library prepared from such other organisms may be screened for DNA which hybridizes with the probes described above and which encodes a parent polypeptide having beta-glucosidase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO: 1 or SEQ ID NO: 71, or a subsequence thereof, the carrier material is used in a Southern blot. For purposes of the present invention, hybridization indicates that the nucleotide sequence hybridizes to a labeled nucleotide probe corresponding to the nucleotide sequence shown in SEQ ID NO: 1 or SEQ ID NO: 71, its complementary strand, or a subsequence thereof, under low to very high stringency conditions. Molecules to which the radioactivity-labeled probe hybridizes can be detected using, for example, X-ray film.

In a preferred embodiment, the nucleotide probe is a nucleotide sequence which encodes the polypeptide of SEQ ID NO: 2 or SEQ ID NO: 70, or a subsequence thereof. In another preferred embodiment, the nucleotide probe is SEQ ID NO: 1 or SEQ ID NO: 71. In another preferred embodiment, the nucleotide probe is nucleotides 58 to 2583 of SEQ ID NO: 1 or nucleotides 58 to 2589 of SEQ ID NO: 71. In another preferred embodiment, the nucleotide probe is the nucleic acid sequence contained in *Escherichia coli* DSM 14240, wherein the nucleic acid sequence encodes a polypeptide having beta-glucosidase activity. In another preferred embodiment, the nucleotide probe is the mature polypeptide coding region contained in *Escherichia coli* DSM 14240. In another preferred embodiment, the nucleotide probe is the nucleic acid sequence contained in plasmid pEJG113 which is contained in *Escherichia coli* NRRL B-30695, wherein the nucleic acid sequence encodes a polypeptide having beta-glucosidase activity. In another preferred embodiment, the nucleotide probe is the mature polypeptide coding region contained in plasmid pEJG113 which is contained in *Escherichia coli* NRRL B-30695.

For long probes of at least 100 nucleotides in length, low to very high stringency conditions are defined as prehybridization and hybridization at 42° C. in 5×SSPE, 0.3% SDS, 200 µg/ml sheared and denatured salmon sperm DNA, and either 25% formamide for low stringencies, 35% formamide for medium and medium-high stringencies, or 50% formamide for high and very high stringencies, following standard Southern blotting procedures.

For long probes of at least 100 nucleotides in length, the carrier material is finally washed three times each for 15 minutes using 2×SSC, 0.2% SDS preferably at least at least at 50° C. (low stringency), more preferably at least at 55° C. (medium stringency), more preferably at least at 60° C. (medium-high stringency), most preferably at least at 65° C. (high stringency), and even most preferably at least at 70° C. (very high stringency).

For short probes which are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

The parent beta-glucosidase may be obtained from microorganisms of any genus. For purposes of the present invention, the term "obtained from" as used herein in connection with a given source shall mean that the parent beta-glucosidase encoded by a nucleotide sequence is produced by the source or by a cell in which the nucleotide sequence from the source has been inserted. In a preferred embodiment, the parent beta-glucosidase is secreted extracellularly.

The parent beta-glucosidase may be a fungal beta-glucosidase. In a more preferred embodiment, the fungal beta-glucosidase is a yeast beta-glucosidase such as a *Candida, Kluyveromyces, Pichia, Saccharomyces, Schizosaccharomyces,* or *Yarrowia* beta-glucosidase. In another more preferred embodiment, the fungal beta-glucosidase is a filamentous fungal beta-glucosidase such as an *Acremonium, Agaricus, Alternaria, Aspergillus, Botryospaeria, Ceriporiopsis, Chaetomidium, Claviceps, Cochliobolus, Coprinopsis, Coptotermes, Corynascus, Cryphonectria, Diplodia, Exidia, Fusarium, Gibberella, Holomastigotoides, Humicola, Irpex, Lentinula, Leptospaeria, Magnaporthe, Melanocarpus, Meripilus, Myceliophthora, Neurospora, Penicillium, Phanerochaete, Poitrasia, Pseudoplectania, Pseudotrichonympha, Rhizomucor, Scytalidium, Talaromyces, Thermoascus, Thielavia, Trichoderma, Trichophaea, Verticillium, Volvariella,* or *Xylaria* beta-glucosidase.

In a more preferred embodiment, the parent beta-glucosidase is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* beta-glucosidase.

In another more preferred embodiment, the parent beta-glucosidase is an *Acremonium cellulolyticus, Aspergillus aculeatus, Aspergillus awamori, Aspergillus fumigatus, Aspergillus foetidus, Aspergillus fumigatus, Aspergillus japonicus, Aspergillus nidulans, Aspergillus niger, Aspergillus oryzae, Fusarium bactridioldes, Fusarium cerealls, Fusarium crookwellense, Fusafuim culmorum, Fusarium graminearum, Fusarium graminum, Fusarium heterosporum, Fusarium negundi, Fusarium oxysporum,*

*Fusafuim reticulatum, Fusafuim roseum, Fusarium sambucinum, Fusafuim sarcochroum, Fusafuim solani, Fusarium sporotrichioldes, Fusarium sulphureum, Fusafuim torulosum, Fusarium trichothecioides, Fusafuim venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Schizophyllum commune, Sclerotium rolfsii, Sporotrichum cellulophilum, Talaromyces emersonii, Thielavia terrestris, Trichoderma harzianum, Trichoderma koningii, Trichoderma longibrachiatum, Trichoderma reesei*, or *Trichoderma viride* beta-glucosidase.

In an even more preferred embodiment, the parent beta-glucosidase is an *Aspergillus oryzae* beta-glucosidase, and most preferably the *Aspergillus oryzae* beta-glucosidase of SEQ ID NO: 2 or the mature polypeptide thereof. In another most preferred embodiment, the parent beta-glucosidase is encoded by the nucleotide sequence contained in *E. coli* DSM 14240, wherein the nucleotide sequence encodes a polypeptide having beta-glucosidase activity. In another most preferred embodiment, the parent beta-glucosidase is encoded by the mature polypeptide coding region contained in *E. coli* DSM 14240.

In an even more preferred embodiment, the parent beta-glucosidase is an *Aspergillus fumigatus* beta-glucosidase, and most preferably the *Aspergillus fumigatus* beta-glucosidase of SEQ ID NO: 70 or the mature polypeptide thereof. In another most preferred embodiment, the parent beta-glucosidase is encoded by the nucleotide sequence contained in plasmid pEJG113 which is contained in *Escherichia coli* NRRL B-30695, wherein the nucleotide sequence encodes a polypeptide having beta-glucosidase activity. In another most preferred embodiment, the parent beta-glucosidase is encoded by the mature polypeptide coding region contained in plasmid pEJG113 which is contained in *Escherichia coli* NRRL B-30695.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

The parent beta-glucosidases may also be identified and obtained from other sources including microorganisms isolated from nature (e.g., soil, composts, water, etc.) or DNA samples obtained directly from natural materials (e.g., soil, composts, water, etc,) using the above-mentioned probes. Techniques for isolating microorganisms and DNA directly from natural habitats are well known in the art. The nucleotide sequence encoding a beta-glucosidase may then be derived by similarly screening a genomic or cDNA library of another microorganism or mixed DNA sample. Once a nucleotide sequence encoding a beta-glucosidase has been detected with suitable probe(s) as described herein, the sequence may be isolated or cloned by utilizing techniques which are known to those of ordinary skill in the art (see, e.g., J. Sambrook, E. F. Fritsch, and T. Maniatis, 1989, *Molecular Cloning, A Laboratory Manual*, 2d edition, Cold Spring Harbor, N.Y.).

As defined herein, an "isolated" beta-glucosidase is a polypeptide which is essentially free of other non-beta-glucosidase polypeptides, e.g., at least about 20% pure, preferably at least about 40% pure, more preferably about 60% pure, even more preferably about 80% pure, most preferably about 90% pure, and even most preferably about 95% pure, as determined by SDS-PAGE.

The parent beta-glucosidases can also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator. Fusion proteins may also be constructed using intein technology in which fusions are created post-translationally (Cooper et al., 1993, *EMBO J.* 12: 2575-2583; Dawson et al., 1994, *Science* 266: 776-779).

Variants

In the present invention, the isolated variants of a parent beta-glucosidase comprise a substitution at one or more positions corresponding to positions 142, 183, 266, and 703 of amino acids 1 to 842 of SEQ ID NO: 2 or corresponding to positions 142, 183, 266, and 705 of amino acids 1 to 844 of SEQ ID NO: 70, wherein the variant, having beta-glucosidase activity, comprises an amino acid sequence which has a degree of identity of at least about 70%, preferably at least about 75%, more preferably at least about 80%, more preferably at least about 85%, even more preferably at least about 90%, most preferably at least about 95%, and even most preferably at least about 97% to the amino acid sequence of the parent beta-glucosidase. For purposes of the present invention, the degree of identity between two amino acid sequences is determined by the Clustal method (Higgins, 1989, *CABIOS* 5: 151-153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=1, gap penalty=3, windows=5, and diagonals=5.

Essential amino acids in the parent beta-glucosidase can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for biological activity (i.e., beta-glucosidase activity) to identify amino acid residues that are critical to the activity of the molecule. See also, Hilton et al., 1996, *J. Biol Chem.* 271: 4699-4708. The active site of the enzyme or other biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309:59-64. The identities of essential amino acids can also be inferred from analysis of identities with polypeptides which are related to a polypeptide according to the invention.

Single or multiple amino acid substitutions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochem.* 30:10832-10837; U.S. Pat. No. 5,223,409; WO 92/06204) and region-directed mutagenesis (Derbyshire et al., 1986, *Gene* 46:145; Ner et al., 1988, *DNA* 7:127).

Mutagenesis/shuffling methods can be combined with high-throughput, automated screening methods to detect activity of cloned, mutagenized polypeptides expressed by host cells. Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

In a preferred embodiment, the number of amino acid substitutions in the variants of the present invention comprise preferably 4 substitutions, more preferably 3 substitutions, even more preferably 2 substitutions, and most preferably 1 substitution. In another preferred embodiment, the number of amino acid substitutions in the variants of the present invention consists of preferably 4 substitutions, more preferably 3 substitutions, even more preferably 2, and most preferably 1 substitution.

In a preferred embodiment, a variant of the present invention consists of 741 to 750, 751 to 760, 761 to 770, 771 to 780, 781 to 790, 791 to 800, 801 to 810, 811 to 820, 821 to 830, 831 to 840, 841 to 850, 851 to 860, 861 to 870, 871 to 880, 881 to 890, 891 to 900, 901 to 910, 911 to 920, 921 to 930, 931 to 940, or 941 to 950 amino acids.

The variants of the present invention may further comprise one or more deletions and/or insertions of the amino acid sequence.

In a preferred embodiment, a variant of a parent beta-glucosidase comprises a substitution at one or more positions corresponding to positions 142, 183, 266, and 703 of amino acids 1 to 842 of SEQ ID NO: 2 or corresponding to positions 142, 183, 266, and 705 of amino acids 1 to 844 of SEQ ID NO: 70. In another preferred embodiment, a variant of a parent beta-glucosidase comprises substitutions at two or more positions corresponding to positions 142, 183, 266, and 703 of amino acids 1 to 842 of SEQ ID NO: 2 or corresponding to positions 142, 183, 266, and 705 of amino acids 1 to 844 of SEQ ID NO: 70. In another preferred embodiment, a variant of a parent beta-glucosidase comprises substitutions at three or more positions corresponding to positions 142, 183, 266, and 703 of amino acids 1 to 842 of SEQ ID NO: 2 or corresponding to positions 142, 183, 266, and 705 of amino acids 1 to 844 of SEQ ID NO: 70. In another preferred embodiment, a variant of a parent beta-glucosidase comprises substitutions at least at positions corresponding to positions 142, 183, 266, and 703 of amino acids 1 to 842 of SEQ ID NO: 2 or corresponding to positions 142, 183, 266, and 705 of amino acids 1 to 844 of SEQ ID NO: 70.

In a preferred embodiment, the variant comprises a substitution at a position corresponding to position 142 of amino acids 1 to 842 of SEQ ID NO: 2 or amino acids 1 to 844 of SEQ ID NO: 70. In a more preferred embodiment, the variant comprises a substitution at a position corresponding to position 142 of amino acids 1 to 842 of SEQ ID NO: 2 or amino acids 1 to 844 of SEQ ID NO: 70 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Ser as a substitution at a position corresponding to position 142 of amino acids 1 to 842 of SEQ ID NO: 2 or amino acids 1 to 844 of SEQ ID NO: 70. In a most preferred embodiment, the variant comprises the substitution G142S of amino acids 1 to 842 of SEQ ID NO: 2 or amino acids 1 to 844 of SEQ ID NO: 70.

In another preferred embodiment, the variant comprises a substitution at a position corresponding to position 183 of amino acids 1 to 842 of SEQ ID NO: 2 or amino acids 1 to 844 of SEQ ID NO: 70. In another more preferred embodiment, the variant comprises a substitution at a position corresponding to position 183 of amino acids 1 to 842 of SEQ ID NO: 2 or amino acids 1 to 844 of SEQ ID NO: 70 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the variant comprises Arg as a substitution at a position corresponding to position 183 of amino acids 1 to 842 of SEQ ID NO: 2 or amino acids 1 to 844 of SEQ ID NO: 70. In another most preferred embodiment, the variant comprises the substitution Q183R of amino acids 1 to 842 of SEQ ID NO: 2 or amino acids 1 to 844 of SEQ ID NO: 70.

In another preferred embodiment, the variant comprises a substitution at a position corresponding to position 266 of amino acids 1 to 842 of SEQ ID NO: 2 or amino acids 1 to 844 of SEQ ID NO: 70. In another more preferred embodiment, the variant comprises a substitution at a position corresponding to position 266 of amino acids 1 to 842 of SEQ ID NO: 2 or amino acids 1 to 844 of SEQ ID NO: 70 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the variant comprises Gln as a substitution at a position corresponding to position 266 of amino acids 1 to 842 of SEQ ID NO: 2 or amino acids 1 to 844 of SEQ ID NO: 70. In another most preferred embodiment, the variant comprises the substitution H266Q of SEQ ID NO: 2 or amino acids 1 to 844 of SEQ ID NO: 70.

In another preferred embodiment, the variant comprises a substitution at a position corresponding to position 703 of amino acids 1 to 842 of SEQ ID NO: 2. In another more preferred embodiment, the variant comprises a substitution at a position corresponding to position 703 of amino acids 1 to 842 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the variant comprises Gly as a substitution at a position corresponding to position 703 of amino acids 1 to 842 of SEQ ID NO: 2. In another most preferred embodiment, the variant comprises the substitution D703G of amino acids 1 to 842 of SEQ ID NO: 2.

In another preferred embodiment, the variant comprises a substitution at a position corresponding to position 705 of amino acids 1 to 844 of SEQ ID NO: 70. In another more preferred embodiment, the variant comprises a substitution at a position corresponding to position 705 of amino acids 1 to 844 of SEQ ID NO: 70 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the variant comprises Gly as a substitution at a position corresponding to position 705 of amino acids 1 to 844 of SEQ ID NO: 70. In another most preferred embodiment, the variant comprises the substitution D705G of amino acids 1 to 844 of SEQ ID NO: 70.

In another preferred embodiment, the variant comprises substitutions at positions corresponding to positions 142 and 183 of amino acids 1 to 842 of SEQ ID NO: 2 or amino acids 1 to 844 of SEQ ID NO: 70. In a more preferred embodiment, the variant comprises substitutions at positions corresponding to positions 142 and 183 of amino acids 1 to 842 of SEQ ID NO: 2 or amino acids 1 to 844 of SEQ ID NO: 70 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Ser and Arg as substitutions at positions corresponding to positions 142 and 183, respectively, of amino acids 1 to 842 of SEQ ID NO: 2 or amino acids 1 to 844 of SEQ ID NO: 70.

In another preferred embodiment, the variant comprises substitutions at positions corresponding to positions 142 and 266 of amino acids 1 to 842 of SEQ ID NO: 2 or amino acids 1 to 844 of SEQ ID NO: 70. In a more preferred embodiment, the variant comprises substitutions at positions corresponding to positions 142 and 266 of amino acids 1 to 842 of SEQ ID NO: 2 or amino acids 1 to 844 of SEQ ID NO: 70 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Ser and Gln as substitutions at positions corresponding to positions 142 and 266, respectively, of amino acids 1 to 842 of SEQ ID NO: 2 or amino acids 1 to 844 of SEQ ID NO: 70.

In another preferred embodiment, the variant comprises substitutions at positions corresponding to positions 142 and 703 of amino acids 1 to 842 of SEQ ID NO: 2. In a more preferred embodiment, the variant comprises substitutions at positions corresponding to positions 142 and 703 of amino acids 1 to 842 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Ser and Gly as substitutions at positions corresponding to positions 142 and 703, respectively, of amino acids 1 to 842 of SEQ ID NO: 2.

In another preferred embodiment, the variant comprises substitutions at positions corresponding to positions 142 and 705 of amino acids 1 to 844 of SEQ ID NO: 70. In a more preferred embodiment, the variant comprises substitutions at positions corresponding to positions 142 and 705 of amino acids 1 to 844 of SEQ ID NO: 70 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Ser and Gly as substitutions at positions corresponding to positions 142 and 705, respectively, of amino acids 1 to 844 of SEQ ID NO: 70.

In another preferred embodiment, the variant comprises substitutions at positions corresponding to positions 183 and 266 of amino acids 1 to 842 of SEQ ID NO: 2 or amino acids 1 to 844 of SEQ ID NO: 70. In a more preferred embodiment, the variant comprises substitutions at positions corresponding to positions 183 and 266 of amino acids 1 to 842 of SEQ ID NO: 2 or amino acids 1 to 844 of SEQ ID NO: 70 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Arg and Gln as substitutions at positions corresponding to positions 183 and 266, respectively, of amino acids 1 to 842 of SEQ ID NO: 2 or amino acids 1 to 844 of SEQ ID NO: 70.

In another preferred embodiment, the variant comprises substitutions at positions corresponding to positions 183 and 703 of amino acids 1 to 842 of SEQ ID NO: 2. In a more preferred embodiment, the variant comprises substitutions at positions corresponding to positions 183 and 703 of amino acids 1 to 842 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Arg and Gly as substitutions at positions corresponding to positions 183 and 703, respectively, of amino acids 1 to 842 of SEQ ID NO: 2.

In another preferred embodiment, the variant comprises substitutions at positions corresponding to positions 183 and 705 of amino acids 1 to 844 of SEQ ID NO: 70. In a more preferred embodiment, the variant comprises substitutions at positions corresponding to positions 183 and 705 of amino acids 1 to 844 of SEQ ID NO: 70 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Arg and Gly as substitutions at positions corresponding to positions 183 and 705, respectively, of amino acids 1 to 844 of SEQ ID NO: 70.

In another preferred embodiment, the variant comprises substitutions at positions corresponding to positions 266 and 703 of amino acids 1 to 842 of SEQ ID NO: 2. In a more preferred embodiment, the variant comprises substitutions at positions corresponding to positions 266 and 703 of amino acids 1 to 842 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Gln and Gly as substitutions at positions corresponding to positions 266 and 703, respectively, of amino acids 1 to 842 of SEQ ID NO: 2.

In another preferred embodiment, the variant comprises substitutions at positions corresponding to positions 266 and 705 of amino acids 1 to 844 of SEQ ID NO: 70. In a more preferred embodiment, the variant comprises substitutions at positions corresponding to positions 266 and 705 of amino acids 1 to 844 of SEQ ID NO: 70 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Gln and Gly as substitutions at positions corresponding to positions 266 and 705, respectively, of amino acids 1 to 844 of SEQ ID NO: 70.

In another preferred embodiment, the variant comprises substitutions at positions corresponding to positions 142, 183, and 266 of amino acids 1 to 842 of SEQ ID NO: 2 or amino acids 1 to 844 of SEQ ID NO: 70. In a more preferred embodiment, the variant comprises substitutions at positions corresponding to positions 142, 183, and 266 of amino acids 1 to 842 of SEQ ID NO: 2 or amino acids 1 to 844 of SEQ ID NO: 70 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Ser, Arg, and Gln as substitutions at positions corresponding to positions 142, 183, and 266, respectively, of amino acids 1 to 842 of SEQ ID NO: 2 or amino acids 1 to 844 of SEQ ID NO: 70.

In another preferred embodiment, the variant comprises substitutions at positions corresponding to positions 142, 266, and 703 of amino acids 1 to 842 of SEQ ID NO: 2. In a more preferred embodiment, the variant comprises substitutions at positions corresponding to positions 142, 266, and 703 of amino acids 1 to 842 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Ser, Gln, and Gly as substitutions at positions corresponding to positions 142, 266, and 703, respectively, of amino acids 1 to 842 of SEQ ID NO: 2.

In another preferred embodiment, the variant comprises substitutions at positions corresponding to positions 142, 266, and 705 of amino acids 1 to 844 of SEQ ID NO: 70. In a more preferred embodiment, the variant comprises substitutions at positions corresponding to positions 142, 266, and 705 of amino acids 1 to 844 of SEQ ID NO: 70 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Ser, Gln, and Gly as substitutions at positions corresponding to positions 142, 266, and 705, respectively, of amino acids 1 to 844 of SEQ ID NO: 70.

In another preferred embodiment, the variant comprises substitutions at positions corresponding to positions 183, 266, and 703 of amino acids 1 to 842 of SEQ ID NO: 2. In a more preferred embodiment, the variant comprises substitutions at positions corresponding to positions 183, 266, and 703 of amino acids 1 to 842 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Arg, Gln, and Gly as substitutions at positions corresponding to positions 183, 266, and 703, respectively, of amino acids 1 to 842 of SEQ ID NO: 2.

In another preferred embodiment, the variant comprises substitutions at positions corresponding to positions 183, 266, and 705 of amino acids 1 to 844 of SEQ ID NO: 70. In a more preferred embodiment, the variant comprises substitutions at positions corresponding to positions 183, 266, and 705 of amino acids 1 to 844 of SEQ ID NO: 70 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Arg, Gln, and Gly as substitutions at positions corresponding to positions 183, 266, and 705, respectively, of amino acids 1 to 844 of SEQ ID NO: 70.

In another preferred embodiment, the variant comprises substitutions at positions corresponding to positions 142, 183, and 703 of amino acids 1 to 842 of SEQ ID NO: 2. In a more preferred embodiment, the variant comprises substitutions at positions corresponding to positions 142, 183, and 703 of amino acids 1 to 842 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Ser, Arg, and Gly as substitutions at positions corresponding to positions 142, 183, and 703, respectively, of amino acids 1 to 842 of SEQ ID NO: 2.

In another preferred embodiment, the variant comprises substitutions at positions corresponding to positions 142, 183, and 705 of amino acids 1 to 844 of SEQ ID NO: 70. In a more preferred embodiment, the variant comprises substitutions at positions corresponding to positions 142, 183, and 705 of amino acids 1 to 844 of SEQ ID NO: 70 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Ser, Arg, and Gly as substitutions at positions corresponding to positions 142, 183, and 705, respectively, of amino acids 1 to 844 of SEQ ID NO: 70.

In another preferred embodiment, the variant comprises substitutions at positions corresponding to positions 142, 183, 266, and 703 of amino acids 1 to 842 of SEQ ID NO: 2. In a more preferred embodiment, the variant comprises substitutions at positions corresponding to positions 142, 183, 266, and 703 of amino acids 1 to 842 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Ser, Arg, Gln, and Gly as substitutions at positions corresponding to positions 142, 183, 266, and 703, respectively, of amino acids 1 to 842 of SEQ ID NO: 2.

In another preferred embodiment, the variant comprises substitutions at positions corresponding to positions 142, 183, 266, and 705 of amino acids 1 to 844 of SEQ ID NO: 70. In a more preferred embodiment, the variant comprises substitutions at positions corresponding to positions 142, 183, 266, and 705 of amino acids 1 to 844 of SEQ ID NO: 70 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Arg and Gly as substitutions at positions corresponding to positions 142, 183, 266, and 705, respectively, of amino acids 1 to 844 of SEQ ID NO: 70.

In a more preferred embodiment, the variant comprises two or more substitutions selected from the group consisting of G142S, Q183R, H266Q, and D703G (or D705G) of amino acids 1 to 842 of SEQ ID NO: 2 or amino acids 1 to 844 of SEQ ID NO: 70.

In a most preferred embodiment, the variant comprises the substitutions G142S+Q183R of amino acids 1 to 842 of SEQ ID NO: 2. In another most preferred embodiment, the variant comprises the substitutions G142S+H266Q of amino acids 1 to 842 of SEQ ID NO: 2. In another most preferred embodiment, the variant comprises the substitutions G142S+D703G of amino acids 1 to 842 of SEQ ID NO: 2. In another most preferred embodiment, the variant comprises the substitutions Q183R+H266Q of amino acids 1 to 842 of SEQ ID NO: 2. In another most preferred embodiment, the variant comprises the substitutions Q183R+D703G of amino acids 1 to 842 of SEQ ID NO: 2. In another most preferred embodiment, the variant comprises the substitutions H266Q+D703G of amino acids 1 to 842 of SEQ ID NO: 2.

In another most preferred embodiment, the variant comprises the substitutions G142S+Q183R of amino acids 1 to 844 of SEQ ID NO: 70. In another most preferred embodiment, the variant comprises the substitutions G142S+H266Q of amino acids 1 to 844 of SEQ ID NO: 70. In another most preferred embodiment, the variant comprises the substitutions G142S+D705G of amino acids 1 to 844 of SEQ ID NO: 70. In another most preferred embodiment, the variant comprises the substitutions Q183R+H266Q of amino acids 1 to 844 of SEQ ID NO: 70. In another most preferred embodiment, the variant comprises the substitutions Q183R+D705G of amino acids 1 to 844 of SEQ ID NO: 70. In another most preferred embodiment, the variant comprises the substitutions H266Q+D705G of amino acids 1 to 844 of SEQ ID NO: 70.

In another most preferred embodiment, the variant comprises the substitutions G142S+Q183R+H266Q of amino acids 1 to 842 of SEQ ID NO: 2. In another most preferred embodiment, the variant comprises the substitutions G142S+H266Q+D703G of amino acids 1 to 842 of SEQ ID NO: 2. In another most preferred embodiment, the variant comprises the substitutions Q183R+H266Q+D703G of amino acids 1 to 842 of SEQ ID NO: 2. In another most preferred embodiment, the variant comprises the substitutions G142S+Q183R+D703G of amino acids 1 to 842 of SEQ ID NO: 2.

In another most preferred embodiment, the variant comprises the substitutions G142S+Q183R+H266Q of amino acids 1 to 844 of SEQ ID NO: 70. In another most preferred embodiment, the variant comprises the substitutions G142S+H266Q+D705G of amino acids 1 to 844 of SEQ ID NO: 70. In another most preferred embodiment, the variant comprises the substitutions Q183R+H266Q+D705G of amino acids 1 to 844 of SEQ ID NO: 70. In another most preferred embodiment, the variant comprises the substitutions G142S+Q183R+D705G of amino acids 1 to 844 of SEQ ID NO: 70.

In another most preferred embodiment, the variant comprises the substitutions G142S+Q183R+H266Q+D703G of amino acids 1 to 842 of SEQ ID NO: 2. In another most preferred embodiment, the variant comprises the substitutions G142S+Q183R+H266Q+D705G of amino acids 1 to 842 of SEQ ID NO: 70.

In another most preferred embodiment, the variant comprising the substitutions G142S+Q183R+H266Q+D703G of amino acids 1 to 842 of SEQ ID NO: 2 is encoded by the nucleotide sequence contained in pSATe111BG53 which is contained in E. coli NRRL B-30652.

As defined herein, an "isolated variant" of a parent beta-glucosidase is a polypeptide which is essentially free of other non-beta-glucosidase polypeptides, e.g., at least about 20% pure, preferably at least about 40% pure, more preferably about 60% pure, even more preferably about 80% pure, most preferably about 90% pure, and even most preferably about 95% pure, as determined by SDS-PAGE.

Plasmids

The plasmid or plasmids used for preparing beta-glucosidase variants may be any plasmid or vector that may be subjected to recombinant DNA procedures. The plasmid comprising a nucleotide sequence encoding a beta-glucosidase may be prepared by ligating the nucleotide sequence into a suitable plasmid, or by any other suitable method. The plasmid preferably contains one or more selectable markers described herein which permit easy selection of transformed cells. The choice of plasmid will often depend on the host cell into which it is to be introduced.

In the present invention, the plasmid may be an autonomously replicating plasmid, i.e. a plasmid which exists as an extrachromosomal entity, the replication of which is distinct from chromosomal replication.

The plasmid replicator may be any plasmid replicator mediating autonomous replication which functions in a cell. The term "plasmid replicator" is defined herein as a sequence that enables a plasmid or vector to replicate in vivo. Examples of a plasmid replicator useful in a yeast cell are the 2 micron origin of replication, ARS1, ARS4, the combination of ARS1 and CEN3, and the combination of ARS4 and CEN6. Examples of a plasmid replicator useful in a filamentous fungal cell are AMA1 and ANS1 (Gems et al., 1991, *Gene* 98:61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

The linearizing of the plasmid(s) can be directed toward any site within the plasmid. The plasmid(s) may be linearized by any suitable methods known in the art, for example, digestion with one or more restriction enzymes. The linearized ends of the plasmid may be filled-in with nucleotides as described by Pompon el al., 1989, *Gene* 83: 15-24. However, it is preferred not to fill in the linearized ends as it might create a frameshift.

To facilitate the screening process, the plasmid is preferably an expression vector in which the nucleotide sequence in question is operably linked to additional segments required for transcription of the DNA. In general, the expression vector is derived from a plasmid, a cosmid or a bacteriophage, or may contain elements of any or all of these. For purposes of the present invention, the terms "plasmid" and "vector" are used interchangeably.

DNA Fragments

The library of DNA fragments to be randomly combined (or "shuffled") with homologous regions in the linearized plasmid(s) by in vivo recombination may be prepared by any suitable method. For instance, the DNA fragment may be prepared by PCR amplification (e.g., error-prone PCR) of a plasmid comprising the nucleotide sequence, using specific primers, for example, as described in U.S. Pat. No. 4,683,202 or Saiki et al., 1988, *Science* 239: 487-491. The DNA fragment may also be isolated from a plasmid comprising the desired nucleotide sequence by digestion with restriction enzymes, followed by isolation using, for example, electrophoresis.

The DNA fragment may alternatively be prepared synthetically by established standard methods, e.g., the phosphoamidite method described by Beaucage and Caruthers, 1981, *Tetrahedron Letters* 22: 1859-1869, or the method described by Matthes et al., 1984, *EMBO Journal* 3: 801-805. According to the phosphoamidite method, oligonucleotides are synthesized in an automatic DNA synthesizer, purified, annealed, ligated, and cloned into suitable plasmids.

The DNA fragment may also be of mixed synthetic and genomic, mixed synthetic and cDNA or mixed genomic and cDNA origins prepared by ligating fragments of synthetic, genomic or cDNA origin, the fragments corresponding to various parts of the entire nucleotide sequence, in accordance with standard techniques.

The library of DNA fragments comprise one or more mutations of the nucleotide sequence, wherein the fragments comprise at least two regions, one or more regions which are homologous to the 5'-region or the 3'-region of the gap in the linearized nucleotide sequence and/or plasmid sequence and one or more second regions which are homologous to the 5'-region or the 3'-region of the DNA fragments of the library.

The regions of the DNA fragment may be any sequence that is homologous with the nucleotide sequence and/or plasmid sequence.

In a preferred embodiment, the regions of the DNA fragment are a 5'-region and/or a 3'-region that flank a gene that encodes a beta-glucosidase; or a 5'-region and/or a 3'-region of a gene that encodes a beta-glucosidase.

In another preferred embodiment of the present invention, the DNA fragment or fragments are prepared under conditions resulting in a low, medium or high random mutagenesis frequency. To obtain low mutagenesis frequency the nucleotide sequence(s) (comprising the DNA fragment(s)) may be prepared by a standard PCR amplification method (U.S. Pat. No. 4,683,202 or Saiki et al., 1988, *Science* 239: 487-491). A medium or high mutagenesis frequency may be obtained by performing the PCR amplification under conditions which reduce the fidelity of replication by the thermostable polymerase and increase the misincorporation of nucleotides, for instance as described by Deshler, 1992, *GATA* 9: 103-106; Leung et al., 1989, *BioTechniques* 1: 11-15.

The PCR amplification may be combined with a mutagenesis step using a suitable physical or chemical mutagenizing agent, e.g., one which induces transitions, transversions, inversions, scrambling, deletions, and/or insertions.

In a preferred embodiment, the DNA fragment(s) to be shuffled preferably have a length of about 15 bp to 8 kb, more preferably about 30 bp to 6 kb, even more preferably about 40 bp to 6 kb, even more preferably about 80 bp to 4 kb, and most preferably about 100 bp to 2 kb, to be able to interact optimally with the linearized plasmid.

Fungal Cells

The fungal cell, into which the mixture of plasmid/fragment nucleotide sequences are to be introduced, may be any fungal cell useful in the present invention. A "recombination fungal cell" is defined herein as a cell capable of mediating shuffling of a number of homologous nucleotide sequences.

In a preferred embodiment, the fungal recombination cell is a yeast cell. In a more preferred embodiment, the yeast recombination cell is a *Candida, Hansenula, Kluyveromyces, Pichia, Saccharomyces, Schizosaccharomyces,* or *Yarrowia* cell.

In a most preferred embodiment, the yeast recombination cell is a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell.

In another preferred embodiment, the fungal recombination cell is a filamentous fungal cell. In a more preferred embodiment, the filamentous fungal recombination cell is an *Acremonium, Aspergillus, Fusarium, Humicola, Mucor, Mycellophthora, Neurospora, Penicillium, Thielavia, Tolypocladium,* or *Trichoderma* cell.

In a most preferred embodiment, the filamentous fungal recombination cell is an *Aspergillus awamori, Aspergillus foetidus, Aspergillus japonicus, Aspergillus nidulans, Aspergillus niger,* or *Aspergillus oryzae* cell. In another most preferred embodiment, the filamentous fungal recombination cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum* cell. In another most preferred embodiment, the filamentous fungal recombination cell is a *Humicola insolens, Humicola lanuginosa, Mucor miehei, Mycellophthora thermophila, Neurospora crassa, Penicillum purpurogenum, Thielavia terrestris, Trichoderma harzianum, Trichoderma koningii, Trichoderma longibrachiatum, Trichoderma reesei,* or *Trichoderma viride* cell.

In another most preferred embodiment, the *Aspergillus* cell is an *Aspergillus oryzae* cell.

In another most preferred embodiment, the *Aspergillus* cell is an *Aspergillus niger* cell.

In another most preferred embodiment, the *Fusarium venenatum* cell is *Fusarium venenatum* A3/5, which was originally deposited as *Fusarium graminearum* ATCC 20334 and recently reclassified as *Fusarium venenatum* by Yoder and Christianson, 1998, *Fungal Genetics and Biology* 23: 62-80 and O'Donnell et al., 1998, *Fungal Genetics and Biology* 23: 57-67; as well as taxonomic equivalents of *Fusarium venentum* regardless of the species name by which they are currently known. In another most preferred embodiment, the *Fusarium venentum* cell is a morphological mutant of *Fusarium venentum* A3/5 or *Fusarium venentum* ATCC 20334, as disclosed in WO 97/26330.

Fungal cells may be transformed by a process involving protoplast formation, transformation of the protoplasts, and regeneration of the cell wall in a manner known perse. Suitable procedures for transformation of *Aspergillus* and *Trichoderma* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

In vivo Recombination

A large number of variants or homologous genes can be combined in one transformation to efficiently create gene chimeras from the homologous genes. The shuffling of these genes, encoding improved variants or wild type genes, results in chimeras that can be expressed and followed by screening to identify those chimeras with the optimal combination of beneficial mutations. The process increases multi-fold the number of further improved variants that can be obtained compared to a process that uses only random mutagenesis (for a review, see Kuchner and Arnold, 1997, *TIBTech* 15: 523-530). Random mutagenesis introduces mutations into a target nucleotide sequence, creating deleterious mutations much more frequently than beneficial ones. In iterative rounds of such mutagenesis, deleterious mutations accumulate more rapidly than beneficial ones, effectively masking the identification of beneficial mutations during screening. The random recombination between two or more homologous nucleotide sequences that contain multiple single nucleotide changes in their nucleotide sequences potentially allows all those nucleotide changes contained in one variant to be separated from one another and to be randomly combined instead with any mutations present on other variants. This shuffling of mutations provides a means by which mutations from different parent sequences can be combined with each other randomly to increase the probability of combining nucleotide changes in a single nucleotide sequence.

Efficient recombination of multiple overlapping fragments using the in vivo recombination method is a means to generate chimeras from variants or homologous genes. An overlap as small as 15 bp is sufficient for recombination, and may be utilized for very easy domain shuffling of even distantly related genes. In domain shuffling, larger blocks of non-homologous DNA are randomly assorted by means of stretches of homology at their termini.

It is preferred that at least one shuffling cycle is a back-crossing cycle with the initially used DNA fragment or fragments, which may be the wild-type DNA fragment. This eliminates non-essential mutations. Non-essential mutations may also be eliminated by using wild-type DNA fragments as the initially used input DNA material.

More than two nucleotide sequences can be shuffled at the same time, and can be advantageous as a vast number of quite different variants can be made rapidly without an abundance of iterative procedures. When recombining many fragments from the same region, multiple overlapping of the fragments will increase the frequency of DNA interchange by itself, but it is also important to have a relatively high number of random crossovers in overlapping regions in order to recombine closely located variants/differences.

An overlap as small as 15 bp between two fragments is sufficient to obtain an efficient recombination. Therefore, overlapping in the range from 15 to 5000 bp, preferably from 30 bp to 500 bp, especially 30 bp to 100 bp is suitable in the present invention.

In the present invention, preferably 2 or more overlapping fragments, more preferably 2 to 50 overlapping fragments, and most preferably 2 to 10 overlapping fragments may advantageously be used as DNA fragments in a shuffling cycle.

Besides allowing creation of chimeric genes, employing overlapping fragments is a useful method for domain shuffling by creating small overlaps between DNA fragments from different domains and screening for the best combination. For example, in the case of three DNA fragments the overlapping regions may be as follows: the first end of the first fragment overlaps the first end of the linearized plasmid, the first end of the second fragment overlaps the second end of the first fragment, and the second end of the second fragment overlaps the first end of the third fragment, the first end of the third fragment overlaps (as stated above) the second end of the second fragment, and the second end of the third fragment overlaps the second end of the linearized plasmid.

It is understood that when using two or more DNA fragments as the starting material, it is preferred to have continuous overlaps between the ends of the plasmid and the DNA fragments.

Even though it is preferred to shuffle homologous nucleotide sequences in the form of DNA fragment(s) and linearized plasmid(s), it is also possible to shuffle two or more linearized plasmids comprising homologous nucleotide sequences encoding polypeptides. However, in such a case it is important to linearize the plasmids at different sites.

In the present invention, two or more linearized plasmids and one or more homologous DNA fragments can be used as the starting material to be shuffled. The ratio between the linearized plasmid(s) and homologous DNA fragment(s) preferably lie in the range from 20:1 to 1:50, preferable from 2:1 to 1:10 (mol plasmid:mol fragments) with the specific concentrations being from 1 pM to 10 M of the DNA.

The linearized plasmids may be gapped in such a way that the overlap between the fragments is deleted in the plasmid. The repair of the gap in the plasmid then requires that the fragments recombine with one another in addition to recombining with the ends of the gapped plasmid in order to reconstitute a circular, autonomously replicating plasmid. In a preferred embodiment, the linearization of the plasmid or vector creates a sufficient gap in the coding sequence of the nucleotide sequence to force the homologous recombination of the DNA fragments with the corresponding regions of the nucleotide sequence, recreating a circular replicating plasmid.

Nucleotide Sequences

The present invention also relates to isolated nucleotide sequences which encode variants of beta-glucosidases, wherein the nucleotide sequence has been modified by a substitution at one or more positions corresponding to positions 142, 183, 266, and 703 of SEQ ID NO: 2 or corresponding to positions 142, 183, 266, and 705 of SEQ ID NO: 70, wherein the beta-glucosidase is (a) a polypeptide having an amino acid sequence which has at least about 70%, preferably at least about 75%, more preferably at least about 80%, more preferably at least about 85%, even more preferably at least about 90%, most preferably at least about 95%, and even most preferably at least about 97% identity with amino acids 1 to 842 of SEQ ID NO: 2 or amino acids 1 to 844 of SEQ ID NO: 70; (ii) a polypeptide encoded by a nucleotide sequence which hybridizes under low, preferably low-medium, more preferably medium, even more preferably medium-high, most preferably high, or even most preferably very high stringency conditions with (i) nucleotides 58 to 2583 of SEQ ID NO: 1 or nucleotides 58 to 2589 of SEQ ID NO: 71, (ii) the genomic nucleotide sequence comprising nucleotides 58 to 2583 of SEQ ID NO: 1 or nucleotides 58 to 2589 of SEQ ID NO: 71, or (iii) a complementary strand of (i) or (ii), wherein the variant has beta-glucosidase activity.

The isolated nucleotide sequences encoding beta-glucosidase variants of the present invention may further comprise one or more deletions and/or insertions of the sequence.

In a preferred embodiment, the isolated nucleotide sequence encodes a beta-glucosidase variant comprising a substitution at one or more positions corresponding to positions 142, 183, 266, and 703 of amino acids 1 to 842 of SEQ ID NO: 2 or corresponding to positions 142, 183, 266, and 705 of amino acids 1 to 844 of SEQ ID NO: 70. In another preferred embodiment, the isolated nucleotide sequence encodes a beta-glucosidase variant comprising substitutions at two or more positions corresponding to positions 142, 183, 266, and 703 of amino acids 1 to 842 of SEQ ID NO: 2 or corresponding to positions 142, 183, 266, and 705 of amino acids 1 to 844 of SEQ ID NO: 70. In another preferred embodiment, the isolated nucleotide sequence encodes a beta-glucosidase variant comprising substitutions at three or more positions corresponding to positions 142, 183, 266, and 703 of amino acids 1 to 842 of SEQ ID NO: 2 or corresponding to positions 142, 183, 266, and 705 of amino acids 1 to 844 of SEQ ID NO: 70. In another preferred embodiment, the isolated nucleotide sequence encodes a beta-glucosidase variant comprising substitutions at least at positions corresponding to positions 142, 183, 266, and 703 of amino acids 1 to 842 of SEQ ID NO: 2 or corresponding to positions 142, 183, 266, and 705 of amino acids 1 to 844 of SEQ ID NO: 70.

In a preferred embodiment, the isolated nucleotide sequence encodes a beta-glucosidase variant comprising a substitution at a position corresponding to position 142 of amino acids 1 to 842 of SEQ ID NO: 2 or amino acids 1 to 844 of SEQ ID NO: 70. In a more preferred embodiment, the isolated nucleotide sequence encodes a beta-glucosidase variant comprising a substitution at a position corresponding to position 142 of amino acids 1 to 842 of SEQ ID NO: 2 or amino acids 1 to 844 of SEQ ID NO: 70 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the isolated nucleotide sequence encodes a beta-glucosidase variant comprising Ser as a substitution at a position corresponding to position 142 of amino acids 1 to 842 of SEQ ID NO: 2 or amino acids 1 to 844 of SEQ ID NO: 70. In a most preferred embodiment, the isolated nucleotide sequence encodes a beta-glucosidase variant comprising the substitution G142S of amino acids 1 to 842 of SEQ ID NO: 2 or amino acids 1 to 844 of SEQ ID NO: 70.

In another preferred embodiment, the isolated nucleotide sequence encodes a beta-glucosidase variant comprising a substitution at a position corresponding to position 183 of amino acids 1 to 842 of SEQ ID NO: 2 or amino acids 1 to 844 of SEQ ID NO: 70. In another more preferred embodiment, the isolated nucleotide sequence encodes a beta-glucosidase variant comprising a substitution at a position corresponding to position 183 of amino acids 1 to 842 of SEQ ID NO: 2 or amino acids 1 to 844 of SEQ ID NO: 70 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the isolated nucleotide sequence encodes a beta-glucosidase variant comprising Arg as a substitution at a position corresponding to position 183 of amino acids 1 to 842 of SEQ ID NO: 2 or amino acids 1 to 844 of SEQ ID NO: 70. In another most preferred embodiment, the isolated nucleotide sequence encodes a beta-glucosidase variant comprising the substitution Q183R of amino acids 1 to 842 of SEQ ID NO: 2 or amino acids 1 to 844 of SEQ ID NO: 70.

In another preferred embodiment, the isolated nucleotide sequence encodes a beta-glucosidase variant comprising a substitution at a position corresponding to position 266 of amino acids 1 to 842 of SEQ ID NO: 2 or amino acids 1 to 844 of SEQ ID NO: 70. In another more preferred embodiment, the isolated nucleotide sequence encodes a beta-glucosidase variant comprising a substitution at a position corresponding to position 266 of amino acids 1 to 842 of SEQ ID NO: 2 or amino acids 1 to 844 of SEQ ID NO: 70 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the isolated nucleotide sequence encodes a beta-glucosidase variant comprising Gln as a substitution at a position corresponding to position 266 of amino acids 1 to 842 of SEQ ID NO: 2 or amino acids 1 to 844 of SEQ ID NO: 70. In another most preferred embodiment, the isolated nucleotide sequence encodes a beta-glucosidase variant comprising the substitution H266Q of SEQ ID NO: 2 or amino acids 1 to 844 of SEQ ID NO: 70.

In another preferred embodiment, the isolated nucleotide sequence encodes a beta-glucosidase variant comprising a substitution at a position corresponding to position 703 of amino acids 1 to 842 of SEQ ID NO: 2. In another more preferred embodiment, the isolated nucleotide sequence encodes a beta-glucosidase variant comprising a substitution at a position corresponding to position 703 of amino acids 1 to 842 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the isolated nucleotide sequence encodes a beta-glucosidase variant comprising Gly as a substitution at a position corresponding to position 703 of amino acids 1 to 842 of SEQ ID NO: 2. In another most preferred embodiment, the isolated nucleotide sequence encodes a beta-glucosidase variant comprising the substitution D703G of amino acids 1 to 842 of SEQ ID NO: 2.

In another preferred embodiment, the isolated nucleotide sequence encodes a beta-glucosidase variant comprising a substitution at a position corresponding to position 705 of amino acids 1 to 844 of SEQ ID NO: 70. In another more preferred embodiment, the isolated nucleotide sequence encodes a beta-glucosidase variant comprising a substitution at a position corresponding to position 705 of amino acids 1 to 844 of SEQ ID NO: 70 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the isolated nucleotide sequence encodes a beta-glucosidase variant comprising Gly as a substitution at a position corresponding to position 705 of amino acids 1 to 844 of SEQ ID NO: 70. In another most preferred embodiment, the isolated nucleotide sequence encodes a beta-glucosidase variant comprising the substitution D705G of amino acids 1 to 844 of SEQ ID NO: 70.

In another preferred embodiment, the isolated nucleotide sequence encodes a beta-glucosidase variant comprising substitutions at positions corresponding to positions 142 and 183 of amino acids 1 to 842 of SEQ ID NO: 2 or amino acids 1 to 844 of SEQ ID NO: 70. In a more preferred embodiment, the isolated nucleotide sequence encodes a beta-glucosidase variant comprising substitutions at positions corresponding to positions 142 and 183 of amino acids 1 to 842 of SEQ ID NO: 2 or amino acids 1 to 844 of SEQ ID NO: 70 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the isolated nucleotide sequence encodes a beta-glucosidase variant comprising Ser and Arg as substitutions at positions corresponding to positions 142 and 183, respectively, of amino acids 1 to 842 of SEQ ID NO: 2 or amino acids 1 to 844 of SEQ ID NO: 70.

In another preferred embodiment, the isolated nucleotide sequence encodes a beta-glucosidase variant comprising substitutions at positions corresponding to positions 142 and 266 of amino acids 1 to 842 of SEQ ID NO: 2 or amino acids 1 to 844 of SEQ ID NO: 70. In a more preferred embodiment, the isolated nucleotide sequence encodes a beta-glucosidase variant comprising substitutions at positions corresponding to positions 142 and 266 of amino acids 1 to 842 of SEQ ID NO: 2 or amino acids 1 to 844 of SEQ ID NO: 70 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the isolated nucleotide sequence encodes a beta-glucosidase variant comprising Ser and Gln as substitutions at positions corresponding to positions 142 and 266, respectively, of amino acids 1 to 842 of SEQ ID NO: 2 or amino acids 1 to 844 of SEQ ID NO: 70.

In another preferred embodiment, the isolated nucleotide sequence encodes a beta-glucosidase variant comprising substitutions at positions corresponding to positions 142 and 703 of amino acids 1 to 842 of SEQ ID NO: 2. In a more preferred embodiment, the isolated nucleotide sequence encodes a beta-glucosidase variant comprising substitutions at positions corresponding to positions 142 and 703 of amino acids 1 to 842 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the isolated nucleotide sequence encodes a beta-glucosidase variant comprising Ser and Gly as substitutions at positions corresponding to positions 142 and 703, respectively, of amino acids 1 to 842 of SEQ ID NO: 2.

In another preferred embodiment, the isolated nucleotide sequence encodes a beta-glucosidase variant comprising substitutions at positions corresponding to positions 142 and 705 of amino acids 1 to 844 of SEQ ID NO: 70. In a more preferred embodiment, the isolated nucleotide sequence encodes a beta-glucosidase variant comprising substitutions at positions corresponding to positions 142 and 705 of amino acids 1 to 842 of SEQ ID NO: 70 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the isolated nucleotide sequence encodes a beta-glucosidase variant comprising Ser and Gly as substitutions at positions corresponding to positions 142 and 705, respectively, of amino acids 1 to 844 of SEQ ID NO: 70.

In another preferred embodiment, the isolated nucleotide sequence encodes a beta-glucosidase variant comprising substitutions at positions corresponding to positions 183 and 266 of amino acids 1 to 842 of SEQ ID NO: 2 or amino acids 1 to 844 of SEQ ID NO: 70. In a more preferred embodiment, the isolated nucleotide sequence encodes a beta-glucosidase variant comprising substitutions at positions corresponding to positions 183 and 266 of amino acids 1 to 842 of SEQ ID NO: 2 or amino acids 1 to 844 of SEQ ID NO: 70 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the isolated nucleotide sequence encodes a beta-glucosidase variant comprising Arg and Gln as substitutions at positions corresponding to positions 183 and 266, respectively, of amino acids 1 to 842 of SEQ ID NO: 2 or amino acids 1 to 844 of SEQ ID NO: 70.

In another preferred embodiment, the isolated nucleotide sequence encodes a beta-glucosidase variant comprising substitutions at positions corresponding to positions 183 and 703 of amino acids 1 to 842 of SEQ ID NO: 2. In a more preferred embodiment, the isolated nucleotide sequence encodes a beta-glucosidase variant comprising substitutions at positions corresponding to positions 183 and 703 of amino acids 1 to 842 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the isolated nucleotide sequence encodes a beta-glucosidase variant comprising Arg and Gly as substitutions at positions corresponding to positions 183 and 703, respectively, of amino acids 1 to 842 of SEQ ID NO: 2.

In another preferred embodiment, the isolated nucleotide sequence encodes a beta-glucosidase variant comprising substitutions at positions corresponding to positions 183 and 705 of amino acids 1 to 844 of SEQ ID NO: 70. In a more preferred embodiment, the isolated nucleotide sequence encodes a beta-glucosidase variant comprising substitutions at positions corresponding to positions 183 and 705 of amino acids 1 to 844 of SEQ ID NO: 70 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the isolated nucleotide sequence encodes a beta-glucosidase variant comprising Arg and Gly as substitutions at positions corresponding to positions 183 and 705, respectively, of amino acids 1 to 844 of SEQ ID NO: 70.

In another preferred embodiment, the isolated nucleotide sequence encodes a beta-glucosidase variant comprising substitutions at positions corresponding to positions 266 and 703 of amino acids 1 to 842 of SEQ ID NO: 2. In a more preferred embodiment, the isolated nucleotide sequence encodes a beta-glucosidase variant comprising substitutions at positions corresponding to positions 266 and 703 of amino acids 1 to 842 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the isolated nucleotide sequence encodes a beta-glucosidase variant comprising Gln and Gly as substitutions at positions corresponding to positions 266 and 703, respectively, of amino acids 1 to 842 of SEQ ID NO: 2.

In another preferred embodiment, the isolated nucleotide sequence encodes a beta-glucosidase variant comprising substitutions at positions corresponding to positions 266 and 705 of amino acids 1 to 844 of SEQ ID NO: 70. In a more preferred embodiment, the isolated nucleotide sequence encodes a beta-glucosidase variant comprising substitutions at positions corresponding to positions 266 and 705 of amino acids 1 to 844 of SEQ ID NO: 70 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the isolated nucleotide sequence encodes a beta-glucosidase variant comprising Gln and Gly as substitutions at positions corresponding to positions 266 and 705, respectively, of amino acids 1 to 844 of SEQ ID NO: 70.

In another preferred embodiment, the isolated nucleotide sequence encodes a beta-glucosidase variant comprising substitutions at positions corresponding to positions 142, 183, and 266 of amino acids 1 to 842 of SEQ ID NO: 2 or amino acids 1 to 844 of SEQ ID NO: 70. In a more preferred embodiment, the isolated nucleotide sequence encodes a beta-glucosidase variant comprising substitutions at positions corresponding to positions 142, 183, and 266 of amino acids 1 to 842 of SEQ ID NO: 2 or amino acids 1 to 844 of SEQ ID NO: 70 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the isolated nucleotide sequence encodes a beta-glucosidase variant comprising Ser, Arg, and Gln as substitutions at positions corresponding to positions 142, 183, and 266, respectively, of amino acids 1 to 842 of SEQ ID NO: 2 or amino acids 1 to 844 of SEQ ID NO: 70.

In another preferred embodiment, the isolated nucleotide sequence encodes a beta-glucosidase variant comprising substitutions at positions corresponding to positions 142, 266, and 703 of amino acids 1 to 842 of SEQ ID NO: 2. In a more preferred embodiment, the isolated nucleotide sequence encodes a beta-glucosidase variant comprising substitutions at positions corresponding to positions 142, 266, and 703 of amino acids 1 to 842 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the isolated nucleotide sequence encodes a beta-glucosidase variant comprising Ser, Gln, and Gly as substitutions at positions corresponding to positions 142, 266, and 703, respectively, of amino acids 1 to 842 of SEQ ID NO: 2.

In another preferred embodiment, the isolated nucleotide sequence encodes a beta-glucosidase variant comprising substitutions at positions corresponding to positions 142, 266, and 705 of amino acids 1 to 844 of SEQ ID NO: 70. In a more preferred embodiment, the isolated nucleotide sequence encodes a beta-glucosidase variant comprising substitutions at positions corresponding to positions 142, 266, and 705 of amino acids 1 to 844 of SEQ ID NO: 70 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the isolated nucleotide sequence encodes a beta-glucosidase variant comprising Ser, Gln, and Gly as substitutions at positions corresponding to positions 142, 266, and 705, respectively, of amino acids 1 to 844 of SEQ ID NO: 70.

In another preferred embodiment, the isolated nucleotide sequence encodes a beta-glucosidase variant comprising substitutions at positions corresponding to positions 183, 266, and 703 of amino acids 1 to 842 of SEQ ID NO: 2. In a more preferred embodiment, the isolated nucleotide sequence encodes a beta-glucosidase variant comprising substitutions at positions corresponding to positions 183, 266, and 703 of amino acids 1 to 842 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the isolated nucleotide sequence encodes a beta-glucosidase variant comprising Arg, Gln, and Gly as substitutions at positions corresponding to positions 183, 266, and 703, respectively, of amino acids 1 to 842 of SEQ ID NO: 2.

In another preferred embodiment, the isolated nucleotide sequence encodes a beta-glucosidase variant comprising substitutions at positions corresponding to positions 183, 266, and 705 of amino acids 1 to 844 of SEQ ID NO: 70. In a more preferred embodiment, the isolated nucleotide sequence encodes a beta-glucosidase variant comprising substitutions at positions corresponding to positions 183, 266, and 705 of amino acids 1 to 844 of SEQ ID NO: 70 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the isolated nucleotide sequence encodes a beta-glucosidase variant comprising Arg, Gln, and Gly as substitutions at positions corresponding to positions 183, 266, and 705, respectively, of amino acids 1 to 844 of SEQ ID NO: 70.

In another preferred embodiment, the isolated nucleotide sequence encodes a beta-glucosidase variant comprising substitutions at positions corresponding to positions 142, 183, and 703 of amino acids 1 to 842 of SEQ ID NO: 2. In a more preferred embodiment, the isolated nucleotide sequence encodes a beta-glucosidase variant comprising substitutions at positions corresponding to positions 142, 183, and 703 of amino acids 1 to 842 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the isolated nucleotide sequence encodes a beta-glucosidase variant comprising Ser, Arg, and Gly as substitutions at positions corresponding to positions 142, 183, and 703, respectively, of amino acids 1 to 842 of SEQ ID NO: 2.

In another preferred embodiment, the isolated nucleotide sequence encodes a beta-glucosidase variant comprising substitutions at positions corresponding to positions 142, 183, and 705 of amino acids 1 to 844 of SEQ ID NO: 70. In a more preferred embodiment, the isolated nucleotide sequence encodes a beta-glucosidase variant comprising substitutions at positions corresponding to positions 142, 183, and 705 of amino acids 1 to 844 of SEQ ID NO: 70 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the isolated nucleotide sequence encodes a beta-glucosidase variant comprising Ser, Arg, and Gly as substitutions at positions corresponding to positions 142, 183, and 705, respectively, of amino acids 1 to 844 of SEQ ID NO: 70.

In another preferred embodiment, the isolated nucleotide sequence encodes a beta-glucosidase variant comprising substitutions at positions corresponding to positions 142, 183, 266, and 703 of amino acids 1 to 842 of SEQ ID NO: 2. In a more preferred embodiment, the isolated nucleotide sequence encodes a beta-glucosidase variant comprising substitutions at positions corresponding to positions 142, 183, 266, and 703 of amino acids 1 to 842 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the isolated nucleotide sequence encodes a beta-glucosidase variant comprising Ser, Arg, Gln, and Gly as substitutions at positions corresponding to positions 142, 183, 266, and 703, respectively, of amino acids 1 to 842 of SEQ ID NO: 2.

In another preferred embodiment, the isolated nucleotide sequence encodes a beta-glucosidase variant comprising substitutions at positions corresponding to positions 142, 183, 266, and 705 of amino acids 1 to 844 of SEQ ID NO: 70. In a more preferred embodiment, the isolated nucleotide sequence encodes a beta-glucosidase variant comprising substitutions at positions corresponding to positions 142, 183, 266, and 705 of amino acids 1 to 844 of SEQ ID NO: 70 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the isolated nucleotide sequence encodes a beta-glucosidase variant comprising Arg and Gly as substitutions at positions corresponding to positions 142, 183, 266, and 705, respectively, of amino acids 1 to 844 of SEQ ID NO: 70.

In a more preferred embodiment, the isolated nucleotide sequence encodes a beta-glucosidase variant comprising two or more substitutions selected from the group consisting of G142S, Q183R, H266Q, and D703G (or D705G) of amino acids 1 to 842 of SEQ ID NO: 2 or amino acids 1 to 844 of SEQ ID NO: 70.

In a most preferred embodiment, the isolated nucleotide sequence encodes a beta-glucosidase variant comprising the substitutions G142S+Q183R of amino acids 1 to 842 of SEQ ID NO: 2. In another most preferred embodiment, the isolated nucleotide sequence encodes a beta-glucosidase variant comprising the substitutions G142S+H266Q of amino acids 1 to 842 of SEQ ID NO: 2. In another most preferred embodiment, the isolated nucleotide sequence encodes a beta-glucosidase variant comprising the substitutions G142S+D703G of amino acids 1 to 842 of SEQ ID NO: 2. In another most preferred embodiment, the isolated nucleotide sequence encodes a beta-glucosidase variant comprising the substitutions Q183R+H266Q of amino acids 1 to 842 of SEQ ID NO: 2. In another most preferred embodiment, the isolated nucleotide sequence encodes a beta-glucosidase variant comprising the substitutions Q183R+D703G of amino acids 1 to 842 of SEQ ID NO: 2. In another most preferred embodiment, the isolated nucleotide sequence encodes a beta-glucosidase variant comprising the substitutions H266Q+D703G of amino acids 1 to 842 of SEQ ID NO: 2.

In another most preferred embodiment, the isolated nucleotide sequence encodes a beta-glucosidase variant comprising the substitutions G142S+Q183R of amino acids 1 to 844 of SEQ ID NO: 70. In another most preferred embodiment, the isolated nucleotide sequence encodes a beta-glucosidase variant comprising the substitutions G142S+H266Q of amino acids 1 to 844 of SEQ ID NO: 70. In another most preferred embodiment, the isolated nucleotide sequence encodes a beta-glucosidase variant comprising the substitutions G142S+D705G of amino acids 1 to 844 of SEQ ID NO: 70. In another most preferred embodiment, the isolated nucleotide sequence encodes a beta-glucosidase variant comprising the substitutions Q183R+H266Q of amino acids 1 to 844 of SEQ ID NO: 70. In another most preferred embodiment, the isolated nucleotide sequence encodes a beta-glucosidase variant comprising the substitutions Q183R+D705G of amino acids 1 to 844 of SEQ ID NO: 70. In another most preferred embodiment, the isolated nucleotide sequence encodes a beta-glucosidase variant comprising the substitutions H266Q+D705G of amino acids 1 to 844 of SEQ ID NO: 70.

In another most preferred embodiment, the isolated nucleotide sequence encodes a beta-glucosidase variant comprising the substitutions G142S+Q183R+H266Q of amino acids 1 to 842 of SEQ ID NO: 2. In another most preferred embodiment, the isolated nucleotide sequence encodes a beta-glucosidase variant comprising the substitutions G142S+H266Q+D703G of amino acids 1 to 842 of SEQ ID NO: 2. In another most preferred embodiment, the isolated nucleotide sequence encodes a beta-glucosidase variant comprising the substitutions Q183R+H266Q+D703G of amino acids 1 to 842 of SEQ ID NO: 2. In another most preferred embodiment, the isolated nucleotide sequence encodes a beta-glucosidase variant comprising the substitutions G142S+Q183R+D703G of amino acids 1 to 842 of SEQ ID NO: 2.

In another most preferred embodiment, the isolated nucleotide sequence encodes a beta-glucosidase variant comprising the substitutions G142S+Q183R+H266Q of amino acids 1 to 844 of SEQ ID NO: 70. In another most preferred embodiment, the isolated nucleotide sequence encodes a beta-glucosidase variant comprising the substitutions G142S+H266Q+D705G of amino acids 1 to 844 of SEQ ID NO: 70. In another most preferred embodiment, the isolated nucleotide sequence encodes a beta-glucosidase variant comprising the substitutions Q183R+H266Q+D705G of amino acids 1 to 844 of SEQ ID NO: 70. In another most preferred embodiment, the isolated nucleotide sequence encodes a beta-glucosidase variant comprising the substitutions G142S+Q183R+D705G of amino acids 1 to 844 of SEQ ID NO: 70.

In another most preferred embodiment, the isolated nucleotide sequence encodes a beta-glucosidase variant comprising the substitutions G142S+Q183R+H266Q+D703G of amino acids 1 to 842 of SEQ ID NO: 2. In another most preferred embodiment, the isolated nucleotide sequence encodes a beta-glucosidase variant comprising the substitutions G142S+Q183R+H266Q+D705G of amino acids 1 to 842 of SEQ ID NO: 70.

In another most preferred embodiment, the isolated nucleotide sequence encoding a beta-glucosidase variant comprising the substitutions G142S+Q183R+H266Q+D703G of amino acids 1 to 842 of SEQ ID NO: 2 is encoded by the nucleotide sequence contained in pSATe111BG53 which is contained in *E. coli* NRRL B-30652.

The term "isolated nucleotide sequence" as used herein refers to a nucleotide sequence which is essentially free of other nucleotide sequences, e.g., at least about 20% pure, preferably at least about 40% pure, more preferably at least about 60% pure, even more preferably at least about 80% pure, and most preferably at least about 90% pure as determined by agarose electrophoresis. For example, an isolated nucleotide sequence can be obtained by standard cloning procedures used in genetic engineering to relocate the nucleotide sequence from its natural location to a different site where it will be reproduced. The cloning procedures may involve excision and isolation of a desired nucleotide fragment comprising the nucleotide sequence encoding the polypeptide, insertion of the fragment into a vector molecule, and incorporation of the recombinant vector into a host cell where multiple copies or clones of the nucleotide sequence will be replicated. The nucleotide sequence may be of genomic, cDNA, RNA, semisynthetic, synthetic origin, or any combinations thereof.

Nucleic Acid Constructs

The present invention also relates to nucleic acid constructs comprising a nucleotide sequence encoding a beta-glucosidase variant of the present invention operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

"Nucleic acid construct" is defined herein as a nucleic acid molecule, either single- or double-stranded, which is isolated from a naturally occurring gene or which has been modified to contain segments of nucleic acid combined and juxtaposed in a manner that would not otherwise exist in nature. The term nucleic acid construct is synonymous with the term expression cassette when the nucleic acid construct contains all the control sequences required for expression of a coding sequence of a variant of the present invention. The term "coding sequence" is defined herein as a nucleotide sequence which directly specifies the amino acid sequence of its protein product. The boundaries of a genomic coding sequence are generally determined by the ATG start codon (eukaryotes), or alternative start codons such as GTG and TTG, located just upstream of the open reading frame at the 5'-end of the mRNA and a transcription terminator sequence located just downstream of the open reading frame at the 3'-end of the mRNA. A coding sequence can include, but is not limited to, DNA, cDNA, and recombinant nucleotide sequences.

An isolated nucleotide sequence encoding a beta-glucosidase variant of the present invention may be manipulated in a variety of ways to provide for expression of the variant. Manipulation of the nucleotide sequence prior to its insertion into a vector may be desirable or necessary depending on the expression vector. The techniques for modifying nucleotide sequences utilizing recombinant DNA methods are well known in the art.

The term "control sequences" is defined herein to include all components which are necessary or advantageous for the expression of a beta-glucosidase variant of the present invention. Each control sequence may be native or foreign to the nucleotide sequence encoding the variant. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a variant beta-glucosidase of the present invention. The term "operably linked" is defined herein as a configuration in which a control sequence is appropriately placed at a position relative to the coding sequence of the nucleotide sequence such that the control sequence directs the expression of a variant beta-glucosidase.

The control sequence may be an appropriate promoter sequence, which is recognized by a host cell for expression of the nucleotide sequence. The promoter sequence contains transcriptional control sequences which mediate the expression of the variant beta-glucosidase. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleotide constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase, *Fusarium oxysporum* trypsin-like protease (WO 96/00787), *Trichoderma reesei* beta-glucosidase, *Trichoderma reesei* cellobiohydrolase I, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); equivalents thereof; and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1,ADH2/GAP), *Saccharomyces cerevisiae* triose phosphate isomerase (TPI), *Saccharomyces cerevisiae* metallothionine (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, which is recognized by a host cell to terminate transcription. The terminator sequence is operably linked to the 3'-terminus of the nucleotide sequence encoding the variant beta-glucosidase. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5'-terminus of the nucleotide sequence encoding the variant beta-glucosidase. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polypeptide-encoding sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding region that codes for an amino acid sequence linked to the amino terminus of a variant beta-glucosidase and directs the encoded polypeptide into the cell's secretory pathway. The 5'-end of the coding sequence of the nucleotide sequence may inherently contain a signal peptide coding region naturally linked in translation reading frame with the segment of the coding region which encodes the secreted variant beta-glucosidase. Alternatively, the 5'-end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the variant beta-glucosidase. However, any signal peptide coding region which directs the expressed polypeptide into the secretory pathway of a host cell of choice may be used in the present invention.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* Cel45A cellulase, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a variant beta-glucosidase. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the variant beta-glucosidase relative to the growth of the host cell. Examples of regulatory systems are those which cause the expression of the gene to be turned on or off in response to a chemical or physical stimulus, including the presence of a regulatory compound. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleotide sequence encoding the variant beta-glucosidase would be operably linked with the regulatory sequence.

Expression Vectors

The present invention also relates to recombinant expression vectors comprising a nucleotide sequence encoding a variant beta-glucosidase of the present invention, a promoter, and transcriptional and translational stop signals. The various nucleotide and control sequences described above may be joined together to produce a recombinant expression vector which may include one or more convenient restriction sites to allow for insertion or substitution of the nucleotide sequence encoding the variant at such sites. Alternatively, the nucleotide sequence may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleotide sequence. The choice of the vector will typically depend on the compatibility of the vector with the host cell into which the vector is to be introduced. The vectors may be linear or closed circular plasmids.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrg (orotidine-5'-phosphate decarboxylase), sC(sulfate adenyltransferase), and trpC(anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vector may be an autonomously replicating vector, i.e., a vector which exists as an extrachromosomal entity, the replication of which is distinct from chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain an element(s) that permits integration of the vector into the host cell's genome or autonomous replication of the vector in the cell independent of the genome.

For integration into the host cell genome, the vector may rely on the nucleotide sequence encoding the variant or any other element of the vector for integration of the vector into the genome by homologous or nonhomologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes functioning temperature-sensitive in the host cell (see, e.g., Ehrlich, 1978, *Proceedings of the National Academy of Sciences USA* 75: 1433). Examples of a plasmid replicator useful in a filamentous fungal cell are AMA1 and ANS1 (Gems et al.,1991, *Gene* 98:61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a nucleotide sequence of the present invention may be inserted into the host cell to increase production of a beta-glucosidase variant. An increase in the copy number of the nucleotide sequence can be obtained by integrating at least one additional copy of the sequence into the host cell genome or by including an amplifiable selectable marker gene with the nucleotide sequence where cells containing amplified copies of the selectable marker gene, and thereby additional copies of the nucleotide sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a nucleotide sequence encoding a variant beta-glucosidase, which are advantageously used in the recombinant production of the variant. A vector comprising a nucleotide sequence of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any eukaryote, such as a mammalian, insect, plant, or fungal cell.

The host cell may be any fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

In a more preferred embodiment, the yeast host cell is a *Candida, Hansenula, Kluyveromyces, Pichia, Saccharomyces, Schizosaccharomyces*, or *Yarrowia* cell.

In a most preferred embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In a more preferred embodiment, the filamentous fungal host cell is, but not limited to, an *Acremonium, Aspergillus, Fusarium, Humicola, Mucor, Myceliophthora, Neurospora, Penicillium, Thielavia, Tolypocladium*, or *Trichoderma* cell.

In a most preferred embodiment, the filamentous fungal host cell is an *Aspergillus awamori, Aspergillus foetidus, Aspergillus japonicus, Aspergillus nidulans, Aspergillus niger* or *Aspergillus oryzae* cell. In another most preferred embodiment, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusafuim sporotrichioldes, Fusarium sulphureum, Fusarium torulosum, Fusarium trichothecioides,* or *Fusarium venentum* cell. In an even most preferred embodiment, the filamentous fungal host cell is a *Fusarium venentum* (Nirenberg sp. nov.) cell. In another most preferred embodiment, the filamentous fungal host cell is a *Humicola insolens, Humicola lanuginosa, Mucor miehei, Myceliophthora thermophila, Neurospora crassa, Penicillium purpurogenum, Thielavia terrestris, Trichoderma harzianum, Trichoderma koningii, Trichoderma longibrachiatum, Trichoderma reesei,* or *Trichoderma viride* cell. In another even most preferred embodiment, the filamentous fungal host cell is *Trichoderma reesei* RutC30.

Fungal cells may be transformed according to the procedures described herein.

Methods of Production

The present invention also relates to methods for producing a beta-glucosidase variant, comprising:

(a) cultivating a host cell under conditions suitable for the expression of the variant, wherein the host cell comprises a nucleotide sequence which has been modified by a substitution at one or more positions corresponding to positions 142, 183, 266, and 703 of SEQ ID NO: 2 or corresponding to positions 142, 183, 266, and 705 of SEQ ID NO: 70, as described herein; and (b) recovering the variant from the cultivation medium.

In the production methods of the present invention, the host cells are cultivated in a nutrient medium suitable for production of the variant beta-glucosidase using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

In an alternative embodiment, the beta-glucosidase variant is not recovered, but rather a host cell of the present invention expressing a variant is used as a source of the variant.

The variant beta-glucosidases may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein in the Examples.

The resulting variant beta-glucosidase may be recovered by methods known in the art. For example, the polypeptide may be recovered from the nutrient medium by conventional procedures including, but not limited to, collection, centrifugation, filtration, extraction, spray-drying, evaporation, or precipitation.

A variant beta-glucosidase of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

Other Polypeptides having Beta-Glucosidase Activity

The present invention also relates to isolated polypeptides having beta-glucosidase activity, wherein the amino acid sequence of the polypeptide differs from SEQ ID NO: 2 or SEQ ID NO: 70 at one or more positions corresponding to positions 142, 183, 266, and 703 of SEQ ID NO: 2 or corresponding to positions 142, 183, 266, and 705 of SEQ ID NO: 70.

In a preferred embodiment, the amino acid sequence of the polypeptide differs from amino acids 1 to 842 of SEQ ID NO: 2 or amino acids 1 to 844 SEQ ID NO: 70 by preferably 4 amino acids, more preferably 3 amino acids, even more preferably 2 amino acids, and most preferably 1 amino acid.

In a preferred embodiment, the polypeptide consists of 741 to 750, 751 to 760, 761 to 770, 771 to 780, 781 to 790, 791 to 800, 801 to 810, 811 to 820, 821 to 830, 831 to 840, 841 to 850, 851 to 860, 861 to 870, 871 to 880, 881 to 890, 891 to 900, 901 to 910, 911 to 920, 921 to 930, 931 to 940, or 941 to 950 amino acids.

In a preferred embodiment, the amino acid sequence of the polypeptide differs from SEQ ID NO: 2 or SEQ ID NO: 70 at one or more positions corresponding to positions 142, 183, 266, and 703 of amino acids 1 to 842 of SEQ ID NO: 2 or corresponding to positions 142, 183, 266, and 705 of amino acids 1 to 844 of SEQ ID NO: 70. In another preferred embodiment, the amino acid sequence of the polypeptide differs from SEQ ID NO: 2 or SEQ ID NO: 70 at two or more positions corresponding to positions 142, 183, 266, and 703 of amino acids 1 to 842 of SEQ ID NO: 2 or corresponding to positions 142, 183, 266, and 705 of amino acids 1 to 844 of SEQ ID NO: 70. In another preferred embodiment, the amino acid sequence of the polypeptide differs from SEQ ID NO: 2 or SEQ ID NO: 70 at three or more positions corresponding to positions 142, 183, 266, and 703 of amino acids 1 to 842 of SEQ ID NO: 2 or corresponding to positions 142, 183, 266, and 705 of amino acids 1 to 844 of SEQ ID NO: 70. In another preferred embodiment, the amino acid sequence of the polypeptide differs from SEQ ID NO: 2 or SEQ ID NO: 70 at least at positions corresponding to positions 142, 183, 266, and 703 of amino acids 1 to 842 of SEQ ID NO: 2 or corresponding to positions 142, 183, 266, and 705 of amino acids 1 to 844 of SEQ ID NO: 70.

In a preferred embodiment, the amino acid sequence of the polypeptide differs from SEQ ID NO: 2 or SEQ ID NO: 70 at a position corresponding to position 142 of amino acids 1 to 842 of SEQ ID NO: 2 or amino acids 1 to 844 of SEQ ID NO: 70. In a more preferred embodiment, the amino acid sequence of the polypeptide differs from SEQ ID NO: 2 or SEQ ID NO: 70 at a position corresponding to position 142 of amino acids 1 to 842 of SEQ ID NO: 2 or amino acids 1 to 844 of SEQ ID NO: 70 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 or SEQ ID NO: 70 by Ser at a position corresponding to position 142 of amino acids 1 to 842 of SEQ ID NO: 2 or amino acids 1 to 844 of SEQ ID NO: 70. In a most preferred embodiment, the amino acid sequence of the polypeptide differs from SEQ ID NO: 2 or SEQ ID NO: 70 by Ser at position 142 of amino acids 1 to 842 of SEQ ID NO: 2 or amino acids 1 to 844 of SEQ ID NO: 70.

In another preferred embodiment, the amino acid sequence of the polypeptide differs from SEQ ID NO: 2 or SEQ ID NO: 70 at a position corresponding to position 183 of amino acids 1 to 842 of SEQ ID NO: 2 or amino acids 1 to 844 of SEQ ID NO: 70. In another more preferred embodiment, the amino acid sequence of the polypeptide differs from SEQ ID NO: 2 or SEQ ID NO: 70 at a position corresponding to position 183 of amino acids 1 to 842 of SEQ ID NO: 2 or amino acids 1 to 844 of SEQ ID NO: 70 by Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the amino acid sequence of the polypeptide differs from SEQ ID NO: 70 by Arg at a position corresponding to position 183 of amino acids 1 to 842 of SEQ ID NO: 2 or amino acids 1 to 844 of SEQ ID NO: 70. In another most preferred embodiment, the amino acid sequence of the polypeptide differs from SEQ ID NO: 2 or SEQ ID NO: 70 by Arg at position 183 of amino acids 1 to 842 of SEQ ID NO: 2 or amino acids 1 to 844 of SEQ ID NO: 70.

In another preferred embodiment, the amino acid sequence of the polypeptide differs from SEQ ID NO: 2 or SEQ ID NO: 70 at a position corresponding to position 266 of amino acids 1 to 842 of SEQ ID NO: 2 or amino acids 1 to 844 of SEQ ID NO: 70. In another more preferred embodiment, the amino acid sequence of the polypeptide differs from SEQ ID NO: 2 or SEQ ID NO: 70 at a position corresponding to position 266 of amino acids 1 to 842 of SEQ ID NO: 2 or amino acids 1 to 844 of SEQ ID NO: 70 by Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the amino acid sequence of the polypeptide differs from SEQ ID NO: 70 by Gln at a position corresponding to position 266 of amino acids 1 to 842 of SEQ ID NO: 2 or amino acids 1 to 844 of SEQ ID NO: 70. In another most preferred embodiment, the amino acid sequence of the polypeptide differs from SEQ ID NO: 2 or SEQ ID NO: 70 by Gln at position 266 of SEQ ID NO: 2 or amino acids 1 to 844 of SEQ ID NO: 70.

In another preferred embodiment, the amino acid sequence of the polypeptide differs from SEQ ID NO: 2 at a position corresponding to position 703 of amino acids 1 to 842 of SEQ ID NO: 2. In another more preferred embodiment, the amino acid sequence of the polypeptide differs from SEQ ID NO: 2 at a position corresponding to position 703 of amino acids 1 to 842 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the amino acid sequence of the polypeptide differs from SEQ ID NO: 2 by Gly at a position corresponding to position 703 of amino acids 1 to 842 of SEQ ID NO: 2. In another most preferred embodiment, the amino acid sequence of the polypeptide differs from SEQ ID NO: 2 by Gly at position 703 of amino acids 1 to 842 of SEQ ID NO: 2.

In another preferred embodiment, the amino acid sequence of the polypeptide differs from SEQ ID NO: 70 at a position corresponding to position 705 of amino acids 1 to 844 of SEQ ID NO: 70. In another more preferred embodiment, the amino acid sequence of the polypeptide differs from SEQ ID NO: 70 at a position corresponding to position 705 of amino acids 1 to 844 of SEQ ID NO: 70 by Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the amino acid sequence of the polypeptide differs from SEQ ID NO: 70 by Gly at a position corresponding to position 705 of amino acids 1 to 844 of SEQ ID NO: 70. In another most preferred embodiment, the amino acid sequence of the polypeptide differs from SEQ ID NO: 70 by Gly at position 705 of amino acids 1 to 844 of SEQ ID NO: 70.

In another preferred embodiment, the amino acid sequence of the polypeptide differs from SEQ ID NO: 2 or SEQ ID NO: 70 at positions corresponding to positions 142 and 183 of amino acids 1 to 842 of SEQ ID NO: 2 or amino acids 1 to 844 of SEQ ID NO: 70. In a more preferred embodiment, the amino acid sequence of the polypeptide differs from SEQ ID NO: 2 or SEQ ID NO: 70 at positions corresponding to positions 142 and 183 of amino acids 1 to 842 of SEQ ID NO: 2 or amino acids 1 to 844 of SEQ ID NO: 70 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 or SEQ ID NO: 70 by Ser and Arg at positions corresponding to positions 142 and 183, respectively, of amino acids 1 to 842 of SEQ ID NO: 2 or amino acids 1 to 844 of SEQ ID NO: 70. In a most preferred embodiment, the amino acid sequence of the polypeptide differs from SEQ ID NO: 2 or SEQ ID NO: 70 by Ser and Arg at positions 142 and 183, respectively, of amino acids 1 to 842 of SEQ ID NO: 2 or amino acids 1 to 844 of SEQ ID NO: 70.

In another preferred embodiment, the amino acid sequence of the polypeptide differs from SEQ ID NO: 2 or SEQ ID NO: 70 at positions corresponding to positions 142 and 266 of amino acids 1 to 842 of SEQ ID NO: 2 or amino acids 1 to 844 of SEQ ID NO: 70. In a more preferred embodiment, the amino acid sequence of the polypeptide differs from SEQ ID NO: 2 or SEQ ID NO: 70 at positions corresponding to positions 142 and 266 of amino acids 1 to 842 of SEQ ID NO: 2 or amino acids 1 to 844 of SEQ ID NO: 70 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 or SEQ ID NO: 70 by Ser and Gln at positions corresponding to positions 142 and 266, respectively, of amino acids 1 to 842 of SEQ ID NO: 2 or amino acids 1 to 844 of SEQ ID NO: 70. In a most preferred embodiment, the amino acid sequence of the polypeptide differs from SEQ ID NO: 2 or SEQ ID NO: 70 by Ser and Gln at positions 142 and 266, respectively, of amino acids 1 to 842 of SEQ ID NO: 2 or amino acids 1 to 844 of SEQ ID NO: 70.

In another preferred embodiment, the amino acid sequence of the polypeptide differs from SEQ ID NO: 2 at positions corresponding to positions 142 and 703 of amino acids 1 to 842 of SEQ ID NO: 2. In a more preferred embodiment, the amino acid sequence of the polypeptide differs from SEQ ID NO: 2 at positions corresponding to positions 142 and 703 of amino acids 1 to 842 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Ser and Gly at positions corresponding to positions 142 and 703, respectively, of amino acids 1 to 842 of SEQ ID NO: 2. In a most preferred embodiment, the amino acid sequence of the polypeptide differs from SEQ ID NO: 2 by Ser and Gly at positions 142 and 703, respectively, of amino acids 1 to 842 of SEQ ID NO: 2.

In another preferred embodiment, the amino acid sequence of the polypeptide differs from SEQ ID NO: 70 at positions corresponding to positions 142 and 705 of amino acids 1 to 842 of SEQ ID NO: 70. In a more preferred embodiment, the amino acid sequence of the polypeptide differs from SEQ ID NO: 70 at positions corresponding to positions 142 and 705 of amino acids 1 to 842 of SEQ ID NO: 70 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 70 by Ser and Gly at positions corresponding to positions 142 and 705, respectively, of amino acids 1 to 842 of SEQ ID NO: 70. In a most preferred embodiment, the amino acid sequence of the polypeptide differs from SEQ ID NO: 70 by Ser and Gly at positions 142 and 705, respectively, of amino acids 1 to 842 of SEQ ID NO: 70.

In another preferred embodiment, the amino acid sequence of the polypeptide differs from SEQ ID NO: 2 or SEQ ID NO: 70 at positions corresponding to positions 183 and 266 of amino acids 1 to 842 of SEQ ID NO: 2 or amino acids 1 to 844 of SEQ ID NO: 70. In a more preferred embodiment, the amino acid sequence of the polypeptide differs from SEQ ID NO: 2 or SEQ ID NO: 70 at positions corresponding to positions 183 and 266 of amino acids 1 to 842 of SEQ ID NO: 2 or amino acids 1 to 844 of SEQ ID NO: 70 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 or SEQ ID NO: 70 by Arg and Gln at positions corresponding to positions 183 and 266, respectively, of amino acids 1 to 842 of SEQ ID NO: 2 or amino acids 1 to 844 of SEQ ID NO: 70. In a most preferred embodiment, the amino acid sequence of the polypeptide differs from SEQ ID NO: 2 or SEQ ID NO: 70 by Arg and Gln at positions 183 and 266, respectively, of amino acids 1 to 842 of SEQ ID NO: 2 or amino acids 1 to 844 of SEQ ID NO: 70.

In another preferred embodiment, the amino acid sequence of the polypeptide differs from SEQ ID NO: 2 at positions corresponding to positions 183 and 703 of amino acids 1 to 842 of SEQ ID NO: 2. In a more preferred embodiment, the amino acid sequence of the polypeptide differs from SEQ ID NO: 2 at positions corresponding to positions 183 and 703 of amino acids 1 to 842 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Arg and Gly at positions corresponding to positions 183 and 703, respectively, of amino acids 1 to 842 of SEQ ID NO: 2. In a most preferred embodiment, the amino acid sequence of the polypeptide differs from SEQ ID NO: 2 by Arg and Gly at positions 183 and 703, respectively, of amino acids 1 to 842 of SEQ ID NO: 2.

In another preferred embodiment, the amino acid sequence of the polypeptide differs from SEQ ID NO: 70 at positions corresponding to positions 183 and 705 of amino acids 1 to 844 of SEQ ID NO: 70. In a more preferred embodiment, the amino acid sequence of the polypeptide differs from SEQ ID NO: 70 at positions corresponding to positions 183 and 705 of amino acids 1 to 844 of SEQ ID NO: 70 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 70 by Arg and Gly at positions corresponding to positions 183 and 705, respectively, of amino acids 1 to 844 of SEQ ID NO: 70. In a most preferred embodiment, the amino acid sequence of the polypeptide differs from SEQ ID NO: 70 by Arg and Gly at positions corresponding to positions 183 and 705, respectively, of amino acids 1 to 844 of SEQ ID NO: 70.

In another preferred embodiment, the amino acid sequence of the polypeptide differs from SEQ ID NO: 2 at positions corresponding to positions 266 and 703 of amino acids 1 to 842 of SEQ ID NO: 2. In a more preferred embodiment, the amino acid sequence of the polypeptide differs from SEQ ID NO: 2 at positions corresponding to positions 266 and 703 of amino acids 1 to 842 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Gln and Gly at positions corresponding to positions 266 and 703, respectively, of amino acids 1 to 842 of SEQ ID NO: 2. In a most preferred embodiment, the amino acid sequence of the polypeptide differs from SEQ ID NO: 2 by Gln and Gly at positions 266 and 703, respectively, of amino acids 1 to 842 of SEQ ID NO: 2.

In another preferred embodiment, the amino acid sequence of the polypeptide differs from SEQ ID NO: 70 at positions corresponding to positions 266 and 705 of amino acids 1 to 844 of SEQ ID NO: 70. In a more preferred embodiment, the amino acid sequence of the polypeptide differs from SEQ ID NO: 70 at positions corresponding to positions 266 and 705 of amino acids 1 to 844 of SEQ ID NO: 70 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 70 by Gln and Gly at positions corresponding to positions 266 and 705, respectively, of amino acids 1 to 844 of SEQ ID NO: 70. In a most preferred embodiment, the amino acid sequence of the polypeptide differs from SEQ ID NO: 70 by Gln and Gly at positions 266 and 705, respectively, of amino acids 1 to 844 of SEQ ID NO: 70.

In another preferred embodiment, the amino acid sequence of the polypeptide differs from SEQ ID NO: 2 or SEQ ID NO: 70 at positions corresponding to positions 142, 183, and 266 of amino acids 1 to 842 of SEQ ID NO: 2 or amino acids 1 to 844 of SEQ ID NO: 70. In a more preferred embodiment, the amino acid sequence of the polypeptide differs from SEQ ID NO: 2 or SEQ ID NO: 70 at positions corresponding to positions 142, 183, and 266 of amino acids 1 to 842 of SEQ ID NO: 2 or amino acids 1 to 844 of SEQ ID NO: 70 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 or SEQ ID NO: 70 by Ser, Arg, and Gln at positions corresponding to positions 142, 183, and 266, respectively, of amino acids 1 to 842 of SEQ ID NO: 2 or amino acids 1 to 844 of SEQ ID NO: 70. In a most preferred embodiment, the amino acid sequence of the polypeptide differs from SEQ ID NO: 2 or SEQ ID NO: 70 by Ser, Arg, and Gln at positions 142, 183, and 266, respectively, of amino acids 1 to 842 of SEQ ID NO: 2 or amino acids 1 to 844 of SEQ ID NO: 70.

In another preferred embodiment, the amino acid sequence of the polypeptide differs from SEQ ID NO: 2 at positions corresponding to positions 142, 266, and 703 of amino acids 1 to 842 of SEQ ID NO: 2. In a more preferred embodiment, the amino acid sequence of the polypeptide differs from SEQ ID NO: 2 at positions corresponding to positions 142, 266, and 703 of amino acids 1 to 842 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Ser, Gln, and Gly at positions corresponding to positions 142, 266, and 703, respectively, of amino acids 1 to 842 of SEQ ID NO: 2. In a most preferred embodiment, the amino acid sequence of the polypeptide differs from SEQ ID NO: 2 by Ser, Gln, and Gly at positions 142, 266, and 703, respectively, of amino acids 1 to 842 of SEQ ID NO: 2.

In another preferred embodiment, the amino acid sequence of the polypeptide differs from SEQ ID NO: 70 at positions corresponding to positions 142, 266, and 705 of amino acids 1 to 844 of SEQ ID NO: 70. In a more preferred embodiment, the amino acid sequence of the polypeptide differs from SEQ ID NO: 70 at positions corresponding to positions 142, 266, and 705 of amino acids 1 to 844 of SEQ ID NO: 70 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 70 by Ser, Gln, and Gly at positions corresponding to positions 142, 266, and 705, respectively, of amino acids 1 to 844 of SEQ ID NO: 70. In a most preferred embodiment, the amino acid sequence of the polypeptide differs from SEQ ID NO: 70 by Ser, Gln, and Gly at positions 142, 266, and 705, respectively, of amino acids 1 to 844 of SEQ ID NO: 70.

In another preferred embodiment, the amino acid sequence of the polypeptide differs from SEQ ID NO: 2 at positions corresponding to positions 183, 266, and 703 of amino acids 1 to 842 of SEQ ID NO: 2. In a more preferred embodiment, the amino acid sequence of the polypeptide differs from SEQ ID NO: 2 at positions corresponding to positions 183, 266, and 703 of amino acids 1 to 842 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Arg, Gln, and Gly at positions corresponding to positions 183, 266, and 703, respectively, of amino acids 1 to 842 of SEQ ID NO: 2. In a most preferred embodiment, the amino acid sequence of the polypeptide differs from SEQ ID NO: 2 by Arg, Gln, and Gly at positions 183, 266, and 703, respectively, of amino acids 1 to 842 of SEQ ID NO: 2.

In another preferred embodiment, the amino acid sequence of the polypeptide differs from SEQ ID NO: 70 at positions corresponding to positions 183, 266, and 705 of amino acids 1 to 844 of SEQ ID NO: 70. In a more preferred embodiment, the amino acid sequence of the polypeptide differs from SEQ ID NO: 70 at positions corresponding to positions 183, 266, and 705 of amino acids 1 to 844 of SEQ ID NO: 70 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 70 by Arg, Gln, and Gly at positions corresponding to positions 183, 266, and 705, respectively, of amino acids 1 to 844 of SEQ ID NO: 70. In a most preferred embodiment, the amino acid sequence of the polypeptide differs from SEQ ID NO: 70 by Arg, Gln, and Gly at positions 183, 266, and 705, respectively, of amino acids 1 to 844 of SEQ ID NO: 70.

In another preferred embodiment, the amino acid sequence of the polypeptide differs from SEQ ID NO: 2 at positions corresponding to positions 142, 183, and 703 of amino acids 1 to 842 of SEQ ID NO: 2. In a more preferred embodiment, the amino acid sequence of the polypeptide differs from SEQ ID NO: 2 at positions corresponding to positions 142, 183, and 703 of amino acids 1 to 842 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Ser, Arg, and Gly at positions corresponding to positions 142, 183, and 703, respectively, of amino acids 1 to 842 of SEQ ID NO: 2. In a most preferred embodiment, the amino acid sequence of the polypeptide differs from SEQ ID NO: 2 by Ser, Arg, and Gly at positions 142, 183, and 703, respectively, of amino acids 1 to 842 of SEQ ID NO: 2.

In another preferred embodiment, the amino acid sequence of the polypeptide differs from SEQ ID NO: 70 at positions corresponding to positions 142, 183, and 705 of amino acids 1 to 844 of SEQ ID NO: 70. In a more preferred embodiment, the amino acid sequence of the polypeptide differs from SEQ ID NO: 70 at positions corresponding to positions 142, 183, and 705 of amino acids 1 to 844 of SEQ ID NO: 70 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 70 by Ser, Arg, and Gly at positions corresponding to positions 142, 183, and 705, respectively, of amino acids 1 to 844 of SEQ ID NO: 70. In a most preferred embodiment, the amino acid sequence of the polypeptide differs from SEQ ID NO: 70 by Ser, Arg, and Gly at positions 142, 183, and 705, respectively, of amino acids 1 to 844 of SEQ ID NO: 70.

In another preferred embodiment, the amino acid sequence of the polypeptide differs from SEQ ID NO: 2 at positions corresponding to positions 142, 183, 266, and 703 of amino acids 1 to 842 of SEQ ID NO: 2. In a more preferred embodiment, the amino acid sequence of the polypeptide differs from SEQ ID NO: 2 at positions corresponding to positions 142, 183, 266, and 703 of amino acids 1 to 842 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Ser, Arg, Gln, and Gly at positions corresponding to positions 142, 183, 266, and 703, respectively, of amino acids 1 to 842 of SEQ ID NO: 2. In a most preferred embodiment, the amino acid sequence of the polypeptide differs from SEQ ID NO: 2 by Ser, Arg, Gln, and Gly at positions 142, 183, 266, and 703, respectively, of amino acids 1 to 842 of SEQ ID NO: 2.

In another preferred embodiment, the amino acid sequence of the polypeptide differs from SEQ ID NO: 70 at positions corresponding to positions 142, 183, 266, and 705 of amino acids 1 to 844 of SEQ ID NO: 70. In a more preferred embodiment, the amino acid sequence of the polypeptide differs from SEQ ID NO: 70 at positions corresponding to positions 142, 183, 266, and 705 of amino acids 1 to 844 of SEQ ID NO: 70 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 70 by Arg and Gly at positions corresponding to positions 142, 183, 266, and 705, respectively, of amino acids 1 to 844 of SEQ ID NO: 70. In a most preferred embodiment, the amino acid sequence of the polypeptide differs from SEQ ID NO: 70 by Arg and Gly at positions 142, 183, 266, and 705, respectively, of amino acids 1 to 844 of SEQ ID NO: 70.

The polypeptide consists of 741 to 750, 751 to 760, 761 to 770, 771 to 780, 781 to 790, 791 to 800, 801 to 810, 811 to 820, 821 to 830, 831 to 840, 841 to 850, 851 to 860, 861 to 870, 871 to 880, 881 to 890, 891 to 900, 901 to 910, 911 to 920, 921 to 930, 931 to 940, or 941 to 950 amino acids.

The isolated polypeptides have one or more improved properties compared to the polypeptide of SEQ ID NO: 2 or SEQ ID NO: 70, wherein the improved properties are selected from the group consisting of thermal activity, thermostability, pH activity, pH stability, substrate specificity, product specificity, and chemical stability, as described herein.

The present invention also relates to isolated nucleotide sequences encoding such polypeptides, nucleic acid constructs, expression vectors, and host cells comprising the nucleotide sequences, and methods of producing the polypeptides having beta-glucosidase acity, according to the same disclosure herein for variants of beta-glucosidases.

Degradation of Biomass to Monosaccharides, Disaccharides, and Polysaccharides

The beta-glucosidase variants and host cells of the present invention may be used in the production of monosaccharides, disaccharides, and polysaccharides as chemical or fermentation feedstocks from biomass for the production of ethanol, plastics, or other products or intermediates. The beta-glucosidase variants may be in the form of a crude fermentation broth with or without the cells removed or in the form of a semi-purified or purified enzyme preparation. Alternatively, a host cell of the present invention may be used as a source of the variant in a fermentation process with the biomass.

Biomass can include, but is not limited to, wood resources, municipal solid waste, wastepaper, and crop residues (see, for example, Wiselogel et al., 1995, in *Handbook on Bioethanol* (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, *Recent Progress in Bioconversion of Lignocellulosics*, in *Advances in Biochemical Engineering/Biotechnology*, T. Scheper, managing editor, Volume 65, pp. 23-40, Springer-Verlag, New York).

The predominant polysaccharide in the primary cell wall of biomass is cellulose, the second most abundant is hemi-cellulose, and the third is pectin. The secondary cell wall, produced after the cell has stopped growing, also contains polysaccharides and is strengthened through polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which helps stabilize the cell wall matrix.

Three major classes of glycohydrolases are used to breakdown cellulosic biomass:

(1) The "endo-1,4-beta-glucanases" or 1,4-beta-D-glucan-4-glucanohydrolases (EC 3.2.1.4), which act randomly on soluble and insoluble 1,4-beta-glucan substrates.

(2) The "exo-1,4-beta-D-glucanases" including both the 1,4-beta-D-glucan glucohydrolases (EC 3.2.1.74), which liberate D-glucose from 1,4-beta-D-glucans and hydrolyze D-cellobiose slowly, and cellobiohydrolases (1,4-beta-D-glucan cellobiohydrolases, EC 3.2.1.91), which liberate D-cellobiose from 1,4-beta-glucans.

(3) The "beta-D-glucosidases" or beta-D-glucoside glucohydrolases (EC 3.2.1.21), which act to release D-glucose units from cellobiose and soluble cellodextrins, as well as an array of glycosides.

These three classes of enzymes work together synergistically resulting in efficient decrystallization and hydrolysis of native cellulose from biomass to yield reducing sugars.

The beta-glucosidase variants of the present invention may be used in conjunction with the above-noted enzymes to further degrade the cellulose component of the biomass substrate, (see, for example, Brigham et al., 1995, in *Handbook on Bioethanol* (Charles E. Wyman, editor), pp. 119-141, Taylor & Francis, Washington D.C.; Lee, 1997, *Journal of Biotechnology* 56: 1-24).

Ethanol can be produced by enzymatic degradation of biomass and conversion of the released saccharides to ethanol. This kind of ethanol is often referred to as bioethanol or biofuel. It can be used as a fuel additive or extender in blends of from less than 1% and up to 100% (a fuel substitute).

Detergent Compositions

The beta-glucosidase variants of the present invention may be added to and thus become a component of a detergent composition.

The detergent composition of the present invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the present invention provides a detergent additive comprising the enzyme of the invention. The detergent additive as well as the detergent composition may comprise one or more other enzymes such as a protease, lipase, cutinase, an amylase, carbohydrase, cellulase, pectinase, mannanase, arabinase, galactanase, xylanase, oxidase, e.g., a laccase, and/or peroxidase.

In general the properties of the chosen enzyme(s) should be compatible with the selected detergent, (i.e., pH-optimum, compatibility with other enzymatic and non-enzymatic ingredients, etc.), and the enzyme(s) should be present in effective amounts.

Proteases: Suitable proteases include those of animal, vegetable or microbial origin. Microbial origin is preferred. Chemically modified or protein engineered mutants are included. The protease may be a serine protease or a metalloprotease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g., of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274.

Preferred commercially available protease enzymes include Alcalase™, Savinase™, Primase™, Duralase™, Esperase™, and Kannase™ (Novo Nordisk A/S), Maxatase™, Maxacal™, Maxapem™, Properase™, Purafect™, Purafect OxP™, FN2™, and FN3™ (Genencor International Inc.).

LiDases: Suitable lipases include those of bacterial or fungal origin. Chemically modified or protein engineered mutants are included. Examples of useful lipases include lipases from *Humicola* (synonym *Thermomyces*), e.g., from *H. lanuginosa* (*T. lanuginosus*) as described in EP 258 068 and EP 305 216 or from *H. insolensas* described in WO 96/13580, a *Pseudomonas* lipase, e.g., from *P. alcaligenes* or *P. pseudoalcaligenes* (EP 218 272), *P. cepacia* (EP 331 376), *P. stutzeri* (GB 1,372,034), *P. fluorescens*, *Pseudomonas* sp. strain SD 705 (WO 95/06720 and WO 96/27002), *P. wisconsinensis* (WO 96/12012), a *Bacillus* lipase, e.g., from *B. subtilis* (Dartois et al., 1993, *Biochemica et Biophysica Acta*, 1131: 253-360), *B. stearothermophilus*(JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include Lipolase™ and Lipolase Ultra™ (Novo Nordisk A/S).

Amylases: Suitable amylases (α and/or β) include those of bacterial or fungal origin. Chemically modified or protein engineered mutants are included. Amylases include, for example, α-amylases obtained from *Bacillus*, e.g., a special strain of *Bacillus licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are Duramyl™, Termamyl™, Fungamyl™ and BAN™ (Novo Nordisk A/S), Rapidase™ and Purastar™ (from Genencor International Inc.).

Cellulases: Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and PCT/DK98/00299.

Commercially available cellulases include Celluzyme™, and Carezyme™ (Novo Nordisk A/S), Clazinase™, and Puradax HA™ (Genencor International Inc.), and KAC-500 (B)™ (Kao Corporation).

Peroxidases/Oxidases: Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/1527.

Commercially available peroxidases include Guardzyme™ (Novo Nordisk A/S).

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid, or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates, or layered silicates (e.g., SKS-6 from Hoechst).

The detergent may comprise one or more polymers. Examples are carboxymethylcellulose, poly(vinylpyrrolidone), poly (ethylene glycol), poly(vinyl alcohol), poly(vinylpyridine-N-oxide), poly(vinylimidazole), polycarboxylates such as polyacrylates, maleic/acrylic acid copolymers, and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of, for example, the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, for example, WO 92/19709 and WO 92/19708.

The detergent may also contain other conventional detergent ingredients such as, e.g., fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

In the detergent compositions any enzyme, in particular the enzyme of the invention, may be added in an amount corresponding to 0.01-100 mg of enzyme protein per liter of wash liquor, preferably 0.05-5 mg of enzyme protein per liter of wash liquor, in particular 0.1-1 mg of enzyme protein per liter of wash liquor.

The enzyme of the invention may additionally be incorporated in the detergent formulations disclosed in WO 97/07202, which is hereby incorporated as reference.

Plants

The present invention also relates to a transgenic plant, plant part, or plant cell which has been transformed with a nucleotide sequence encoding a variant beta-glucosidase of the present invention so as to express and produce the variant in recoverable quantities. The variant may be recovered from the plant or plant part. Alternatively, the plant or plant part containing the recombinant variant may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as Festuca, Lolium, temperate grass, such as Agrostis, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilisation of the invention are also considered plant parts, e.g., embryos, endosperms, aleurone and seeds coats.

Also included within the scope of the present invention are the progeny of such plants, plant parts, and plant cells.

The transgenic plant or plant cell expressing a variant of the present invention may be constructed in accordance with methods known in the art. In short, the plant or plant cell is constructed by incorporating one or more expression constructs encoding a variant of the present invention into the plant host genome and propagating the resulting modified plant or plant cell into a transgenic plant or plant cell.

Conveniently, the expression construct is a nucleic acid construct which comprises a nucleic acid sequence encoding a variant of the present invention operably linked with appropriate regulatory sequences required for expression of the nucleic acid sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the variant is desired to be expressed. For instance, the expression of the gene encoding a variant of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, and the rice actin 1 promoter may be used (Franck et al., 1980, *Cell* 21: 285-294, Christensen et al., 1992, *Plant Mo. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards & Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant and Cell Physiology* 39: 885-889), a Vicia faba promoter from the legumin B4 and the unknown seed protein gene from Vicia faba (Conrad et al., 1998, *Journal of Plant Physiology* 152: 708-711), a promoter from a seed oil body protein (Chen et al., 1998, *Plant and Cell Physiology* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991-1000, the chlorella virus adenine methyltransferase gene promoter (Mitra and Higgins, 1994, *Plant Molecular Biology* 26: 85-93), or the aldP gene promoter from rice (Kagaya et al., 1995, *Molecular and General Genetics* 248: 668-674), or a wound inducible promoter such as the potato pin2 promoter (Xu et al., 1993, *Plant Molecular Biology* 22: 573-588). Likewise, the promoter may inducible by abiotic treatments such as temperature, drought, or alterations in salinity or induced by exogenously applied substances that activate the promoters e.g., ethanol, oestrogens, plant hormones such as ethylene, abscisic acid, and gibberellic acid, and heavy metals.

A promoter enhancer element may also be used to achieve higher expression of a polypeptide of the present invention in the plant. For instance, the promoter enhancer element may be an intron which is placed between the promoter and the nucleotide sequence encoding a polypeptide of the present invention. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275-281; Shimamoto, 1994, *Current Opinion Biotechnology* 5: 158-162; Vasil et al., 1992, *Bio/Technology* 10: 667-674). An alternative method for transformation of monocots is based on protoplast transformation as described by Omirulleh et al., 1993, *Plant Molecular Biology* 21: 415-428.

Following transformation, the transformants having incorporated the expression construct are selected and regenerated into whole plants according to methods well-known in the art. Often the transformation procedure is designed for the selective elimination of selection genes either during regeneration or in the following generations by using, for example, co-transformation with two separate T-DNA constructs or site specific excision of the selection gene by a specific. recombinase.

The present invention also relates to methods for producing a variant of the present invention comprising (a) cultivating a transgenic plant or a plant cell comprising a nucleic acid sequence encoding a variant having beta-glucosidase activity of the present invention under conditions conducive for production of the variant; and (b) recovering the variant.

Other Uses

The beta-glucosidase variants of the present invention may also be used in the treatment of textiles as biopolishing agents and for reducing of fuzz, pilling, texture modification, and stonewashing (N. K. Lange, in P. Suominen, T. Reinikainen (Eds.), *Trichoderma reesei Cellulases and Other Hydrolases*, Foundation for Biotechnical and Industrial Fermentation Research, Helsinki, 1993, pp. 263-272). In addition, the described variants may also be used in wood processing for biopulping or debarking, paper manufacturing for fiber modification, bleaching, and reduction of refining energy costs, whitewater treatment, important to wastewater recycling, lignocellulosic fiber recycling such as deinking and secondary fiber processing, and wood residue utilization (S. D, Mansfield and A. R. Esteghlalian in S. D, Mansfield and J. N. Saddler (Eds.), *Applications of Enzymes to Lignocellulosics*, ACS Symposium Series 855, Washington, D.C., 2003, pp. 2-29).

The present invention is further described by the following examples which should not be construed as limiting the scope of the invention.

EXAMPLES

Materials

Chemicals used as buffers and substrates were commercial products of at least reagent grade.

Strains

The yeast strain *Saccharomyces cerevisiae* YNG318 (MATα, ura3-52, leu-2Δ2, pep4Δ1, his4-539, cir$^+$) was used to express the *Aspergillus oryzae* and *Aspergillus fumigatus* beta-glucosidases and their variants. Bacterial strains used to generate plasmids were *Epicurian coli* XL-10 Gold ultracompetent cells, *Epicurian coli* XL1-Blue subcloning-competent cells, and *Epicurian coli* SURE electroporation-competent cells (Stratagene, La Jolla, Calif.). *Aspergillus oryzae* Jal250 strain (WO 99/61651) was used for expression of the *Aspergilius otyzae* beta-glucosidase. *Aspergillus fumigatus* PaHa34 was used as the source of the Family GH3A beta-glucosidase.

Media and Solutions

YPD medium was composed per liter of 10 g of yeast extract, 20 g of bacto tryptone, and 40 ml of 50% glucose.

Yeast selection medium was composed per liter of 6.7 g of yeast nitrogen base, 0.8 g of complete supplement mixture (CSM, Qbiogene, Inc., Carlsbad, Calif.; missing uracil and containing 40 mg/ml of adenine), 5 g of casamino acids (without amino acids), 100 ml of 0.5 M succinate pH 5.0, 40 ml of 50% glucose, 1 ml of 100 mM $CuSO_4$, 50 mg of ampicillin, and 25 mg of chloramphenicol.

Yeast selection plate medium was composed per liter of yeast selection medium supplemented with 20 g of bacto agar and 150 mg of 5-bromo-4-chloro-3-indolyl-beta-D-glucopyranoside (X-Glc, INALCO SPA, Milano, Italy) but lacking both ampicillin and chloramphenicol.

M400 medium is composed per liter of 50 g of maltodextrin, 2 g of $MgSO_4.7H_2O$, 2 g of $KH_2PO_4$, 4 g of citric acid, 8 g of yeast extract, 2 g of urea, 0.5 ml of AMG trace metals solution, and 0.5 g $CaCl_2$.

AMG trace metals solution was composed per liter of 14.3 g of $ZnSO_4.7H_2O$, 2.5 g of $CuSO_4.5H_2O$, 0.5 g of $NiCl_2.6H_2O$, 13.8 g of $FeSO_4.7H_2O$, 8.5 g of 1×BS was composed per liter of 2 g of MgSO$_4$.7H$_2$O, 2 g of K$_2$SO$_4$, and 10 g of KH$_2$PO$_4$.

Minimal medium *Aspergillus oryzaes* election plates were composed per liter of 6 g of NaNO$_3$, 0.52 g of KCl, 1.52 g of KH$_2$PO$_4$, 1 ml of COVE trace elements solution, 20 g of agar Noble, 20 ml of 50% glucose, 2.5 ml of 20% MgSO$_4$.7H$_2$O.

COVE trace elements solution was composed per liter of 0.04 g of NaB$_4$O$_7$.10H$_2$O, 0.4 g of CuSO$_4$.5H$_2$O, 1.2 g of FeSO$_4$.7H$_2$O, 0.7 g of MnSO$_4$.H$_2$O, 0.8 g of Na$_2$MoO$_2$.2H$_2$O and 10 g of ZnSO$_4$.7H$_2$O.

Yeast lysis buffer was composed of 1% sodium dodecyl sulfate (SDS), 10 mM Tris-HCl, and 1 mM EDTA, pH 8.0.

Potato dextrose medium was composed per liter of 39 grams of potato dextrose (Difco).

PDA plates were composed per liter of 39 grams of potato dextrose agar (Difco).

MDU2BP medium was composed per liter of 45 g of maltose, 1 g of MgSO$_4$.7H$_2$O, 1 g of NaCl, 2 g of K$_2$SO$_4$, 12 g of KH$_2$PO$_4$, 7 g of yeast extract, 2 g of urea, and 0.5 ml of metals solution, pH to 5.0.

Plasmid DNA Preparation and DNA Sequencing

Plasmid DNA from *E. coli* strains was prepared using a BioRobot 9600 (QIAGEN, Inc., Chatsworth, Calif.).

DNA sequencing was performed on an ABI3700 (Applied Biosystems, Foster City, Calif.) using dye terminator chemistry (Giesecke et al., 1992, *Journal of Virol. Methods* 38: 47-60). Sequences were assembled using phred/phrap/consed (University of Washington, Seattle Wash.) with sequence specific primers.

Example 1

Construction of pSATe111 *Saccharomyces cerevisiae* Expression Vector

A 2,605 bp DNA fragment comprising the region from the ATG start codon to the TAA stop codon of the *Aspergillus oryzae* beta-glucosidase coding sequence (SEQ ID NO: 1 for cDNA sequence and SEQ ID NO: 2 for the deduced amino acid sequence) was amplified by PCR from pJaL660 (WO 2002/095014) as template with primers 992127 (sense) and 992328 (antisense) shown below.

```
992127: 5'-GCAGATCTACCATGAAGCTTGGTTGGATCGAG-3'  (SEQ ID NO: 3)
992328: 5'-GCCTCGAGTTACTGGGCCTTAGGCAGCGAG-3'    (SEQ ID NO: 4)
```

Primer 992127 has an upstream BglII site and the primer 992328 has a downstream XhoI site.

The amplification reactions (50 µl) were composed of 1×PCR buffer containing MgCl$_2$ (Roche Applied Science, Manheim, Germany), 0.25 mM dNTPs, 50 µM primer 992127, 50 µM primer 992328, 80 ng of pJaL660, and 2.5 units of Pwo DNA Polymerase (Roche Applied Science, Manheim, Germany). The reactions were incubated in an Eppendorf Mastercycler 5333 (Eppendorf Scientific, Inc., Westbury, N.Y.) programmed for 1 cycle at 94° C. for 5 minutes followed by 25 cycles each at 94° C. for 60 seconds, 55° C. for 60 seconds, and 72° C. for 120 seconds (10 minute final The PCR product was then subcloned into the PCR-Blunt II-TOPO vector using the PCR-Blunt II-TOPO Cloning Kit (Invitrogen, Carlsbad, Calif.) following the manufacturer's instructions to generate plasmid pSATe101 (FIG. 1). Plasmid pSATe101 was digested with Bgl II and Xho I to liberate the beta-glucosidase gene. The reaction products were isolated on a 1.0% agarose gel using 40 mM Tris-acetate-1 mM EDTA (TAE) buffer where a 2.6 kb product band was excised from the gel and purified using a QIAquick Gel Extraction Kit (QIAGEN Inc., Valencia, Calif.) according to the manufacturer's instructions.

Figure 2:
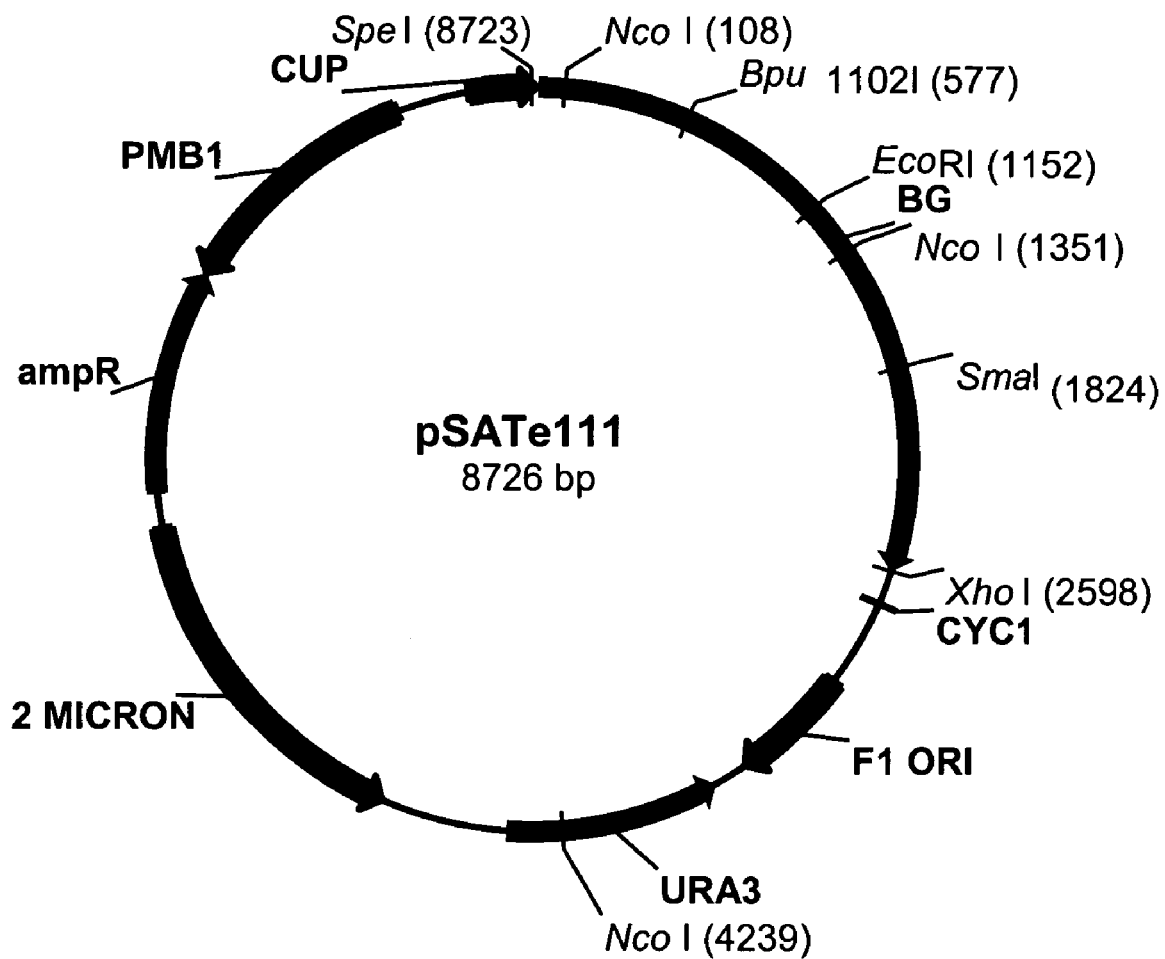
FIG. 2 shows a restriction map of pSATe111.

The 2.6 kb PCR product was digested and cloned into the Bam HI and Xho I sites of the copper inducible 2 µm yeast expression vector pCu426 (Labbe and Thiele, 1999, *Methods Enzymol.* 306: 145-53) to generate pSATe111 (FIG. 2).

Example 2

Construction of pMJ04 Expression Vector

Expression vector pMJ04 was constructed by PCR amplifying the *Trichoderma reesei* exocellobiohydrolase 1 gene (cbh1) terminator from *Trichoderma reesei*RutC30 (Montenecourt and Eveleigh, 1979, *Adv. Chem. Ser.* 181: 289-301) genomic DNA using primers 993429 (antisense) and 993428 (sense) shown below. The antisense primer was engineered to have a PacI site at the 5'-end and a Spe I site at the 3'-end of the sense primer.

```
Primer 993429 (antisense): 5'-AACGTTAATTAAGGAATCGTTTTGTGTTT-3'  (SEQ ID NO: 5)
Primer 993428 (sense):     5'-AGTACTAGTAGCTCCGTGGCGAAAGCCTG-3'  (SEQ ID NO: 6)
```

*Trichoderma reesei* RutC30 genomic DNA was isolated using a DNeasy Plant Maxi Kit (Qiagen, Chatsworth, Calif.).

The amplification reactions (50 µl) were composed of 1×ThermoPol Reaction Buffer (New England Biolabs, Beverly, Mass.), 0.3 mM dNTPs, 100 ng of *Trichoderma reesei* RutC30 genomic DNA, 0.3 µM primer 993429, 0.3 µM primer 993428, and 2 units of Vent DNA polymerase (New England Biolabs, Beverly, Mass.). The reactions were incubated in an Eppendorf Mastercycler 5333 programmed as follows: 5 cycles each for 30 seconds at 94° C., 30 seconds at 50° C., and 60 seconds at 72° C., followed by 25 cycles each for 30 seconds at 94° C., 30 seconds at 65° C., and 120 seconds at 72° C. (5 minute final extension). The reaction products were isolated on a 1.0% agarose gel using TAE buffer where a 229 bp product band was excised from the gel and purified using a QIAquick Gel Extraction Kit.

Figure 3:
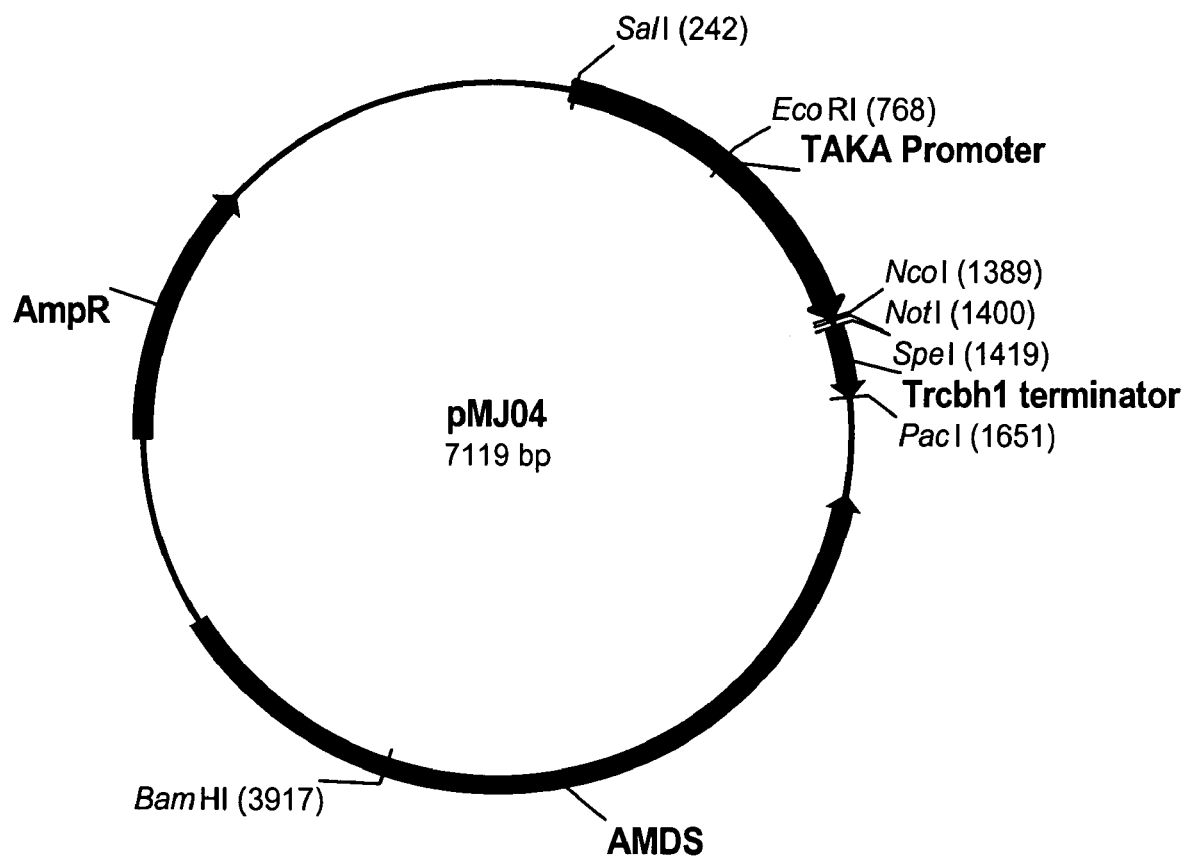
FIG. 3 shows a restriction map of pMJ04.

The resulting PCR fragment was digested with PacI and SpeI and ligated into pAlLo01 digested with the same restriction enzymes using a Rapid Ligation Kit (Roche, Indianapolis, Ind.), to generate pMJ04 (FIG. 3).

Example 3

Construction of pCaHj568 Expression Vector

Expression plasmid pCaHj568 was constructed from pCaHj170(U.S. Pat. No. 5,763,254) and pMT2188. Plasmid pCaHj170 comprises the *Humicola insolens* endoglucanase V (EGV) coding region. Plasmid pMT2188 was constructed as follows: The pUC19 origin of replication was PCR amplified from pCaHj483 (WO 98/00529) with primers 142779 and 142780 shown below. Primer 142780 introduced a Bbu I site in the PCR fragment.

```
142779:  5'-TTGAATTGAAAATAGATTGATTTAAAACTTC-3'  (SEQ ID NO: 7)

142780:  5'-TTGCATGCGTAATCATGGTCATAGC-3'        (SEQ ID NO: 8)
```

The Expand PCR system (Roche Molecular Biochemicals, Basel, Switserland) was used for the amplification following the manufacturer's instructions and the subsequent PCR amplifications. PCR products were separated on a 1% agarose gel using TAE buffer and an 1160 bp fragment was isolated and purified using a Jetquick gel extraction spin kit (Genomed, Wielandstr, Germany).

The URA3 gene was amplified from the *Saccharomyces serevisiae* cloning vector pYES2 (Invitrogen, Carlsbad, Calif.) using primers 140288 and 142778 below. Primer 140288 introduced an EcoRI site in the PCR fragment.

```
140288:  5'-TTGAATTCATGGGTAATAACTGATAT-3'        (SEQ ID NO: 9)

142778:  5'-AAATCAATCTATTTTCAATTCAATTCATCATT-3'  (SEQ ID NO: 10)
```

PCR products were separated on a 1% agarose gel using TAE buffer and an 1126 bp fragment was isolated and purified using a Jetquick gel extraction spin kit.

The two PCR fragments were fused by mixing and amplification using primers 142780 and 140288 shown above by overlap method splicing (Horton et al., 1989, *Gene* 77: 61-68). PCR products were separated on a 1% agarose gel using TAE buffer and a 2263 bp fragment was isolated and purified using a Jetquick gel extraction spin kit.

Figure 4:
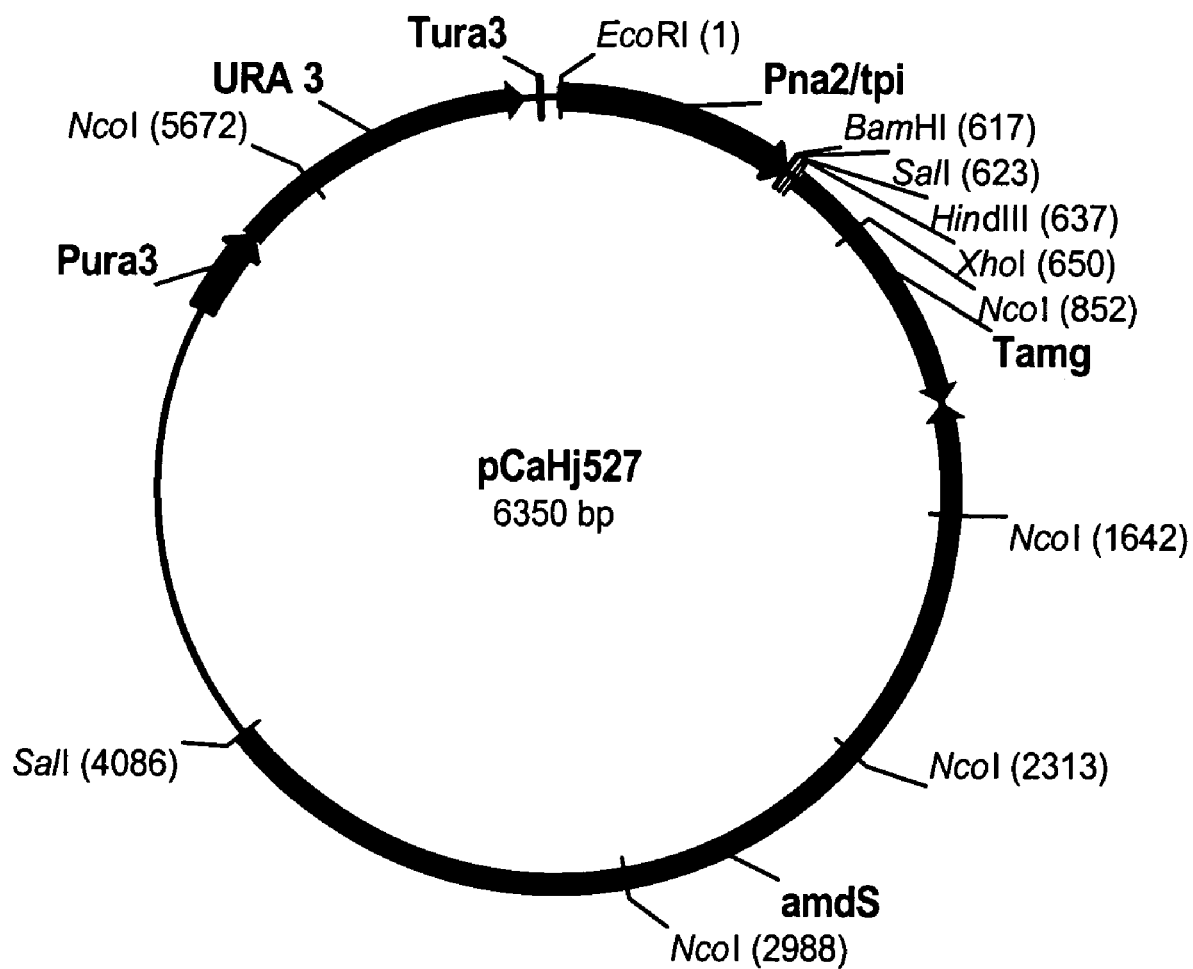
FIG. 4 shows a restriction map of pCaHj527.

The resulting fragment was digested with Eco RI and Bbu I and ligated to the largest fragment of pCaHj483 digested with the same enzymes. The ligation mixture was used to transform pyrF-negative *E. coli* strain DB6507 (ATCC 35673) made competent by the method of Mandel and Higa, 1970, *J. Mol. Biol.* 45: 154. Transformants were selected on solid M9 medium (Sambrook et al., 1989, *Molecular Cloning, A Laboratory Manual*, 2nd edition, Cold Spring Harbor Laboratory Press) supplemented per liter with 1 g of casaminoacids, 500 µg of thiamine, and 10 mg of kanamycin. A plasmid from one transformant was isolated and designated pCaHj527 (FIG. 4).

The NA2-tpi promoter present on pCaHj527 was subjected to site directed mutagenesis by a simple PCR approach. Nucleotides 134-144 were converted from GTACTAAAACC to CCGTTAAATTT using mutagenic primer 141223:

```
Primer 141223:  5'-GGATGCTGTTGACTCCGGAAATTTAACGGTTTGGTCTTGCATCCC-3'  (SEQ ID NO: 11)
```

Nucleotides 423-436 were converted from ATGCAATTTAAACT to CGGCAATTTAACGG using mutagenic primer 141222:

```
Primer 141222:  5'-GGTATTGTCCTGCAGACGGCAATTTAACGGCTTCTGCGAATCGC-3'   (SEQ ID NO: 12)
```

Figure 5:
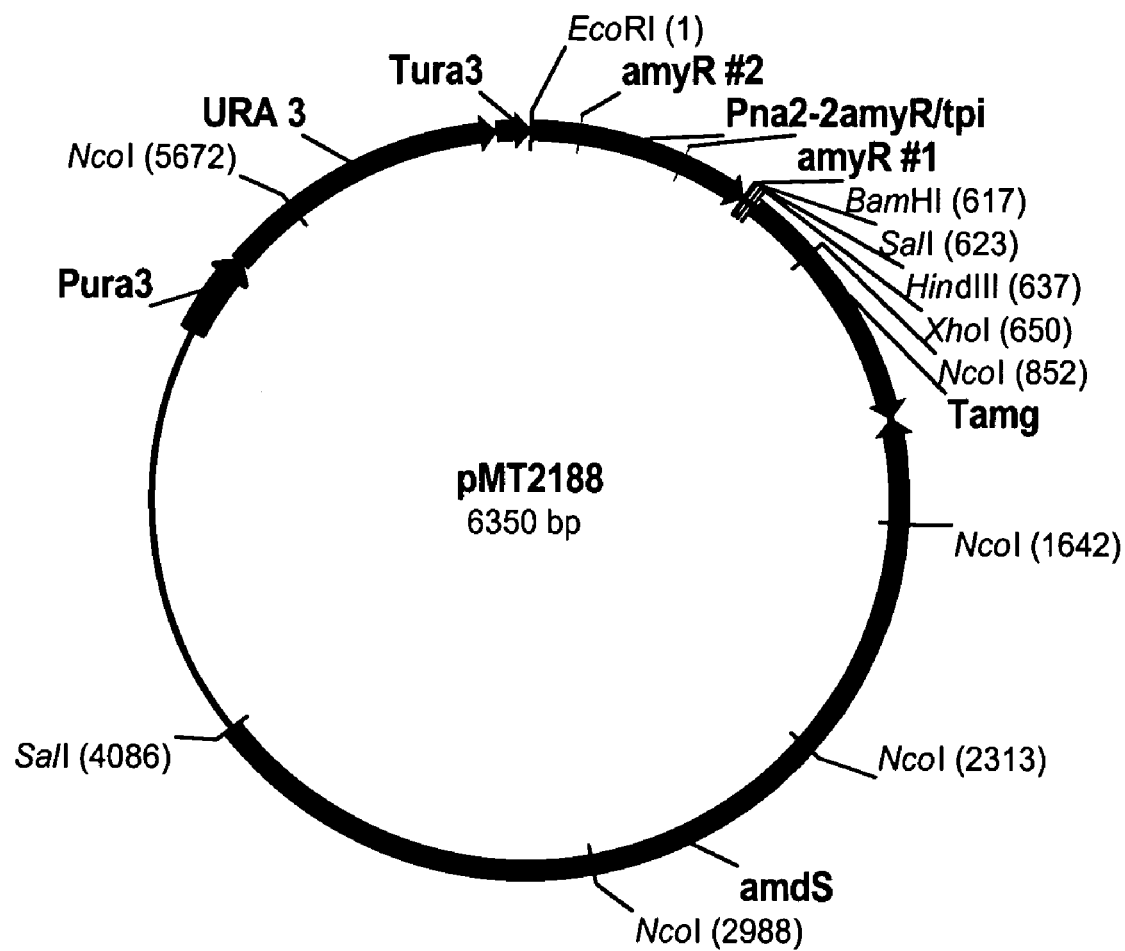
FIG. 5 shows a restriction map of pMT2188.
Figure 6:
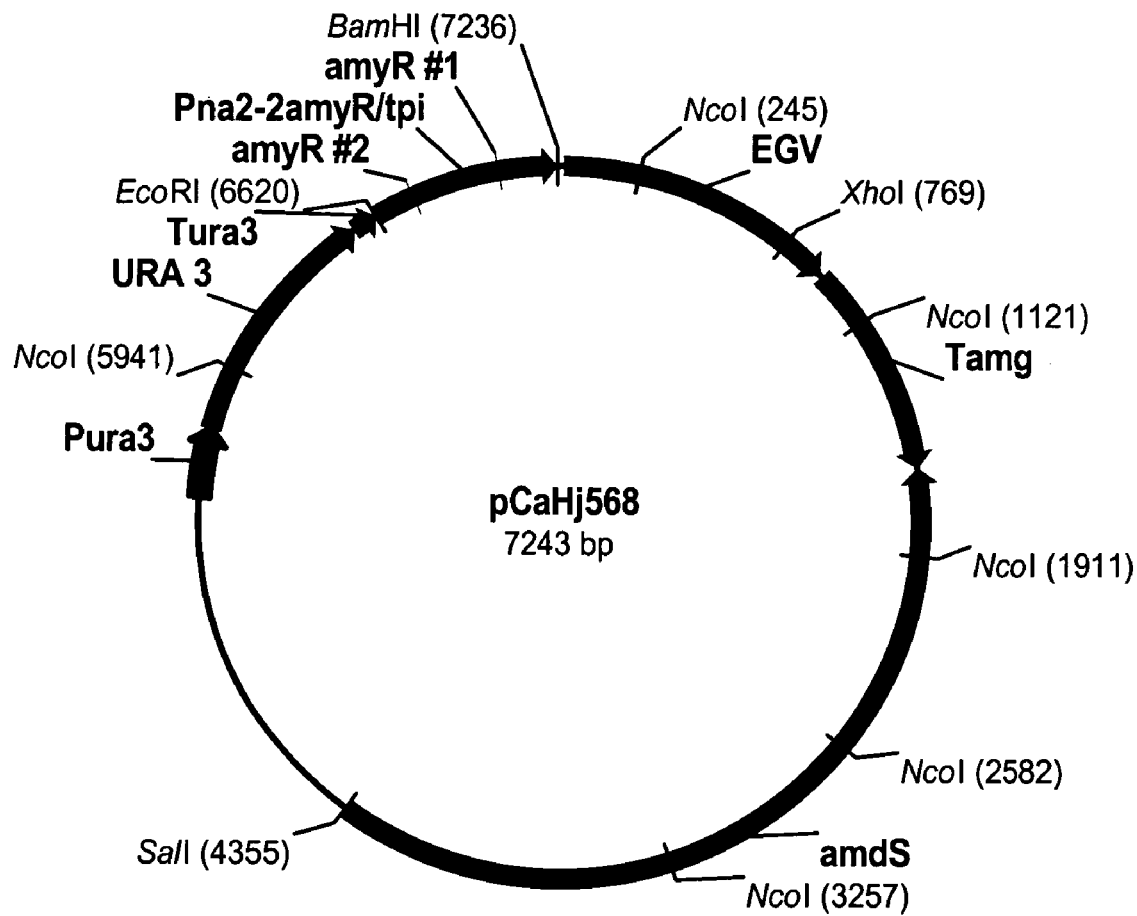
FIG. 6 shows a restriction map of pCaHj568.

The resulting plasmid was designated pMT2188 (FIG. 5).
The *Humicola insolens* endoglucanase V coding region was transferred from pCaHj170as a Bam HI-Sal I fragment into pMT2188 digested with Bam HI and Xho I to generate pCaHj568 (FIG. 6).

Example 4

Construction of pMJ05 Expression Vector

Expression vector pMJ05 was constructed by PCR amplifying the 915 bp *Humicola insolens* endoglucanase V coding region from pCaHj568 using primers HiEGV-F and HiEGV-R shown below.

the promoter and the coding sequence allowed precise fusion of the 994 bp fragment comprising the *Trichoderma reesei* cbh1 promoter to the 918 bp fragment comprising the *Humicola insolens* endoglucanase V open reading frame.

The amplification reactions (50 µl) were composed of 1×ThermoPol Reaction Buffer, 0.3 mM dNTPs, 1 ul of 937 bp purified PCR fragment, 0.3 µM HiEGV-F-overlap primer, 0.3 µM HiEGV-R primer, and 2 units of Vent DNA polymerase. The reactions were incubated in an Eppendorf Mastercycler 5333 programmed as follows: 5 cycles each for 30 seconds at 94° C., 30 seconds at 50° C., and 60 seconds at 72° C.,

```
HiEGV-F (sense):       5'-AAGCTTAAGCATGCGTTCCTCCCCCCTCC-3'    (SEQ ID NO: 13)

HiEGV-R (antisense):   5'-CTGCAGAATTCTACAGGCACTGATGGTACCAG-3'  (SEQ ID NO: 14)
```

The amplification reactions (50 µl) were composed of 1×ThermoPol Reaction Buffer, 0.3 mM dNTPs, 10 ng of pCaHj568 plasmid, 0.3 µM HiEGV-F primer, 0.3 µM HiEGV-R primer, and 2 units of Vent DNA polymerase. The reactions were incubated in an Eppendorf Mastercycler 5333 programmed as follows: 5 cycles each for 30 seconds at 94° C., 30 seconds at 50° C., and 60 seconds at 72° C., followed by 25 cycles each for 30 seconds at 94° C., 30 seconds at 65° C., and 120 seconds at 72° C. (5 minute final extension). The reaction products were isolated on a 1.0% agarose gel using TAE buffer where a 937 bp product band was excised from the gel and purified using a QIAquick Gel Extraction Kit according to the manufacturer's instructions.

This 937 bp purified fragment was used as template DNA for subsequent amplifications using the following primers:

followed by 25 cycles each for 30 seconds at 94° C., 30 at 65° C., and 120 seconds at 72° C. (5 minute final extension). The reaction products were isolated on a 1.0% agarose gel using TAE buffer where a 945 bp product band was excised from the gel and purified using a QIAquick Gel Extraction Kit according to the manufacturer's instructions.

A separate PCR was performed to amplify the *Trichoderma reesei* cbh1 promoter sequence extending from 994 bp upstream of the ATG start codon of the gene from *Trichoderma reesei* RutC30 genomic DNA using the following primers (sense primer was engineered to have a Sal I restriction site at the 5'-end):

```
HiEGV-R (antisense):    5'-CTGCAGAATTCTACAGGCACTGATGGTACCAG-3'     (SEQ ID NO: 15)

HiEGV-F-overlap (sense): 5'-ACCGCGGACTGCGCATCATGCGTTCCTCCCCCCTCC-3'  (SEQ ID NO: 16)
```

Primer sequences in italics are homologous to 17 bp of the *Trichoderma reesei* cbh1 promoter and underlined primer

```
                 TrCBHIpro-F (sense):    5'-AAACGTCGACCGAATGTAGGATTGTTATC-3'   (SEQ ID NO: 17)

TrCBHIpro-R (antisense): 5'-GATGCGCAGTCCGCGGT-3'              (SEQ ID NO: 18)
``` sequences are homologous to 29 bp of the *Humicola insolens* endoglucanase V coding region. The 36 bp overlap between The amplification reactions (50 µl) were composed of 1×ThermoPol Reaction Buffer, 0.3 mM dNTPs, 100 ng of

*Trichoderma reesei* RutC30 genomic DNA, 0.3 µM TrCB-HIpro-F primer, 0.3 µM TrCBHIpro-R primer, and 2 units of Vent DNA polymerase. The reactions were incubated in an Eppendorf Mastercycler 5333 programmed as follows: 30 cycles each for 30 seconds at 94° C., 30 seconds at 55° C., and 120 seconds at 72° C. (5 minute final extension). The reaction products were isolated on a 1.0% agarose gel using TAE buffer where a 998 bp product band was excised from the gel and purified using a QIAquick Gel Extraction Kit according to the manufacturer's instructions.

The 998 bp purified PCR fragment was used to as template DNA for subsequent amplifications using the following primers:

```
TrCBHIpro-F:        5'-AAACGTCGACCGAATGTAGGATTGTTATC-3'         (SEQ ID NO: 19)

TrCBHIpro-R-overlap: 5'-GGAGGGGGGAGGAACGCATGATGCGCAGTCCGCGGT-3'  (SEQ ID NO: 20)
```

Sequences in italics are homologous to 17 bp of the *Trichoderma reesei* cbh1 promoter and underlined sequences are homologous to 29 bp of the *Humicola insolens* endoglucanase V coding region. The 36 bp overlap between the promoter and the coding sequence allowed precise fusion of the 994 bp fragment comprising the *Trichoderma reesei* cbh1 promoter to the 918 bp fragment comprising the *Humicola insolens* endoglucanase V open reading frame.

The amplification reactions (50 µl) were composed of 1×ThermoPol Reaction Buffer, 0.3 mM dNTPs, 1 µM of 998 bp purified PCR fragment, 0.3 µM TrCBH1pro-F primer, 0.3 µM TrCBH1pro-R-overlap primer, and 2 units of Vent DNA polymerase. The reactions were incubated in an Eppendorf Mastercycler 5333 programmed as follows: 5 cycles each for 30 seconds at 94° C., 30 seconds at 50° C., and 60 seconds at 72° C., followed by 25 cycles each for 30 seconds at 94° C., 30 at 65° C., and 120 seconds at 72° C. (5 minute final extension). The reaction products were isolated on a 1.0% agarose gel using TAE buffer where a 1017 bp product band was excised from the gel and purified using a QIAquick Gel Extraction Kit according to the manufacturer's instructions.

The 1017 bp *Trichoderma reesei* cbh1 promoter PCR fragment and the 945 bp *Humicola insolens* endoglucanase V PCR fragments were used as template DNA for subsequent amplification using the following primers to precisely fuse the 994 bp *Trichoderma reesei* cbh1 promoter to the 918 bp *Humicola insolens* endoglucanase V coding region using overlapping PCR.

```
TrCBHIpro-F: 5'-AAACGTCGACCGAATGTAGGATTGTTATC-3'      (SEQ ID NO: 21)

HiEGV-R:     5'-CTGCAGAATTCTACAGGCACTGATGGTACCAG-3'   (SEQ ID NO: 22)
```

The amplification reactions (50 µl) were composed of 1×ThermoPol Reaction Buffer, 0.3 mM dNTPs, 0.3 µM TrCBHIpro-F primer, 0.3 µM HiEGV-R primer, and 2 units of Vent DNA polymerase. The reactions were incubated in an Eppendorf Mastercycler 5333 programmed as follows: 5 cycles each for 30 seconds at 94° C., 30 seconds at 50° C., and 60 seconds at 72° C., followed by 25 cycles each for 30 seconds at 94° C., 30 seconds at 65° C., and 120 seconds at 72° C. (5 minute extension). The reaction products were isolated on a 1.0% agarose gel using TAE buffer where a 1926 bp product band was excised from the gel and purified using a QIAquick Gel Extraction Kit according to the manufacturer's instructions.

Figure 7:
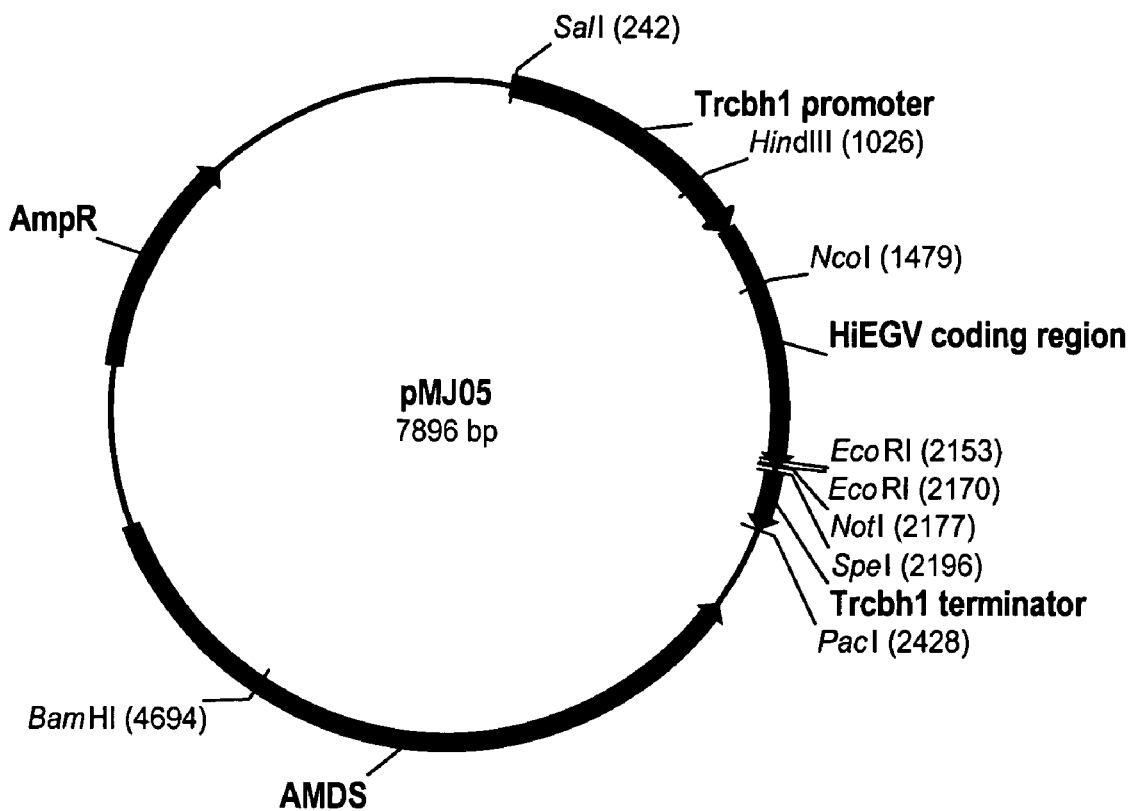
FIG. 7 shows a restriction map of pMJ05.

The resulting 1926 bp fragment was cloned into pCR-Blunt-II-TOPO vector (Invitrogen, Carlsbad, Calif.) using the ZeroBlunt TOPO PCR Cloning Kit following the manufacturer's protocol. The resulting plasmid was digested with Not I and Sal I and the 1926 bp fragment purified and ligated into pMJ04 expression vector, which was also digested with the same two restriction enzymes, to generate pMJ05 (FIG. 7).

Example 5

Construction of pSMai130 Expression Vector

A 2586 bp DNA fragment spanning from the ATG start codon to the TAA stop codon of the *Aspergillus oryzae* beta-glucosidase coding sequence (SEQ ID NO: 1 for cDNA sequence and SEQ ID NO: 2 for the deduced amino acid sequence; *E. coli* DSM 14240) was amplified by PCR from pJaL660 (WO 2002/095014) as template with primers 993467 (sense) and 993456 (antisense) shown below. A Spe I site was engineered at the 5' end of the antisense primer to facilitate ligation. Primer sequences in italics are homologous to 24 bp of the *Trichoderma reesei* cbh1 promoter and underlined sequences are homologous to 22 bp of the *Aspergillus oryzae* beta-glucosidase coding region.

```
Primer 993467: 5'-ATAGTCAACCGCGGACTGCGCATCATGAAGCTTGGTTGGATCGAGG-3'  (SEQ ID NO: 23)

Primer 993456: 5'-ACTAGTTTACTGGGCCTTAGGCAGCG-3'                       (SEQ ID NO: 24)
```

The amplification reactions (50 µl) were composed of Pfx Amplification Buffer (Invitrogen, Carlsbad, Calif.), 0.25 mM dNTPs, 10 n of pJaL660, 6.4 µM primer 993467, 3.2 µM primer 993456, 1 mM MgCl$_2$, and 2.5 units of Pfx polymerase (Invitrogen, Carlsbad, Calif.). The reactions were incubated in an Eppendorf Mastercycler 5333 programmed as follows: 30 cycles each for 60 seconds at 94° C., 60 seconds at 55° C., and 180 seconds at 72° C. (15 minute final extension). The reaction products were isolated on a 1.0% agarose gel using TAE buffer where a 2586 bp product band was excised from the gel and purified using a QIAquick Gel Extraction Kit according to the manufacturer's instructions.

A separate PCR was performed to amplify the *Trichoderma reesei* cbh1 promoter sequence extending from 1000 bp upstream of the ATG start codon of the gene, using primer 993453 (sense) and primer 993463 (antisense) shown below to generate a 1000 bp PCR fragment. Primer sequences in italics are homologous to 24 bp of the *Trichoderma reesei* cbh1 promoter and underlined primer sequences are homologous to 22 bp of the *Aspergillus oryzae* beta-glucosidase coding region. The 46 bp overlap between the promoter and the coding sequence allowed precise fusion of the 1000 bp fragment comprising the *Trichoderma reesei* cbh1 promoter to the 2586 bp fragment comprising the *Aspergillus oryzae* beta-glucosidase open reading frame.

```
Primer 993453: 5'-GTCGACTCGAAGCCCGAATGTAGGAT-3'            (SEQ ID NO: 25)
```

```
Primer 993463: 5'-CCTCGATCCAACCAAGCTTCATGATGCGCAGTCCGCGGTTGACTA-3'   (SEQ ID NO: 26)
```

The amplification reactions (50 µl) were composed of Pfx Amplification Buffer, 0.25 mM dNTPs, 100 ng of *Trichoderma reesei* RutC30 genomic DNA, 6.4 µM primer 993453, 3.2 µM primer 993463, 1 mM MgCl$_2$, and 2.5 units of Pfx polymerase. The reactions were incubated in an Eppendorf Mastercycler 5333 programmed as follows: 30 cycles each for 60 seconds at 94° C., 60 seconds at 55° C., and 180 seconds at 72° C. (15 minute final extension). The reaction products were isolated on a 1.0% agarose gel using TAE buffer where a 1000 bp product band was excised from the gel and purified using a QIAquick Gel Extraction Kit according to the manufacturer's instructions. The purified fragments were used as template DNA for subsequent amplification using primer 993453 (sense) and primer 993456 (antisense) shown above to precisely fuse the 1000 bp *Trichoderma reesei* cbh1 promoter to the 2586 bp *Aspergillus oryzae* beta-glucosidase by overlapping PCR.

The amplification reactions (50 µl) were composed of Pfx Amplification Buffer, 0.25 mM dNTPs, 6.4 µM primer 99353, 3.2 µM primer 993456, 1 mM MgCl$_2$, and 2.5 units of Pfx polymerase.

The reactions were incubated in an Eppendorf Mastercycler 5333 programmed as follows: 30 cycles each for 60 seconds at 94° C., 60 seconds at 60° C., and 240 seconds at 72° C. (15 minute extension).

Figure 8:
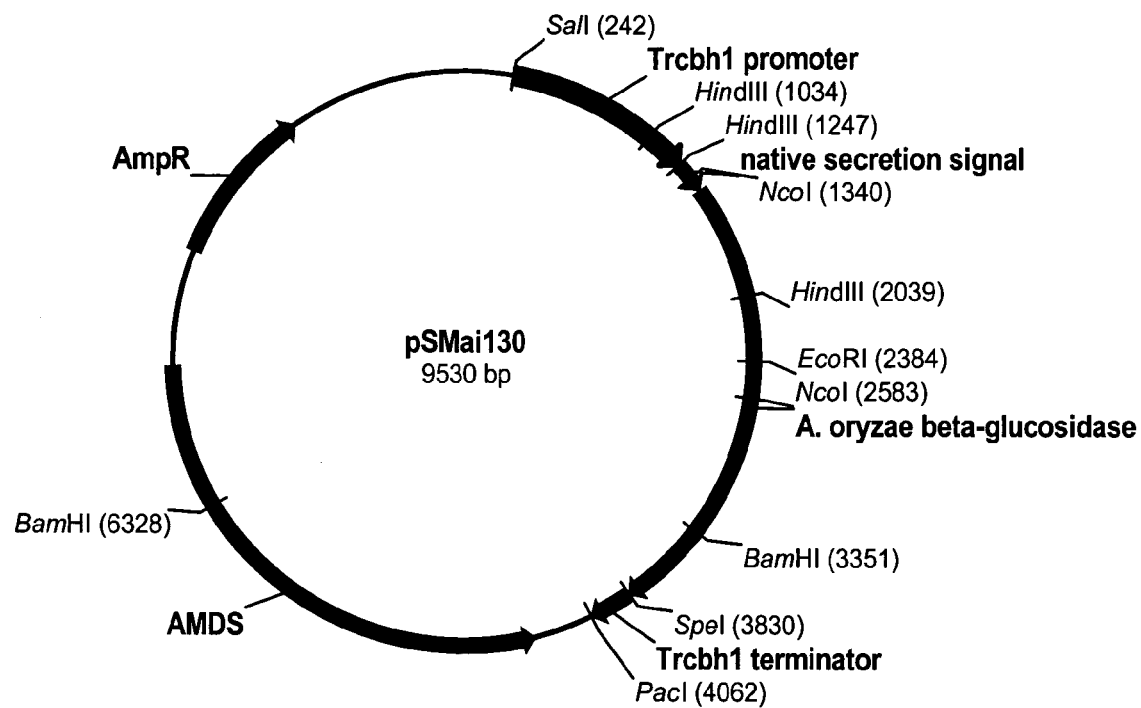
FIG. 8 shows a restriction map of pSMai130.

The resulting 3586 bp fragment was digested with Sal I and Spe I and ligated into pMJ04, digested with the same two restriction enzymes, to generate pSMai130 (FIG. 8).

Example 6

Construction of pSMai135

The *Aspergillus oryzae* beta-glucosidase coding region (minus the putative native signal sequence, see FIG. 9) from Lys-20 to the TAA stop codon was PCR amplified from pJaL660 (WO 2002/095014) as template with primer 993728 (sense) and primer 993727 (antisense) shown below. Sequences in italics are homologous to 20 bp of the *Humicola insolens* endoglucanase V signal sequence and sequences underlined are homologous to 22 bp of the *Aspergillus oryzae* beta-glucosidase coding region. A Spe I site was engineered into the 5' end of the antisense primer.

```
Primer 993728: 5'-TGCCGGTGTTGGCCCTTGCCAAGGATGATCTCGCGTACTCCC-3'   (SEQ ID NO: 27)
```

```
Primer 993727: 5'-GACTAGTCTTACTGGGCCTTAGGCAGCG-3'            (SEQ ID NO: 28)
```

The amplification reactions (50 µl) were composed of Pfx Amplification Buffer, 0.25 mM dNTPs, ng of pJaL660, 6.4 µM primer 993728, 3.2 µM primer 993727, 1 mM MgCl$_2$, and 2.5 units of Pfx polymerase. The reactions were incubated in an Eppendorf Mastercycler 5333 programmed as follows: 30 cycles each for 60 seconds at 94° C., 60 seconds at 55° C., and 180 seconds at 72 (15 minute final extension). The reaction products were isolated on a 1.0% agarose gel using TAE buffer where a 2523 bp product band was excised from the gel and purified using a QIAquick Gel Extraction Kit according to the manufacturer's instructions.

A separate PCR amplification was performed to amplify 1000 bp of the *Trichoderma reesei* cbh1 promoter and 63 bp of the putative *Humicola insolens* endoglucanase V signal sequence (ATG start codon to Ala-21, FIG. 10, SEQ ID NO: 29), using primer 993724 (sense) and primer 993729 (antisense) shown below. Primer sequences in italics are homologous to 20 bp of the *Humicola insolens* endoglucanase V signal sequence and underlined primer sequences are homologous to 22 bp of the *Aspergillus oryzae* beta-glucosidase coding region. Plasmid pMJ05, which comprises the *Humicola insolens* endoglucanase V coding region under the control of the cbh1 promoter, was used as a template to generate a 1063 bp fragment comprising the *Trichoderma reesei* cbh1 promoter/*Humicola insolens* endoglucanase V signal sequence fragment. A 42 bp of overlap was shared between the *Trichoderma reesei* cbh1 promoter/*Humicola insolens* endoglucanase V signal sequence and the *Aspergillus oryzae* coding sequence to provide a perfect linkage between the promoter and the ATG start codon of the 2523 bp *Aspergillus oryzae* beta-glucosidase.

Primer 993724: 5'-ACGCGTCGACCGAATGTAGGATTGTTATCC-3' (SEQ ID NO: 30)

Primer 993729: 5'-<u>GGGAGTACGCGAGATCATCCTT</u>GGCAAGGGCCAACACCGGCA-3' (SEQ ID NO: 31)

The amplification reactions (50 µl) were composed of Pfx Amplification Buffer, 0.25 mM dNTPs, 10 ng/µl pMJ05, 6.4 µM primer 993728, 3.2 µM primer 993727, 1 mM MgCl$_2$, and 2.5 units of Pfx polymerase. The reactions were incubated in an Eppendorf Mastercycler 5333 programmed as follows: 30 cycles each for 60 seconds at 94° C., 60 seconds at 60° C., and 240 seconds at 72° C. (15 minute final extension). The reaction products were isolated on a 1.0% agarose gel using TAE buffer where a 1063 bp product band was excised from the gel and purified using a QIAquick Gel Extraction Kit according to the manufacturer's instructions.

The purified overlapping fragments were used as a template for amplification using primer 993724 (sense) and primer 993727 (antisense) described above to precisely fuse the 1063 bp fragment comprising the *Trichoderma reesei* cbh1 promoter/*Humicola insolens* endoglucanase V signal sequence to the 2523 bp fragment comprising the *Aspergillus oryzae* beta-glucosidase open reading frame by overlapping PCR.

The amplification reactions (50 µl) were composed of Pfx Amplification Buffer, 0.25 mM dNTPs, 6.4 µM primer 993724, 3.2 µM primer 993727, 1 mM MgCl$_2$, and 2.5 units of Pfx polymerase. The reactions were incubated in an Eppendorf Mastercycler 5333 programmed as follows: 30 cycles each for 60 seconds at 94° C., 60 seconds at 60° C., and 240 seconds at 72° C. (15 minute extension). The reaction products were isolated on a 1.0% agarose gel using TAE buffer where a 3591 bp product band was excised from the gel and purified using a QIAquick Gel Extraction Kit according to the manufacturer's instructions.

Figure 11:
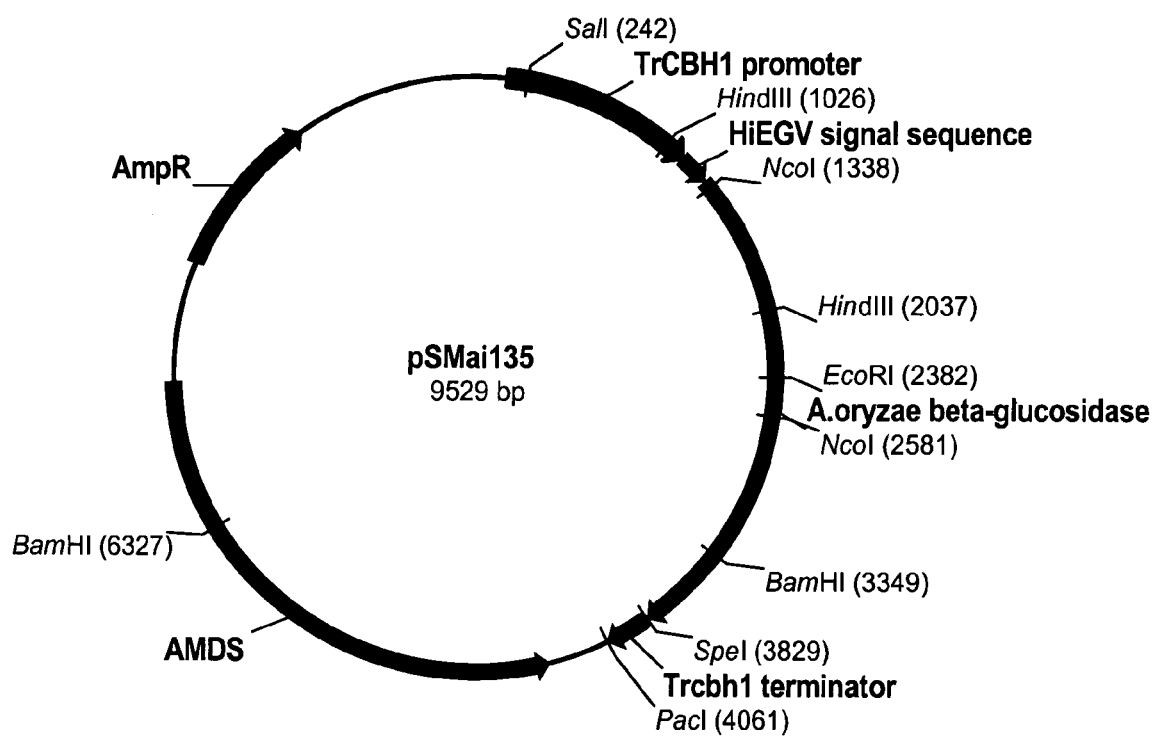
FIG. 11 shows a restriction map of pSMai135.

The resulting 3591 bp fragment was digested with Sal I and Spe I and ligated into pMJ04 digested with the same restriction enzymes to generate pSMai135 (FIG. 11).

Example 7

Construction of pALFd1 *Saccharomyces cerevisiae* Expression Vector

Plasmid pALFd1 was generated from pSATe111 to swap the native *Aspergillus oryzae* beta-glucosidase secretion signal with the secretion signal of the *Humicola insolens* endoglucanase V to enhance *Aspergillus oryzae* beta-glucosidase production and secretion in *Saccharomyces cerevisiae*. Plasmid pSATe111 was digested with Xho I and Spe I to release a 2.6 kb fragment (*Aspergillus oryzae* beta-glucosidase) and a 6 kb (rest of the vector) fragment. The digestion was run in a 0.7% agarose gel using TAE buffer and the 6 kb fragment was isolated by gel purification using a QIAquick Gel Extraction Kit (QIAGEN Inc., Valencia, Calif.) following the manufacturer's protocol and ligated to the 2.6 kb PCR fragment, containing the *Aspergillus oryzae* beta-glucosidase coding region (minus the secretion signal sequence) and the *Humicola insolens* endoglucanase V signal sequence, which was amplified from pSMai135 using primers 993950 and 993951 shown below. The primers contain Spe I and Xho I restriction sites at their ends for subsequent subcloning into the SpeI and Xho I restriction sites of pSATe111.

Primer 993950: 5'-AATCCGACTAGTGGATCTACCATGCGTTCCTCCCCCCTCC-3' (SEQ ID NO: 32)

Primer 993951: 5'-GCGGGCCTCGAGTTACTGGGCCTTAGGCAGCG-3' (SEQ ID NO: 33)

Figure 12:
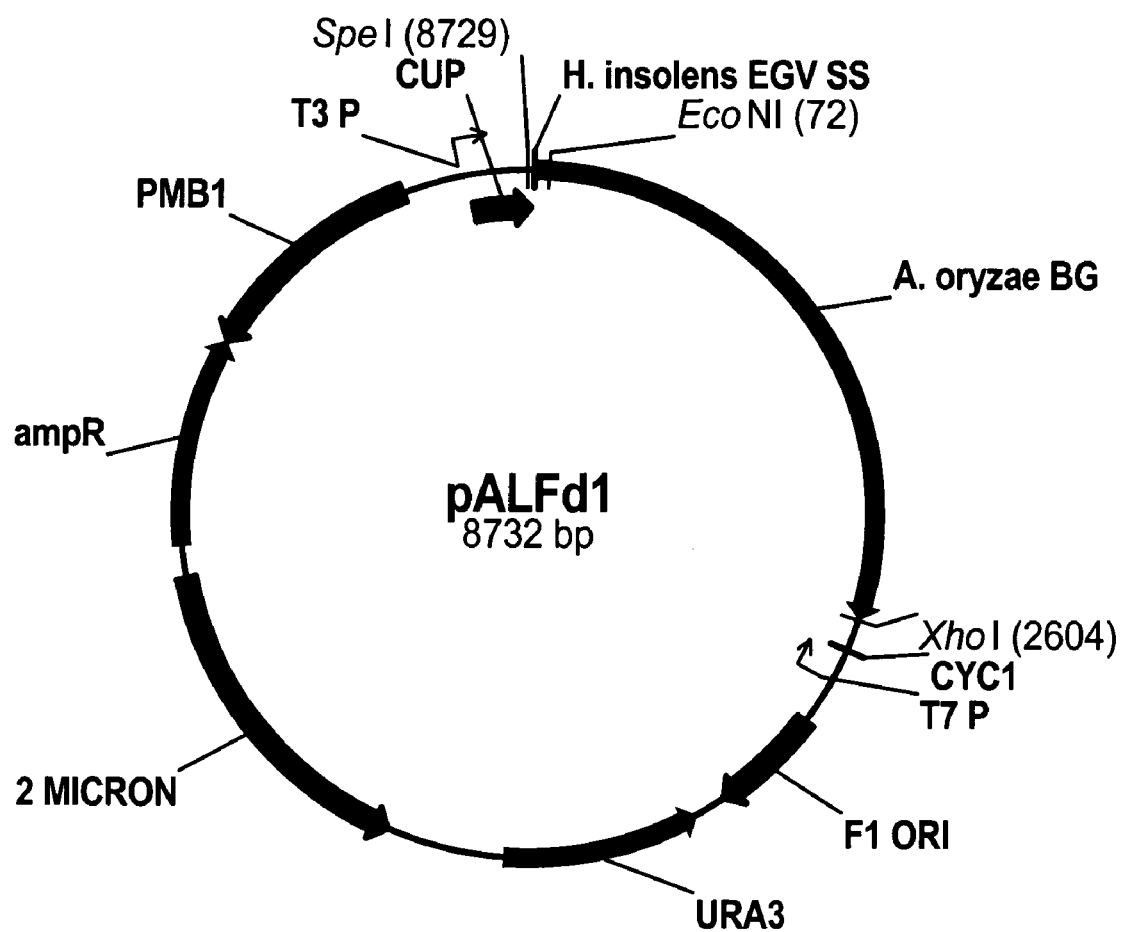
FIG. 12 shows a restriction map of pALFd1.

The amplification reactions (100 µM) were composed of PCR Thermo Pol Buffer, 0.20 mM dNTPs, 0.14 µg of pSMai135 µlasmid DNA, 50 µM primer 993950, 50 µM primer 993951, and 2 units of Vent DNA polymerase. The reactions were incubated in a RoboCycler Gradient 40 Thermal Cycler (Stratagene, La Jolla, Calif.) programmed as follows: one cycle of 1 minute at 95° C., and 25 cycles each for 1 minute at 95° C., 1 minute at 60 or 64° C., and 3 minutes at 72° C. (10 extension). The reaction products were visualized on a 0.7% agarose gel using TAE buffer. The resulting 2.6 kb fragments were purified using a PCR MinElute PCR Purification (QIAGEN, Chatsworth, Calif.) according to the manufacturer's instructions. The purified fragments were combined and digested with Spe I and Xho I and ligated into pSATe111 digested with the same two restriction enzymes to generate pALFd1 (FIG. 12).

Example 8

Generation of Primary Libraries of Mutagenized Beta-glucosidase in *Saccharomyces cerevisiae*

In an effort to identify regions on the *Aspergillus oryzae* beta-glucosidase that are critical for protein thermostability, the entire wild-type *Aspergillus oryzae* beta-glucosidase gene was mutagenized using error-prone PCR with homologous sequences to the yeast expression vector pSATe111, which can undergo in vivo recombination between homologous domains of distinct fragments. This process generated circular, replicating plasmids from a combination of linearized vector and PCR products.

Primer 992328 (from Example 1) and primer AoJal660.2, shown below, were used in the error-prone PCR amplification of the beta-glucosidase gene from pSATe101 to generate mutagenized sequences that could be cloned into pSATe111 for expression of the beta-glucosidase enzyme in yeast.

Primer AoJal660.2: 5'-AGGGTGAATGGGCGGAA-3' (SEQ ID NO: 34)

The error-prone PCR amplifications (50 µl) were composed of 1×Taq buffer containing 1.5 mM MgCl$_2$ (Promega Corporation, Madison, Wis.), 60 ng of pSATe101, 0.16 mM dATP, 0.07 mM each of dCTP, dGTP, and dTTP, 50 µM of primer AoJA1660.2, 50 µM of primer 992328, 0.1 mM MnCl$_2$, and 5 units of Taq DNA polymerase (Promega Corporation, Madison, Wis.). The amplification reactions were incubated as described in Example 1.

Plasmid pSATe111 was gapped by digestion with Eco RI and Sma I, and then gel purified using QiaexII resin (QIAGEN Inc., Valencia, Calif.). The digestion was verified by fractionating an aliquot of the digestion on a 0.7% agarose gel using TAE buffer and staining with ethidium bromide where expected fragments of 8,054 bp (gapped vector containing part of the beta-glucosidase coding sequence) and 672 bp (from the beta-glucosidase gene) were obtained. The digestion was purified using QiaexII resin.

Three µl aliquots of the above PCR reactions were mixed with 0.5 µl of the gapped pSATe111 vector for cotransformation into *Saccharomyces cerevisiae* YNG318 competent cells. The co-transformed fragments contained at least 250 bp of homologous DNA sequence at the ends to facilitate gap repair of the expressed plasmid. Competent cells of *Saccharomyces serevisiae* YNG 318 were prepared prior to each transformation following the YEASTMAKER Yeast Transformation Protocol (CLONTECH Laboratories, Inc., Palo Alto, Calif.) with the following modifications: (1) The volume of yeast culture used to inoculate the overnight incubation (16-20 hours) was between 100-1,000 µl; (2) recovery of cells upon transformation was performed in YPD medium for 45 minutes at 30° C.; and (3) the transformation mixture was aliquoted for plating onto yeast selection plate medium while the remainder of the transformants were frozen at −80° C. in a controlled rate freezer (Nalge Nunc International, Rochester, N.Y.).

Plates were incubated at 30° C. for approximately 4 days. Colonies producing active beta-glucosidase turned blue after incubation due to beta-glucosidase hydrolysis of X-Glc. Activity of the library was estimated by the percentage of blue colonies obtained. The library was 67% active.

Example 9

Screening of Beta-glucosidase Libraries

The primary beta-glucosidase library was spread on Genetix QTray's (22×22 cm Petri dishes, Genetics Ltd., Hampshire, United Kingdom) and incubated for 5 days at 30° C. Using a Genetix QPix (Genetix Ltd., Hampshire, United Kingdom), active colonies were picked using X-Glc selection into 96-well plates containing yeast selection medium. Plates were incubated for 7 days at 30° C. Screening buffer (0.1 M succinate pH 5) was added to the growth plates prior to the start of the screen. Using an ORCA robot (Beckman Coulter, Fullerton, Calif.), the growth plates were transported to a Multimek (Beckman Coulter, Fullerton, Calif.) and samples were taken from the growth plate and mixed into 96-well polycarbonate v-bottom plates. Samples were then taken from the v-bottom plates and dispensed into empty 96-well flat bottom plates for an initial plate assay with p-nitrophenyl-beta-D-glucopyranoside as substrate in 0.1 M succinate pH 5 at ambient temperature. The v-bottom plate was transported to a custom 96-well heating block and incubated at 65° C. for a total of 10 minutes. Samples were then taken from the v-bottom plates subjected to the heating block and dispensed into empty 96-well flat bottom plates for a final plate assay with p-nitrophenyl-beta-D-glucopyranoside as substrate in 0.1 M succinate pH 5 at ambient temperature. The initial and final assay plates were then transported to a Multidrop (Labsystems, Vantaa, Finland) where the p-nitrophenyl-beta-D-glucopyranoside substrate was added. After the predetermined assay incubation time had expired, between 30-120 minutes, the initial and final assay plates were quenched with 2 M Tris pH 8 buffer. Both plates were read using a Spectramax plate reader (Molecular Devices, Sunnyvale, Calif.) at 405 nm. The ratio of the final read to the initial read was calculated using Microsoft Excel (Microsoft Corporation, Redmond, Wash.) to determine the percent residual activity (% RA). Based on % RA measurements, screening of the libraries constructed in Example 8 generated two variants: BG13 and BG14. The residual activity produced by these variants was 13% and 17% for BG13 and BG14, respectively.

Example 10

Shuffled Library of Beta-glucosidase Variants BG13 and BG14

To shuffle the DNA of beta-glucosidase variants BG13 and BG14 of Example 9, plasmid DNA was isolated from the variants. Each variant was grown at 30° C. overnight in 3 ml of yeast selection medium containing 75 µg of chloramphenicol to prevent contamination. Samples of 100 µl from the overnight cultures were centrifuged for 3 minutes at 13,200× g. The supernatant was removed and DNA was isolated from the remaining pellet according to the protocol described by Kaiser and Auer, 1993, *BioTechniques* 14 (4): 552, except 20 µl of yeast lysis buffer was used.

The *Aspergillus oryzae* beta-glucosidase genes from variants BG13 and BG14 were amplified by PCR using the following primers:

```
pSATe1115'nested primer: 5'-GACATTTTTGCTGTCAGTCA-3' (SEQ ID NO: 35)
pSATe1113'nested primer: 5'-AATGTTACATGCGTACACGC-3' (SEQ ID NO: 36)
```

Three PCR reactions using DNA rescued from variant BG13 as a template and 5 reactions using DNA rescued from variant BG14 were conducted. The amplification reactions (100 µl) were composed of 0.5 µl of yeast plasmid DNA, 1×AmpliTaq buffer not containing MgCl$_2$, 125 µM each of dATP, dCTP, dGTP, and dTTP, 50 pmole of each primer, 1.5 mM MgCl$_2$, and 1 unit of AmpliTaq DNA polymerase (PE Applied Biosystems, Foster City, Calif.). The reactions were incubated in an Eppendorf Mastercycler 5333 programmed for 1 cycle at 95° C. for 5 minutes; 25 cycles each at 95° C. for 1 minute, 50° C. for 1 minute; and 72° C. for 3 minutes; and a final extension cycle at 72° C. for 10 minutes. The three PCR reactions for BG13 and five PCR reactions for BG14 were combined and purified using a QIAquick PCR Purification Kit (QIAGEN Inc., Valencia, Calif.). DNA was eluted into 30 µl of EB buffer (QIAGEN Inc., Valencia, Calif.). The concentration of the purified PCR products obtained after amplification of each variant was verified by visualization in a 0.7% agarose gel run in TAE buffer and stained with ethidium bromide. Each variant yielded 125 ng of DNA per microliter.

For shuffling of the DNA of BG13 and BG14 variants, 3.2 µl (400 ng) of the BG13 PCR product and 3.2 µl (400 ng) of the BG14 PCR product were combined with 2 µl (400 ng) of gapped pSATe111 prepared as described in Example 8, except Spe I and Xho I were used to gap the vector and then transformed into freshly made competent *Saccharomyces serevisiae* YNG 318 cells as described in Example 8. The generated library was 78% active based on the percentage of blue colonies generated.

Totally, 6,336 active colonies from this library were picked and screened as described in Example 9, which resulted in the isolation of 6 improved thermostable variants, four of which were designated BG40, BG41, BG42, and BG43. For sequencing of the DNA of variants BG40, BG41, BG42, and BG43, DNA was isolated from a 100 µl sample of yeast selection broth according to the procedure of Kaiser and Auer, 1993, supra. The isolated DNA was transformed into *E. coli* SURE electroporation-competent cells according to the manufacturer's instructions. Plasmid DNA was isolated as described previously and then sequenced.

The entire coding region of each *Aspergillus oryzae* beta-glucosidase variant gene was sequenced using 0.5 µl of plasmid DNA and 3.2 µmol of the following primers:

Variant BG42 possessed three mutations with two being silent. The only actual amino acid substitution was H266Q.

Variant BG43 possessed three mutations, one being silent. The E-13V amino acid substitution was located in the predicted signal sequence and the H266Q amino acid substitution was found in the active site of the protein.

The only common amino acid substitution found in all of the isolated variants was H266Q.

Example 11

Second Round of Shuffling of Beta-glucosidase Improved Variants

To generate a shuffled library with several of the mutants previously isolated, the beta-glucosidase coding regions of the BG41 and BG43 variants were amplified using plasmid DNA isolated as described previously. A 100 µl PCR reaction was performed as described in Example 10 except 200 µM of each dATP, dCTP, dGTP, and dTTP and 1×AmpliTaq buffer

```
AoJa1660.1:    5'-GTTTCGGCTCAGGACTG-3'      Position: 2492 Forward (SEQ ID NO: 37)

AoJa1660.1a:   5'-ACTTCCGCCCATTCACC-3'      Position: 141 Reverse (SEQ ID NO: 38)

AoJa1660.2:    5'-AGGGTGAATGGGCGGAA-3'      Position: 123 Forward (SEQ ID NO: 39)

AoJa1660.2a:   5'-GGCGGAAATGCTCTTGT-3'      Position: 614 Reverse (SEQ ID NO: 40)

AoJa1660.3:    5'-GGATGGCGGTAGAAACT-3'      Position: 469 Forward (SEQ ID NO: 41)

AoJa1660.3a:   5'-GCGGTCCAATCACTCAT-3'      Position: 861 Reverse (SEQ ID NO: 42)

AoJa1660.4:    5'-GCTACGGTTGCGAGAAT-3'      Position: 774 Forward (SEQ ID NO: 43)

AoJa1660.4a:   5'-CTCAAGGGCAAGGCACC-3'      Position: 1232 Reverse (SEQ ID NO: 44)

AoJa1660.5:    5'-GGTGCCTTGCCCTTGAG-3'      Position: 1232 Forward (SEQ ID NO: 45)

AoJa1660.5a:   5'-TTCGCTGCGGTCTTGAC-3'      Position: 1629 Reverse (SEQ ID NO: 46)

AoJa1660.6:    5'-GTGGAAGAACGGCGACA-3'      Position: 1591 For (SEQ ID NO: 47)

AoJa1660.6a:   5'-CCCAGCCGTAGTTAGAA-3'      Position: 2195 Rev (SEQ ID NO: 48)

AoJa1660.7:    5'-CGTCCCGATACACTCCC-3'      Position: 2019 For (SEQ ID NO: 49)

AoJa1660.7a:   5'-CCTGGAGCGGCAGTTTC-3'      Position: 2573 Rev (SEQ ID NO: 50)

AoJa1660.8:    5'-GGTCGGTGTCCTTAACGG-3'     Position 964 For (SEQ ID NO: 51)

AoJaI.660.8a:  5'-ACTATCCTGCAAACACAAGC-3'   Position: 292 Rev (SEQ ID NO: 52)

AoJa1660.9:    5'-CCTTTCACTTGGGGCA-3'       Position 1802 For (SEQ ID NO: 53)

AoJa1660.9a:   5'-GGAGTTACCAGACTCCTGGC-3'   Position 1756 Rev (SEQ ID NO: 54)

AoJa1660.10a:  5'-ACCTTCCGAAACATGGTTAT-3'   Position 1132 Rev (SEQ ID NO: 55)
```

Sequencing indicated there were consistent mutations in the mutants isolated that led to amino acid substitutions. Variant BG40 possessed 5 mutations, in which 3 of them led to amino acid substitutions. The first mutation, which led to the substitution G4S, was found in the predicted signal peptide sequence of beta-glucosidase. Three mutations were found in the active site of the protein, but only 1 of the mutations led to an amino acid substitution: H266Q. A final mutation was found in the X-domain of the protein: D365N. The X-domain is the region outside of the active site region.

Variant BG41 possessed three mutations with two of them leading to amino acid substitutions: G142S and H266Q. All substitutions were found in the active site of the protein.

containing 1.5 mM $MgCl_2$ were used. The amplified beta-glucosidase inserts (BG41 and BG43) were purified as described in Example 10 each yielding an estimated DNA concentration of 125 ng per microliter. The coding regions of BG13 and BG14 variants were also further amplified and purified for shuffling by using 1 µl of plasmid DNA in a PCR reaction as described in Example 10. The yield of each purified product was 1,250 ng per microliter for BG13 and 125 ng per microliter for BG14.

A fifth variant designated BG2 was generated as described in Example 8 using the primers described in Example 10, and isolated by screening as described in Example 9. DNA of variant BG2 was also added to the shuffle with the DNA of BG13, BG14, BG41, BG43, but later analysis showed that BG2 was a false-positive. The purified PCR product for each mutant was combined (125 ng each, except for BG14 where 12.5 ng was used) with 400 ng of pSATe111 gapped with Spe I/Xho I for transformation by gap repair into 50 µl of *Saccharomyces cerevisiae* YNG318 competent cells as described in Example 8. The resulting library was 93.9% active based on the percentage of blue colonies.

Screening of the library was performed as described in Example 9, except plates were incubated at 68° C. Totally, 15,439 active clones were picked from the library and screened, which resulted in the isolation of variants BG47, BG48, and BG 49, which had 53%, 87%, and 21% residual activity after incubation for 10 minutes at 68° C. using p-nitrophenyl-beta-D-glucopyranoside as substrate as described in Example 9.

For sequencing of the DNA of variants BG47, BG48, and BG 49, DNA was isolated as described in Example 10, except DNA was isolated from a 500 µl sample of yeast selection broth and transformed into *E. coli* XL-10 Gold ultracompetent cells.

Sequencing of these mutants revealed that variant BG47 contained an E-13V amino acid substitution in the signal sequence, a silent mutation, and two amino acid substitutions at G142S and H266Q in the active site. Variant BG48 contained the same mutations as found in variant BG41 plus amino acid substitutions at A16T in the active site and at D703G in the X domain. Variant BG49 was identical to BG43.

Example 12

Generation of a Site-specific Randomized Library at Positions G142 and H266

In an effort to identify the best substitutions at positions 142 and 266, which were present in the BG41 variant, the nucleotides that encode the amino acids at these positions, G166S and H266Q, in BG41, were randomized by replacing them with NN(G/C). Therefore, the region that encodes these amino acids in the *Aspergillus oryzae* beta-glucosidase gene was amplified by PCR and transformed with the pSATe111BG41 which was digested with BlpI, so that the amplified PCR fragments which are homologous to the linearized yeast expression vector pSATe111BG41, with the exception of the degenerated nucleotides, could undergo in vivo recombination when transformed into *Saccharomyces cerevisiae*. This process generated circular, replicating plasmids from a combination of linearized vector and PCR products.

Primer BG41SDMUpper (which contains degenerated nucleotides at the position which encodes the amino acid 143, in bold) and primer BG41SDMLower (which contains degenerated nucleotides at the position which encodes the amino acid 266, in bold), shown below, were used in the PCR amplification of the beta-glucosidase gene from pSATe111BG41 to generate a partial sequence of the beta-glucosidase gene that contains these randomized positions and could be cloned into pSATe111BG41 for expression of the beta-glucosidase enzyme in yeast.

The PCR amplifications (100 µl) were composed of 1×Pfx Amplification Buffer, 150 ng of pSATe111BG41, 2 µM of 10 mM blend of dATP, dTTP, dGTP, and dCTP, 3 µM of 50 mM MgSO$_4$ 50 µM of primer BG41SDMUpper, 50 µM of primer BG41LowerLower, 2.5 units of Platinum Pfx DNA Polymerase (Invitrogen, Carlsbad, Calif.). The amplification conditions were one cycle at 95° C. for 5 minutes; 25 cycles each at 95° C. for 1 minute, 52, 55, 58, or 61° C. for 1 minute, and 72° C. for 30 seconds; and a final cycle of 72° C. for 10 minutes. The heat block then went to a 4° C. soak cycle.

Plasmid pSATe 111BG41 was linearized by digestion with Blp I, and then cleaned up using the QIAquick Nucleotide Removal Kit (QIAGEN Inc., Valencia, Calif.) following the manufacturer's instructions. The four above PCR reactions were combined and cleaned up using a QIAquick PCR Purification Kit and eluted in 10 µl of EB buffer following manufacturer's instructions. An aliquot of 7 µl of the cleaned PCR product (3.5 µg) was combined with 560 ng of the linearized pSATe111BG41 vector for cotransformation into *Saccharomyces cerevisiae* YNG318 competent cells as described as in Example 8. The library was 82.8% active. The high activity of this library suggested the randomization of the G142 and H266 positions was not successful. However, this library was still screened as described in Example 9.

Example 13

Third Round of Shuffling of Beta-glucosidase Improved Variants

To obtain a further improved variant, a shuffled library with the DNA of the previously described variants BG2, BG13, BG14, and BG48 was constructed as well as with variant BG50, which arose from generation of a site-specific randomized library as described in Example 12 and was isolated by screening as described in Example 9. The DNA of this variant was partially sequenced and had the same mutations as present in its parental sequence, BG41, but with an extra mutation: Q183R. Therefore, this variant was a product of mutagenesis in the amplification reaction of the pSATe111BG41 vector. Generation of the library was performed as described in Example 10. Screening of the library was performed as described in Example 9, except plates were incubated at 70° C. The library led to the isolation of variants BG52, BG53, and BG54, which had a % RA of 60%, 65%, 50%, respectively, at 70° C. Sequencing of the DNA of these variants was performed as described in Example 10. Variant BG52 had the same substitutions as BG48 with a S-5P substitution in the predicted signal sequence. Variant BG53 had the same substitutions as BG41 with the addition of a Q183R substitution and the same D703G amino acid substitution present in BG48. BG54 contained the following substitutions: S-5P, G142S, Q183R, and H266Q.

Table 1 summarizes the variants obtained from screening of either the primary or shuffled libraries and their amino acid substitutions. Table 2 shows the thermostability of the variants at 65° C., 68° C., and 70° C. for 10 minutes. Mutations in the DNA sequence that led to amino acid substitutions are in bold. Mutations in the DNA sequence that did not led to amino acid substitutions are in plain text.

```
Primer BG41SDMUpper:    5'-GGTAGAAACTGGGAANNSTTCTCACCAGATCCAGCCCTC-3'   (SEQ ID NO: 56)

Primer BG41LowerLower:  5'-GCCTACGCCGCTGTGNNSAGCGGTCCAATCACT-3'          (SEQ ID NO: 57)
```

TABLE 1

Thermostable Beta-Glucosidase Variants

| Mutant | Amino acid substitutions | Library origin |
|---|---|---|
| BG13 | N/A | Primary of WT BG |
| BG14 | N/A | Primary of WT BG |
| BG40 | G-16S; V226V; H266Q; P335P; D365N | Shuffling BG13 and BG14 |
| BG41 | G142S; V226V; H266Q | Shuffling BG13 and BG14 |
| BG42 | V226V; H266Q; N514N | Shuffling BG13 and BG14 |
| BG43 | E-13V; V226V; H266Q | Shuffling BG13 and BG14 |
| BG47 | E-13V; C55C; G142S; H266Q | Shuffling "BG2", BG13, BG14, BG 43 |
| BG48 | A16T; A132A; G142S; V226V; H266Q; D703G | Shuffling "BG2", BG13, BG14, BG 43 |
| BG49 | E-13V, V226V; H266Q | Shuffling "BG2", BG13, BG14, BG 43 |
| BG50 | Partial seq. G142S; Q183R; V226V; H266Q | Primary of BG41 |
| BG52 | S-5P; A16T; G142S; H266Q; D703G | Shuffling "BG2", BG13, BG14, BG48, BG50 |
| BG53 | G142S; Q183R; H266Q; D703G | Shuffling "BG2", BG13, BG14, BG48, BG50 |
| BG54 | S-5P; G142S; Q183R; H266Q | Shuffling "BG2", BG13, BG14, BG48, BG50 |

TABLE 2

Thermostability of Beta-Glucosidase Variants

| Mutant | Amino acid substitutions | % RA at 65° C. | % RA at 68° C. | % RA at 70° C. |
|---|---|---|---|---|
| BG13 | N/A | 13% | N/A | N/A |
| BG14 | N/A | 17% | N/A | N/A |
| BG40 | G-16S; V226V; H266Q; P335P; D365N | 54% | N/A | N/A |
| BG41 | G142S; V226V; H266Q | 79% | 45% | N/A |
| BG42 | V226V; H266Q; N514N | 45% | N/A | N/A |
| BG43 | E-13V; V226V; H266Q | 45% | 31% | N/A |
| BG47 | E-13V; C55C; G142S; H266Q | 85% | 53% | N/A |
| BG48 | A16T; A132A; G142S; V226V; H266Q; D703G | 100% | 87% | 44% |
| BG49 | E-13V; V226V; H266Q | N/A | 69% (at 69° C.) | N/A |
| BG50 | Partial seq. G142S; Q183R; H266Q | N/A | 21% | N/A |
| BG52 | S-5P; A16T; G142S; H266Q; D703G | N/A | N/A | 60% |
| BG53 | G142S; Q183R; H266Q; D703G | N/A | N/A | 65% |
| BG54 | S-5P; G142S; Q183R; H266Q | N/A | N/A | 50% |

Samples of beta-glucosidase were diluted in the same buffer as used in Example 9 to the same activity relative to each other. The sample was divided into two polypropylene test tubes, one part of the sample was incubated submerged in a temperature controlled water bath, and the other part was incubated at ambient temperature, both for a period of up to 42 hours. At the end of the incubation period, samples of both were placed into a 96-well plate. Methylumbelliferyl-beta-D-glucopyranoside (MUG) substrate (200 µl of 0.5 µM solution of MUG) was added to the 96-well plate of samples and incubated at ambient temperature for 15 minutes. The reaction was stopped with the addition of 2M Tris pH 9.0 buffer, and the plate was read on a fluorometer to obtain Relative Fluorescent Units (RFU) at excitation 365, emission 454. The percent residual activity was determined using the same method as described in Example 9. The results are shown in Table 3. Overall, the results correlated with the results shown in Table 2.

TABLE 3

Thermostability of beta-glucosidase variants at longer incubation times

| Mutations as appropriate | Other ID as appropriate | % RA at 55° C. for 42 hr | % RA at 60° C. for 15 hr | % RA at 60° C. for 23.5 hr | % RA at 65° C. for 1 hr |
|---|---|---|---|---|---|
| A. niger WT | ANBG | 12% | 0% | 0% | 5% |
| A. oryzae WT | AOBG | 69% | 2% | 0% | 0% |
| H266Q | BG43 | Not Done | 9% | Not Done | 1% |
| G142S; H266Q | BG41 | 88% | 40% | 35% | 40% |
| A16T; G142S; H266Q; D703G | BG48 | 87% | 41% | 37% | 48% |

Example 14

Construction of pAlLo2 Expression Vector

Expression vector pAlLo1 was constructed by modifying pBANe6 (U.S. Pat. No.6,461,837), which comprises the NA2-tpi promoter, *Aspergillus niger* amyloglucosidase terminator sequence (AMG terminator), and *Aspergillus nidulans* acetamidase gene (amdS). Modification of pBANe6 was performed by first eliminating three Nco I restriction sites at positions 2051, 2722, and 3397 bp from the amdS selection marker by site directed mutagenesis. All changes were designed to be "silent" leaving the actual protein sequence of the amdS gene product unchanged. Removal of these three sites was performed simultaneously with a GeneEditor Site-Directed Mutagenesis Kit (Promega, Madison, Wis.) according to the manufacturer's instructions using the following primers (underlined nucleotide represents the changed base):

```
AMDS3NcoMut (2050): 5'-GTGCCCCATGATACGCCTCCGG-3'       (SEQ ID NO: 58)

AMDS2NcoMut (2721): 5'-GAGTCGTATTTCCAAGGCTCCTGACC-3'   (SEQ ID NO: 59)

AMDS1NcoMut (3396): 5'-GGAGGCCATGAAGTGGACCAACGG-3'     (SEQ ID NO: 60)
```

A plasmid comprising all three expected sequence changes was then submitted to site-directed mutagenesis, using a QuickChange Mutagenesis Kit (Stratagene, La Jolla, Calif.), to eliminate ac I the Nco I restriction site at the end of the AMG terminator at position 1643. The following primers (underlined nucleotide represents the changed base) were used for mutagenesis:

Upper Primer to mutagenize the *Aspergillus niger* amyloglucosidase (AMG) terminator sequence:

```
5'-CACCGTGAAAGCCATGCTCTTTCCTTCGTGTAGAAGACCAGACAG-3'   (SEQ ID NO: 61)
```

Lower Primer to mutagenize the *Aspergillus niger* amyloglucosidase (AMG) terminator sequence:

```
5'-CTGGTCTTCTACACGAAGGAAAGAGCATGGCTTTCACGGTGTCTG-3'   (SEQ ID NO: 62)
```

Figure 13:
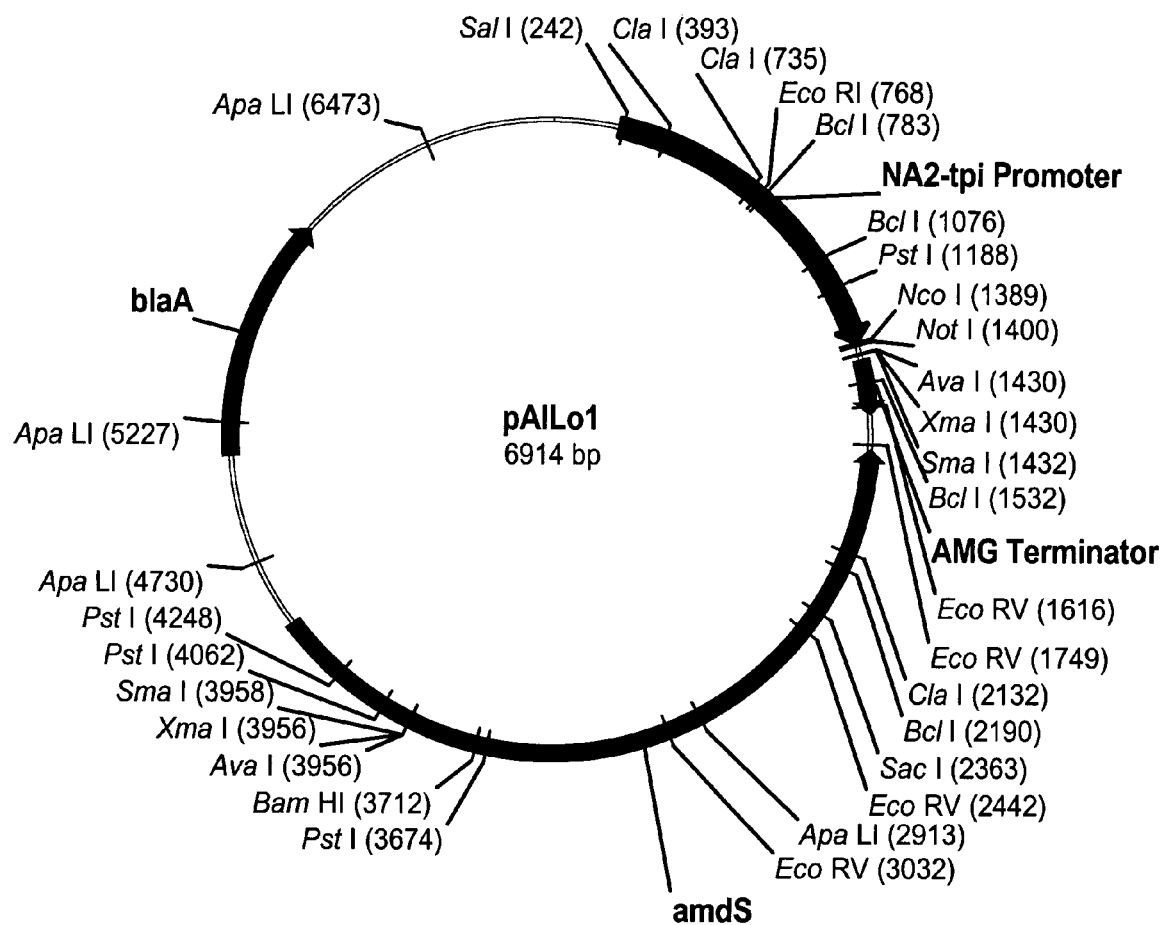
FIG. 13 shows a restriction map of pAILo1.

The last step in the modification of pBANe6 was the addition of a new Nco I restriction site at the beginning of the polylinker using a QuickChange mutagenesis kit and the following primers (underlined nucleotides represent the changed bases) to yield pAlLo1 (FIG. 13).

Upper Primer to mutagenize the *Aspergillus niger* amylase promoter (NA2-tpi):

```
5'-CTATATACACAACTGGATTTACCATGGGCCCGCGGCCGCAGATC-3'    (SEQ ID NO: 63)
```

Lower Primer to mutagenize the *Aspergillus niger* amylase promoter (NA2-tpi):

```
5'-GATCTGCGGCCGCGGGCCCATGGTAAATCCAGTTGTGTATATAG-3'    (SEQ ID NO: 64)
```

Figure 14:
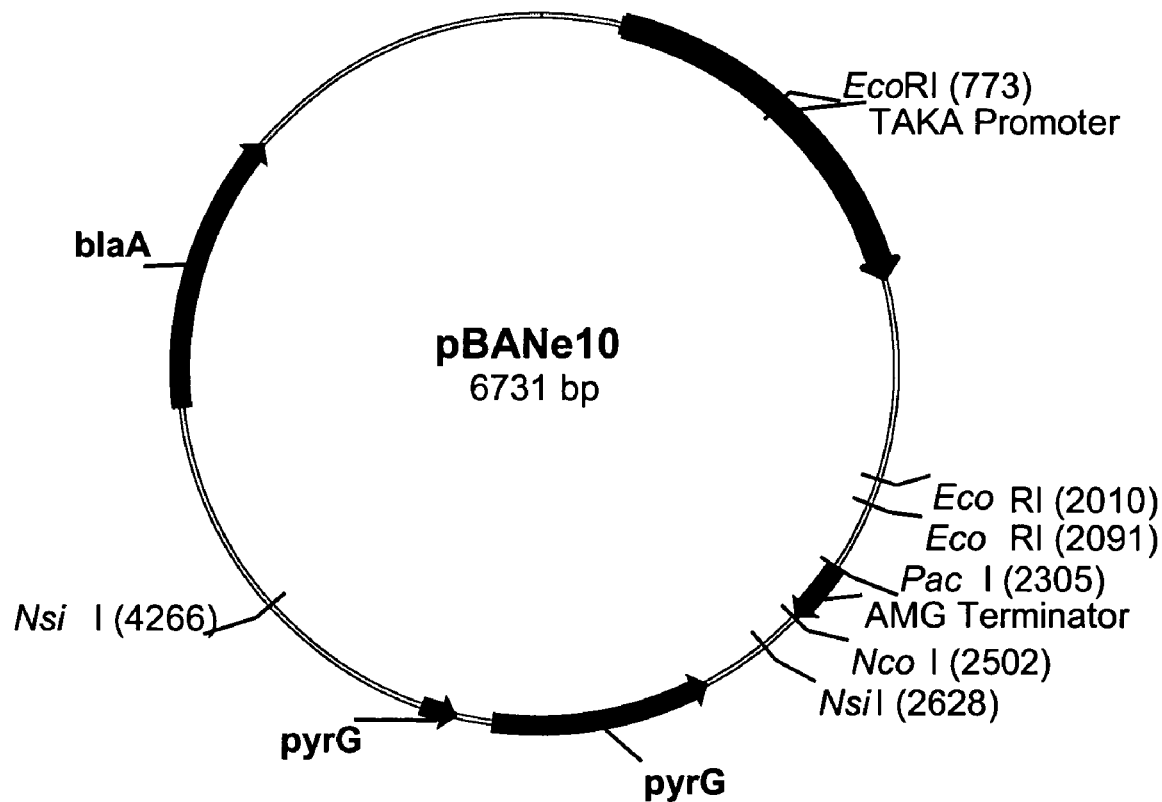
FIG. 14 shows a restriction map of pBANe10.
Figure 15:
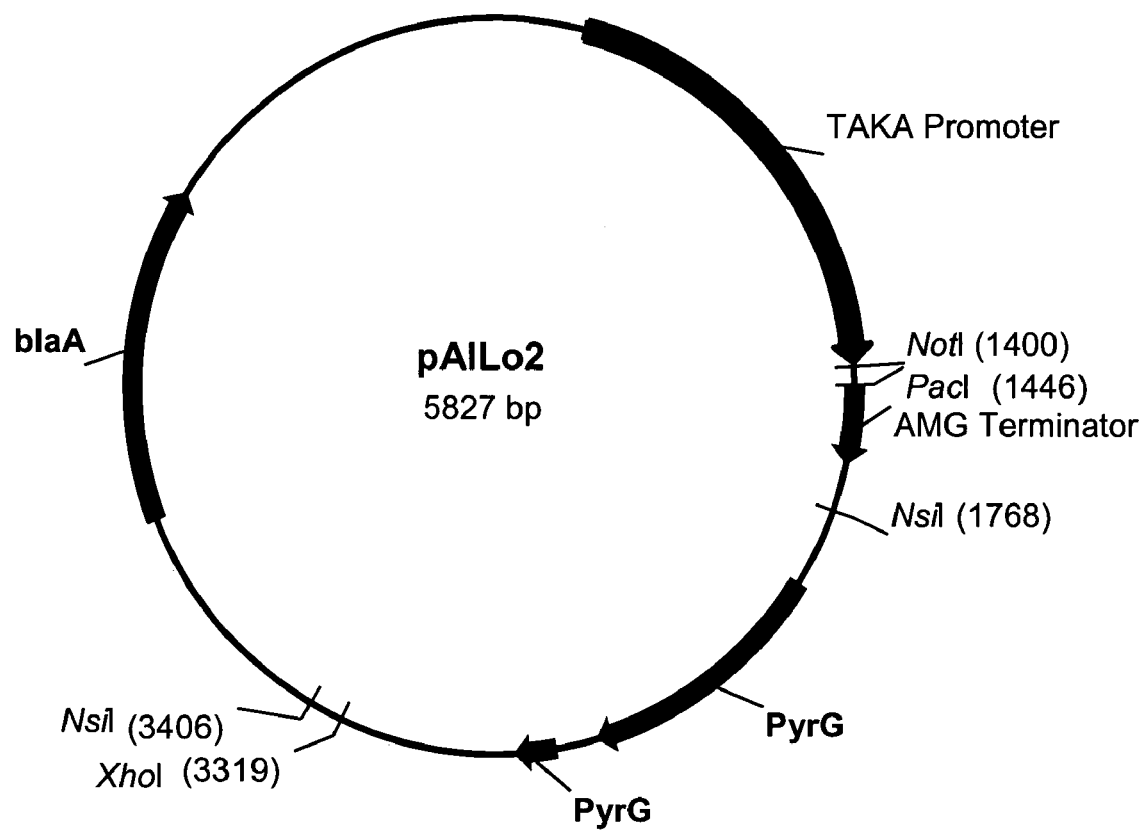
FIG. 15 shows a restriction map of pAILo2.

The amdS gene of pAlLo1 was swapped with the *Aspergillus nidulans* pyrG gene. Plasmid pBANe10 (FIG. 14) was used as a source for the pyrG gene as a selection marker. Analysis of the sequence of pBANe10 showed that the pyrG marker was contained within an Nsi I restriction fragment and does not contain either Nco I or Pac I restriction sites. Since the amdS is also flanked by Nsi I restriction sites the strategy to switch the selection marker was a simple swap of Nsi I restriction fragments. Plasmid DNA from pAlLo1 and pBANe10 were digested with the restriction, enzyme Nsi I and the products purified by agarose gel electrophoresis. The Nsi I fragment from pBANe10 containing the pyrG gene was ligated to the backbone of pAlLo1 to replace the original Nsi I DNA fragment containing the amdS gene. Recombinant clones were analyzed by restriction digest to determine that they had the correct insert and also its orientation. A clone with the pyrG gene transcribed in the counterclockwise direction was selected. The new plasmid was designated pAlLo2 (FIG. 15).

Example 15

Subcloning of the Improved Thermostable Beta-glucosidase BG41 and BG48 Variants into *Aspergillus oryzae* for Protein Characterization The coding regions of beta-glucosidase variants BG41 and BG48 were subcloned into the *Aspergillus oryzae* vector pAlLo02 digested with Nco I and Pac I to form a perfect junction with the ATG of the gene and the *Aspergillus niger* amylase promoter (NA2-tpi) and the *Aspergillus niger* amyloglucosidase terminator sequence. Since the beta-glucosidase coding region possessed two Nco I sites, subcloning of the beta-glucosidase gene into pAlLo2 was accomplished by designing two primers, shown below, that expand the beta-glucosidase gene in pSATe111 and also anneal to pAlLo2 close to the Nco I and Pac I sites.

Aoryzaebeta-glucosidaseUpper: 5'-ACTGGATTTACCATGAAGCTTGGTTGGATC-3' (SEQ ID NO: 65)

ACTGGATTTACCATG anneals to pAILo2 and AAGCTTGGTTGGATC anneals to pSATe111.

Aoryzaebeta-glucosidaseLower: 5'-AGTCACCTCTAGTTATTACTGGGCCTTAGG-3' (SEQ ID NO: 66)

AGTCACCTCTAGTTA anneals to pAILo2 and TTACTGGGCCTTAGG anneals to pSATe111.

To amplify the DNA of variants BG41 and BG48, 0.5 μl of each plasmid DNA template was used in a 100 μl reaction containing 1×ThermoPol Reaction buffer containing 2 mM MgSO₄, 0.05 mM of each dATP, dGTP, dCTP, and dTTP, 50 μmole of each primer (Aoryzaebeta-glucosidaseUpper and Aoryzaebeta-glucosidaseLower primers), and 1 unit of Vent DNA polymerase. Two amplification reactions were performed where the first reaction was subjected to 1 cycle at 95° C. for 5 minutes; 25 cycles each at 95° C. for 1 minute, 50° C. for 1 minute, 72° C. for 3 minutes; and cycle at 72° C. for 10 minutes, and the second reaction was performed under the same conditions but at an annealing temperature of 56° C. An aliquot of each PCR product was run on a 0.7% agarose gel using TAE buffer, as previously described, generating expected bands of approximately 3 kb. Both PCR reactions were combined and were purified using a MinElute PCR Purification Kit and DNA and eluting the DNA into 10 μl of EB buffer. The yield of each purified PCR product was estimated to be 250 ng per microliter by visualization on a 0.7% agarose gel using TAE buffer.

Plasmid pAILo2 digested with Pac I and blunted at the Nco I site was concentrated by precipitation with 0.1 volume of 3 M sodium acetate pH 5.0 and 2 volumes of 95% ethanol overnight at −20° C. The precipitated plasmid was centrifuged at 13,200×g using a microcentrifuge for 15 minutes. The supernatant was removed, and the pellet was washed with 1 ml of 70% ethanol. The precipitated pellet was centrifuged again at 13,200×g for 15 minutes, followed by removal of the supernatant, drying of the pellet under vacuum, and resuspension in 20 μl of water. The plasmid had a concentration of 80 ng per microliter. The concentration was verified by visualization on a 0.7% agarose gel using TAE buffer. Cloning of the beta-glucosidase PCR product described above and the digested pAILo2 vector was accomplished by using a BD In-Fusion PCR Cloning Kit (Stratagene, La Jolla, Calif.).

Figure 16:
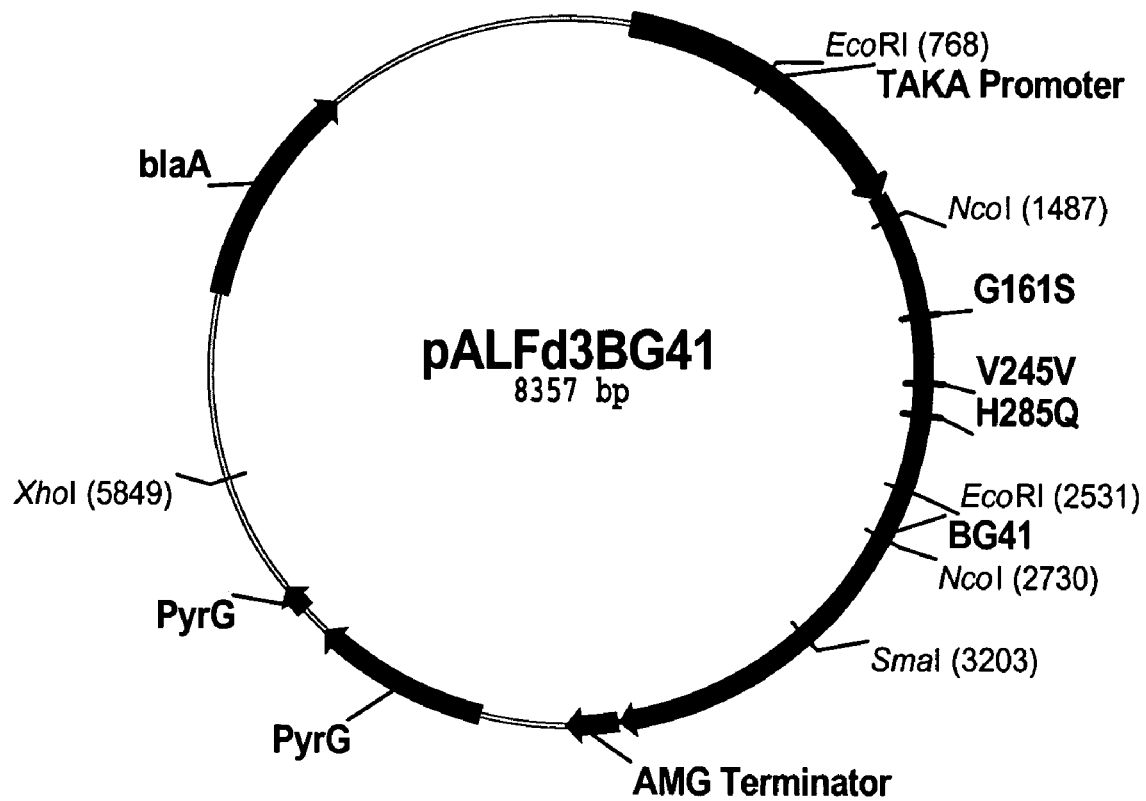
FIG. 16 shows a restriction map of pALFd3BG41.
Figure 17:
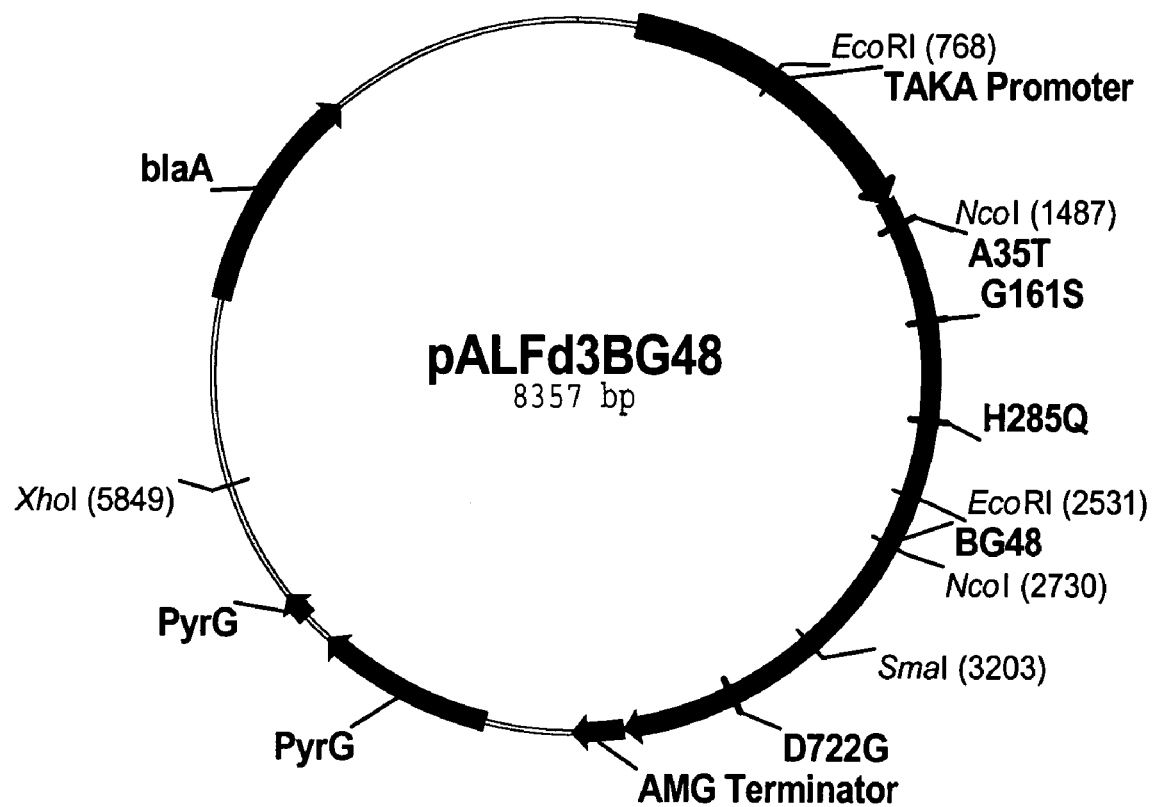
FIG. 17 shows a restriction map of pALFd3BG48.

The resulting expression vectors containing the coding regions of variant BG41 or BG48 were designated pALFd3BG41 (FIG. 16) and pALFd3BG48 (FIG. 17), respectively.

Example 16

Expression of Beta-glucosidase Variants BG41 and BG48 in *Aspergillus oryzae*

Approximately 4.5 μg of pALFd3BG41 and 6.25 μg of pALFd3BG48 μlasmid DNA were used to independently transform *Aspergillus oryzae* Jal250 protoplasts. *Aspergillus oryzae* Jal250 protoplasts were prepared according to the method of Christensen et al., *Bio/Technology* 6: 1419-1422.

The transformation of *Aspergillus oryzae* Jal250 with pALFd3BG41 yielded 5 independent transformants, while transformation with pALFd3BG48 yielded 15 independent transformants, where 9 of them were further subcultured. Four days after each independent transformant had been transferred to 100 mm minimal medium selection plates, spores were transferred from the selection plates to 24-well plates containing M400 medium diluted 1 to 5 with 1×BS and incubated at 34° C. Seven days after incubation, 10 μM of each supernatant were analyzed using 8-16% SDS-PAGE gels (Invitrogen, Carlsbad, Calif.) according to the manufacturer's instructions. SDS-PAGE profiles of the cultures of the four pALFd3BG41 transformants showed a major band of approximately 120 kDa which corresponded to the molecular weight of *Aspergillus oryzae* beta-glucosidase. SDS-PAGE profiles of the cultures of the six pALFd3BG48 transformants also showed a major band of approximately 120 kDa.

Example 17

Thermostability Determinations of Beta-glucosidase Variants BG41 and BG48 with Cellobiose The thermostability of beta-glucosidase variants BG41 and BG48 (unpurified fermentation broths) was determined by incubating the broth with 10 mM cellobiose in 100 mM sodium citrate buffer with 0.01% Tween-20 at pH 5.0 up to 21 hours at 65° C.

Figure 18:
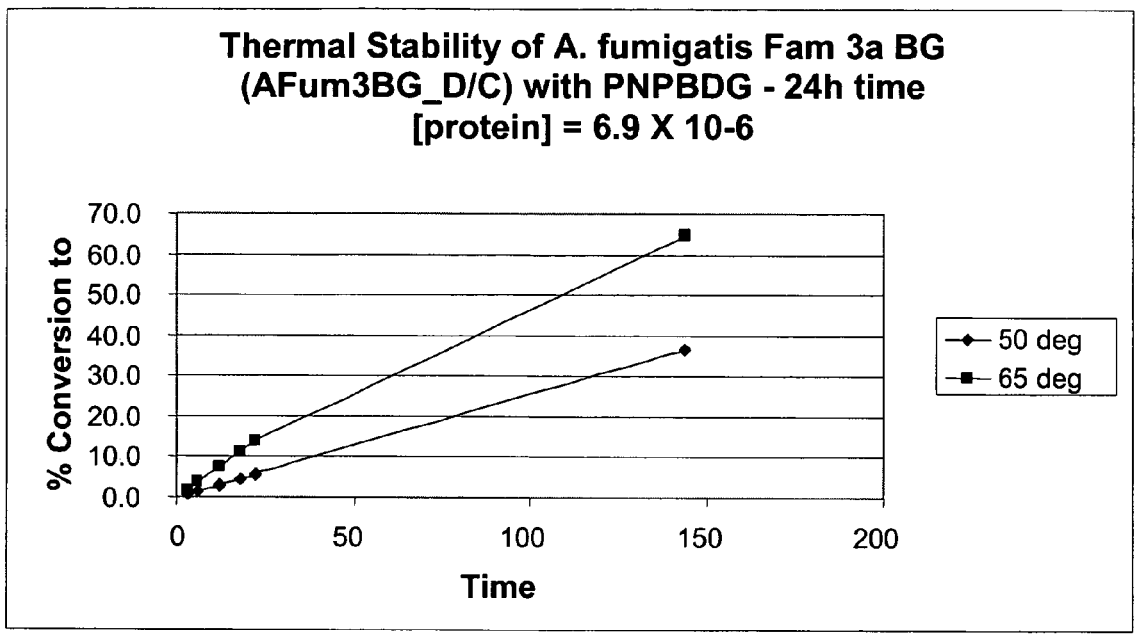
FIG. 18 shows a thermostability determination of *Aspergillus oryzae* beta-glucosidase variants BG41 and BG48.

Results of the thermostability determination of beta-glucosidase variants BG41 and BG48, as shown in FIG. 18, demonstrated that the variants were significantly more stable over time than either *Aspergillus niger* beta-glucosidase (Novozym 188) or *Aspergillus oryzae* beta-glucosidase.

Example 18

Construction of a Beta-glucosidase Variant with the G142S Substitution

The nucleotide region containing the G to A mutation to produce the G142S substitution was subcloned into the coding sequence of pSATe111 for further characterization of the effects of this single amino acid substitution. The G to A mutation was located between the Spe I and Bpu 1102 I unique sites of the pSATe111 vector. Plasmids pSATe111 (approximately 50 μg) and pSATe111BG41 (approximately 300 μg) were digested with Spe I and Blp I, an isoschizomer of Bpu 1102 I. The reactions yielded two fragments: one containing most of pSATe111 (8146 bp) and a smaller fragment of 580 bp from the beta-glucosidase coding sequence containing the G to A mutation. Digested pSATe111 was treated with shrimp alkaline phosphatase for dephosphorylation of the digested DNA products by adding 1×SAP buffer and 2 μl of SAP (Roche Applied Science, Manheim, Germany) and incubating the reaction for 10 minutes at 37° C. followed by incubation at 85° C. for 10 minutes for enzyme inactivation. Both digestions were run on 0.7% agarose gel and purified using a QIAGEN Gel purification kit according to the manufacturer's instructions.

Digested pSATe111 was ligated to the 580 bp fragment from the pATe111BG41 digestion containing the position that encoded amino acid 142 with the nucleotide mutation that led to the G142S amino acid substitution. Ligation was accomplished by using the Rapid DNA Ligation Kit (Roche Applied Science, Manheim, Germany) following the manufacturer's instructions.

The ligation reaction was transformed into XL1-Blue *E. coli* subcloning-competent cells according to the manufacturer's instructions (Stratagene, La Jolla, Calif.). Upon transformation, plasmid DNA from an isolated colony was isolated as described in Example 10 and sequenced, confirming the presence of the unique G to A mutation in the entire coding region of the gene. Subsequently, the plasmid DNA was transformed into yeast competent cells as described in Example 8, which resulted in isolation of a beta-glucosidase variant containing the G142S substitution. This beta-glucosidase variant was designated the G142S mutant. Since BG43 contained only the H266Q substitution and the G142S mutant contained only the G142S substitution, the effects of each substitution, G142S and H266Q, could be individually characterized.

Example 19

Assay of the Effects of G142S and H266Q Mutations

A thermal stability test was performed at 60° C. for 23 hours demonstrating the synergistic effect of the mutations. Samples of the beta-glucosidase variants were diluted in the same buffer as used in Example 9 to the same enzyme activities relative to each other. Each sample was divided into two polypropylene test tubes, one tube of the samples was incubated submerged in a temperature controlled water bath at 60° C. and the other part was incubated at ambient temperature, both for a period of up to 42 hours. At the end of the incubation period, samples of both were placed into a 96-well plate. Methylumbelliferyl-beta-D-glucopyranoside (MUG) substrate (200 µl of 0.5 µM solution of MUG) was added to the 96-well plate of samples and incubated at ambient temperature for 15 minutes. The reaction was stopped with the addition of 2 M Tris buffer, pH 9.0 and the plate was read on a fluorometer to obtain the Relative Fluorescent Units (RFU) at excitation 365, emission 454. The percent residual activity was determined using the same method described in Example 9.

Figure 19:
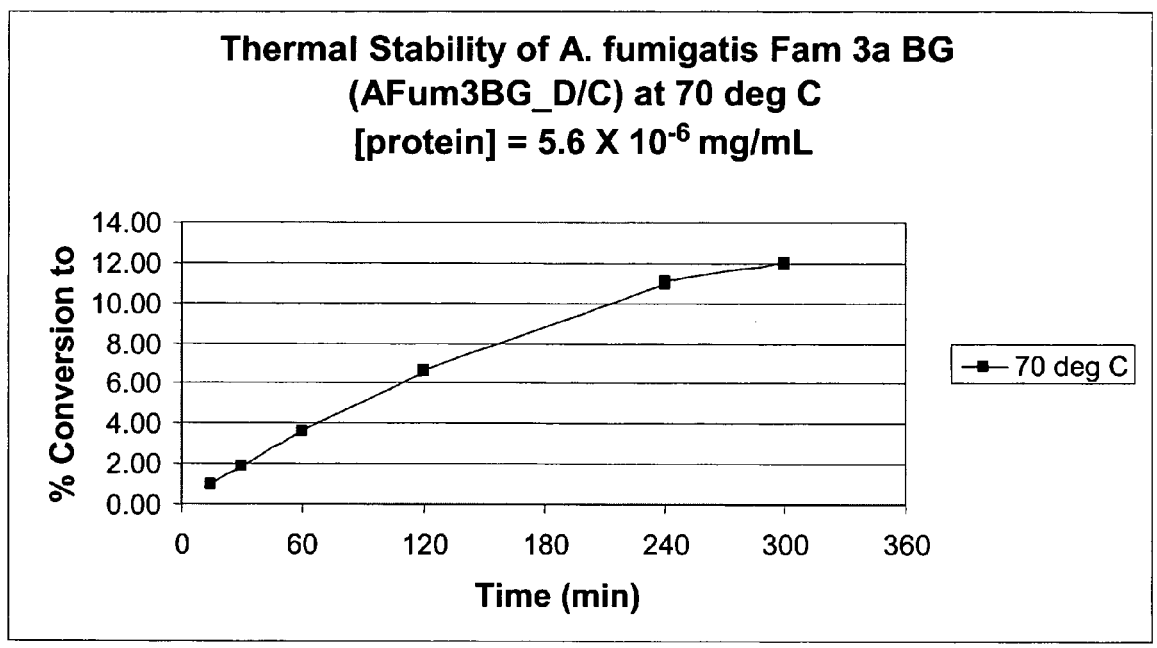
FIG. 19 shows the thermostability effects of mutations G142S and H266Q individually and combined.

The effects of mutations G142S and H266Q individually and combined into one molecule are shown in FIG. 19. Individual testing of these mutations showed that the combination of them in one molecule had a greater effect on thermal stability of beta-glucosidase activity in buffer than either of them individually as shown in FIG. 19. The bar is the mathematical composite of these two amino acid substitutions.

Example 20

Identification of a Glycosyl Hydrolase Family GH3A Gene in the Genomic Sequence of *Aspergillus fumigatus*

A tblastn search (Altschul et al., 1997, *Nucleic Acids Res.* 25: 3389-3402) of the *Aspergillus fumigatus* partial genome sequence (The Institute for Genomic Research, Rockville, Md.) was carried out using as query a beta-glucosidase protein sequence from *Aspergillus aculeatus* (Accession No. P48825). Several genes were identified as putative Family GH3A homologs based upon a high degree of similarity to the query sequence at the amino acid level. One genomic region of approximately 3000 bp with greater than 70% identity to the query sequence at the amino acid level was chosen for further study.

Example 21

*Aspergillus fumigatus* Genomic DNA Extraction

*Aspergillus fumigatus* was grown in 250 ml of potato dextrose medium in a baffled shake flask at 37° C. and 240 rpm. Mycelia were harvested by filtration, washed twice in TE buffer (10 mM Tris-1 mM EDTA), and frozen under liquid nitrogen. Frozen mycelia were ground by mortar and pestle to a fine powder, which was resuspended in pH 8.0 buffer containing 10 mM Tris, 100 mM EDTA, 1% Triton X-100, 0.5 M guanidine-HCl, and 200 mM NaCl. DNase free RNase A was added at a concentration of 20 mg/liter and the lysate was incubated at 37° C. for 30 minutes. Cellular debris was removed by centrifugation, and DNA was isolated by using a Qiagen Maxi 500 column (QIAGEN Inc., Chatsworth, Calif.). The columns were equilibrated in 10 ml of QBT washed with 30 ml of QC, and eluted with 15 ml of QF (all buffers from QIAGEN Inc., Chatsworth, Calif.). DNA was precipitated in isopropanol, washed in 70% ethanol, and recovered by centrifugation. The DNA was resuspended in TE buffer.

Example 22

Cloning of the Family GH3A Beta-glucosidase Gene and Construction of an *Aspergillus oryzae* Expression Vector Two synthetic oligonucleotide primers shown below were designed to PCR amplify a *Aspergillus fumigatus* gene encoding a putative Family GH3A beta-glucosidase from the genomic DNA prepared in Example 21. An InFusion Cloning Kit (BD Biosciences, Palo Alto, Calif.) was used to clone the fragment directly into the expression vector, pAILo2, without the need for restriction digests and ligation.

```
Forward primer: 5'-ACTGGATTTACCATGAGATTCGGTTGGCTCG-3' (SEQ ID NO: 67)

Reverse primer: 5'-AGTCACCTCTAGTTACTAGTAGACACGGGGC-3' (SEQ ID NO: 68)
```

Bold letters represent coding sequence. The remaining sequence is homologous to the insertion sites of pAILo2.

Fifty picomoles of each of the primers above were used in a PCR reaction containing 100 ng of *Aspergillus fumigatus* genomic DNA, 1×Pfx Amplification Buffer, 1.5 µl of 10 mM blend of dATP, dTTP, dGTP, and dCTP, 2.5 units of Platinum Pfx DNA Polymerase, 1 µl of 50 mM MgSO$_4$ and 2.5 µl of 10×pCRx Enhancer solution (Invitrogen, Carlsbad, Calif.) in a final volume of 50 µl. The amplification conditions were one cycle at 94° C. for 2 minutes; and 30 cycles each at 94° C. for 15 seconds, 55° C. for 30 seconds, and 68° C. for 3 minutes. The heat block then went to a 4° C. soak cycle.

The reaction products were isolated on a 1.0% agarose gel using TAE buffer where a 3 kb product band was excised from the gel and purified using a QIAquick Gel Extraction Kit according to the manufacturer's instructions.

Figure 20:
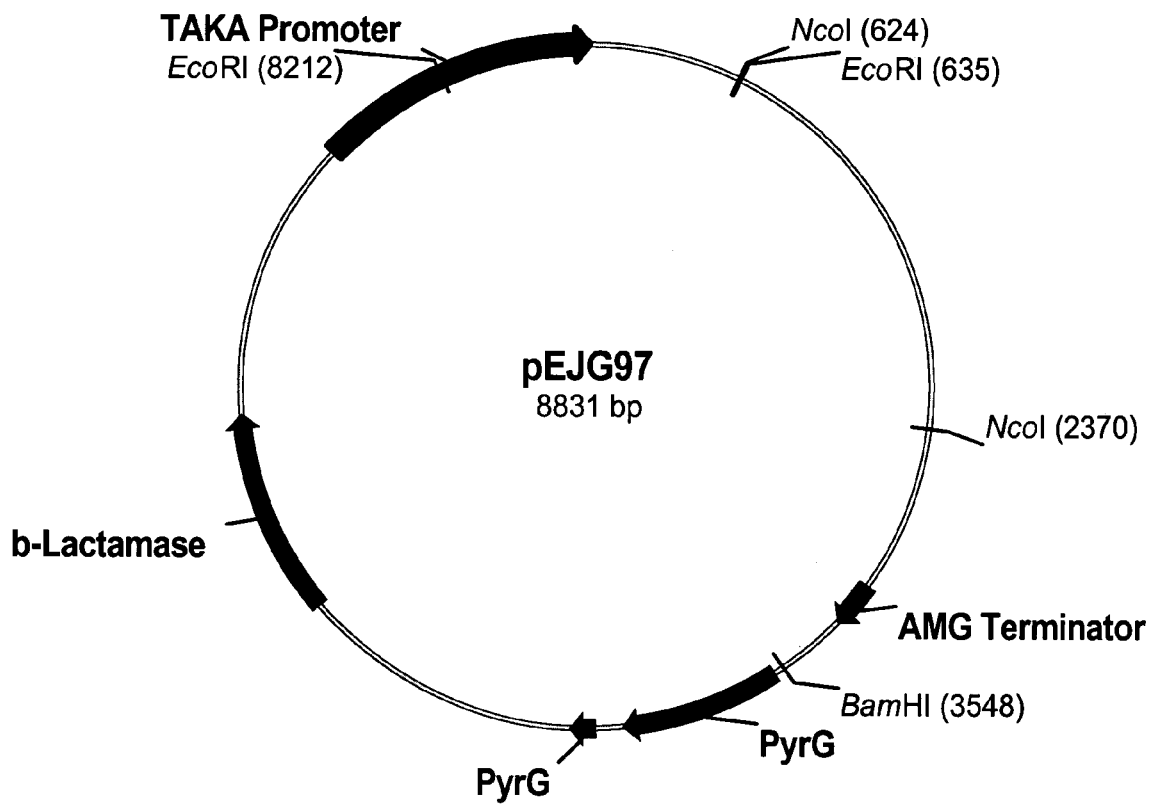
FIG. 20 shows a restriction map of pEJG97.

The fragment was then cloned into the pAILo2 expression vector using an Infusion Cloning Kit. The vector was digested with Nco I and Pac I. The fragment was purified by gel electrophoresis and Qiaquick gel purification. The gene fragment and the digested vector were ligated together in a reaction resulting in the expression plasmid pEJG97 (FIG. 20) in which transcription of the Family GH3A beta-glucosidase gene was under the control of the NA2-tpi promoter. The ligation reaction (50 µl) was composed of 1×InFusion Buffer (BD Biosciences, Palo Alto, Calif.), 1×BSA (BD Biosciences, Palo Alto, Calif.), 1 µl of Infusion enzyme (diluted 1:10) (BD Biosciences, Palo Alto, Calif.), 150 ng of pAlLo2 digested with Nco I and Pac I, and 50 ng of the *Aspergllius fumigatus* beta-glucosidase purified PCR product. The reaction was incubated at room temperature for 30 minutes. One µl of the reaction was used to transform *E. coli* XL10 Solopac Gold cells (Stratagene, La Jolla, Calif.). An *E. coli* transformant containing the pEJG97 plasmid was detected by restriction digestion of the plasmid DNA.

Example 23

Characterization of the *Aspergillus fumigatus* Genomic Sequence Encoding a Family GH3A Beta-glucosidase DNA sequencing of the *Aspergillus fumigatus* beta-glucosidase gene from pEJG97 was performed as described previously using a primer walking strategy. A gene model for the *Aspergillus fumigatus* sequence was constructed based on similarity to homologous genes from *Aspergillus aculeatus*, *Aspergillus niger*, and *Aspergillus kawachii*. The nucleotide sequence (SEQ ID NO: 69) and deduced amino acid sequence (SEQ ID NO: 70) of the *Aspergillus fumigatus* beta-glucosidase gene are shown in FIG. 21. The genomic fragment encoded a polypeptide of 863 amino acids, interrupted by 8 introns of 62, 55, 58, 63, 58, 58, 63 and 51 bp. The % G+C content of the gene is 54.3%. Using the SignalP software program (Nielsen et al, 1997, *Protein Engineering* 10: 1-6), a signal peptide of 19 residues was predicted. The predicted mature protein contains 844 amino acids with a molecular mass of 91.7 kDa.

A comparative alignment of beta-glucosidase sequences was determined using the Clustal W method (Higgins, 1989, *CABIOS* 5: 151-153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=1, gap penalty=3, windows=5, and diagonals=5. The alignment showed that the deduced amino acid sequence of the *Aspergillus fumigatus* beta-glucosidase gene shared 78%, 76%, and 76% identity to the deduced amino acid sequences of the *Aspergillus aculeatus*(accession number P48825), *Aspergillus niger*(accession number 000089), and *Aspergillus kawachii*(accession number P87076) beta-glucosidases.

Example 24

Expression of the *Aspergillus fumigatus* Family GH3A Beta-glucosidase Gene in *Aspergillus oryzae* JAL250

*Aspergillus oryzae* Jal250 protoplasts were prepared according to the method of Christensen et al., 1988, *Bio/Technology* 6: 1419-1422. Five µg of pEJG97 (as well as pAlLo2 as a vector control) was used to transform *Aspergillus oryzae* JAL250.

The transformation of *Aspergillus oryzae* Jal250 with pEJG97 yielded about 100 transformants. Ten transformants were isolated to individual PDA plates.

Confluent PDA plates of five of the ten transformants were washed with 5 ml of 0.01% Tween 20 and inoculated separately into 25 ml of MDU2BP medium in 125 ml glass shake flasks and incubated at 34° C., 250 rpm. Five days after incubation, 0.5 µl of supernatant from each culture was analyzed using 8-16% Tris-Glycine SDS-PAGE gels (Invitrogen, Carlsbad, Calif.) according to the manufacturer's instructions. SDS-PAGE profiles of the cultures showed that one of the transformants (designated transformant 1) had a major band of approximately 130 kDa.

Example 25

Extraction of Total RNA from *Aspergillus oryzae*

The *Aspergillus oryzae* transformant described in Example 22 was frozen with liquid nitrogen and stored at −80° C. Subsequently, the frozen tissue was ground in an electric coffee grinder with a few chips of dry ice added to keep the powdered mycelia frozen. Then, the ground material was transferred with a spatula to a 50 ml sterile conical tube which had been previously filled with 20 ml of Fenozol (Active Motif, Inc., Carlsbad, Calif.). This mixture was mixed rapidly to dissolve the frozen material to a thick solution, and placed in a 50° C. water bath for 15 minutes. Five ml of RNase free chloroform was added to the mixture and vortexed vigorously. Then, the mixture was allowed to stand at room temperature for 10 minutes. Next the mixture was centrifuged at 2700 rpm in a Sorvall RT7 centrifuge (Sorvall, Inc, Newtown, Conn.) at room temperature for 20 minutes. The top phase was transferred to a new conical tube and an equal volume of phenol-chloroform-isoamylalcohol (25:24:1) was added. The mixture was vortexed and centrifuged for 10 minutes. This procedure was repeated twice so that three phenol-chloroform isoamylalcohol extractions were done. Then, the top phase was transferred to a new tube and an equal volume of chloroform:isoamylalcohol (24:1), was added. The mixture was vortexed once again and centrifuged for 10 minutes. After centrifugation, the aqueous phase, approximately 5 ml at this point, was transferred to a new Oak Ridge tube and 0.5 ml of 3 M sodium acetate pH 5.2 and 6.25 ml of isopropanol were added. The mixture was mixed and incubated at room temperature for 15 minutes. Subsequently, the mixture was centrifuged at 12,000×g for 30 minutes, at 4° C. in a Sorvall RC5B (Sorvall, Inc, Newtown, Conn.). Following centrifugation, the supernatant was removed and 18 ml of 70% ethanol was carefully added to the pellet. Another centrifugation step was done for 10 minutes at 4° C. at 12,000×g. The supernatant was carefully removed and the pellet was air dried. The RNA pellet was resuspended in 500 µM diethyl pyrocarbonate (DEPC) treated water. At this point heating at 65° C. for 10 minutes aided in resuspension. The total RNA was stored at −80° C. Quantitation and assessing RNA quality was done on an Agilent Bioanalyzer 2100 (Englewood, Colo.) using RNA chips. All the materials and reagents used in this protocol were RNAse free.

Example 26

Cloning of the *Aspergillus fumigatus* Beta-glucosidase cDNA Sequence

The total RNA extracted from the *Aspergillus oryzae* transformant containing pEJG97 was used to clone the *Aspergillus fumigatus* beta-glucosidase cDNA sequence (SEQ ID NO: 71 for cDNA sequence and SEQ ID NO: 70 for the deduced amino acid sequence). The mRNA from the total RNA was purified using the Poly(A)Purist Mag kit (Ambion, Inc., Austin, Tex.) following the manufacturer's instructions. The *Aspergllus fumigatus* beta-glucosidase cDNA sequence, was then amplified in two fragments: a 1,337 bp DNA fragment spanning from the ATG start codon to the 1,332 position (labeled as 5' fragment) and a second 1,300 bp DNA fragment (labeled 3'fragment) spanning from the 1,303 position until the stop codon using the ProStar UltraHF RT-PCR System (Stratagene), following the manufacturer's protocol for a 50 μl reaction using 200 ng of poly-A mRNA, the primers Afuma (sense) and Afumc (antisense) for the 5' fragment, and primers Afumd (sense) and Afumb (antisense) for the 3'fragment as shown below:

```
Afuma: 5'-GGCTCATGAGATTCGGTTGGCTCGAGGTC-3'      (SEQ ID NO: 72)

Afumc: 5'-GCCGTTATCACAGCCGCGGTCGGGGCAGCC-3'     (SEQ ID NO: 73)

Afumd: 5'-GGCTGCCCCGACCGCGGCTGTGATAACGGC-3'     (SEQ ID NO: 74)

Afumb: 5'-GCTTAATTAATCTAGTAGACACGGGGCAGAGGCGC-3' (SEQ ID NO: 75)
```

Primer Afuma has an upstream BspHI site and the primer Afumb has a downstream Pac I site. Twenty nine nucleotides at the 3'-end of the 1,337 fragment overlapped with the 5'-end of the 1,303 fragment. In the overlap region there was a unique Sac II site.

Figure 22:
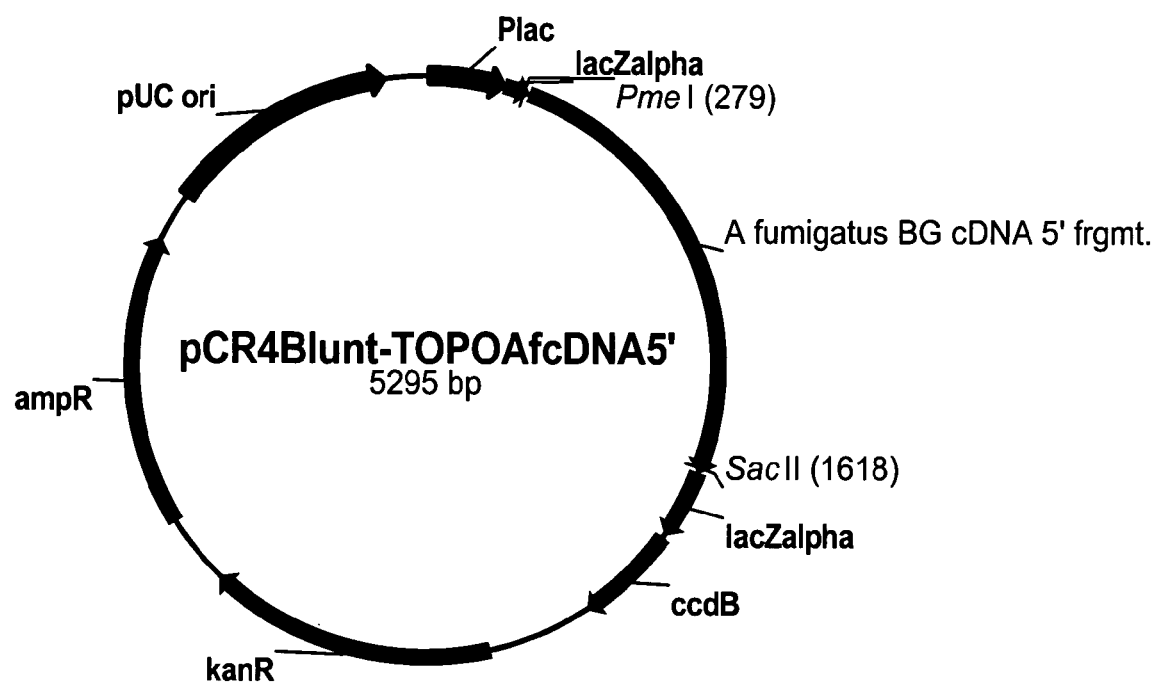
FIG. 22 shows a restriction map of pCR4Blunt-TOPOAf-cDNA5'.
Figure 23:
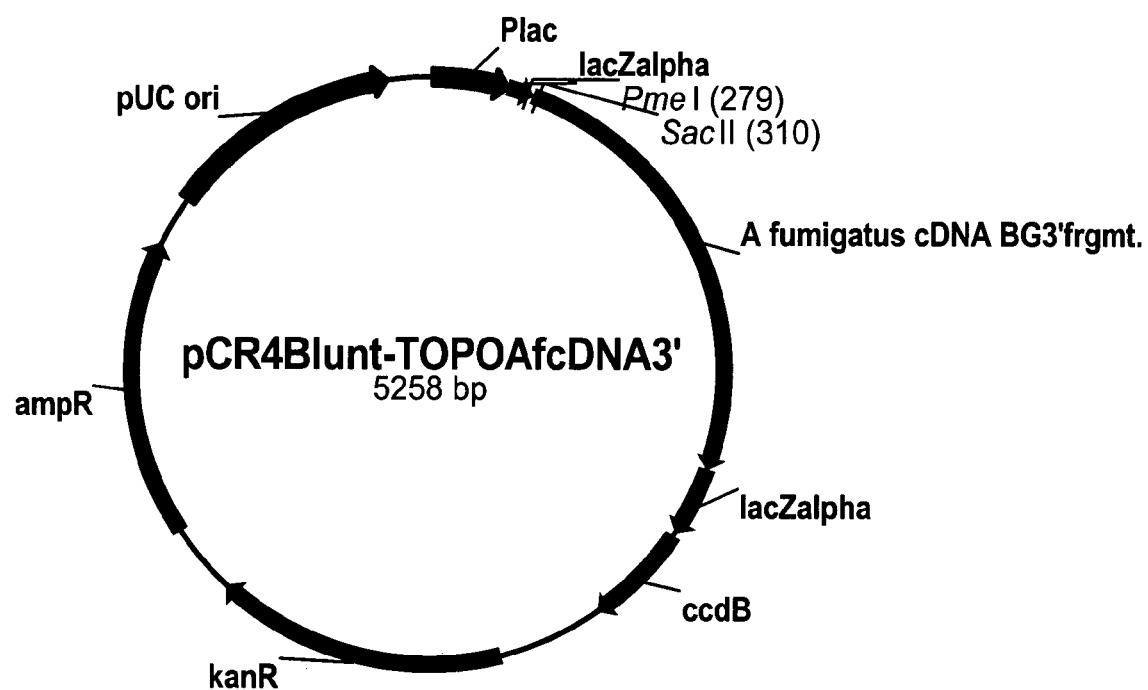
FIG. 23 shows a restriction map of pCR4Blunt-TOPOAf-cDNA3'.

Both fragments were subcloned individually into the pCR4Blunt-TOPO vector (Invitrogen, Carlsbad, Calif.) using the Zero Blunt TOPO PCR Cloning Kit for sequencing (Invitrogen, Carlsbad, Calif.), following the manufacturer's protocol, generating plasmids pCR4Blunt-TOPOAfcDNA5' and pCR4Blunt-TOPOAfcDNA3', containing the 5' and 3' fragments respectively (FIGS. 22 and 23).

The entire coding region of both *Aspergillus fumigatus* beta-glucosidase fragments was confirmed by sequencing using 0.5 μl of each plasmid DNA and 3.2 pho I mol of the following primers:

```
BGLU1.for:    5'-ACACTGGCGGAGAAGG-3'       (SEQ ID NO: 76)

BGLU2.for:    5'-GCCCAGGGATATGGTTAC-3'     (SEQ ID NO: 77)

BGLU3.for:    5'-CGACTCTGGAGAGGGTTTC-3'    (SEQ ID NO: 78)

BGLU4.rev:    5'-GGACTGGGTCATCACAAAG-3'    (SEQ ID NO: 79)

BGLU5.rev:    5'-GCGAGAGGTCATCAGCA-3'      (SEQ ID NO: 80)

M13 forward:  5'-GTAAAACGACGGCCAGT-3'      (SEQ ID NO: 81)

M13 reverse:  5'-CAGGAAACAGCTATGA-3'       (SEQ ID NO: 82)
```

Sequencing results indicated the presence of several nucleotide changes when comparing the *Aspergillus fumigatus* beta-glucosidase cDNA sequence obtained to the *Aspergillus fumigatus* beta-glucosidase cDNA sequence deduced from genome data of The Institute for Genomic Research (Rockville, Md.). At position 500, T was replaced by C, so that the coding sequence GTT was changed to GCT, so that valine was replaced by alanine. At position 903, T was replaced by C, so that the coding sequence CCC was changed to CCT, however, this change was silent. At position 2,191, G was replaced by C, so that the coding sequence CAG was changed to GAG, so that glutamic acid was replaced by glutamine. Finally, at position 2,368, C was replaced by T, so that the coding sequence CTG was changed to TrG, however, this change was also silent.

Once the two fragments had been sequenced, both clones containing each fragment were digested with Sac II and PmeI using approximately 9 μg of each plasmid DNA. Digestion of pCR4Blunt-TOPOAfcDNA5' with the above enzymes generated a fragment of 3,956 bp (containing most of the vector) and a second fragment of 1,339 bp (containing the *Aspergillus fumigatus* beta-glucosidase cDNA 5' fragment). Digestion of the pCR4Blunt-TOPOAfcDNA3' vector with the same enzymes generated a 5,227 bp fragment (containing most of the pCR4Blunt-TOPO vector and the *Aspergillus fumigatus* beta-glucosidase cDNA 3' fragment) and a second fragment of 31 bp. Digested pCR4Blunt-TOPOAfcDNA3' was treated with shrimp alkaline phosphatase for dephosphorylation of the digested DNA products by adding 1×SAP buffer and 1 μl of shrimp alkaline phosphatase (Roche Applied Science, Manheim, Germany) and incubating the reaction for 10 minutes at 37° C. followed by incubation at 85° C. for 10 minutes for enzyme inactivation. Both digestions were run on 0.7% agarose gel using TAE buffer and purified using a QIAGEN Gel purification kit according to the manufacturer's instructions.

Figure 24:
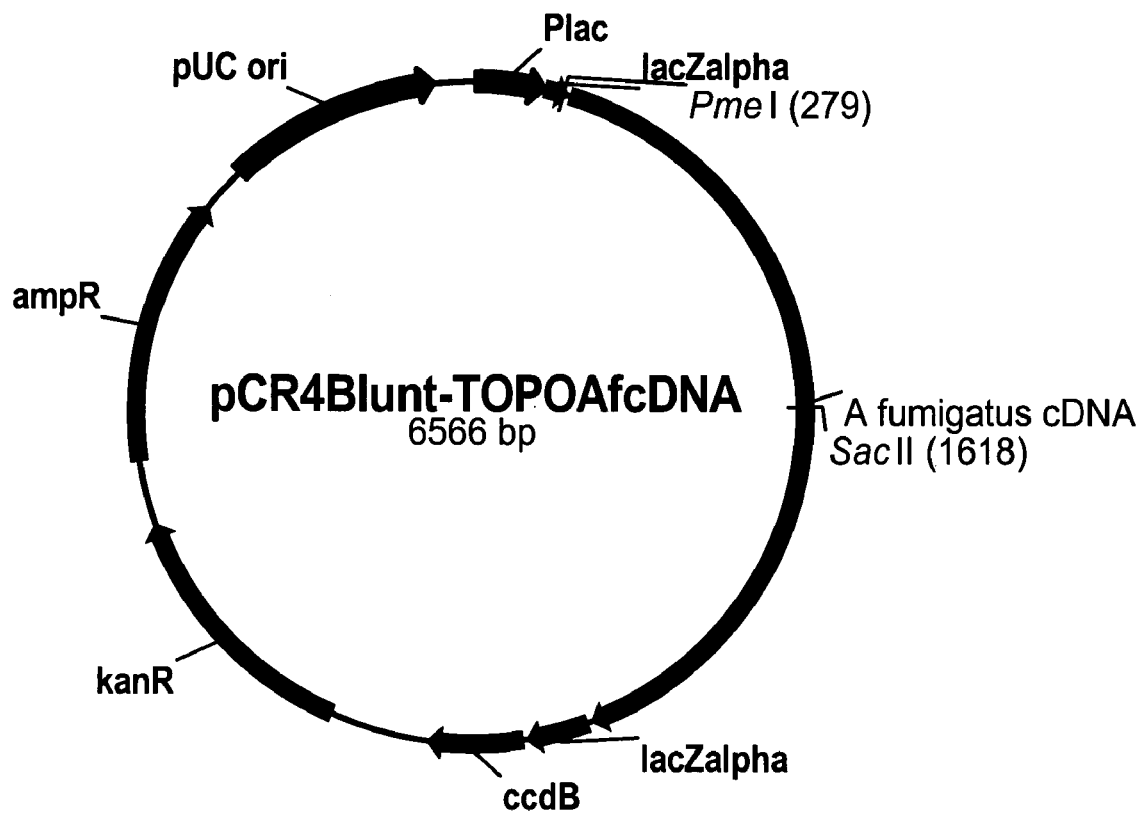
FIG. 24 shows a restriction map of pCR4Blunt-TOPOAf-cDNA.

The 1,339 bp band generated from the pCR4Blunt-TOPOAfcDNA5' digestion and the 5,527 bp fragment generated from the pCR4Blunt-TOPOAfcDNA3' digestion were ligated by using the Rapid DNA Ligation Kit following the manufacturer's instructions. The ligation reaction was transformed into XL1-Blue *E. coli* subcloning-competent cells according to the manufacturer's instructions. Upon transformation, plaasmid DNA from an isolated colony was sequenced to confirm that both the 5' and 3' fragments of the *Aspergillus fumigatus* beta-glucosidase cDNA were subcloned in tandem generating a 6,566 bp pCR4Blunt-TOPOAfcDNA vector (FIG. 24).

Example 27

Construction of the pALFd6 and pALFd7 Sacharomyces cerevisiae Expression Vectors The *Aspergillus fumigatus* beta-glucosidase full length cDNA was amplified by PCR using the following primers that have homology to the pCU426 vector and the 5' and 3' sequences of the *Aspergillus fumigatus* beta-glucosidase cDNA as indicated:

AfumigatusBGUpper:

5'-CTTCTTGTTAGTGCAATATCATATAGAAGTCATCGACTAGTGGATCTACCATGAGATTCGGTTGGCTCG-3' (SEQ ID NO: 83)

ATGAGATTCGGTTGGCTCG has Homology to the 5' End of the *Aspergillus fumigatus* cDNA AfumigatusBGLower:

5'-GCGTGAATGTAAGCGTGACATAACTAATTACATGACTCGAGCTAGTAGACACGGGGCAGAG-3' (SEQ ID NO: 84)

CTAGTAGACACGGGGCAGAG has Homology to the 3' End of the *Aspergillus fumigatus* cDNA The amplification reaction (100 µl) was composed of 0.5 µl of the pCR4Blunt-TOPOAfcDNA plasmid containing the *Aspergillus fumigatus* cDNA sequence, 1×Pfx Amplification Buffer, 50 µM each of dATP, dCTP, dGTP, and dTTP, 50 µmole of each of the above primers, 1.5 mM MgSO$_4$, and 2.5 units of Platinum Pfx DNA polymerase. The reactions were incubated in an RoboCycler Gradient 40 programmed for 1 cycle at 95° C. for 5 minutes; 25 cycles each at 95° C. for 1 minute, 50° C. for 1 minute; and 72° C. for 3 minutes; and a final extension cycle at 72° C. for 10 minutes. The PCR reaction was purified using a QIAquick PCR Purification Kit. DNA was eluted into 30 µl of EB buffer. The PCR product had 37 bp of homologous DNA sequence which was mixed with 1 µl of the pCU426 vector gapped with Spe I and Xho I for cotransformation into *Saccharomyces cerevisiae* YNG318 competent cells as described in Example 8. These colonies did not turn blue as expected, suggesting some sequencing error in the *Aspergillus fumigatus* beta-glucosidase cDNA sequence. Further sequencing of the *Aspergillus fumigatus* cDNA sequence indicated an insertion of an extra nucleotide in the cDNA sequence, which disrupted the open-reading frame of the enzyme.

Simultaneously to expressing the *Aspergillus fumigatus* beta-glucosidase cDNA in *Saccharomyces serevisiae*, the *Humicola insolens* endoglucanase V signal sequence was swapped with the native signal sequence of the *Aspergillus fumigatus* cDNA sequence also for expression in *Saccharomyces serevisiae* to compare the expression of the *Aspergillus fumigatus* beta-glucosidase with each signal sequence. The *Aspergillus fumigatus* cDNA sequence was amplified by PCR with a primer that has homology to the *Humicola insolens* endoglucanase V signal sequence in the vector pALFd1 and homology to the 5' end of the mature *Aspergillus fumigatus* beta-glucosidase cDNA sequence. The primers used for amplification of the *Aspergillus fumigatus* beta-glucosidase cDNA sequence are the AfumigatusBGLower primer described before and the HiEGVAfumigatus primer described below:

HiEGVAfumigatus:

5'-CCGCTCCGCCGTTGTGGCCGCCCTGCCGGTGTTGGCCCTTGCCGAATTGGCTTTCTCTCC-3' (SEQ ID NO: 85)

GAATTGGCTTTCTCTCC has Homology to the 5' End of the *Aspergillus fumigatus* Mature Sequence.

Figure 25:
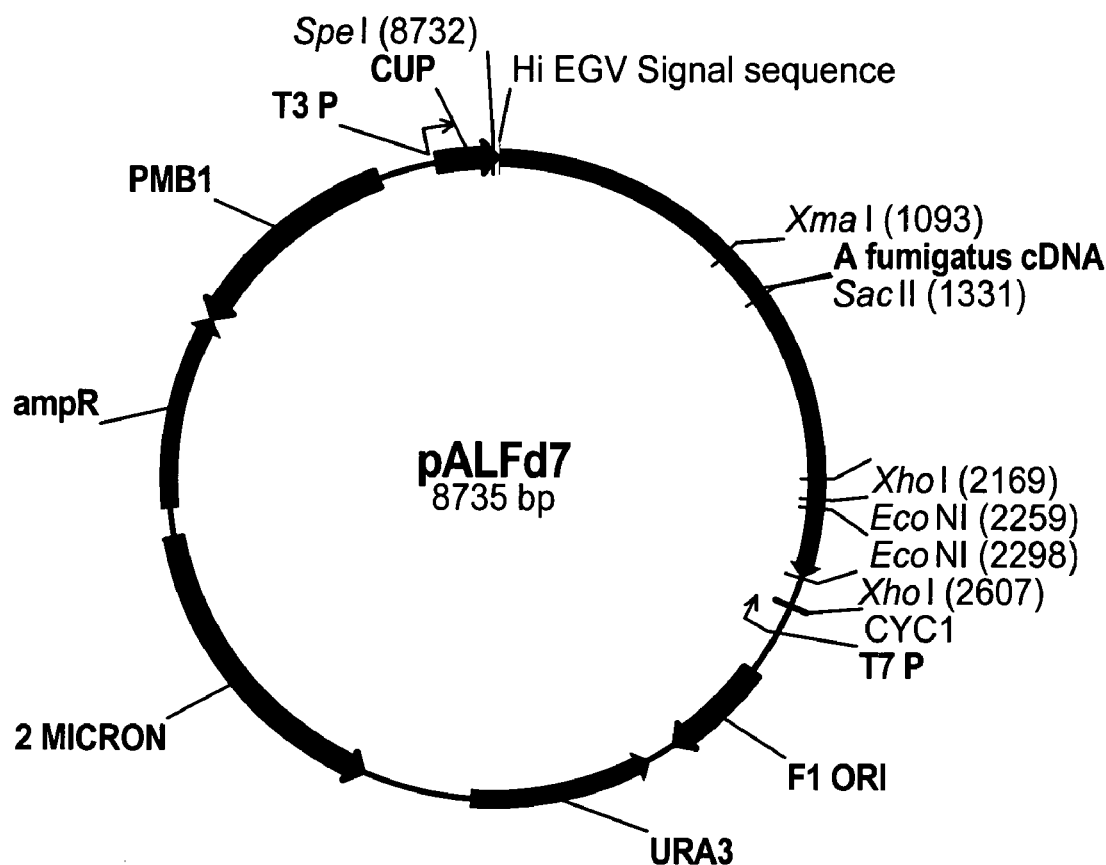
FIG. 25 shows a restriction map of pALFd7.

The amplification reaction (100 µl) was composed of 0.5 µl of pCR4Blunt-TOPOAfcDNA, 1×Pfx Amplification Buffer, 50 µM each of dATP, dCTP, dGTP, and dTTP, 50 µmole of each above primer, 1.5 mM MgSO$_4$, and 2.5 unit of Platinum Pfx DNA polymerase. The reactions were incubated in an RoboCycler Gradient 40 programmed for 1 cycle at 95° C. for 5 minutes; 25 cycles each at 95° C. for 1 minute, 50° C. for 1 minute; and 72° C. for 3 minutes; and a final extension cycle at 72° C. for 10 minutes. The PCR reaction was purified using a QIAquick PCR Purification Kit. DNA was eluted into 10 µl of EB buffer. Three µl of the purified PCR product was mixed with 1.8 µl of the gapped pALFd1 vector with Eco RI and Xho I for cotransformation into *Saccharomyces cerevisiae* YNG318 competent cells as described as in Example 8. These colonies turned light blue. However, one colony stood out as very blue. DNA rescue from this colony was done as described in Example and the plasmid was transformed into *E. coli* SURE electroporation-competent cells (Stratagene, La Jolla, Calif.) for sequencing. Full-length sequencing indicated the *Aspergillus fumigatus* beta-glucosidase cDNA sequence was correct. This plasmid was designated pALFd7 (FIG. 25), which contained the *Aspergillus fumigatus* beta-glucosidase cDNA sequence with the *Humicola insolens* endoglucanase V signal sequence for yeast expression.

To produce a yeast expression vector containing the correct *Aspergillus fumigatus* cDNA sequence with its native signal sequence, the region containing the correct nucleotide sequence from the yeast expression vector containing the *Aspergillus fumigatus* cDNA sequence with the *Humicola insolens* endoglucanase V signal sequence (pALFd7) was amplified by PCR using the above BGLU.5rev primer and the following primer:

BGL.7for:

```
5'-CTGGCGTTGGCGCTGTC-3'      (SEQ ID NO: 86)
```

The amplification reaction (100 µl) was composed of 0.5 µl of pALFd7, 1×Pfx Amplification Buffer, 50 µM each of dATP, dCTP, dGTP, and dTTP, 50 µmole of each above primer, 1.5 mM MgSO$_4$, and 2.5 units of Platinum Pfx DNA polymerase. The reactions were incubated in an RoboCycler Gradient 40 programmed for 1 cycle at 95° C. for 5 minutes; 25 cycles each at 95° C. for 1 minutes, 50° C. for 1 minute; and 72° C. for 1 minutes; and a final extension cycle at 72° C. for 10 minutes.

Figure 26:
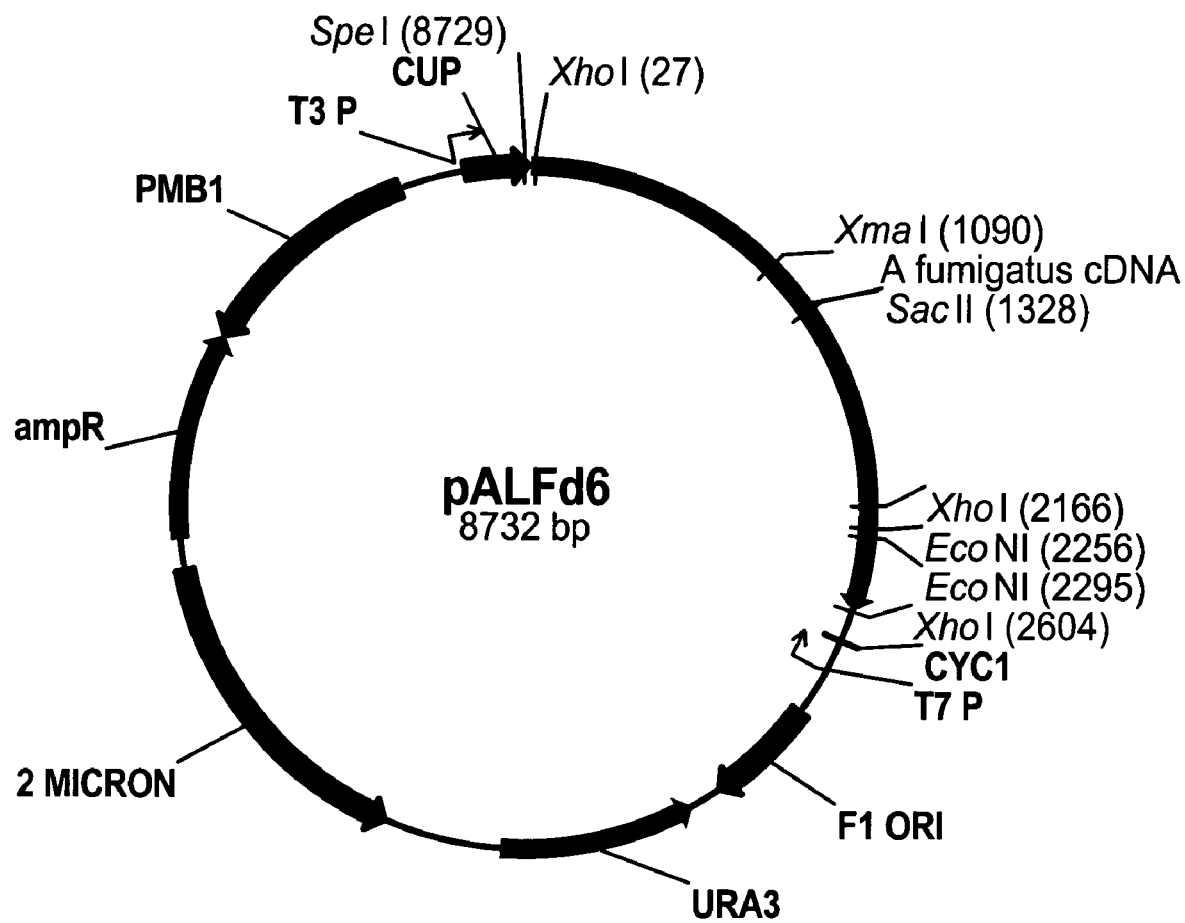
FIG. 26 shows a restriction map of pALFd6.

The 701 bp PCR fragment was purified using a QIAquick PCR Purification Kit. DNA was eluted into 10 µl of EB buffer. Three µl of the purified PCR product was mixed with 3 µl of the yeast expression vector containing the *Aspergillus fumigatus* cDNA sequence with the native signal sequence and the extra nucleotide gapped with the Sac II and XmaI vector for cotransformation into *Saccharomyces serevisiae* YNG318 competent cells as described as in Example 8. These colonies turned blue. Plasmid DNA was rescued from one randomly picked blue colony as described in Example 10, and transformed into *E. coli* SURE electroporation-competent cells (Stratagene, La Jolla, Calif.) for sequencing. Full-length sequencing indicated the *Aspergillus fumigatus* beta-glucosidase cDNA sequence was correct. This yeast expression vector was designated pALFd6 (FIG. 26), which contained the *Aspergillus fumigatus* cDNA sequence with its native signal sequence.

Example 28

Construction of an *Aspergillus fumigatus* Beta-glucosidase Variant with G142S Substitution The nucleotide region that encoded the G142 amino acid in the *Aspergillus fumigatus* coding sequence of pEJG97AfumFAM3A was mutagenized to produce a G to A mutation that encoded a G142S substitution present in the *Aspergillus oryzae* beta-glucosidase sequence variant BG53. The mutagenesis was performed using the QuickChange Site-Directed Mutagenesis Kit (Stratagene, La Jolla, Calif.) and the following primers (underlined nucleotides represents the codon with the changed base that encoded the new amino acid substitution):

```
SDMG142SUpper:  5'-GCGGCAGAATCTGGGAAAGCTTCTCTCCTG-3'  (SEQ ID NO: 87)

SDMG142SLower:  5'-CAGGAGAGAAGCTTTCCCAGATTCTGCCGC-3'  (SEQ ID NO: 88)
```

Figure 27:
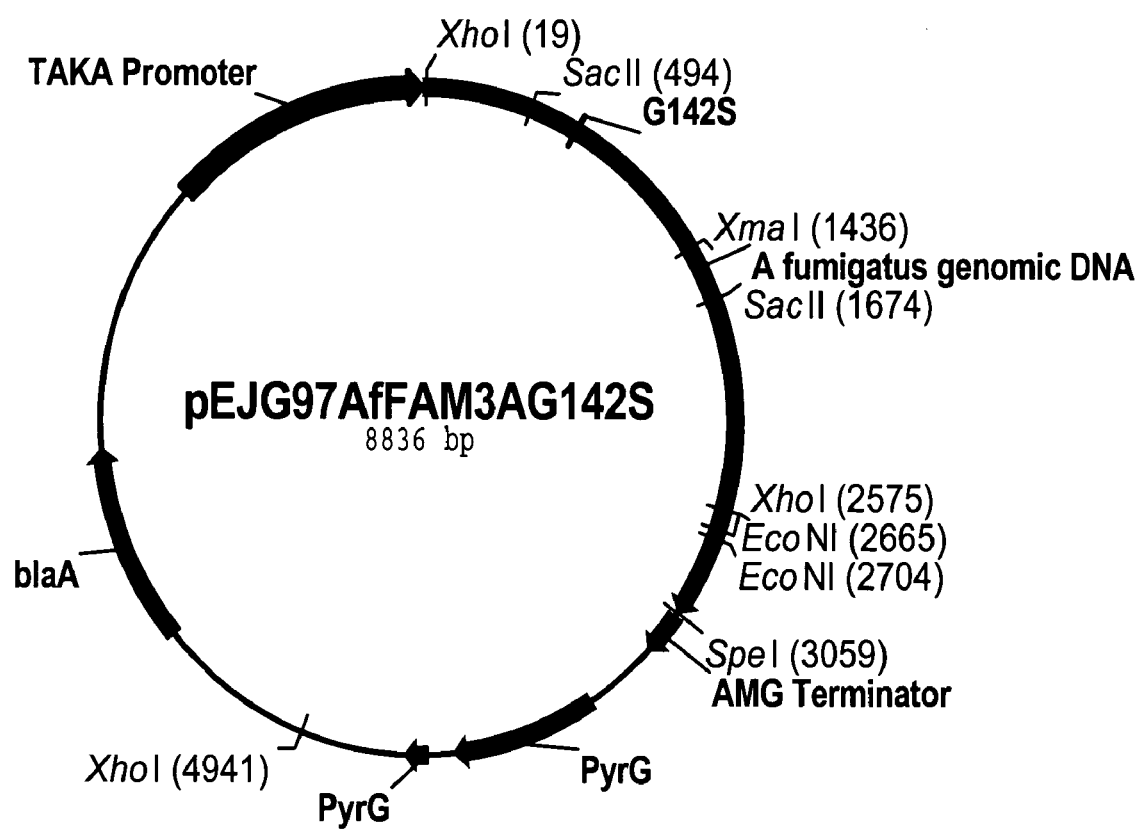
FIG. 27 shows a restriction map of pEJG97AfumFAM3AG142S.

The presence of the G to A mutation was confirmed by sequencing. The new vector was designated pEJG97AfumFAM3AG142S (FIG. 27). The G to A mutation was located between the 231 bp fragment obtained by digestion of the pEJG97AfumFAM3AG142S vector with Eco RI and Bst XI. These sites were unique in the pALFd7 vector.

Both pEJG97AfumFAM3AG142S and pALFd7 (approximately 6 µg each) were digested with Eco RI and Bst XI. The reaction with pALFd7 yielded two fragments, one containing most of vector (8504 bp) and a smaller fragment of 231 bp from the beta-glucosidase coding sequence containing the wild-type location where the G to A mutation was created in the pEJG97AfumFAM3AG142S vector. The reaction with pEJG97AfumFAM3AG142S yielded three fragments, one containing most of vector (7351 bp), a second smaller fragment of 1254 bp, and a smaller fragment of 231 bp from the beta-glucosidase coding sequence containing the G to A mutation. Digested pALFd7 was treated with shrimp alkaline phosphatase for dephosphorylation of the digested DNA products by adding 1×SAP buffer and 1 µl of SAP from Roche (Roche Applied Science, Manheim, Germany) and incubating the reaction for 10 minutes at 37° C. followed by incubation at 85° C. for 10 minutes for enzyme inactivation. Both digestions were run on 0.7% agarose gel and purified using a QIAGEN Gel purification kit according to the manufacturer's instructions.

Digested pALFd7 was ligated to the 231 bp fragment from the pEJG97AfumFAM3AG142S digestion containing the position that encoded amino acid 142 with the nucleotide mutation that led to the G142S amino acid substitution. Ligation was accomplished by using the Rapid DNA Ligation Kit following the manufacturer's instructions.

Figure 28:
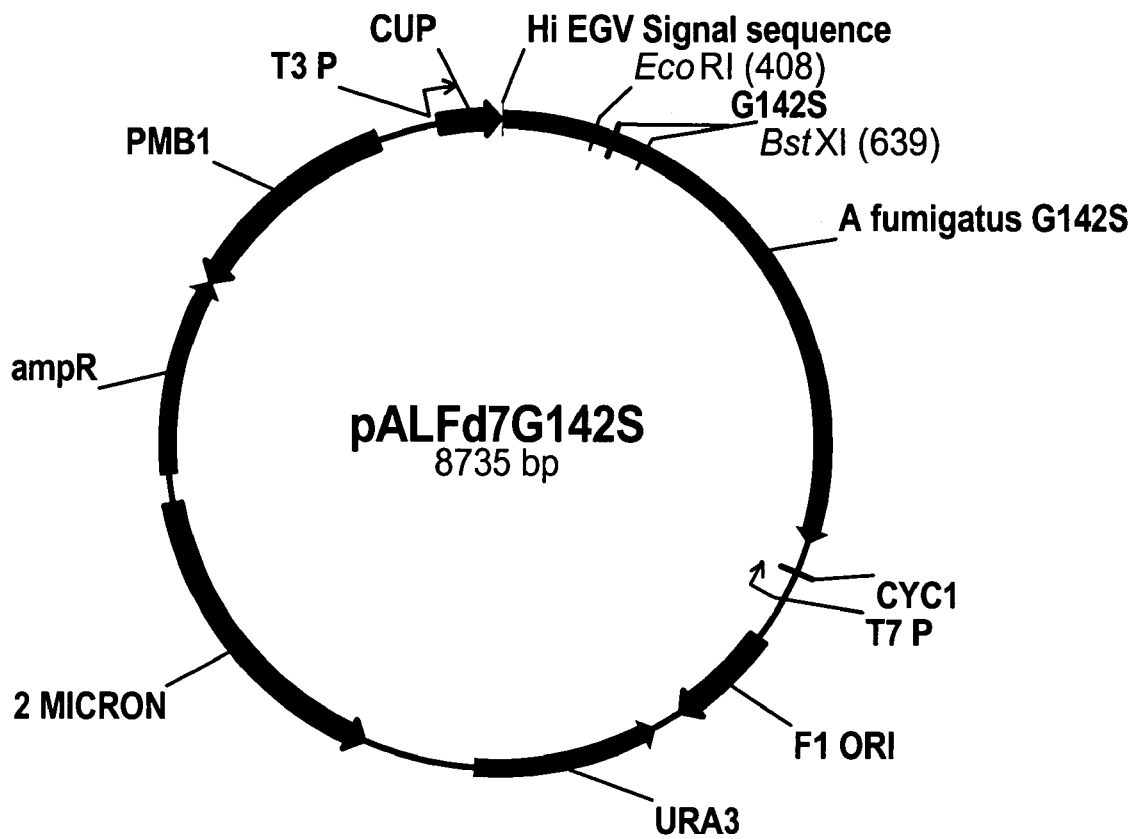
FIG. 28 shows a restriction map of pALFd7G142S.

The ligation reaction was transformed into XL1-Blue *E. coli* subcloning-competent cells according to the manufacturer's instructions. Upon transformation, plasmid DNA from an isolated colony was sequenced as described in Example 10 and the presence of the unique G to A mutation in the entire coding region of the gene was confirmed. Subsequently, the plasmid DNA was transformed into yeast competent cells as described in Example 8, which resulted in isolation of an *Aspergillus fumigatus* beta-glucosidase variant containing the G142S substitution. The yeast expression vector containing the *Aspergillus fumigatus* beta-glucosidase variant with the G142S substitution was designated pALFd7G142S (FIG. 28).

Example 29

Construction of an *Aspergillus fumigatus* Beta-glucosidase Variant with H266Q Substitution The nucleotide region that encoded the H266 amino acid in the *Aspergillus fumigatus* coding sequence of the pEJG97AfumFAM3A vector was mutagenized to produce a C to A mutation that encoded a H266Q substitution present in the *Aspergillus oryzae* beta-glucosidase variant BG53. The mutagenesis was performed using the QuickChange Site-Directed Mutagenesis Kit with the following primers (underlined nucleotides represents the codon with the changed base that encoded the new amino acid substitution):

```
SDMH266QUpper: 5'-TGACTGGAGCGCTCAACACAGCGGTGTCG-3' (SEQ ID NO: 89)

SDMH266QLower: 5'-CGACACCGCTGTGTTGAGCGCTCCAGTCA-3' (SEQ ID NO: 90)
```

Figure 29:
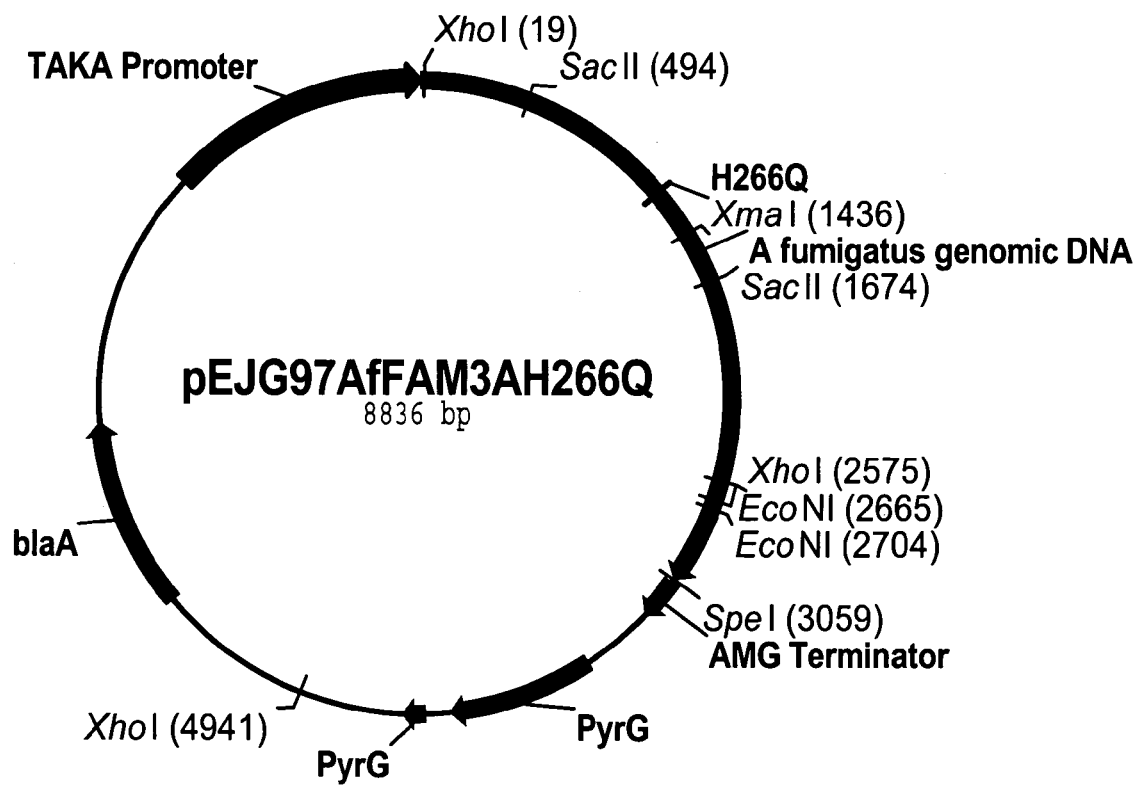
FIG. 29 shows a restriction map of pEJG97AfumFAM3AH266Q.

The presence of the C to A mutation was confirmed by sequencing. The new vector was designated pEJG97AfumFAM3AH266Q (FIG. 29). The C to A mutation was located between the 270 bp fragment obtained by digestion of pEJG97AfumFAM3AH266Q with Blp I, an isoschizomer of Bpu 1102 I, and XmaI. These sites were unique in the pALFd7 vector. Both pEJG97AfumFAM3AH266Q and pALFd7 (approximately 6 µg each) were digested with Blp I and Xma I. The reaction with pALFd7 yielded two fragments, one containing most of vector (8465 bp) and a smaller fragment of 270 bp from the beta-glucosidase coding sequence containing the wild-type location where the C to A mutation was created in the pEJG97AfumFAM3AH266Q vector. The reaction with pEJG97AfumFAM3AH266Q yielded three fragments, one containing most of vector (6,331 bp), a second smaller fragment of 2,235 bp, and a smaller fragment of 270 bp from the beta-glucosidase coding sequence containing the C to A mutation. Digested pALFd7 was treated with shrimp alkaline phosphatase for dephosphorylation of the digested DNA products by adding 1×SAP buffer and 2 ul of SAP from Roche (Roche Applied Science, Manheim, Germany) and incubating the reaction for 10 minutes at 37° C. followed by incubation at 85° C. for 10 minutes for enzyme inactivation. Both digestions were run on 0.7% agarose gel and purified using a QIAGEN Gel purification kit according to the manufacturer's instructions.

Digested pALFd7 was ligated to the 270 bp fragment from the pEJG97AfumFAM3AH266Q digestion containing the position that encoded amino acid 142 with the nucleotide mutation that led to the H266Q amino acid substitution. Ligation was accomplished by using the Rapid DNA Ligation Kit following the manufacturer's instructions.

The ligation reaction was transformed into XL1-Blue *E. coli* subcloning-competent cells according to the manufacturer's instructions. Upon transformation, plasmid DNA from an isolated colony was sequenced as described in Example 10 and the presence of the unique C to A mutation in the entire coding region of the gene was confirmed. Subsequently, the plasmid DNA was transformed into yeast competent cells as described in Example 8, which resulted in isolation of an *Aspergillus fumigatus* beta-glucosidase variant containing the H266Q substitution. The yeast expression vector containing the *Aspergillus fumigatus* beta-glucosidase variant with the G142S substitution was designated pALFd7H266Q.

Example 30

Construction of an *Aspergillus fumigatus* Beta-glucosidase Variant with G142S and H266Q Substitutions Plasmid pEJG97AfumFAM3AH266Q contained the C to A mutation located in the 270 bp fragment obtained by digestion of pEJG97AfumFAM3AH266Q with Blp I and Xma I. The pALFd7G142S vector contained the G to A mutation that produced the G142S substitution in the *Aspergillus fumigatus* beta-glucosidase sequence. Both pEJG97AfumFAM3AH266Q and pALFd7G142S (approximately 6 µg each) were digested with Blp I and Xma I. The reaction with pALFd7 yielded two fragments, one containing most of vector (8,465 bp) and a smaller fragment of 270 bp from the beta-glucosidase coding sequence containing the wild-type location where the C to A mutation was created in the pEJG97AfumFAM3AH266Q vector. The reaction with pEJG97AfumFAM3AH266Q yielded three fragments, one containing most of vector (6,331 bp), a second smaller fragment of 2,235 bp, and a smaller fragment of 270 bp from the beta-glucosidase coding sequence containing the C to A mutation. Digested pALFd7G142S was treated with shrimp alkaline phosphatase for dephosphorylation of the digested DNA products by adding 1×SAP buffer and 2 ul of SAP from Roche (Roche Applied Science, Manheim, Germany) and incubating the reaction for 10 minutes at 37° C. followed by incubation at 85° C. for 10 minutes for enzyme inactivation. Both digestions were run on 0.7% agarose gel using TAE buffer and purified using a QIAGEN Gel purification kit according to the manufacturer's instructions.

Digested pALFd7G142S was ligated to the 270 bp fragment from the pEJG97AfumFAM3AH266Q digestion containing the nucleotide mutation that led to the H266Q amino acid substitution. Ligation was accomplished by using the Rapid DNA Ligation Kit following the manufacturer's instructions.

The ligation reaction was transformed into XL1-Blue *E. coli* subcloning-competent cells according to the manufacturer's instructions. Upon transformation, plasmid DNA from an isolated colony was sequenced as described in Example 10 and the presence of the G to A mutation that encoded the G142S substitution and the C to A mutation which encoded the H266Q substitution in the entire coding region of the gene was confirmed. Subsequently, the plasmid DNA was transformed into yeast competent cells as described in Example 8, which resulted in isolation of an *Aspergillus fumigatus* beta-glucosidase variant containing the G142S and H266Q substitutions. The yeast expression vector containing the *Aspergil-* lus fumigatus beta-glucosidase variant with both the G142S and H266Q substitutions was designated pALFd7G142SH266Q.

Example 31

Construction of an *Aspergillus fumigatus* Beta-glucosidase Variant with H266Q and D705G Substitutions The nucleotide region that encoded the D705 amino acid in the *Aspergillus fumigatus* coding sequence of pEJG97AfumFAM3A was mutagenized to produce a A to G mutation that encoded a homologous D703G substitution present in the *Aspergillus oryzae* beta-glucosidase variant BG53. The mutagenesis was performed using the Quick-Change Site-Directed Mutagenesis Kit according to the manufacturer's instructions and the following primers (underlined nucleotides represents the codon with the changed base that encoded the new amino acid substitution):

```
SDMD705GUpper:  5'-GAGGATTCTTCTGGCGACCCGAACTACGGC-3' (SEQ ID NO: 91)

SDMD705GLower:  5'-GCCGTAGTTCGGGTCGCCAGAAGAATCCTC-3' (SEQ ID NO: 92)
```

The presence of the A to G mutation was confirmed by sequencing. The new vector was designated pEJG97AfumFAM3AD705G. The A to G mutation was located in the 711 bp fragment obtained by digestion of the pEJG97AfumFAM3AD705G vector with Bst EII which has 2 sites in the pEJG97AfumFAM3AD705G. To clone the 711 bp fragment containing the mutation in the pALFd7H266Q vector, both pEJG97AfumFAM3AD705G and pALFd7H266Q vectors (approximately 6 µg each) were digested with Bst EII. The digestion with pALFd7H266Q yielded two fragments, one containing most of vector (8,024 bp) and a smaller fragment of 711 bp from the beta-glucosidase coding sequence containing the wild-type location encoding the D705 amino acid. The digestion with pEJG97AfumFAM3AD705G yielded two fragments, one containing most of vector (8,125 bp), and a smaller fragment of 711 bp from the beta-glucosidase coding sequence containing the A to G mutation. Digested pALFd7H266Q was treated with shrimp alkaline phosphatase for dephosphorylation of the digested DNA products by adding 1×SAP buffer and 2 ul of SAP and incubating the reaction for 10 minutes at 37° C. followed by incubation at 85° C. for 10 minutes for enzyme inactivation. Both digestions were run on 0.7% agarose gel and purified using a QIAGEN Gel purification kit according to the manufacturer's instructions.

Digested pALFd7H266Q was ligated to the 711 bp fragment from the pEJG97AfumFAM3AD705G digestion containing the nucleotide mutation that led to the D705G amino acid substitution. Ligation was accomplished by using the Rapid DNA Ligation Kit following the manufacturer's instructions. The ligation reaction was transformed into XL1-Blue *E. coli* subcloning-competent cells according to the manufacturer's instructions. Upon transformation, plasmid DNA from an isolated colony was sequenced as described in Example 10 and the presence of the unique C to A and A to G mutations that encode the G166S and H266Q amino acid substitutions, respectively, in the entire coding region of the gene was confirmed. Subsequently, the plasmid DNA was transformed into yeast competent cells as described in Example 8, which resulted in isolation of an *Aspergillus fumigatus* beta-glucosidase variant containing the H266Q and D705G substitutions. The yeast expression vector containing the *Aspergillus fumigatus* beta-glucosidase variant with the H266Q and D705G substitutions was designated pALFd7H266QD705G.

Example 32

Assay of the Effects of the G142S, H266Q, G142S and H266Q, and H266Q and D705G Mutations in *Aspergillus fumigatus* Beta-glucosidase Residual activity measurements of the *Aspergillus fumigatus* beta-glucosidases encoded by the following vectors was carried out as described in Example 9 at 80° C. after 10 minutes: pALFd7, which contains the wild-type *Aspergillus fumigatus* beta-glucosidase cDNA core sequence with the *Humicola insolens* endoglucanase V signal sequence, and the same constructs with the following mutations, labeled respectively, pALFd7G142S, with the G142S amino acid substitution; pALFd7H266Q, with the H266Q amino acid substitution; pALFd7G142SH266Q, with the G142S and H266Q amino acid substitutions; and pALFd7H266QD705G, with the H266Q and D705G amino acid substitutions. Table 4 below shows the relative residual activity of the beta-glucosidases at 80° C. The results showed that the amino acid substitutions improved the residual activity of *Aspergillus fumigatus* beta-glucosidase enzyme at 80° C. The G61S and H266Q amino acid substitution combination had the highest impact in improving the thermostability of the *Aspergillus fumigatus* beta-glucosidase enzyme.

TABLE 4

Relative Residual Activity of *Aspergillus fumigatus* Beta-Glucosidase Variants

| Amino acid substitutions | Relative residual activity at 80° C. |
|---|---|
| *A. fumigatus* WT | 1.00 |
| *A. fumigatus* G142S | 1.37 |
| *A. fumigatus* H266Q | 1.08 |
| *A. fumigatus* G142S; H266Q | 1.73 |
| *A. fumigatus* H266Q; D705G | 1.57 |

Deposit of Biological Material

The following biological material has been deposited under the terms of the Budapest Treaty with the Agricultural Research Service Patent Culture Collection, Northern Regional Research Center, 1815 University Street, Peoria, Ill., 61604, and given the following accession numbers:

| Deposit | Accession Number | Date of Deposit |
|---|---|---|
| *E. coli* TOP10 (pEJG113) | NRRL B-30695 | Oct. 17, 2003 |
| *E. coli* (pSATe111BG53) | NRRL B-30652 | May 2, 2003 |

The strains have been deposited under conditions that assure that access to the cultures will be available during the pendency of this patent application to one determined by the Commissioner of Patents and Trademarks to be entitled thereto under 37 C.F.R. §1.14 and 35 U.S.C. §122. The deposits represent substantially pure cultures of the deposited strains. The deposits are available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. An isolated variant of a parent beta-glucosidase, comprising a substitution at one or more positions corresponding to positions 142, 183, 266, and 703 of amino acids 1 to 842 of SEQ ID NO: 2 or corresponding to positions 142, 183, 266, and 705 of amino acids 1 to 844 of SEQ ID NO: 70, wherein the variant has beta-glucosidase activity, the parent beta-glucosidase comprises an amino acid sequence which has at least 95% identity to amino acids 1 to 842 of SEQ ID NO: 2 or amino acids 1 to 844 of SEQ ID NO: 70, and the variant beta-glucosidase comprises an amino acid sequence which has at least 95% identity to amino acids 1 to 842 of SEQ ID NO: 2 or amino acids 1 to 844 of SEQ ID NO: 70.

2. The variant of claim 1, which comprises one or more substitutions selected from the group consisting of G142S, Q183R, H266Q, and D703G or D705G.

3. The variant of claim 1, wherein the number of substitutions is 4, 3, 2, or 1.

4. The variant of claim 1, which has one or more improved properties compared to the parent beta-glucosidase, wherein the improved properties are selected from the thermostability.

5. The variant of claim 1, wherein the variant consists of 801 to 810, 811 to 820, 821 to 830, 831 to 840, 841 to 850, 851 to 860, 861 to 870, 871 to 880, 881 to 890 amino acids.

6. The variant of claim 1, which is encoded by a nucleotide sequence which is contained in E. coli NRRL B-30652.

7. The variant of claim 1, wherein the parent beta-glucosidase comprises an amino acid sequence which has at least 97% identity to amino acids 1 to 842 of SEQ ID NO: 2 or amino acids 1 to 844 of SEQ ID NO: 70.

8. The variant of claim 1, wherein the parent beta-glucosidase comprises the amino acid sequence of amino acids 1 to 842 of SEQ ID NO: 2 or amino acids 1 to 844 of SEQ ID NO: 70.

9. The variant of claim 1, which comprises an amino acid sequence which has at least 97% identity to amino acids 1 to 842 of SEQ ID NO: 2 or amino acids 1 to 844 of SEQ ID NO: 70.

10. The variant of claim 1, which comprises substitutions at positions corresponding to positions 142 and 183; positions 142 and 266; positions 142 and 703; positions 183 and 266; positions 183 and 703; or positions 266 and 703 of amino acids 1 to 842 of SEQ ID NO: 2 or to positions 142 and 183; positions 142 and 266; positions 142 and 705; positions 183 and 266; positions 183 and 705; or positions 266 and 705 of amino acids 1 to 844 of SEQ ID NO: 70.

11. The variant of claim 10, wherein the substitution corresponding to position 142 is Ser, the substitution corresponding to position 183 is Arg, the substitution corresponding to position 266 is Gln, and/or the substitution corresponding to position 703 or 705 is Gly.

12. The variant of claim 1, which comprises substitutions at positions corresponding to positions 142, 183, and 266; positions 142, 266, and 703; positions 183, 266, and 703; or positions 142, 183, and 703 of amino acids 1 to 842 of SEQ ID NO: 2 or to positions 142, 183, and 266; positions 142, 266, and 705; positions 183, 266, and 705; or positions 142, 183, and 705 of amino acids 1 to 844 of SEQ ID NO: 70.

13. The variant of claim 12, wherein the substitution corresponding to position 142 is Ser, the substitution corresponding to position 183 is Arg, the substitution corresponding to position 266 is Gln, and/or the substitution corresponding to position 703 or 705 is Gly.

14. The variant of claim 1, which comprises substitutions at positions corresponding to positions 142, 183, 266, and 703 of amino acids 1 to 842 of SEQ ID NO: 2 or positions 142, 183, 266, and 705 of amino acids 1 to 844 of SEQ ID NO: 70.

15. The variant of claim 14, wherein the substitution corresponding to position 142 is Ser, the substitution corresponding to position 183 is Arg, the substitution corresponding to position 266 is Gln, and/or the substitution corresponding to position 703 or 705 is Gly.

16. The variant of claim 1, which comprises the substitutions G142S+Q183R+H266Q+D703G or D705G; G142S+Q183R+H266Q; G142S+H266Q+D703G or D705G; Q183R+H266Q+D703G or D705G; G142S+Q183R+D703G or D705G; G142S+Q183R; G142S+H266Q; G142S+D703G or D705G; Q183R+H266Q; Q183R+D703G or D705G; or H266Q+D703G or D705G.

* * * * *